(12) United States Patent
Antoniou et al.

(10) Patent No.: US 8,058,028 B2
(45) Date of Patent: *Nov. 15, 2011

(54) POLYNUCLEOTIDE

(75) Inventors: Michael Antoniou, Middlesex (GB); Robert L Crombie, Stroke-on-Trent (GB)

(73) Assignee: Millipore Corporation, Billerica, MA (US)

( * ) Notice: Subject to any disclaimer, the term of this patent is extended or adjusted under 35 U.S.C. 154(b) by 193 days.

This patent is subject to a terminal disclaimer.

(21) Appl. No.: 12/235,058

(22) Filed: Sep. 22, 2008

(65) Prior Publication Data

US 2010/0112640 A1 May 6, 2010

Related U.S. Application Data

(60) Division of application No. 11/087,052, filed on Mar. 22, 2005, now Pat. No. 7,442,787, which is a continuation of application No. 10/225,418, filed on Aug. 21, 2002, now Pat. No. 6,964,951, which is a division of application No. 09/358,082, filed on Jul. 21, 1999, now Pat. No. 6,689,606.

(60) Provisional application No. 60/134,016, filed on May 12, 1999, provisional application No. 60/127,410, filed on Apr. 1, 1999, provisional application No. 60/107,688, filed on Nov. 9, 1998.

(30) Foreign Application Priority Data

Jul. 21, 1998  (GB) .................. 9815879.3
Mar. 23, 1999  (GB) .................. 9906712.6
Apr. 23, 1999  (GB) .................. 9909494.8

(51) Int. Cl.
*C12P 21/02* (2006.01)
(52) U.S. Cl. ................. 435/69.1; 435/91.5; 435/91.41; 435/320.1; 536/24.1
(58) Field of Classification Search ........................ None
See application file for complete search history.

(56) References Cited

U.S. PATENT DOCUMENTS

| 6,881,556 B2 * | 4/2005 | Antoniou et al. | 435/69.1 |
| 6,949,361 B2 * | 9/2005 | Antoniou et al. | 435/69.1 |
| 7,812,148 B2 * | 10/2010 | Crombie et al. | 536/24.1 |

* cited by examiner

*Primary Examiner* — Jim Ketter

(57) ABSTRACT

The present invention relates to a polynucleotide comprising a ubiquitous chromatin opening element (UCOE) which is not derived from 13. The polynucleotide of any one of claims 1 to 7, wherein the UCOE comprises the sequence of FIG. 20 between nucleotides 1 to 7627 or a functional homologue or fragment thereof an LCR. The present invention also relates to a vector comprising the polynucleotide sequence, a host cell comprising the vector, use of the polynucleoticle, vector or host cell in therapy and in an assay, and a method of identifying UCOEs. The UCOE opens chromatin or maintains chromatin in an open state and facilitates reproducible expression of an operably-linked gene in cells of at least two different tissue types.

15 Claims, 83 Drawing Sheets

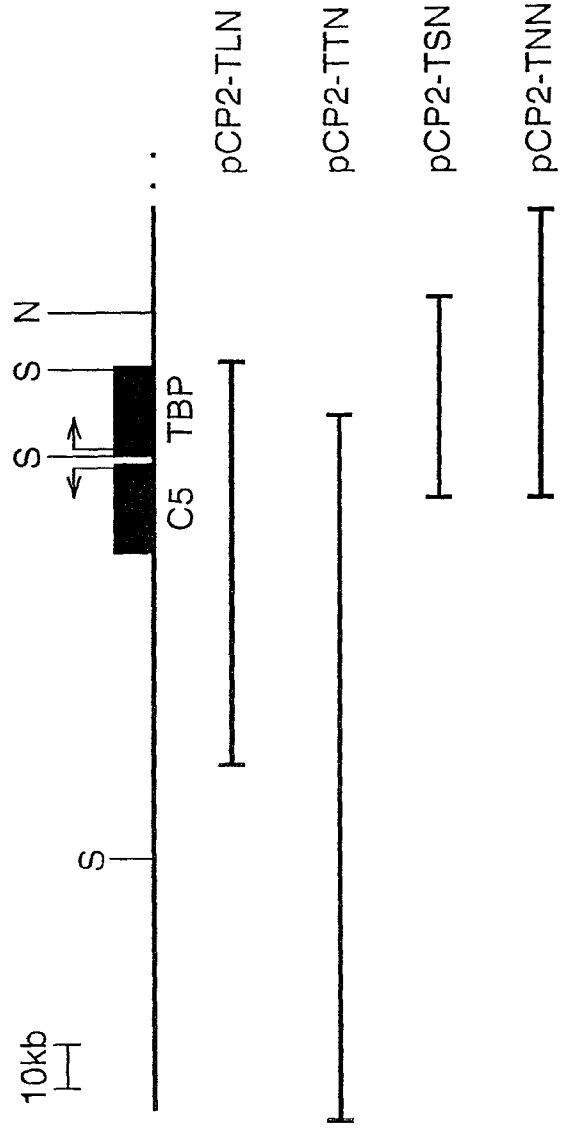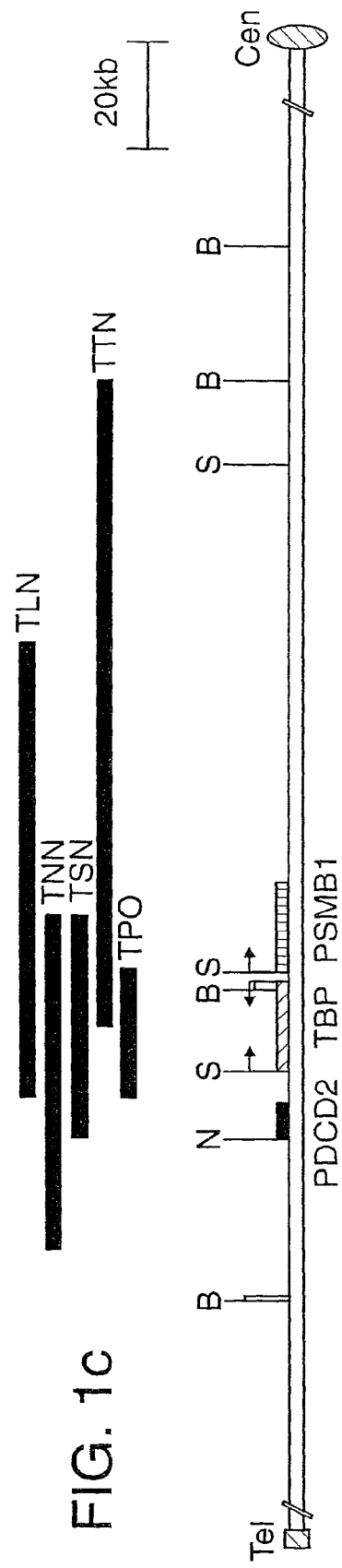
FIG. 1a
FIG. 1c

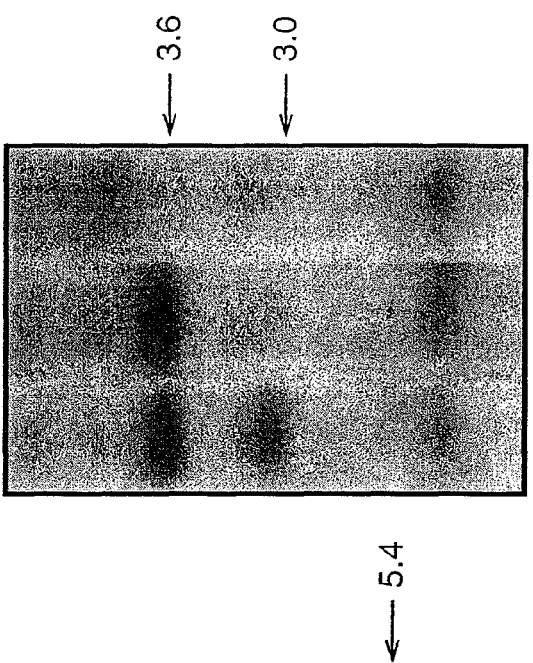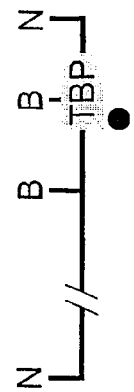
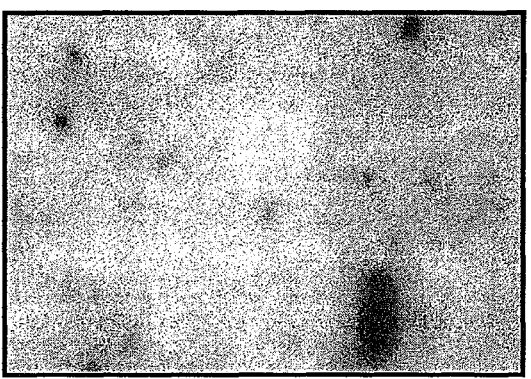
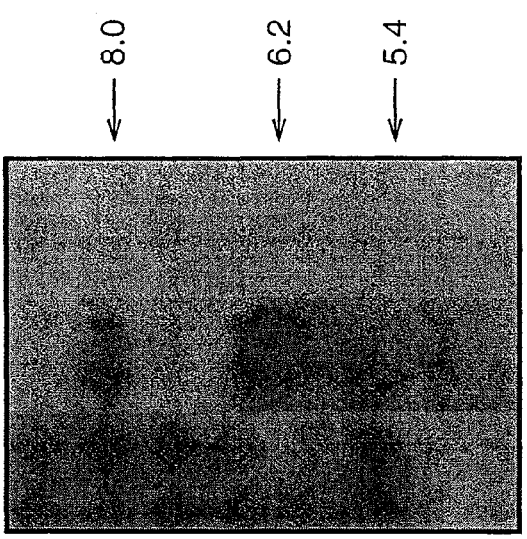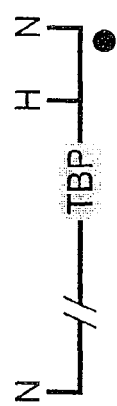

FIG. 2(d)
*Hind III*
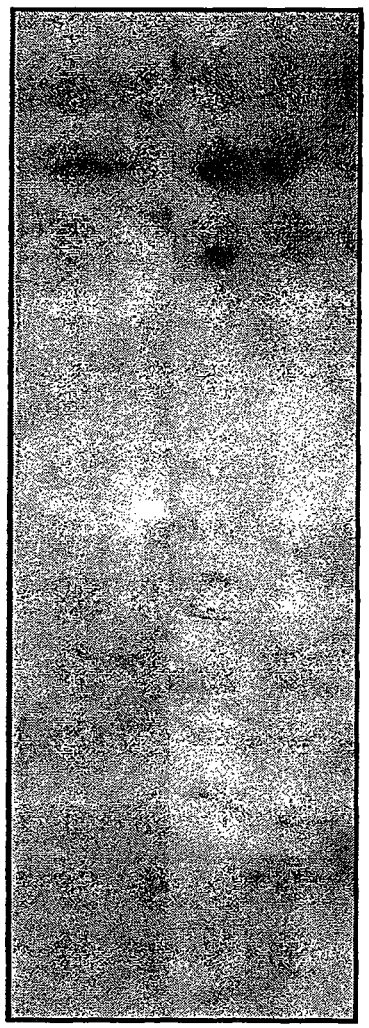
← 7.0
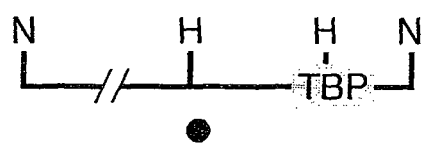
FIG. 2(e)
*Bam HI*
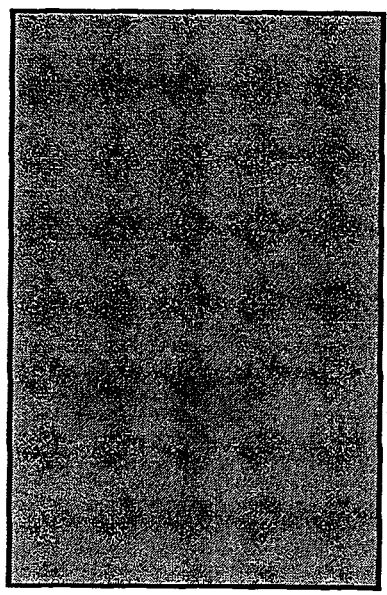
← 2.5
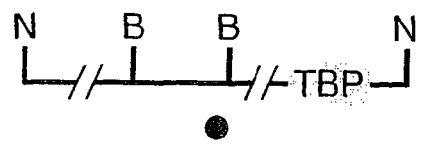

TLN:3

TLN:8

TLN:28

FIG. 5(a)
C5 mRNA

```
         C5RTF
Hu: 5'-ATTGCTGCAATGCTGTCTACAATCCTGTATTCAAGGGCGCTTCTTCCATACTATGTGTTACAACATCATCGGTGACTTGATGAAGAAGGAAAGGGGGCTGTATACAGCT
         ||||||||||||||||||||||||||||||||||||||||||||||||||||||||||||||||||||||||||||||||||||| ||||||||||||||||||||||||
Mo: 5'-ATTGCTGCAATGCTGTCTACCATCCTGTACTCACGGGCGCTTCTTCCCTTCTTCCTACTATGTGTTTACAACATCATCATTGGAGGACTTGATGAAGAAGGAAAGGGGAGCTGTGTACAGCT

TTGATCCAGTAGGGCTTACCAGAGAGACTCCTTCAAGGCTGGAGGCTCAGCATGCAAGTGCCATGTCAGCAGGTTGTTTAAGAACATGCAGAATGTGGA
||||||||||||||||||||||||||||||||||||||||||||||||||||||||||||||||||||| ||||||||||||| |||||||||||||
TTGACCCAGTGGGCTCTACCAGAGAGACTCTTTCAAGGCGGGAGGCTCAGCATGCAAGTGCCATGTCAGCAGGTTGCTTCTTGACAACCAGGTTGTTTAAGAACATGCAGAATGTGGA

GCATGTTCCGGCTGTCCTTGGACAGAGCCATGGGCTGGCTGGTGAAAGATGTCTTCATTTCTGCGGGGACCACTCCGGATCCGCATAGTGTGACCAAA
||||||||||||||||||||||||||||||||||||||||||||||||||||||||||||||||   |||||||||||||||||||||||||| |||
GCACGTCCCCCTGACGCTGGACAGAGCCATGAGGCTGGTGAAAGATGTCTTCATTTCTGCAGCCGAGAGGGATGTGTATACTGGAGATGCTCTCAGGATGCATCGTGACCAAA
                                                                    PstI

GAGGGCATCAGG-3'
|||||||||||
GAGGGCATCAGG-3'
     C5R
```

FIG. 5(b)
TBP mRNA

*TB-22*　　　　　　　　　　　　　　　*Bsp1407I*

Hu:5'-ATGGTGTGCACAGGAGCCAAGAGTGTAGAACAGTTCCAGAGACAATGCTAGAGTTGTACAGAAGTTGGGTTTTCCAGCTAAGTCTTGGACTTCAAG
      |||||||||||||||||||||||| ||||||||||||| |||||||||| |||||||||||||||||||||||||||||||||||| |||||||||||
Mo:5'-ATGGTGTTGACAGGAGCCAACAGTGAAGAACAGTTCCAGAGACAAGAATATGCTAGAGTTGTGCAGAAGTTGGGCTTCCCAGCTAAGTCTTAGACTTCAAG

ATTCAGAACATGGTGGGGAGCTGTGATGTGAAGTTCCCTATAAGGTTAGAAGGCCTTGTGCTCACCCACCAACAATTTCGTATGTATGAGCCAGAGTGTATTTCCTGGTTAATCT
|||||||||||||||||||||||||||||||||||||||||||||||||||||||||||||||||||||||||||||||||    |||||||||||||||| |||||||||||
ATCCAGAACATGGTGGGGAGCTGTGATGTGAAGTTCCCCATAAGGCCTGAAGGCCTTGTGCTGACCCACCAGCAGTTCCGTAGCTATGAGCCAGAGAATTATTTCCTGATTAATCT
                                                                                GATC

ACAGAATGATCAAACCCAGAATTGTTCTCCCTTATTTTTGTTCTGGAAAAAGTTGTATTAACAGGTG-3'
||||||||||||||||||||||||||||||||||||||||||||||||| |||||||||||||||||
ACAGAATGATCAAACCCAGAATTGTTCTCCCTTATTTTTGTTCTGGAAAAGTTGTATTAACAGGTG-3'

*TB-14*

(TLN3)

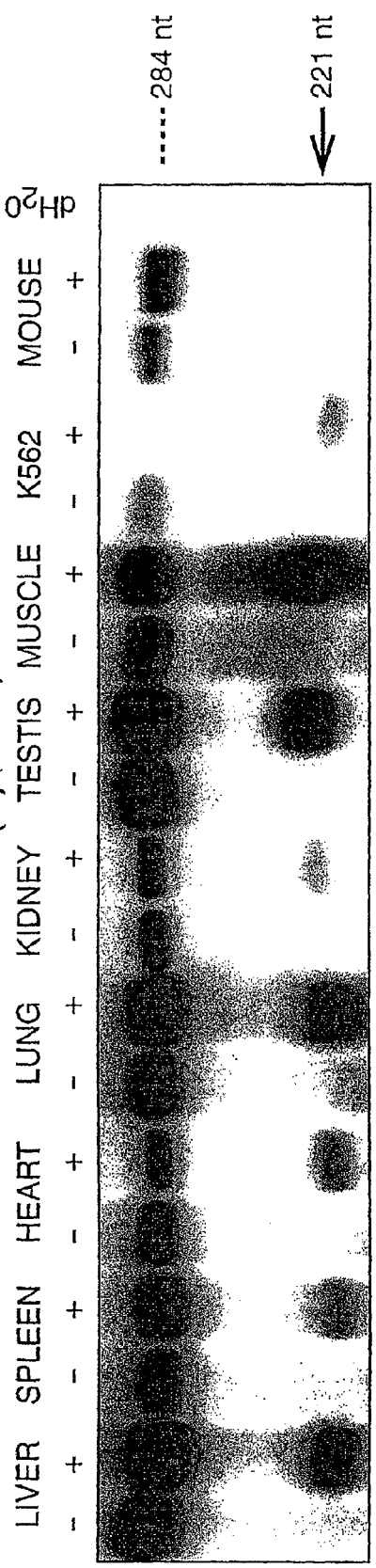
FIG. 6(c) (TLN8)
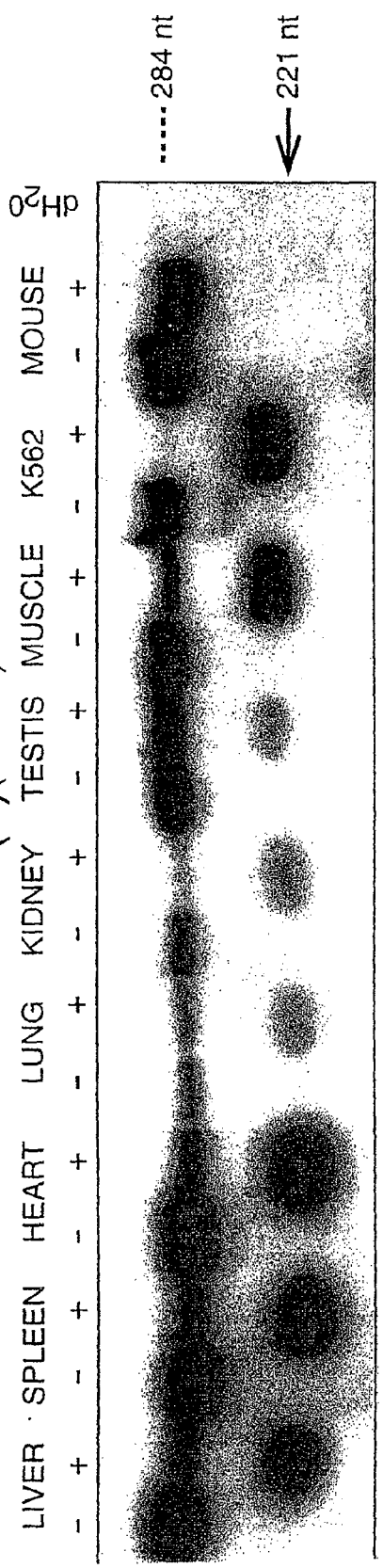
FIG. 6(d) (TLN28)

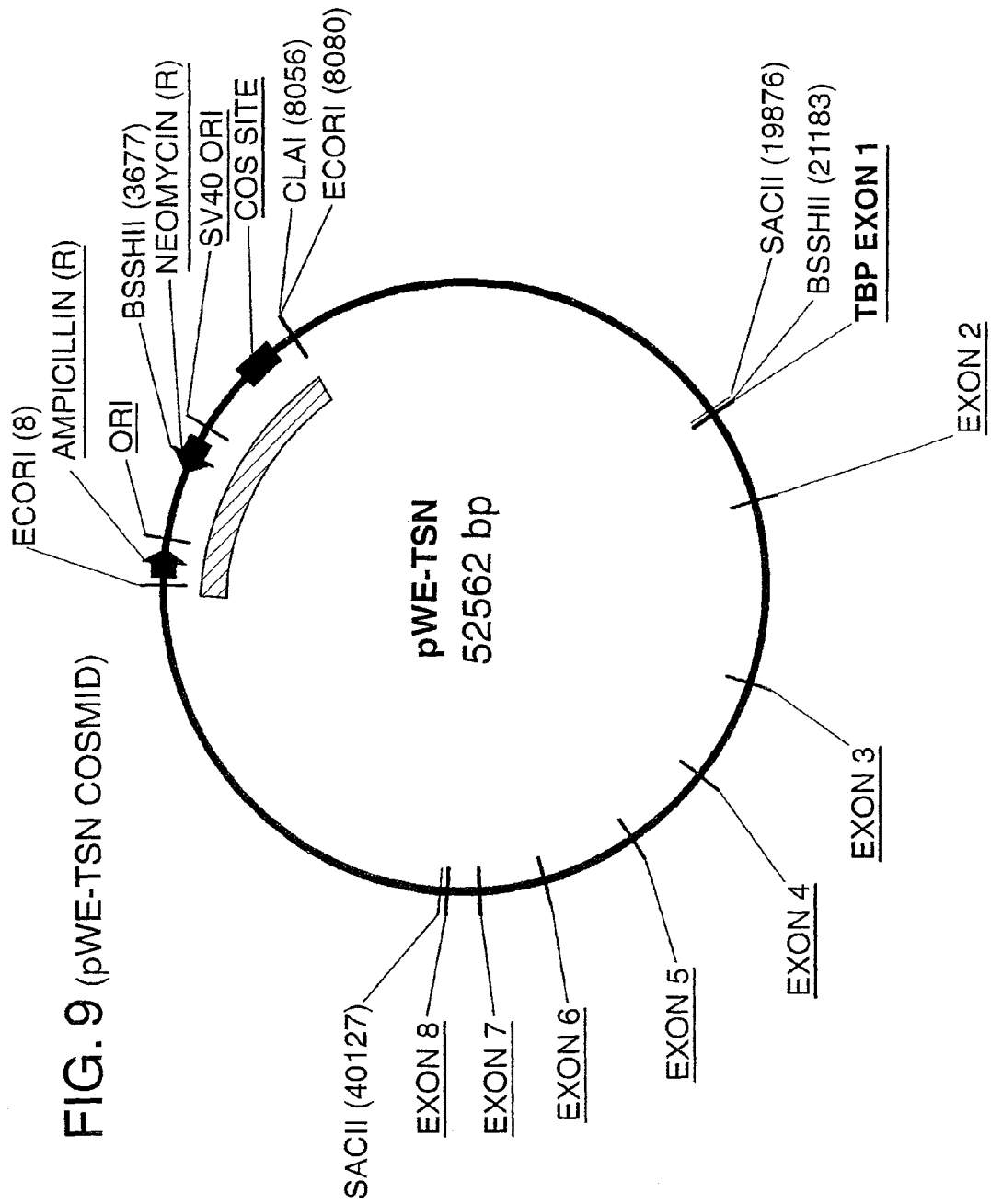
FIG. 9 (pWE-TSN COSMID)

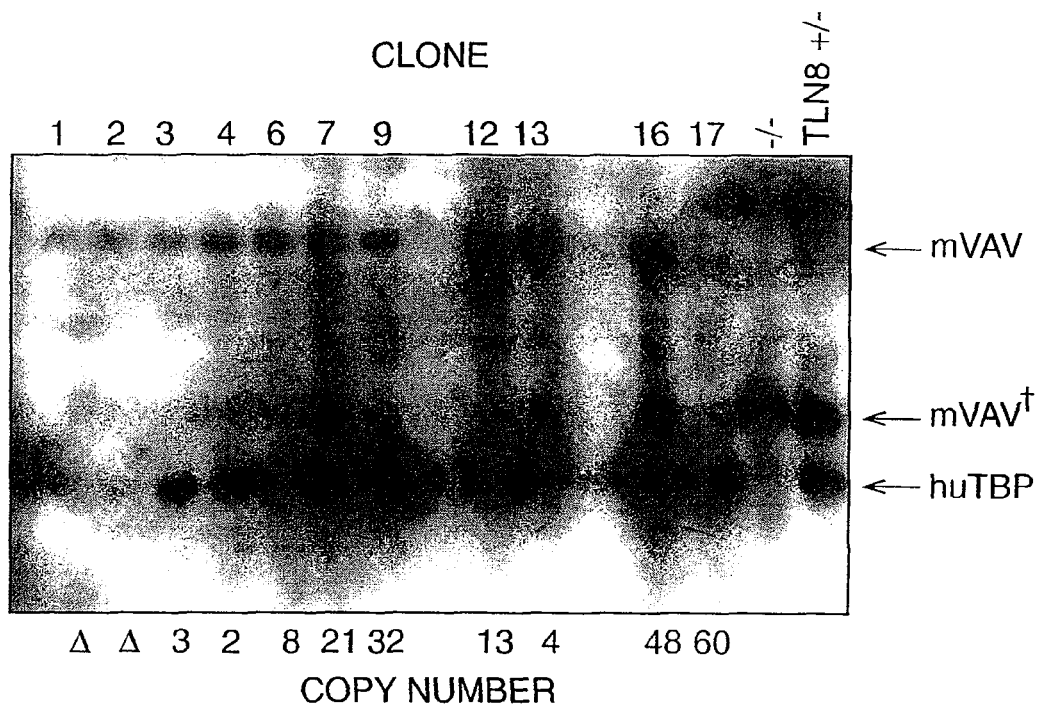
FIG.10
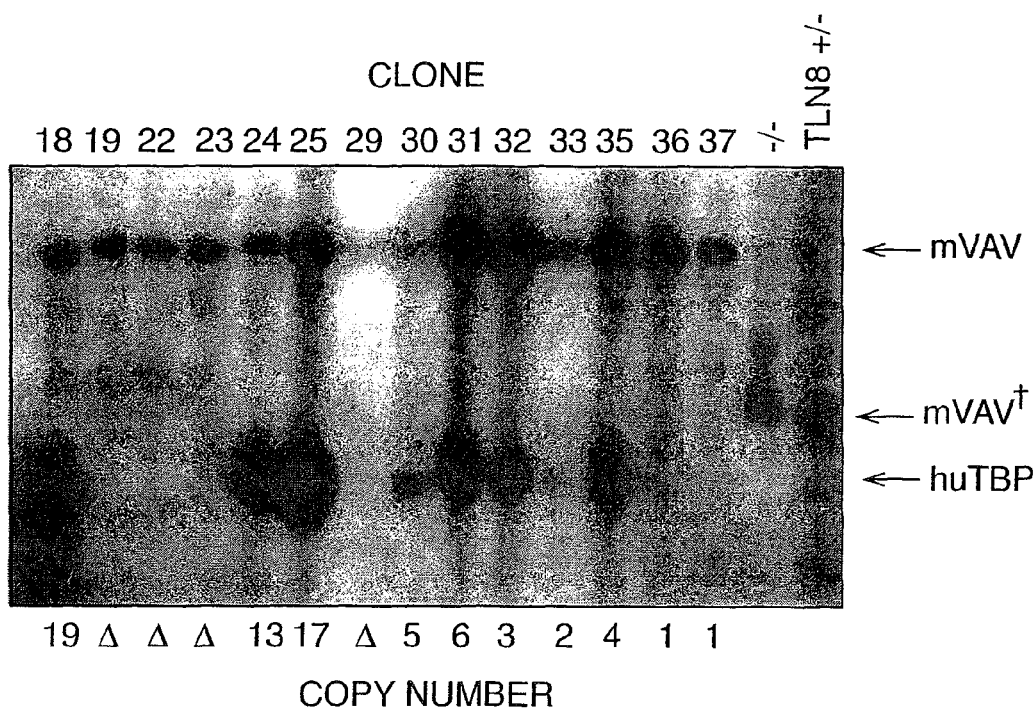

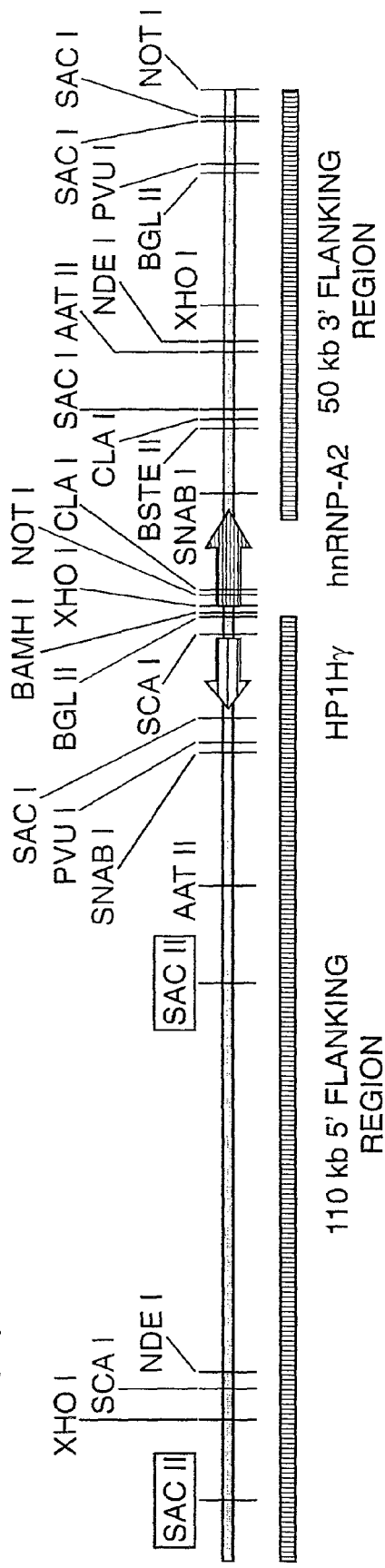

FIG. 14(a)
PRIMERS USED FOR RT AND PCR REACTIONS

Hn 9

```
 9801  GAAGTGGAAA TTACAATGAT TTTGGAAATT ATAACCAGCA ACCTTCTAAC
 9851  TACGGTCCAA TGAAGAGTGG AAACTTTGGT GGTAGCAGGA ACATGGGGGG    EXON 10
 9901  ACCATATGGT GGAGGTAATT TATAAAAATT GAGGTTATTC AGATTTTTGT
 9951  GATTAAAGGA TTAGCCTTTT GTGACTTAAA GGGAAGATAA CATACTAAGT
10001  AGTTTGTACT GTGGGCAGTG CTCCATGTAC GGTCTTAGTG AAAATAAAGA
10051  AATTTTGCAT AAATCTCCAC AGAAGTACTC AGCAAGCAGT TATGACATCA
10101  AATTGGGATT AGGTAGTTGG AGGTGGGTGT CAGTAGTTTA ATTTCTGGTG
10151  GGACTCATAA ACAGCTAAAT ACAGTTGCAA CCCACATTGC AAGTGGTATA
10201  CATTGGAATG AGGGTCTTTG AAGTTAAATC CTTAAACCAT GATTCAAACC
10251  ATTGCTTAGC TTATTTTTGA GGTTTTTAGC TAGGAGTAAA CTAGCTTTGT
10301  CTTGGGCTTG ATGTACTTTT AAAAAAATCC CTTACTCAGT CCAAATGAGG
10351  ATGAGAGGGT GAAAGGACCC TTTATTTAAA AGAATAGGGT CAGCCACGAA
10401  ATAAAAATGT CTATGAACCC GAGTAATTTA TCTCCTGAGT AATTCTGCTA
10451  ACTGGCTGCA AAGGATTAGG ATCTGCTTGT TTAAAAGACT GGATGGATAT
10501  AAAATAGAAT CAACTGTAGT GTTAGGCTGA TCATGGGAAA TCAAAGTAAG
10551  TTTGTTTTCT CTTGCTGTTC CAACAATTAT AGGAAACTAT GGTCCAGGAG
10601  GCAGTGGAGG AAGTGGGGGT TATGGTGGGA GGAGCCGATA CTGAGCTTCT    EXON 11
10651  TCCTATTTGC CATGGGTAAG TAGCTTTTGA GTTTTACAAT TATTATTATC
10701  TTGGGAGACA TAGCTGCAGG AGTAAAAGCT TTTTAGGATC ATGGTTATCT
10751  TTCCTTAAAA TCTGGTTAGA TGGATAATTT CATAACCCAT TTTTTTTTTA
10801  CCCTTTACTT CTGTTGAAAC AGGCTTCACT GTATAAATAG GAGAGGATGA
10851  GAGCCCAGAG GTAACAGAAC AGCTTCAGGT TATCGAAATA ACAATGTTAA
10901  GGAAACTCTT ATCTCAGTCA TGCATAAATA TGCAGTGATA TGGCAGAAGA
10951  CACCAGAGCA GATGCAGAGA GCCATTTTGT GAATGGATTG GATTATTTAA    EXON 12
11001  TAACATTACC TTACTGTGGA GGAAGGATTG TAAAAAAAAA TGCCTTTGAG
```

[Hn 11]

DIGESTION OF RT-PCR PRODUCTS

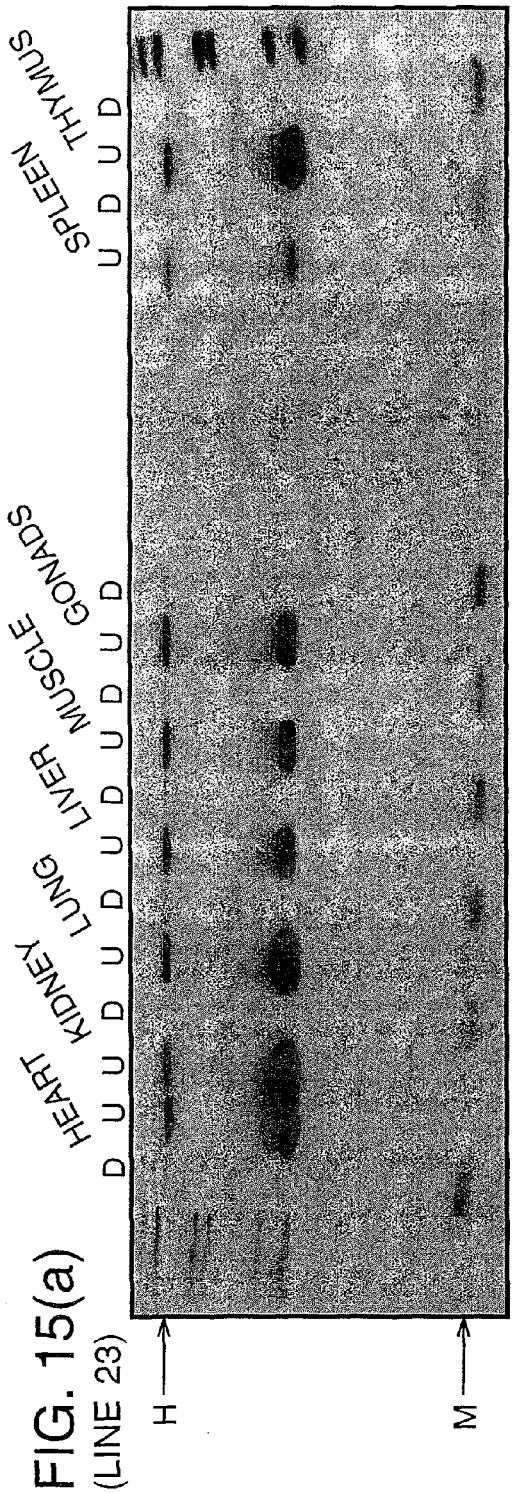
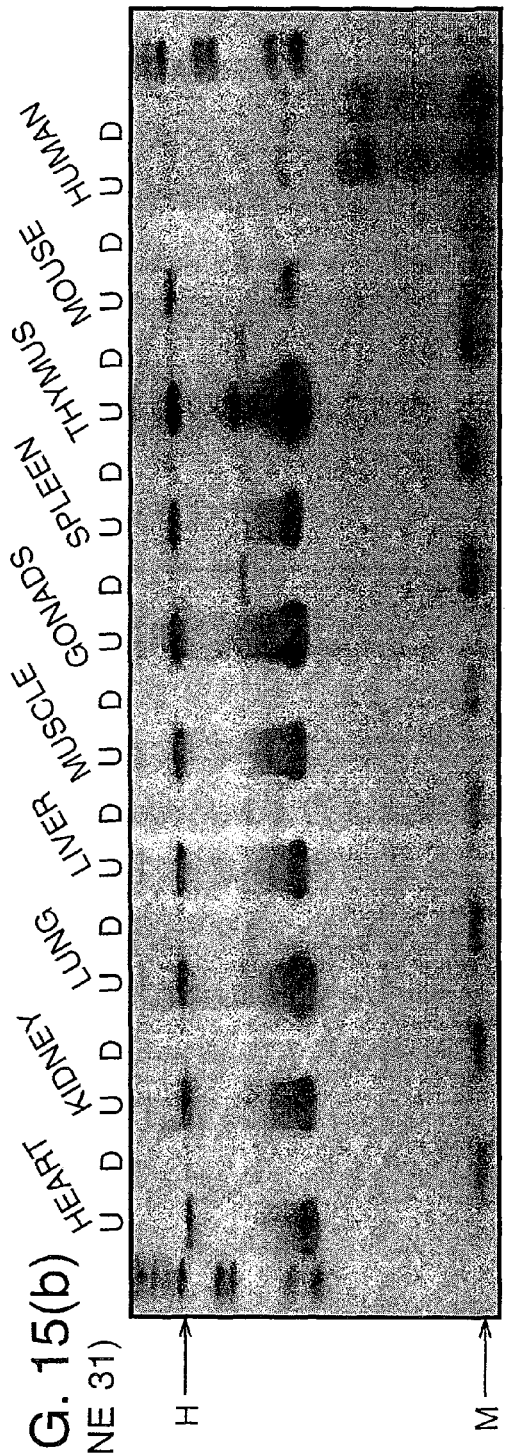
FIG. 15(a) (LINE 23)
FIG. 15(b) (LINE 31)

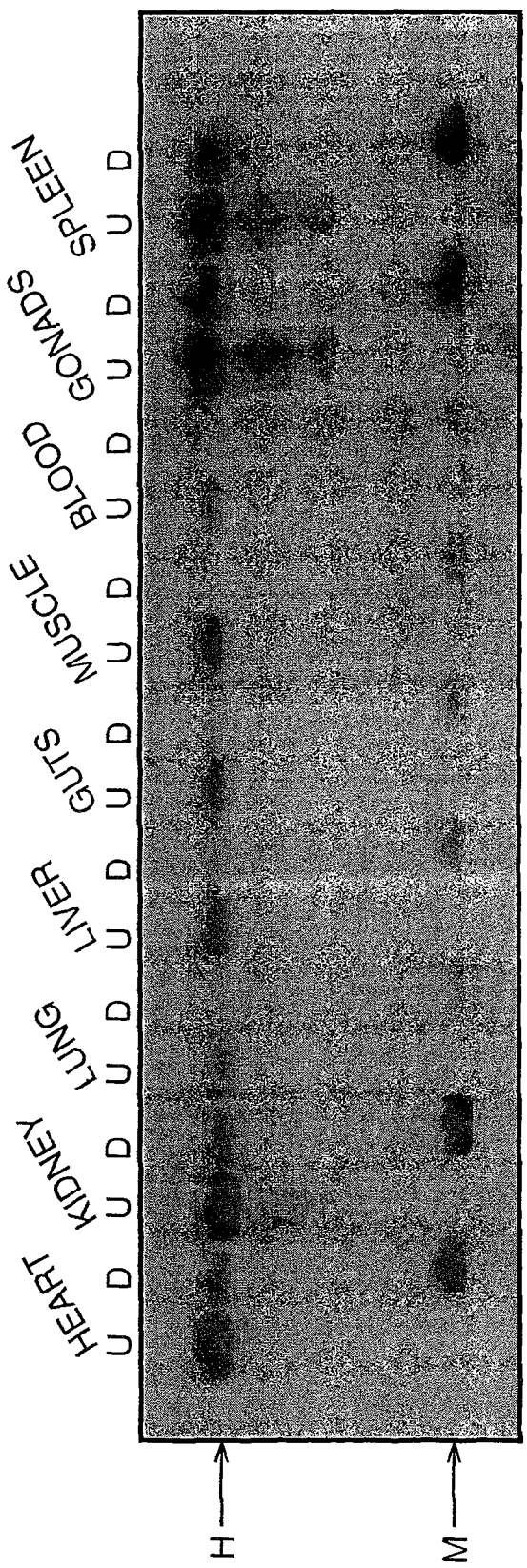

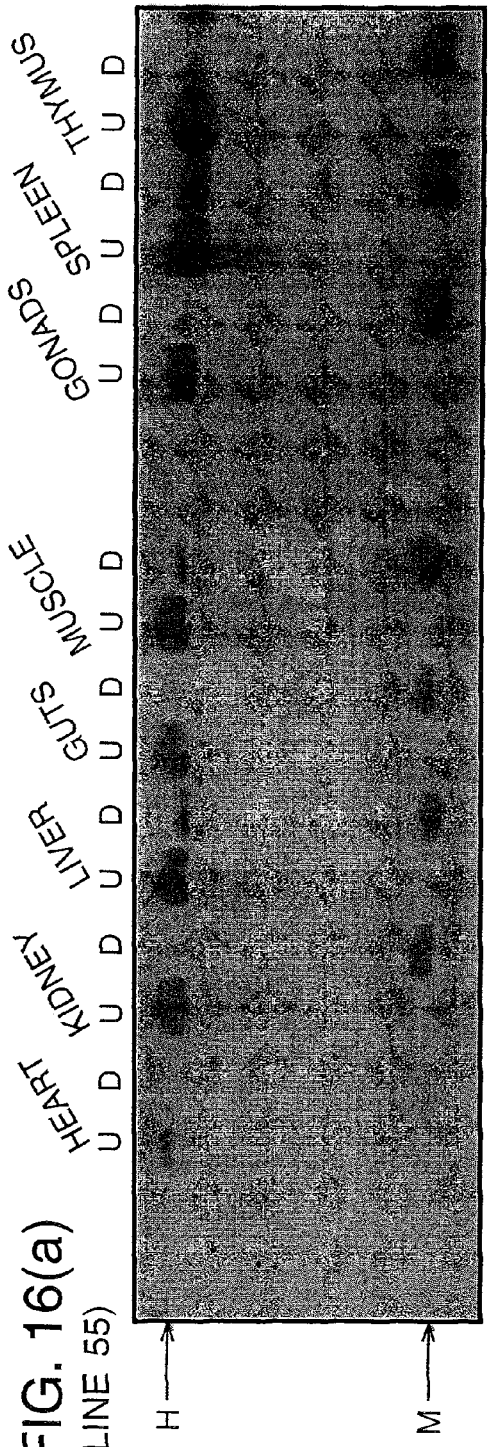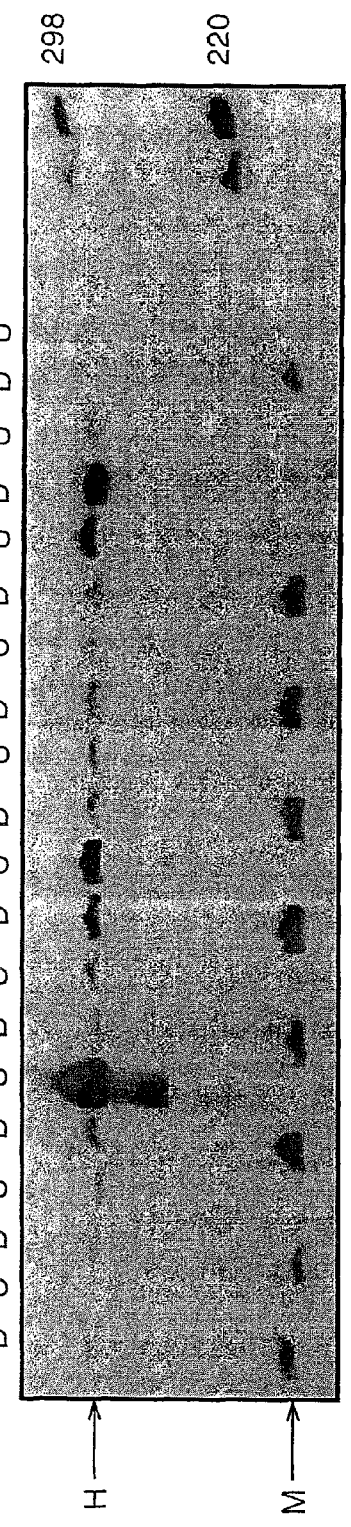
FIG. 16(a) (LINE 55)
FIG. 16(b) (LINE 35)

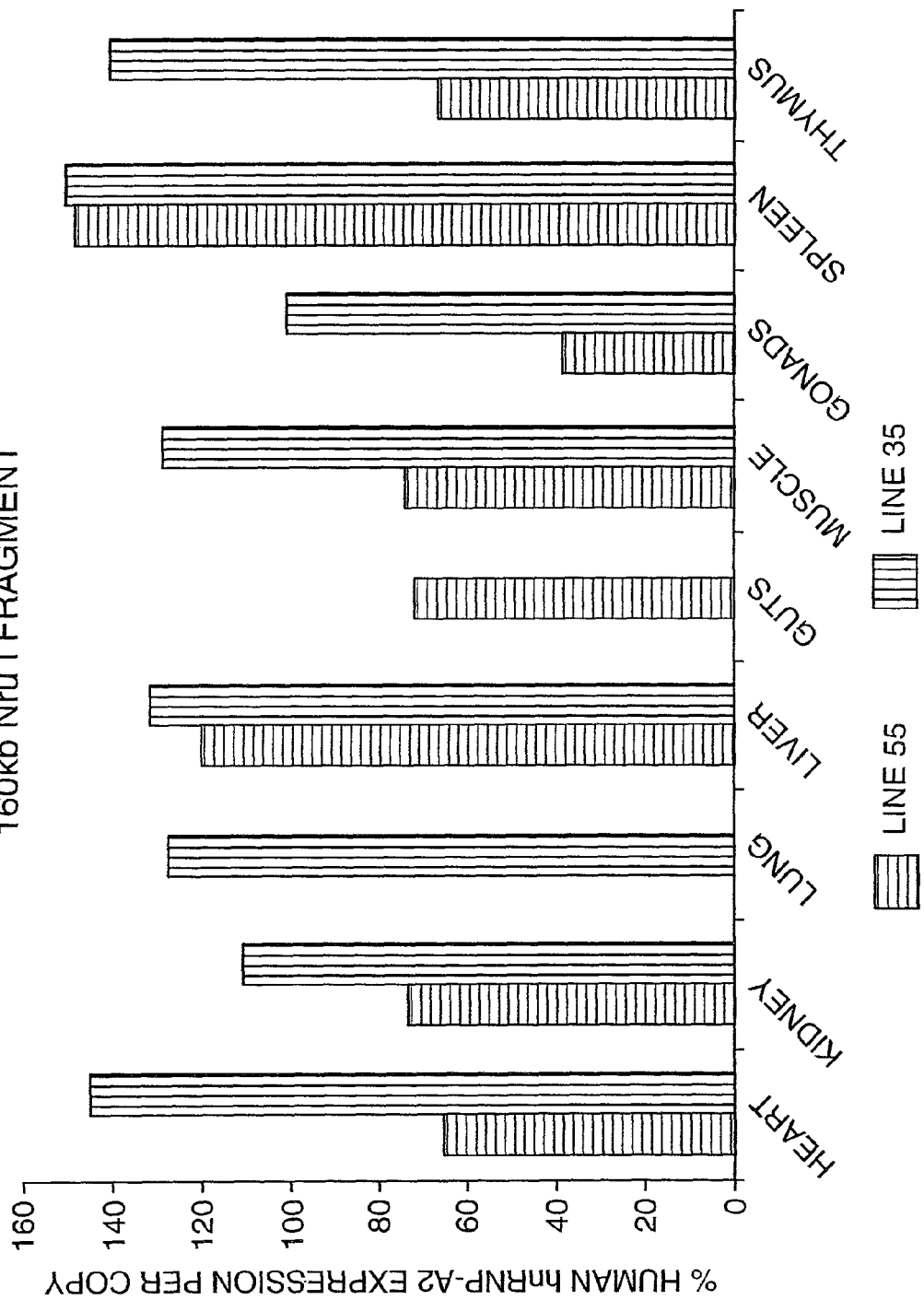

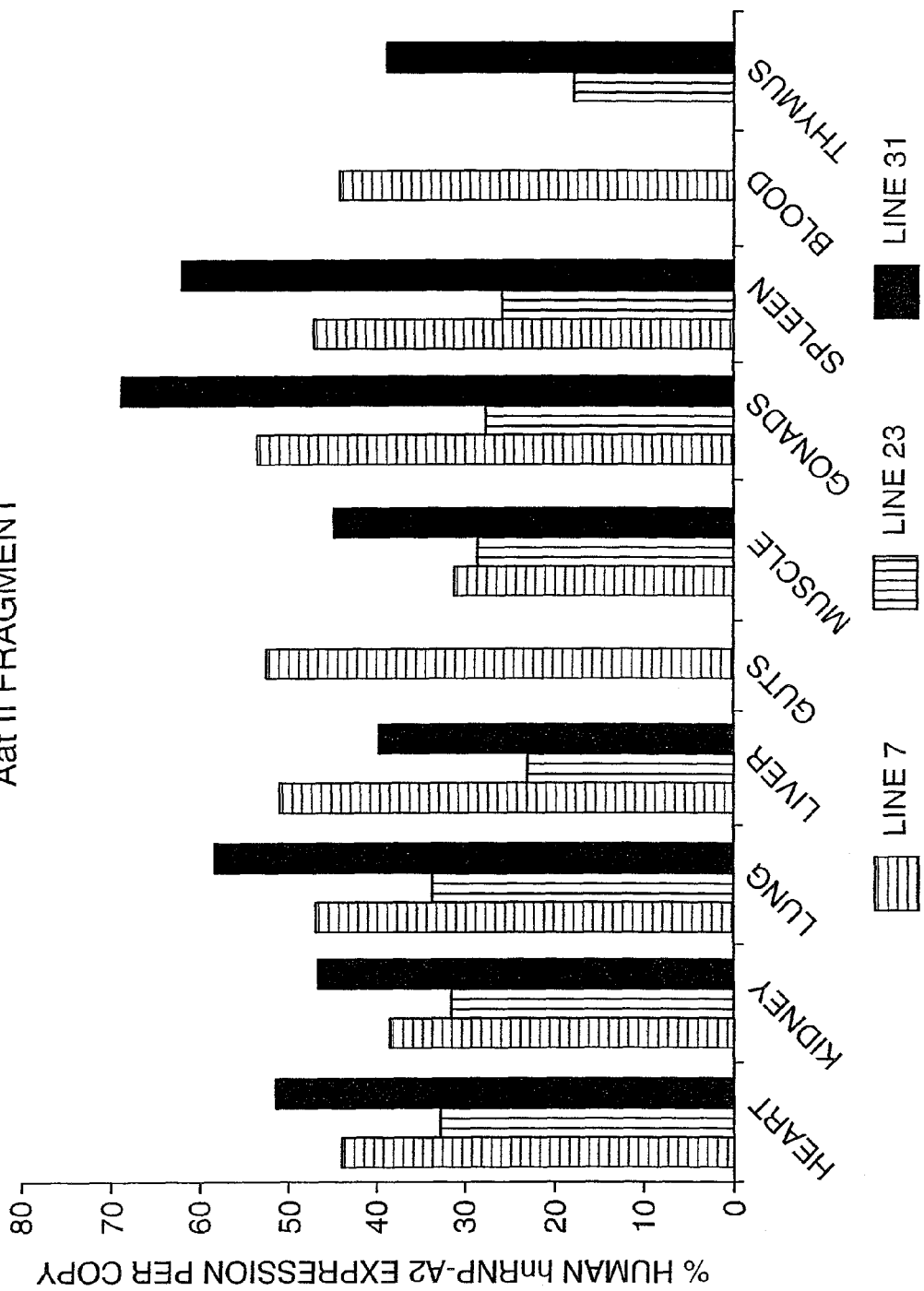

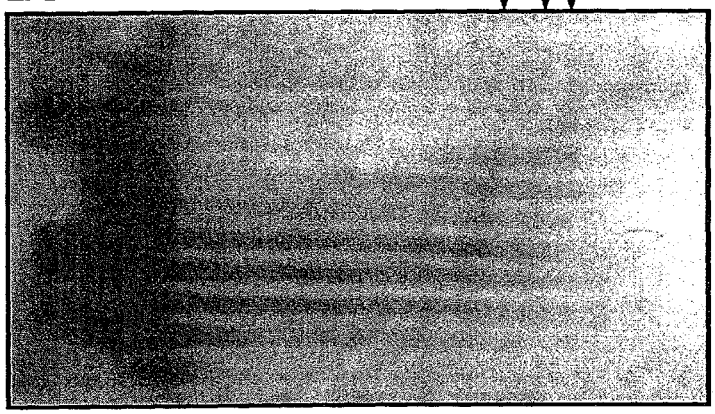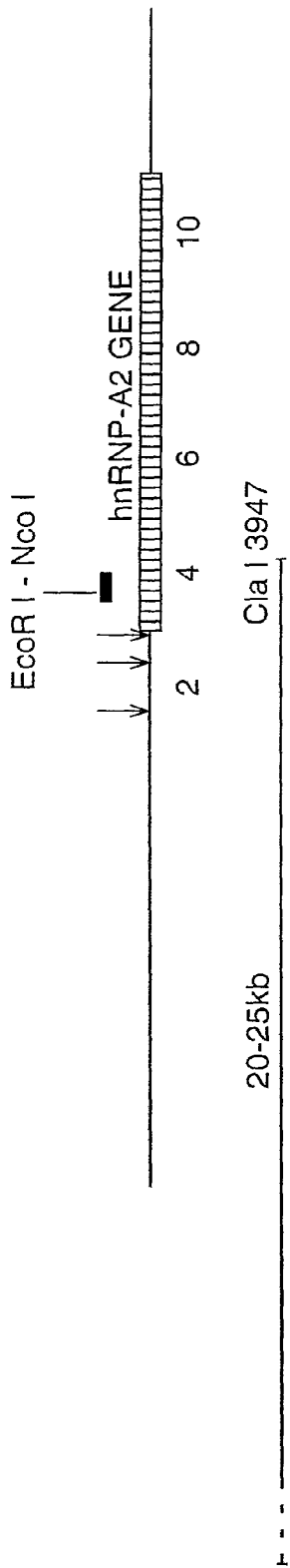
FIG. 18

FIG. 20(I)
Hind III 7725

```
         10        20        30        40        50        60        70
AAGCTTAGTTCTAGGTCAGCCCCACAGGACGTGGGATGAGGGATATATACAGGCATTCGTTAATGCTGCA  70
TTGTTCTTATTCTCTATCTCTATATCTGACGTGTTTCACAAAAAAAAAAAAAAAAAAAAAAAGTGCTCAC 140
TTCACCAGCAAACGTAACTAAAGCAATATTTAAAAGATGAGTAAAAGCTAGTACAAGGATGGTATCCATA 210
AAGTTGTTTTAAAATCTTATTTCTAATATTTACTACTTTCAAGTTGTACAAGTGTCGTCCTTGAGGAGAA 280
AAAAAGGTAACACAAGAGCACCATAAACAGAAAGCAGAAAGGGGGTATCAAAAGATGCAAGTGGAGAGAA 350
        360       370       380       390       400       410       420
ACAGAACTGGGAAGACGAAAACAAACTTCATTGCTTTTTAAGATGTGGGCCATCCCTAGGAGCAGGAAAG 420
ACAACGTATCTTTTCTTCTGTACCTACTTCCTACAATACAAGGAGGGTCCATCCAAAGGACCTAAACCTC 490
GTAAGTCCCATTCCTATTACAATTCAAGTTTAATTAACCCAGGAATTCATGACCATTTATAAGCATTTCC 560
AAAACTGGTAAATACAGACCACTGCCAATCTGCAGTATGTATTCAGTATTTATGCAGGCTTTTTGTTTTT 630
TTAAGTTTTGGCTTTATTTTCATGTTTTAGGAAAAACATAGCTAGCCTATTAAAACTGAGCTGTGGACAT 700
        710       720       730       740       750       760       770
AATTGCTTAGGATATTTCTAAAACGAATGTTTCAGGTAAAAAAAAAAAGTGTGGGGAGGCAGATTTAAAA 770
AAAATATCATTTAATGGATTAATGGTGCTGTGGTTTGAATATTCCCTTCAAAACTCATGTTGAAATTTAA 840
TTGCCATTGTGATGGTACTGGGAGTTGGGACCAGGTGTTTAGGTCCTAGGGCTCAGCTTTCATGAATGGA 910
CATTATCACAGCAGTGGGTTCGCTTGCTCTTCTTTCTTTCTCTGGCCTTCCACCATGTTAAGACACAGCA 980
GGAAATTTTTCATGGTAAAATGCTGGGGTGAACACATTTAGGTTACCGAAAGCACTTTTGGTACCCTGAA 1050
        1060      1070      1080      1090      1100      1110      1120
TACAGCAAATATTATTAAGACTGCACATTAAATTATTAGGAAACATTAACTTAGAAAATGGTTTTCTAAT 1120
AAAAATGCTCCCAACAGCAACTTAAAAACTCATGAAACAAATCATTTAGAAGTAGAAACTCTCACAACAT 1190
TAAATCATTACAAAGGCATTGTGAAATGTCTTTAGAAATATTTACTTACAATTGTAACATTTGGGGCTA  1260
TCCCGCGTATGAATTGAAAACCCTTCACTCAATCGAGTATCAGAAGCAACAATTGCAAAATCTTCTCCAG 1330
CAATTGCCAGTATAGTACTGAGGAAAAAGAAAAAAATTAATTCTCCAGGGTGGTAATCCTATCCCTACA  1400
        1410      1420      1430      1440      1450      1460      1470
AATAGAAGAATGCTCCATAGTACATAATGGGATAAAATACTCTAGATGTCAACAAAAACATGATTCAAAT 1470
GGGAAGAGGAAAGATGAGCGGGAAGAGAATGAACGCCTGGCTACGAGTTGTCTGGGAAAAAAAATTATT  1540
AATAAGCCAAATCAGGGCAAAGTCTCCTTGGCAGAGTTAACAGAAAAGCCAATGAATTATCATCACCAAC 1610
ACATTAAATACTTACTCGCGCAAGGTACTACTAATACAGAACAACTAAATACCCCATCTGTGCCCTTGAG 1680
GATCAGGTATAGACAGTGGTACTACAACGCAAGCTCTATGAGTTTAGAGAAGATGAGATTTTTTTTTCTT 1750
```

FIG. 20(II)

```
         1760      1770      1780      1790      1800      1810      1820
GCTTCATTTCTTTATATCCAAGTCCTTATATAACGCCTATATAATGCTTATTTCTTTATACCCAATCCCT 1820
TATATAATGACAAATAGATGGACAAACAGTAAATTTTTCCCTCTGTGGCTGTACAATTTGACAGCTTATC 1890
AAAGAGACTTACAGTAGAATTCCAAAAGCAGACTGCCTGGGTTCTAATTCTGGCTTTCCCGTTTCGCAGA 1960
TATGAGACTGTGGGTAAGTTACTTCTCAAAGCGTCAATTTCATCATATATACAACAGAGATCACTGCAGT 2030
TGCTACCTCATTAGGGTGTTCAAAGGATCAAATATGTAAGCCCTTATAGCAGTCCCTGACATGTAACTGG 2100
         2110      2120      2130      2140      2150      2160      2170
TCCTCTAGTAAGTGTTAGCTATAAGTGCTATGGCACTGGAGTATGACTAAGCACCTGGGCTCTGGAATTA 2170
CATGAGACAGAGACCCACTCTTGCTACTTACTAGGTATGTGATCTTGGACAAATCCTCCAAATGCAAGTT 2240
GATGATAACAGTACCTGTGTCACAAGGTGTGTATATATATTTGGGTGTGTATATTTTAATGTACAAGGCT 2310
TGACTGATAACTATAACCACTGCTTCAATGCAATAGTGGAAATTAAAGGCATGGTGCCTCACAGACGTAA 2380
GCACTCAGGAAACTTAAGCCACTATTTTTACTGAGGAGGGATTTGTGCTAAAGCTCTCAAGAAGAAAAGG 2450
         2460      2470      2480      2490      2500      2510      2520
ATGGCATTCCAGGTAATATAAACAGCAAGCAATGGCAAACAGGTAATTATTCAAATAGTACATACATTCA 2520
AGCAACTCATTCAGGCAGCCCTTTTTGCATAAGCACATGTAGTGACGTTAAGGTTTATGTGATGGACAGG 2590
GTTCCTACTGTAGAAAATCCCAAATGCCAAGCTAAAGATTTTGGAATTTTAGCAAGAAATCATGAAGGTA 2660
TTCTGAGCAAGAATGATCTGTAGTTGTAACTACTCAAGAGGCTGAGGTGGGAGGACTGCTTGAGCCCAGG 2730
TGTTCAAGGCTGCAGTGAGCTATGATCGTGCCTGGGCATTAGAGTGAGACCTGGTCTTTAAAAAGGAAT 2800
         2810      2820      2830      2840      2850      2860      2870
GCAAGAGAGAGAAAAGTTCCATTTACAAAGTGGGGTTTTAGGAAGACTGCTCTGACAACAACATAGTATG 2870
TGAAATGGGACAGAAACACTGTTCTAATACTACTAATGCAATAGTAAGGTAGCAGGGTGAACAGTAAATC 2940
CAAAATCATCACAAACACACAAAATAGACAAATTTTTATATCTACGCAAATGTTTTAGGAACTGGGAAAA 3010
CCAATTATGACATCCAAGATTTAGAACTTAGATGAGCAGAATGATGGCATAATTATAAGTATTTTAAAGG 3080
AGAGGAGGCCGGGCACGGTGGCTCACACCTGTAATCCCAACACTTTGGGAGGCTGAGGGGGGGGGGGTC 3150
         3160      3170      3180      3190      3200      3210      3220
AATTGCCTGAGATCAGGAGTTCGAGACCAGCCTGGCCAACATGGTGAAACCCATCTCTACTAAAAATACA 3220
AAAATTAGCCAGGCGTGGTGGCAGGCACCTGTAATCCCAGCTACTCGGGAGGCTGAGGCAGAAATGCGTG 3290
AACCCAGGAGTTCGAGGTTGCAGTGAGCTGAGATCGCACCGCTGCACTCCGGCCTGGGTGACAGAGTGAG 3360
ACTCTGTCTCAAAAAATAAGAAGAAAGGAGAAGAGGAGATGAAGGGAATAATTAGCTTGCTTTTTGTTT 3430
TGCTAGCTGTCTTGAGTTGCCCTGAGAGCAGAAAAACCAGTTAAAAATGTTTTACTGAAGAAGCCGAATC 3500
```

FIG. 20(III)

```
         3510      3520      3530      3540      3550      3560      3570
GAGGGACTCATGAGAGGCAGAACTGGAAAACCAGATTTGGGAGTAATCCTCCCAGCAATGAGACATGAAA 3570
GAGTGCTGAGCGATAAACAAGGCGGTAATGACTTAACTACATTTAAAGACAAGTAGGAAAAGAGAATGAG 3640
GCCTCATTTTGCGGAAGCGAAGGCTGCCTGAGAGCCAGCTGCAGTAATCACTAAAGAAAAAGAACAATGA 3710
CTGAGAAAAAGTAATCAGAAAGATCTAAGTAATTTTTAGGGCAGTAATGGCTTAAACTGGATTACAAGGA 3780
TTAAAAAGTGAGTAACGAGTAGGGCATACTGAACACTGAAAATTCTTATTTATAGAGAATAGCCTTACGA 3850
         3860      3870      3880      3890      3900      3910      3920
AACGGGTCCAATAACCCTCCCTACAATATACAACTTAATTAGTCATCACAGGAAGTGTTAAGGTGTATAA 3920
TGGAAAAGCATCCATAAACTCAGTGGTGAAATAGCTATGAATTAAGTCCTGGCTCAACTTCACACCAGCT 3990
CTCTGACCCTGACAGTTTAACGTCTAATATAACCCTAGGATGCTAATATCATCTAACATTCACTTTTCAT 4060
GAGGATTAAATAAGATGACAGCTTGCAATTTACAAAATGCATCTCTCTTGATTCTCACCAAAAACTATGA 4130
AGCTACTAAGGAAGATAAGGAAATTTAGGTTCAAGAAGTTCAGAAGTACCCAAAGTGTCCTTTAGTGGCA 4200
         4210      4220      4230      4240      4250      4260      4270
GAACCAAGGCTAAAATCAGACTTTCGTTATCTTTCTAACACACTCCCAAAATGTGCATTTATATTTCAAA 4270
TTTATGAGGAACCAATTAACATTTTTGCTTTGTTTTTAAAATTTATTTTTGTAGAGATGGGGTCTTGCTA 4340
TGCTGCGCAGGCTGGTCTTCAACTCCTGGCCTCAAGCGATGATCCTCCTGCCTTGGCTTCCCAAAGTCCT 4410
GGGATTACAGGTGCGAGCCACACTGCCCAGCCAATATTTTCTGTTTTAAGAACCATCGGTTCGTTCAAAT 4480
TGCGTGTGTATATTTTAATGTACAAGGCTTGATTGGTAACTATAACCACTGTTTCAATTTACAGCTCTTC 4550
         4560      4570      4580      4590      4600      4610      4620
CCTGTCAAGAGTCTTAAACAGAGCATCTTTCTATAACCCTAAATCTCTGGCGTGCCACCACGGAAAATTA 4620
TACTACTCAAGATAAAGCTGGTAATTAAAATAAAAACCAAAACTTGAACATAACATACAAGAACACACAT 4690
ACTAAAAGGTCCATCTTCTGAGTATTTTGTTTTCCTGAACTTAAGCTAAACGTTAAAAAAAAAAGCACTT 4760
ATCTATGAAACTAAGTTTGCTCAGCCAATCCCACCTTCTATTTGAAATAAAACAAAATGATTAAACTGCT 4830
ACAATTACAAATAACAGAAATCAGGCGGCTACAATTAGACATCTGGCTACCAACCCAGCTATGCATCTA 4900
         4910      4920      4930      4940      4950      4960      4970
ACAACACAGACCAAACAACCCTAACTTTTAAGTTTCAGACGCTAACCCTCTACCCTCGCCGGCTGGCATA 4970
AGAAACGTGTACATGAGGTCCAGTTTTAATGGTCTTCCACAGAGCAGAGGCTATGTTTCAATTTCTACTT 5040
TACTGTCTTACAGCAGCAAGGAGCACGGAGTGGCGGTCCACATAAAAACTCAAATGACATGACTGTAATG 5110
GGAAACCCTAAAAACCAAGGCTGTATCGCAATCACCAAGTAAACTTGAGCAAAGCGAGCCTGAAGAGGGA 5180
AACACAGCGCATGAGAGGACGGCAGGGAGACCGGCCTTGTGCGGACCCCCTCAGCTCAGGGTTCTGAGGC 5250
```

FIG. 20(IV)

```
C5 ATG 5470                                          5642 of 9081
     5260      5270      5280      5290      5300      5310      5320
     |    |    |    |    |    |    |    |    |    |    |    |    |
CTGCAGGAGCCCGGGGCAGCGCCATCACGGCGGTGACTCCTAAATAGGCTTCAGCAGATGGGGGAAGGGC 5320
GAAAGTGAAAGCCGCAGCTCTCTGGGGTTTTTACCCTCCGTTGAAAACGTAGGGCGAAAATCGCAGCTTG 5390
CAAAGGGCCCGCGGCTCTGTGCGGTTCCATCCCCAAGTCTCTGCCAGCAGCCCGAATACATGGCTTGTAG 5460
                                   —————BAMHI—————
AGGACAACATCGCACGGCTTGCGCCTGCGGATCCGACACTTGCTGTCTCACGGCGAGATGGCTGCCTTGA 5530
CCGGACGTTACGCCACTTCCGGCTTCTCCTGAAGTTCGCTTCCCGGCCTCTCTATCTCACGCTAGTCGTT 5600
     5610      5620      5630      5640      5650      5660      5670
     |    |    |    |    |    |    |    |    |    |    |    |    |
GCTCCTGGAGGCTTGCACGGCGGCTTGTCCTTTGGTAAGTGAatcccgcccattccaaaaagcgctgaca 5670
gggatgtaaagggttttttttgtttgttttttgttttttttccccctcgaagaaaacattggaattcaccc 5740
caatggacaaaaatttaagtctgaccatacaaaaaaattgtcagaactatggcgcaacggcaactcgaat 5810 Sac I
aacggtgggaacgttaattgtcctggctaataaaaaatgtatataacatttcctatccttaaagagctca 5880
caacctcactgataataaaaagtacaaagaaaacaagcagtataacatatgattacgccacaatgaacta 5950
     5960      5970      5980      5990      6000      6010      6020
     |    |    |    |    |    |    |    |    |    |    |    |    |
cagaagggaaaatcaaggcgtgctgaagtcccactaagaaacaactgcggaaagagccatgtgacaacag 6020
tgcatgaactgggagtggcagaactgaatatataaatgcatgtgtaaacacaagctgtttgttttgcttagt 6090
gttccttgtcattctacacgcttgaagatcagctagcgttcttgctgacaggtaaggaggacgcgcttac 6160
tgagtgccaagcactgctcaggcactgattctgtcaatctctgtcaatctcccgacagcccaagggtaag 6230
cactgttatcattattcaattttacagaaaaaaaatgcgggggagaggtcaggtaacttgtcgaaggtaa 6300
     6310      6320      6330      6340      6350      6360      6370
     |    |    |    |    |    |    |    |    |    |    |    |    |
cgccgctagttgctttaaacaacaacaacaacaacaaaacacactcacacatatacacacacacgcc 6370
atttaaaaaatcgatctttcctacgtccagcaagggccaattagagatggctgtggcacggcggcccogcc 6440
ccggaactcctcaagagcttccgcccctccttacctatggaaacacaggaagtgacctatgctcacactt 6510
ctcacggcctcggccctagtgggagcaactcgctgaagccgagggcagaactggcggaagtgacattatc 6580
aacgcgcgccaggggttcagtgaggtcgggcaggttcgctgtggcgggcgcctgggccgcggctgttta 6650
     6660      6670      6680      6690      6700 TBP 6710 EXON 1 6720 NON-
     |    |    |    |    |    |    |    |    |    |    |    |    |    CODING
acttcgcttccgctggcccatagtgatctttgcagtgaccaggtaacagattgtactcttttctgacgg 6720
ttcgggcgaaggccaccactgcactgaggcctgggggcaatggtggggaagagactaggaattggcgcgc 6790
gtgcaggcccctcggggggacgttcctcccttttcgtgctgccgccgttccggcctgtaacggccactgg 6860
ccgccactcccgcctggtgccctactctgctgtgtttcgcaggcagcttcccatcgtacgattgtggggc 6930
tcagggtactactggctggctgggcggcggcaggcggggacaggacagtcccttgcatcgaagaccctaag 7000
```

FIG. 20(V)

```
         7010      7020      7030      7040      7050      7060      7070
         |         |         |         |         |         |         |
tttaccctgccctgtcctgccatccgcttcttctccatgttagaagcagattcacccagatctgtgcccg 7070
cctgttttgctgccaacattgagacttaaatattttgtcagaagcctgagacagcgggcacggtagcgct 7140
taagatataatacacaccacttttatttgcagggtctcccgtctctcggttcaggccatcatggttttcca 7210
aatctctagggtagacttttctgtgaaaagactgtgcttcatttagttatacagacactagaaggctatg 7280
cagaattaatttgattgcctccaaaaaatatcggatttgatgtttcaatttccaggagatgaagataccc 7350

7360      7370      7380      7390      7400      7410      7420
         |         |         |         |         |         |         |
agcaaacaactcttttctgaggataaattagtgcagtaatcactgtgcgtttcttctgtagacttacttg 7420
caaaaagtggcctgaagccaccgaagtccctggataaatctctaatcatacttataatggctttaaatcc 7490
tgccgtcattatctcttgcctcaaccttagattcctgaaacgaaacttccgtcctccagttttactcctc 7560
tcaaattcatctagtcttgccaaattagatctgttcatactgcacttccaaaattccataactgttatta 7630
ttgcctatgcaataacattgaaaactcctgatagtatgagcccaccaatatgtgctgtctcatctgctgc 7700

7710   7720 7725 7730    7740      7750      7760      7770
         |         |         |         |         |         |         |
agtgaccttctatacagtcatactaagcttgtcgcctgcatactgcatgctttttcaatctgtctctttc 7770
tgcttgatttctcttttgtctgaagccctgatgtgtaaattcctactcaccttgtgagacccaagttaga 7840
tggtccctgctttgtgaaaacactgcgccacagtgattggctgttagtctatattgtcttctcttccagg 7910
ggtgtatatgggctcattcatgatcacatactgtattccaggcatagtgctagatgcagagatcacaaag 7980
acatgtaggctggtttctgcattcaaggaacttagcttagaccatacctgctgttataatactatgtttt 8050

8060      8070      8080      8090      8100      8110      8120
         |         |         |         |         |         |         |
acagtagttatttgcatacccttcatattgaacactttgatgccaaggactatatcctcctatctttata 8120
tcctcatctgcaggacttctgttattgttattataggataactgtcaaaaaaaaagtatatttttaaaaaa 8190
tatctctgatatatttatttccagaagcagagcttgcttttctttttttggtctgtttttcagtgatgagta 8260
tgtaggatagatagtctttgggggcatttgcccttttcaaagtgatcgtcagagtcttttcatacattcagc 8330
aaatatctgagtgtctgttctgtaccagcacatgcttgaagtgcatatgcctgaaggatctttggacata 8400

8410      8420      8430      8440      8450      8460      8470
         |         |         |         |         |         |         |
taatttgtaactttgagacctctaagttctatgtgagaatatgttgttataaatcatttcagatgtgtag 8470
tgagtaaagcgatgtgatttagaaaagtcagataacaggcacagtttgcattaatgtgttctaaagaggt 8540
aaggttattacatttataaaaattcagggctttatctttgtgcggcttttttttttttacagtttcattac 8610
agtaggagcttgataaatgatcactctgaagtatattggattgaatttgatatttacttaatttttttgcc 8680
caagacattgtagaggatgtaaaattggaatatttaaagatctaaactttgcctaacagtgctgtgtata 8750
```

FIG. 21(I)
8286 HIND III

```
HIND
III    10        20        30        40        50        60        70
AAGCTTCAATGTTTTTAGCACCCTCTGTGTGGAGGAAAATAATGCAGATTATTCTAATTAGTGTAATATC  70
TAACCACATTAAAATATATTACATAGTAAACTACACTCCATAATTTTATAAATTTGACTCCCCAGGGTAA 140
TAAACTAGTCTCTAGTCTGCTCACCTTCAACTGTACAATAAAGTCTTGGTTCTTTTGAAATAGACCTCAA 210
ATGAGACACCTAAAATTCAAAGTGTCTTTACATTTAAAGACACCTACAGGAAAGCAGGTAAAAGAGCCAG 280
GTTAAAAACAAATTCTAAAACCACTTAGCTGCAGTTAAACATATAGTAAAGATGCACTAAAGTTTCTTAC 350

360       370       380       390       400       410       420
TCTGTAAATCCCTTCCACTTCAGGAAATATTCCACTTTCCCATTCACTACACGTCGATCTAGTACTTTTT 420
CCACGACAAATTCTTCAGGCTCTGCCTCTTCAACTTTTTTACTCTTTTCCATTCGTTTTTTTTCCCATTTT 490
TTGCTAAAATAAAACAAAAGAGAAATTAAGAAATATTCCTCTTGAATTTTGAGCACATTTTCAAGGCTCA 560
ATTGCTTATATTATTATCACATTCGACATAAATTTTTACTTCTATATCCCAGGGCAGACACCTTCTGGAA 630
AGATTAAAAGTCAACAGACAATAAAATAAAAGAATGCTTTATCTTGTTCATTTAGTTCAAACTTACAACC 700

710       720       730       740       750       760       770
CACCACCAAAATAATACAATAAAAAAAACACTATCTGGAAACAGTTATTTTTTTCCAGTCTTTTTTTTTGA 770
GACAGGGTCTCACACTCTTGTCGCCCAGGCTGGAGTGCAGTGGCGTGATCTCAGCTCACTGCAACCTCCG 840
CCTCCCCAGGTTCAAGCAGTTCTCATGCCTCAGCCTCCAGAGTAGCTGGGATTATAGGCGGATGCCACCA 910
TGCCCGGCTAATTTTTTTTGTGTTTTTATTAGAAACAGGGTTTCACCATGTTGACCAGGCTGGTCTCAAA 980
CTCCTGACCTGAAGTGATTCACCAGCCTGGGCCTCCCAAAGTGCTGGCATTACAGGCGTGAGCCACTGCG 1050

1060      1070      1080      1090      1100      1110      1120
CCCGGCCCTGTAGTCTTAAAAGACCAAGTTTACTAATTTTCACTCATTTTAACAACACTGCAACAAACAA 1120
CTATGCAGGAAGTACCTAAAGGGTGATCCAGAGAAGCAAGTAGTAGTGACAGGTCTTAGGTGAACCTATG 1190
ACAGACCTTGTATCCACCCCCAGATGGTAAAAGCCCCAGCCCCCTTCTCAATTCAAATATTAATGTCAAA 1260
AGCATCAATGATACAGAGAAAAGATAAATGCAGAATGAAAACATGGTTCAAAATCCTGATACCAACTGCA 1330
GGGTCAACTATAGAGACCACTAGGAGGTTCAATTAAAGGACAAGATTATTTTTCCATAATCTCTGTAGAT 1400

1410      1420      1430      1440      1450      1460      1470
AATATTTCCTACCACTTAGAACAAAACTATAAAGCTATCACTTCAAGAGACCAACATTACAAATTTATTT 1470
TAATTCCCTAAGGTGAAAAAAATCCTTCCTTCCTGGTTTCTCAAGAGAAAGTCTATACTGGTAACCAAAT 1540
TCACTTTAAACAGGCATTTTCTTTGGTATGACACTATTTAAGAGAAGCAGGAAACCAACGTGAACCAGCT 1610
CTTTCCAATGGCTCAAGATTTCCTATGAGAGGACTAAAAATGGGAAAATTTTTATGAGAGGATTAAAAA 1680
TGGGGGAAAAAAAACCCTGAAATGGTTAATCAGAAGATCCTATGGGCTGAGAAGGAATCCATCTTAACAT 1750
```

FIG. 21(II)

```
       1760      1770      1780      1790      1800      1810      1820
     ..|....|....|....|....|....|....|....|....|....|....|....|....|....|
TTCATCTTAAAGCAAATGCTATTGCCGGGGGCAGTGGCTCATGCCTGTAATCCCAGCACTTTGGGAGGCC 1820
GAGGTGGGCAGATCATCTGAGGTCAGGAGTTTGAGACCAGCCTGACCAACATGGAGAAACCCCGTTTCTA 1890
CTAAAAATACAAAATTAGCCAGGCATAGTGGTGCATGCCTGTAATCCCAGCTACTTGGGAGGCTGAGGCA 1960
GGAGAACTGCTTGAACCCAGGAGGCTTAAGTTGCGGTGAGCCAAGATCACGCCATTGCACTCTAGCCTGG 2030
ACAACAAGAGAAAAACTCTGTCTCAAAAAAACACAAAAACAAAAAACCCAAATACTATTTAAAAAGATA 2100

2110      2120      2130      2140      2150      2160      2170
     ..|....|....|....|....|....|....|....|....|....|....|....|....|....|
AACCTTAATTGCTCAATCATTAAAGCCATCCCACAAGTAAAGCAGCAAGCAGAAAAAAGTTAAGAACACC 2170
TCAAGGCTACAGAAGGACATTTCAAGCTATGCAGGCATATGAAGTGTGCAGACAGATATGTAAGAAAGGC 2240
CTCAAGACTGCAAAAGGGCATTTCAAGCTATGCAAGCATATAGGTAACACATACACACACAAAATAAA 2310
ATCCCCTGAAATACAAAAACATGCAGCAAACACCTGACGTTTTTGGATACCATTTCTAAGTCAGGTGTTA 2380
TGATTCTCATTAGTCAAGATACTTGAGTACTGGGCCCAAACAGCTTTCTGCCACTGTACAGTACAAGAAG 2450

2460      2470      2480      2490      2500      2510      2520
     ..|....|....|....|....|....|....|....|....|....|....|....|....|....|
GTAGGAATAATGGTGGGAGGAGCAAAGACAAACTGTAATAGACAGAAGTGTATCAGATACCTATACTACA 2520
TGAAAAACAAAACAGCTACTGCCACAAAGGGAGAAGGCTAACAAAATAAAGTCAACAATAAATACAGAAA 2590
ATGAAAAGGATACACACTAAGGTTTACAAAAAAAAAAGGCAGACAAAATGCCATACAGTATTCATTCAC 2660
TACTATGGCATTCATAAGCTAGTTTCAAATGCTCACTATTTTCTTTTATAGTATATATTTGCCTTAACCC 2730
AGCACTTTTTTCCAAAAGTGGATGAGTCAAAATAAATTTCCCATTATTTAAGTGAAATTAACAGCACACA 2800

2810      2820      2830      2840      2850      2860      2870
     ..|....|....|....|....|....|....|....|....|....|....|....|....|....|
TATCTCACAACACTAATGAATTTTTAAAATGGAAAGTTAAGAACTTTTAAAGTGGCCAACCTGTGATCCT 2870
TCACAAAATAAACTAAATACAATAACAGACCCCAAAGGCTATCAATTGCGTGCAAAAACAACTTCTGTTT 2940
TCCAGGGTAAACAGAATCTAATGCAGAATCTAATGCAGGGTAAACAGACTTAATGCAGAATCTAATGATG 3010
GCACAAATTAAAAATCACTAACGTGCCCTTTTTAGTGTGAAACCCAGAGAGAGCACATACAAGCCAAAAA 3080
CAAATGCTTTATTTTACCTAGGAGACATTAACATTCACCTTTACGTGTTTAAGATTAATGCAATGTTAAA 3150

3160      3170      3180      3190      3200      3210      3220
     ..|....|....|....|....|....|....|....|....|....|....|....|....|....|
TATTGTGAAAACTGTAACTTTGAATTTCATGATTTTTATGTGAATATTCCAGGGTTTAAAAAAACTTGTA 3220
ACATGACATGGCTGAATAAGATAAAAAAAAAATCTAGCCTTTTCTCCCTTCTGGCTCATATTTGCGATTT 3290
CGATCATTTGTTTAAAAAACAAAACACTGCAATGAATTAAACTTAATATTCTTCTATGTTTTAGAGTAA 3360
GTTAAAACAAGATAAAGTGACCAAAGTAATTTGAAAGATTCAATGACTTTTGCTCCAACCTAGGTGCACA 3430
AGGTACCTTGTTCTTTAAATTGGGCTTTAATGAAAATACTTCTCCAGAATTCTGGGGATTTAAGAAAAAT 3500
```

FIG. 21(III)

```
          3510      3520      3530      3540      3550      3560      3570
       ...|....|....|....|....|....|....|....|....|....|....|....|....|....|
       TATGCCAACCAACAAGGGCTTTACCATTTTATGTAACATTTTTCAACGCTGCAAAAATGTGTGTATTTCT  3570
       ATTTGAAGATAAAAATCCTCAGCAAAATCCACATTGCACTGTCCTTCAAAGATTAGCCTTCTTTGAACTA  3640
       GTTAAGACACTATTAAGCCAAGCCAGTATCTCCCTGTAATGAATTCGTTTTTCTCTTAATTTTCCCCTGT  3710
       AATTTACACTGGGAGAGCTGGGAAATATGTGGATGTAAATTTCTCAGCCACAGAGATGCAAAGTTATACT  3780
       GTGGGGAAAAAAAACTTGAGTTAAATCCTTACATATTTTAGGTTTTCATTAACTTACCAATGTAGTTTTG  3850
          3860  3865  3870     3880      3890      3900    3836 3910      3920
       ...|....|....|....|....|....|....|....|....|....|....|....|....|....|
       TTGGAGGCCATTTTTTTTATTGCAGACTTGAAGAGCTATTACTAGAAAAATGCATGACAGTTAAGGTAAG  3920
       TTTGCATGACACAAAAAAGGTAACTAAATACAAATTCTGTTTGGATTCCAACCCCCAAGTAGAGAGCGCA  3990
       CACTTTCAAACGTGAATACAAATCCAGAGTAGATCTGCGCTCCTACCTACATTGCTTATGATGTACTTAA  4060
       GTACGTGTCCTAACCATGTGAGTCTAGAAAGACTTTACTGGGGATCCTGGTACCTAAAACAGCTTCACAT  4130
       GGCTTAAAATAGGGGACCAATGTCTTTTCCAATCTAAGTCCCATTTATAATAAAGTCCATGTTCCATTTT  4200
          4210      4220      4230      4240      4250      4260      4270
       ...|....|....|....|....|....|....|....|....|....|....|....|....|....|
       TAAAGGACAATCCTTTCGGTTTAAAACCAGGCACGATTACCCAAACAACTCACAACGGTAAAGCACTGTG  4270
       AATCTTCTCTGTTCTGCAATCCCAACTTGGTTTCTGCTCAGAAACCCTCCCTCTTTCCAATCGGTAATTA  4340
       AATAACAAAAGGAAAAAACTTAAGATGCTTCAACCCCGTTTCGTGACACTTTGAAAAAAGAATCACCTCT  4410
       TGCAAACACCCGCTCCCGACCCCCGCGCTGAAGCCCGGCGTCCAGAGGCCTAAGCGCGGGTGCCCGCCC  4480
       CCACCCGGGAGCGCGGGCCTCGTGGTCAGCGCATCCGCGGGAGAAACAAAGGCCGCGGCACGGGGCTC  4550
          4560      4570      4580      4590      4600      4610      4620
       ...|....|....|....|....|....|....|....|....|....|....|....|....|....|
       AAGGGCACTGCGCCACACCGCACGCGCCTACCCCGCGCGGCCACGTTAACTGGCGGTCGCCGCAGCCTC  4620
       GGGACAGCCGGCCGCGCGCCGCCAGGCTCGCGGACGCGGGACCACGCGCCGCCCTCCGGGAGGCCCAAGT  4690
       CTCGACCCAGCCCCGCGTGGCGCTGGGGAGGGGGCGCCTCCGCCGGAACGCGGGTGGGGAGCGGAGGG  4760
       GGAAATGCGCTTTGTCTCGAAATGGGCAACCGTCGCCACAGCTCCCTACCCCCTCGAGGCAGAGCAGT  4830
       CCCCCCACTAACTACCGGGCTGGCCGCGCGCCAGGCCAGCCGCGAGGCCACCGCCCGACCCTCCACTCCT  4900
          4910      4920      4930      4940      4950      4960      4970
       ...|....|....|....|....|....|....|....|....|....|....|....|....|....|
       TCCCGCAGCTCCCGGCGCGGGGTCCGGCGAGAAGGGGAGGGGAGGGGAGCGGAGAACCGGGCCCCCGGGA  4970
       CGCGTGTGGCATCTGAAGCACCACCAGCGAGCGAGAGCTAGAGAGAAGGAAAGCCACCGACTTCACCGCC  5040
       TCCGAGCTGCTCCGGGTCGCGGGTCTGCAGCGTCTCCGGCCCTCCGCGCCTACAGCTCAAGCCACATCCG  5110
       AAGGGGGAGGGAGCCGGGAGCTGCGCGCGGGCGCCGGGGGAGGGGTGGCACCGCCCACGCCGGGCGG  5180
       CCACGAAGGGCGGGGCAGCGGCGCGCGCGCGCGGGGGGAGGGGCCGGCGCCGCGCCCGCTGGGAATTG  5250
```

FIG. 21(IV)

```
        5260      5270      5280      5290      5300      5310      5320
     |....|....|....|....|....|....|....|....|....|....|....|....|....|
GGGCCCTAGGGGGAGGGCGGAGGCGCCGACGACCGCGGCACTTACCGTTCGCGGCGTGGCGCCCGGTGGT 5320
CCCCAAGGGGAGGGAAGGGGGAGGCGGGGCGAGGACAGTGACCGGAGTCTCCTCAGCGGTGGCTTTTCTG 5390
CTTGGCAGCCTCAGCGGCTGGCGCCAAAACCGGACTCCGCCCACTTCCTCGCCCGCCGGTGCGAGGGTGT 5460
GGAATCCTCCAGACGCTGGGGGAGGGGGAGTTGGGAGCTTAAAAACTAGTACCCCTTTGGGACCACTTTC 5530
AGCAGCGAACTCTCCTGTACACCAGGGGTCAGTTCCACAGACGCGGCCAGGGGTGGGTCATTGCGGCGT 5600
        5610      5620      5630      5640      5650      5660      5670
     |....|....|....|....|....|....|....|....|....|....|....|....|....|
GAACAATAATTTGACTAGAAGTTGATTCGGGTGTTTCCGGAAGGGGCCGAGTCAATCCGCCGAGTTGGGG 5670
CACGGAAAACAAAAAGGGAAGGCTACTAAGATTTTTCTGGCGGGGGTTATCATTGGCGTAACTGCAGGGA 5740
CCACCTCCCGGGTTGAGGGGGCTGGATCTCCAGGCTGCGGATTAAGCCCCTCCCGTCGGCGTTAATTTCA 5810
AACTGCGGGACGTTTCTCACCTGCCTTCGCCAAGGCAGGGGCCGGGACCCTATTCCAAGAGGTAGTAACT 5880
AGCAGGACTCTAGCCTTCCGCAATTCATTGAGCGCATTTACGGAAGTAACGTCGGGTACTGTCTCTGGCC 5950
        5960      5970      5980      5990      6000      6010      6020
     |....|....|....|....|....|....|....|....|....|....|....|....|....|
GCAAGGGTGGGAGGAGTACGCATTTGGCGTAAGGTGGGGCGTAGAGCCTTCCCGCCATTGGCGGCGGATA 6020
GGGCGTTTACGCGACGGCCTGACGTAGCGGAAGACGCGTTAGTGGGGGGGAAGGTTCTAGAAAAGCGGCG 6090
GCAGCGGCTCTAGCGGCAGTAGCAGCAGCGCCGGGTCCCGTGCGGAGGTGCTCCTCGCAGAGTTGTTTCT 6160
CGAGCAGCGGCAGTTCTCACTACAGCGGCCAGGACGAGTCCGGTTCGTGTTCGTCCGCGGAGATCTCTCTC 6230
ATCTCGCTCGGCTGCGGGAAATCGGGCTGAAGCGACTGAGTCCGCGATGGAGGTAACGGGTTTGAAATCA 6300
        6310      6320      6330      6340      6350      6360      6370
     |....|....|....|....|....|....|....|....|....|....|....|....|....|
ATGAGTTATTGAAAAGGGCATGGCGAGGCCGTTGGCGCCTCAGTGGAAGTCGGCCAGCCGCCTCCGTGGG 6370
AGAGAGGCAGGAAATCGGACCAATTCAGTAGCAGTGGGCTTAAGGTTTATGAACGGGGTCTTGAGCGGA 6440
GGCCTGAGCGTACAAACAGCTTCCCCACCCTCAGCCTCCCGGCGCCATTTCCCTTCACTGGGGGTGGGG 6510
ATGGGGAGCTTTCACATGGCGGACGCTGCCCCGCTGGGGTGAAAGTGGGGCGCGGAGGCGGGAATTCTTA 6580
TTCCCTTTCTAAAGCACGCTGCTTCGGGGGCCACGGCGTCTCCTCGGCGAGCGTTTCGGCGGGCAGCAGG 6650
        6660      6670      6680      6690      6700      6710      6720
     |....|....|....|....|....|....|....|....|....|....|....|....|....|
TCCTCGTGAGCGAGGCTGCGGAGCTTCCCCTCCCCCTCTCTCCCGGGAACCGATTTGGCGGCCGCCATTT 6720
TCATGGCTCGCCTTCCTCTCAGCGGTTTCCTTATAACTCTTTTATTTTCTTAGTGTGCTTTCTCTATCAA 6790
GAAGTAGAAGTGGTTAACTATTTTTTTTTTTCTTCTCGGGCTGTTTTCATATATCGTTTCGAGGTGGATTTGG 6860
AGTGTTTTGTGAGCTTGGATCTTTAGAGTCCTGCGCACCTCATTAAAGGCGCTCAGCCTTCCCCCTCGATG 6930
AAATGGCGCCATTGCGTTCGGAAGCCACACCGAAGAGCGGGGAGGGGGGGTGCTCCGGGTTTGCGGGCCC 7000
```

FIG. 21(V)

```
         7010      7020      7030      7040      7050      7060      7070
GGTTTCAGAGAAGATATCACCACCCAGGGCGTCGGGCCGGGTTCAATGCGAGCCGTAGGACAAAGAAACC 7070
ATTTTATGTTTTTCCTGTCTTTTTTTTCCTTTGAGTAACGGTTTTATCTGGGTCTGCAGTCAGTAAAACG 7140
ACAGATGAACCGCGGCAAAATAAACATAAATTGGAAGCCATCGGCCACGAGGGGCAGGGACGAAGGTGGT 7210
TTTCTGGGCGGGGAGGGATATTCGCGTCAGAATCCTTTACTGTTCTTAAGGATTCCGTTTAAGTTGTAG 7280
AGCTGACTCATTTTAAGTAATGTTGTTACTGAGAAGTTTAACCCTTACGGGACAGATCCATGGACCTTTA 7350
         7360      7370      7380      7390      7400      7410      7420
TAGATGATTACGAGGAAAGTGAAATAACGATTTTGTCCTTAGTTATACTTCGATTAAAACATGGCTTCAG 7420
AGGCTCCTTCCTGTAATGCGTATGGATTGATGTGCAAAACTGTTTTGGGCCTGGGCCGCTCTGTATTTGA 7490
ACTTTGTTACTTTTCTCATTTTGTTTGCAATCTTGGTTGAACATTACATTGATAAGCATAAGGTCTCAAG 7560
CGAAGGGGGTCTACCTGGTTATTTTTCTTTGACCCTAAGCACGTTTATAAAATAACATTGTTTAAAATCG 7630
ATAGTGGACATCGGGTAAGTTTGGATAAATTGTGAGGTAAGTAATGAGTTTTGCTTTTTGTTAGTGATT 7700
         7710      7720      7730      7740      7750      7760      7770
TGTAAAACTTGTTATAAATGTACATTATCCGTAATTTCAGTTTAGAGATAACCTATGTGCTGACGACAAT 7770
TAAGAATAAAAACTAGCTGAAAAAATGAAAATAACTATCGTGACAAGTAACCATTTCAAAAGACTGCTTT 7840
GTGTCTCATAGGAGCTAGTTTGATCATTTCAGTTAATTTTTTCTTTAATTTTTACGAGTCATGAAAACTA 7910
CAGGAAAAAAAATCTGAACTGGGTTTTACCACTACTTTTTAGGAGTTGGGAGCATGCGAATGGAGGGAGA 7980
GCTCCGTAGAACTGGGATGAGAGCAGCAATTAATGCTGCTTGCTAGGAACAAAAAATAATTGATTGAAAA 8050
         8060      8070      8080      8090      8100      8110      8120
TTACGTGTGACTTTTTAGTTTGCATTATGCGTTTGTAGCAGTTGGTCCTGGATATCACTTTCTCTCGTTT 8120
GAGGTTTTTTAACCTAGTTAACTTTTAAGACAGGTTTCCTTAACATTCATAAGTGCCCAGAATACAGCTG 8190
TGTAGTACAGCATATAAAGATTTCAGCTCTGAGGTTTTTCCTATTGACTTGGAAAATTGTTTTGTGCCTG 8260
                                HIND III
TCGCTTGCCACATGGCCAATCAAGTAAGCTTCAGCTTTCAGTAATTGTTATCTTAGAGATTATGCCACGT 8330
GAATGTATTTTATTGTACATATGGTTAAGCTGAGTAATTCATATTCTGTATTGTCATATATCAAATATAG 8400
         8410      8420      8430      8440      8450      8460      8470
ACATGTCCACCAAAAATTAAACTTTTTAAGCTTCGAGTGCTGCTGGTCATAAAAATTAATTTGTCCTGGT 8470
TATAAGAGTAATTTTTAAGGTTATTTCTAATGCATATCTTTAAATATTTTCGTAACTGAGAGTCATATGG 8540
AGAAACTTAGTGTTTGTTGTAAAAGTTGTGTTTTTTTGGCTGAGATACTTAGAATCACCACCAGAGGGG 8610
GCAGTTAAGGGAAAATAAATGATACTTTTCAGATATTGAATAGTGAAATAAAAACTTTGGGTCATAAGTA 8680
ATGAACCAAGAGTTATTTCTGATGTTTAAAAATAGAAATTTGCGTTTTTAGGTTGTAGGGTTGAAATTT 8750
```

FIG. 21(VI)

```
        8760      8770      8780      8790      8800      8810      8820
       |....|....|....|....|....|....|....|....|....|....|....|....|....|
TTGGTAAAGATTCTTTAATAATCCTTTGATAATCACGGTCTACATTTGTTTATTTTTCCTTAGAAAGTTT 8820
TTTTTTTAATTAATAATTTAAGATAATTTAATGTTGAGTAAATTTATATCAAGCATTAATGACTTTGAAA 8890
CTTGTGTAGATCAGCTGAGGCAATTTTTTGGTGTAACACAACTAATATGCAGTTTAACATATGGTTTAAA 8960
TTTGATGTAAGTTTTTTTTTCCCCCCAGAAAACTTTAGAAACTGTTCCTTTGGAGAGGAAAAAGGTACTC 9030
TGCCAGCAGGTCACCTCATATTTAAGAATTTAATTTCCTGCATACAAAGAGGAAAATGTAAATAAAAATT 9100
        9110      9120      9130      9140      9150      9160      9170
       |....|....|....|....|....|....|....|....|....|....|....|....|....|
GAAATGGTATTTTCCTTTGCAGAGAGAAAAGGAACAGTTCCGTAAGCTCTTTATTGGTGGCTTAAGCTTT 9170
GAAACCACAGAAGAAAGTTTGAGGAACTACTACGAACAATGGGGAAAGCTTACAGACTGTGTGGTATGTA 9240
AATTACTGAATTGTTACTGGATATTAGTCTTTTAGCTGTATGTTAAGTGAATCATGGAGGAATAACTATC 9310
AGCATAGTAAAAAATTCTATTATGACTTCACTTATAAGCTATAATGAGATTAAATGCTAAAGTTTACCCT 9380
TTGGTTTGAAAGGTAATGAGGGATCCTGCAAGCAAAAGATCAAGAGGATTTGGTTTTGTAACTTTTTCAT 9450
        9460      9470      9480      9490      9500      9510      9520
       |....|....|....|....|....|....|....|....|....|....|....|....|....|
CCATGGCTGAGGTTGATGCTGCCATGGCTGCAAGACCTCATTCAATTGATGGGAGAGTAGTTGAGCCAAA 9520
ACGTGCTGTAGCAAGAGAGGTAAGCAAACAATGACTGTCTTGTGCATTAACATGAAGAACGCTGCCCTGC 9590
TGAAAATCAGAAACTATTTCTGAATTTAGTTTTAACTCAAGATTTTTTCTCTTATTAAAGGTGTGTTGGG 9660
TTTCTGGACCATTTTCTTAAGCTAGCTTATTTTTCAAAAGCTAGGTCCCTAAAAGCTATTTTATATCTGG 9730
TAGTTTTAAGGTGGATACAAGCGAAGTATGGTACTACGGTTGGGTGCTTTGAATTATGCTTGTGTTTTTT 9800
        9810      9820      9830      9840      9850      9860      9870
       |....|....|....|....|....|....|....|....|....|....|....|....|....|
TCTGTTTGGATGACTTTTACCCCACCACTATTTTAGGAATCTGGAAAACCAGGGGCTCATGTAACTGTGA 9870
AGAAGCTGTTTGTTGGCGGAATTAAAGAAGATACTGAGGAACATCACCTTAGAGATTACTTTGAGGAATA 9940
TGGAAAAATTGATACCATTGAGATAATTACTGATAGGCAGTCTGGAAAGAAAAGAGGCTTTGGCTTTGTT 1001
ACTTTTGATGACCATGATCCTGTGGATAAAATCGTATGTAAGTGTCTAACCACAAATGTACTGTTTTTTT 1008
CCAGTGTATCAATTTTGTGTATGTTAACATCTGTAACTTTATTGAAAGGTAAACTTTTGAAGCTGCTTAA 1015
       10160     10170     10180     10190     10200     10210     10220
       |....|....|....|....|....|....|....|....|....|....|....|....|....|
TATTGTTGATTTAATTTAAAAGGAGTCTGAATTTTTCATTCCAGTGCAGAAATACCATACCATCAATGGT 1022
CATAATGCAGAAGTAAGAAAGGCTTTGTCTAGACAAGAAATGCAGGAAGTTCAGAGTTCTAGGAGTGGAA 1029
GAGGAGGTAATTTAATTCTGTTCTCTCTTTATTTTGTTCATATATAAGGGCTTGCTTCTAACTGGGGCATT 1036
TATTGTAGGCAACTTTGGCTTTGGGGATTCACGTGGTGGCGGTGGAAATTTCGGACCAGGACCAGGAAGT 1043
AACTTTAGAGGAGGATCTGGTGAGTTTCAAGTTCTACGTGTTTAAAGGATGAGTGTGCTTTTATTTTAAA 1050
```

FIG. 21(VII)

```
          10510     10520     10530     10540     10550     10560     10570
         ....|....|....|....|....|....|....|....|....|....|....|....|....|....|
TATGATTAGGTTTTCATTAGTAGAATCAAGAAATCCAACCTAAGTCAATTTTCCTAAGACTTCAAATAGA 1057
TTGTATCCTGGCAAGCTCTTGTGATTTGGCCAGACAAGAAGTTAATAGAGTTGTATTAATAACAGTTGTA 1064
TTTATCTGGATTAATAATGTAACATGAAGTGTCATCCGAAAAGCTTTGACCCCCATCAAGTGTCATTCTT 1071
ACGTATAAATAGGATGGAATCTCTAAGATTGAGACTTGTTAAGAGAGCCCAAAATTAGCTGGAGATTAAT 1078
TATATGCTTCATGTTTTGTGGGTAAACTGGTAGCACTGGTGTGTCCTTTTCTGCGGTTCTTAATTATTGT 1085
          10860     10870     10880     10890     10900     10910     10920
         ....|....|....|....|....|....|....|....|....|....|....|....|....|....|
GCTGAGGTAGTAAGAGAACTGAAAATGAATATTAGCAATAATGCTGAACAGTTTATAGTAAACGTAATCT 1092
TTTTTTGGCCCCTAACAGATGGATATGGCAGTGGACGTGGATTTGGGGATGGCTATAATGGGTATGGAGG 1099
AGGACCTGGAGGTCAGTTTTCCTCTACGTTTTGGTTTGTTTATGTGACTAATACTTAACTATATCGTATA 1106
TTTACTTCATTTATATTTTGAGTTTTTAAACATTTTATATTAGTGTCTATAAATGGCTTGGGTGATAGTG 1113
GTCCAGTTATTTCTAAGTAGTTTTGCCATCTTAGCTGTTATAGCCTAAGGAATAGAGTGCCATTTTAAAT 1120
          11210     11220     11230     11240     11250     11260     11270
         ....|....|....|....|....|....|....|....|....|....|....|....|....|....|
GAAAATGTAAAGATAACCATCAGAGTATCTCATCTTTTCTCAAGCAAAATGATTGGATCTAGATATATCT 1127
TTGTACGTGCCTTCTCTGGAAAAGTACAGAATACTGGATTTAACAGAGTAAAACCTAAGGGGGTGGTATA 1134
TGTAGGAAAAAATATGAAATATGTCTAAACCCGTAACTAGATGGGAAGCATCCCAGGATAACTTTCAAAA 1141
AGCCGTAACCTACGGAAATGTTCCAAAATGTTTAGTGTGCTCCTGGCTGCAGATAAGGTTGTGAACTACCA 1148
TTAAACATGAAGTGTGATATATCATTGGCGTACAGAAAAGGCTGATACACACTGACAGATTTTGTAACAA 1155
          11560     11570     11580     11590     11600     11610     11620
         ....|....|....|....|....|....|....|....|....|....|....|....|....|....|
GGGACATTTAAAACTGAGCTGGTAATAGACTTGATTTCTGGTGTTGCCACTCAATAGGCATGACTAAATA 1162
GTGTATCTCACTGTTCTACTTTTTATAATTAAAATTTTAGAGGAAGCTGAGTTCTTGTATTTAACTACAA 1169
GTTAGAGACTCAGCCCACAAGCTTTTTTTTTTTTTTTAATATGGTTTCTTTTTTTTTTTTTTTTTTTGAGA 1176
CGGAGCCTTGCTCTGTCACCCAGGCTGGAGTGTAGTGGCGCGTCTCTGCTCACTGCAATCTCTGCCTTCC 1183
CGGTCCAAGTGATTCTCCTGCCTCAGCCTCCTGAGTAGCTGGGATTACCGGCGTGCACCACCACGCCAGC 1190
          11910     11920     11930     11940     11950     11960     11970
         ....|....|....|....|....|....|....|....|....|....|....|....|....|....|
TAATTTTAGTATTTTTAGTAGAGACGGGGTTTCCCATGTTGGTCAGGCTGGTCTTGAACTCCTGACCTCGT 1197
GAACTGCCCACCTTGGCCTCCCAAAAACGCTGGGGTTACAGGCGTGAGCAACCATGCCCAGCCTTTTTTT 1204
TTTTTTTATTTTTGTTTTGCCAGTATGTGAATGTGTAAATTTTGTTTATGTCCGCACTTCTATTTACAGT 1211
AAAGAACATACTGTGTGGAGTGTTGGGTCTGTTTTTTTTCTTTGAAATGGGGTCTGGCTTTGTTGCTCAG 1218
ACTGGAGTGCAGTGGTGTGATCTTGGCTTACTGCAATCTTAGTCTCAAGCCATCCTCCCACCTCAGCCCTC 1225
```

FIG. 21(VIII)

```
       12260     12270     12280     12290     12300     12310     12320
     |....|....|....|....|....|....|....|....|....|....|....|....|....|....|
CTGGGTAGCTGGAACTACGGGGTGTGCCACCATGACCGGCTAATTTTGTGTTTTTTTGTAGAGGTGTGGG 1232
GGTTTTGCTGTGTTGCCCTGGCTGGTCTTGAATTCCTGGGCTCAAGCAATCCACCCGCCTCAACTTCCCG 1239
TACTGCTGGGATTACAGGTGTGAGCTGCTGCGCCCAGCCAAGAACATTGTTTCGTTTTTTGAGAGGGAGT 1246
CTCTCTCTGTCGCCCAGGCTGGAGTGCAGTGGTGTGATCTCAGCTCACTGCAACCTCTGCCTCCCGGGTT 1253
CACGCCATTCTCCTGCCTCAGCCTCCAGAGTAGCTAGTACTACAGGTTGCTGCCACCATGTCCGGCTAAT 1260

12610     12620     12630     12640     12650     12660     12670
     |....|....|....|....|....|....|....|....|....|....|....|....|....|....|
GTTTTGTATTTTTAGTAGAGATGGGGTTTCACCGTGTTAGCCAGGGTGGTCTCAATCTCTTGACCTCGTG 1267
ATCCGTCCGCCTCGGCCTTCCCAAAGTGCTGGGATTACAGGCATGAGCCACTGTGCCCAACCGAGAACAT 1274
TGTTTTAAGATATGTAATTCGTAGAGAGACATAATAGAAACTTTATCTTTTGGGCCAGTAGGAGGAAGTG 1281
CTCTTTTACTTTCCCTCTAGCCCACACTACTAGTCTAGCCTCACAGTCCTTACCCACAATATACATGAAG 1288
TATTTCAAGATACTTAAGATTTTTAGTTTTGAGGGAAAGCTGTGGAATTACAGGTATTTAACTGTGTGCA 1295

12960     12970     12980     12990     13000     13010     13020
     |....|....|....|....|....|....|....|....|....|....|....|....|....|....|
CATGGTGTTATCCATTTGGCTGAGTAACCCCAGCCACCAAATGTTTACCAAGGATAGTTATTCAGTCCTT 1302
GAAGCTATTTTAGAGGAATTTCATTAAATATTTCACATGGAAACTTGGAAAGCTGGAAATGGATGTGAGG 1309
AGACAGTTCAAAATGGTATTGAAAATATTAAGTGATTACTTAAAGGCTTATTTTATAATAGGTGGCAATT 1316
TTGGAGGTAGCCCCGGTTATGGAGGAGGAAGAGGAGGATATGGTGGTGGAGGACCTGGATATGGCAACCA 1323
GGGTGGGGGCTACGGAGGTGGTTATGACAACTATGGAGGAGGTAATAAATTCACCTGCAACCTTTATGTG 1330

13310     13320     13330     13340     13350     13360     13370
     |....|....|....|....|....|....|....|....|....|....|....|....|....|....|
GGAATTTGGAATTAATGTCTTTGTAACACTTGATCTTTTGTTTCCATGTTTGTCACTAGATGCCCATAAA 1337
ATTGTGGATAAGTGTTTGCTTTTATTGTTTTTATGGGAGCTTGTCCTAAGTCCTTGGTTTAATGTTT 1344
GTATTGTTCTGAGTATTCCAATTTTTTAATAGGAAATTATGGAAGTGGAAATTACAATGATTTTGGAAAT 1351
TATAACCAGCAACCTTCTAACTACGGTCCAATGAAGAGTGGAAACTTTGGTGGTAGCAGGAACATGGGGG 1358
GACCATATGGTGGAGGTAATTTATAAAAATTGAGGTTATTCAGATTTTGTGATTAAAGGATTAGCCTTT 1365

13660     13670     13680     13690     13700     13710     13720
     |....|....|....|....|....|....|....|....|....|....|....|....|....|....|
TGTGACTTAAAGGGAAGATAACATACTAAGTAGTTTGTACTGTGGGCAGTGCTCCATGTACGGTCTTAGT 1372
GAAAATAAAGAAATTTGCATAAATCTCCACAGAAGTACTCAGCAAGCAGTTATGACATCAAATTGGGAT 1379
TAGGTAGTTGGAGGTGGGTGTCAGTAGTTTAATTTCTGGTGGGACTCATAAACAGCTAAATACAGTTGCA 1386
ACCCACATTGCAAGTGGTATACATTGGAATGAGGGTCTTTGAAGTTAAATCCTTAAACCATGATTCAAAC 1393
CATTGCTTAGCTTATTTTTGAGGTTTTTAGCTAGGAGTAAACTAGCTTTGTCTTGGGCTTGATGTACTTT 1400
```

FIG. 21(IX)

```
       14010     14020     14030     14040     14050     14060     14070
TAAAAAAATCCCTTACTCAGTCCAAATGAGGATGAGAGGGTGAAAGGACCCTTTATTTAAAAGAATAGGG 1407
TCAGCCACGAAATAAAAATGTCTATGAACCCGAGTAATTTATCTCCTGAGTAATTCTGCTAACTGGCTGC 1414
AAAGGATTAGGATCTGCTTGTTTAAAAGACTGGATGGATATAAAATAGAATCAACTGTAGTGTTAGGCTG 1421
ATCATGGAAATCAAAGTAAGTTTGTTTTCTCTTGCTGTTCCAACAATTATAGGAAACTATGGTCCAGGA 1428
GGCAGTGGAGGAAGTGGGGGTTATGGTGGGAGGAGCCGATACTGAGCTTCTTCCTATTTGCCATGGGTAA 1435
       14360     14370     14380     14390     14400     14410     14420
GTAGCTTTTGAGTTTTACAATTATTATTATCTTGGGAGACATAGCTGCAGGAGTAAAAGCTTTTTAGGAT 1442
CATGGTTATCTTTCCTTAAAATCTGGTTAGATGGATAATTTCATAACCCATTTTTTTTTTACCCTTTACT 1449
TCTGTTGAAACAGGCTTCACTGTATAAATAGGAGAGGATGAGAGCCCAGAGGTAACAGAACAGCTTCAGG 1456
TTATCGAAATAACAATGTTAAGGAAACTCTTATCTCAGTCATGCATAAATATGCAGTGATATGGCAGAAG 1463
ACACCAGAGCAGATGCAGAGAGCCATTTTGTGAATGGATTGGATTATTTAATAACATTACCTTACTGTGG 1470
       14710     14720     14730     14740     14750     14760     14770
AGGAAGGATTGTAAAAAAAAATGCCCTTTGAGACAGTTTCTTAGCTTTTTAATTGTTGTTTCTTTCTAGTG 1477
GTCTTTGTAAGAGTGTAGAAGCATTCCTTCTTTGATAATGTTAAATTTGTAAGTTTCAGGTGACATGTGA 1484
AACCTTTTTTAAGATTTTTCTCAAAGTTTTGAAAAGCTATTAGCCAGGATCATGGTGTAATAAGACATAA 1491
CGTTTTTCCTTTAAAAAAATTTAAGTGCGTGTGTAGAGTTAAGAAGCTGTTGTACATTTATGATTTAATA 1498
AAATAATTCTAAAGGAAATTGTGTAATTATAGACTTTTTATTTTTAAATAAGTTAAGGAGTGGGTAGTAT 1505
       15060     15070     15080     15090     15100     15110     15120
AATTAAGGTCGTTCAAAGCTG 15071
```

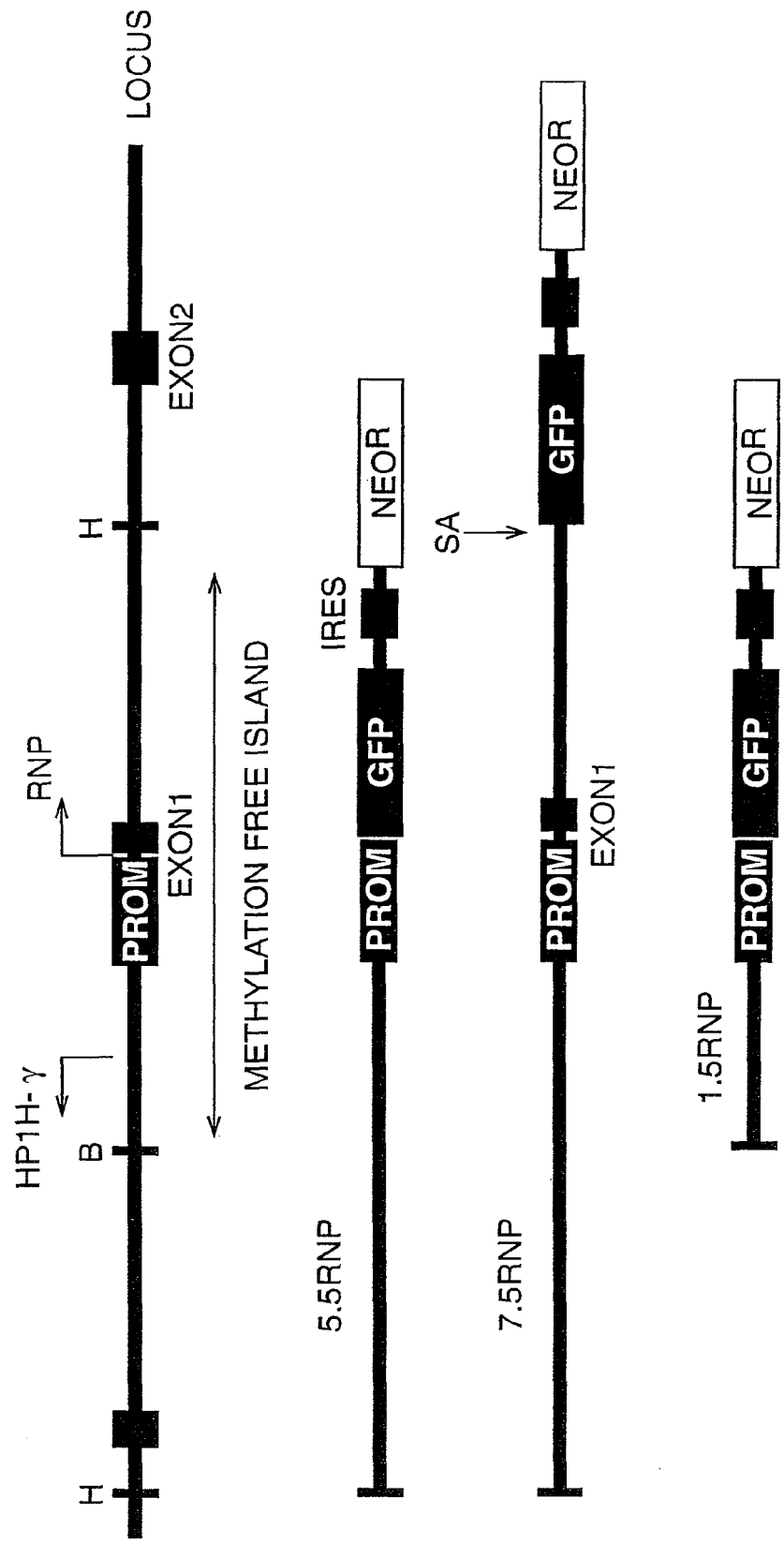

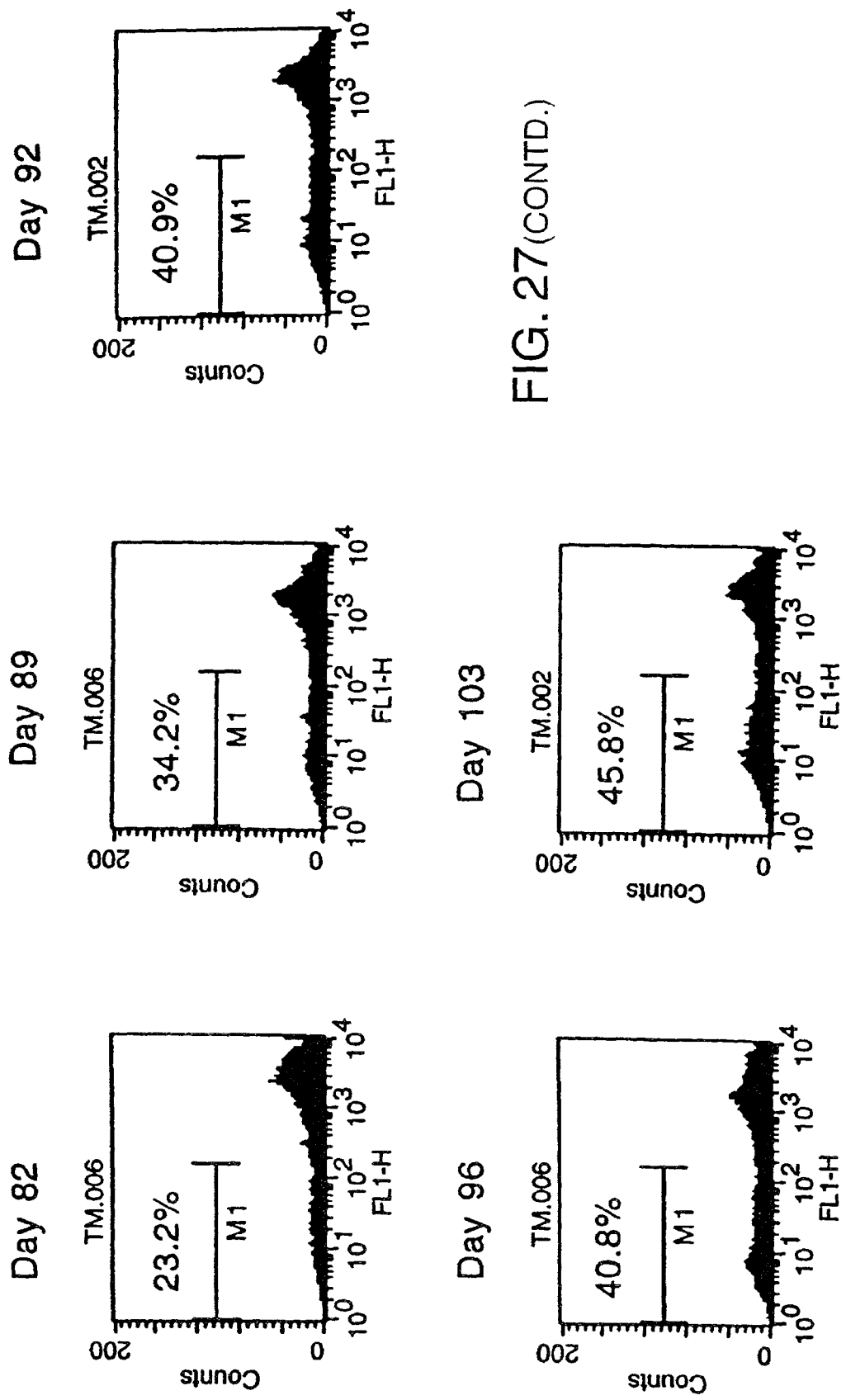
FIG. 27 (CONTD.)

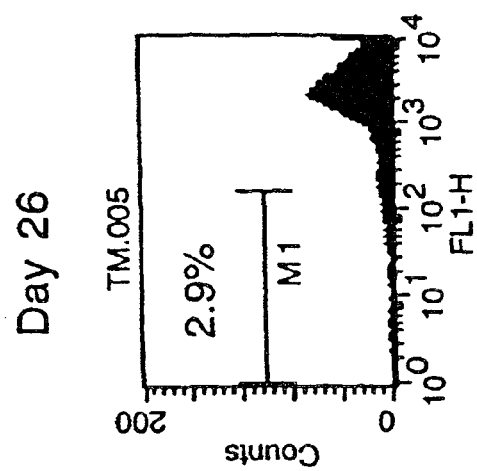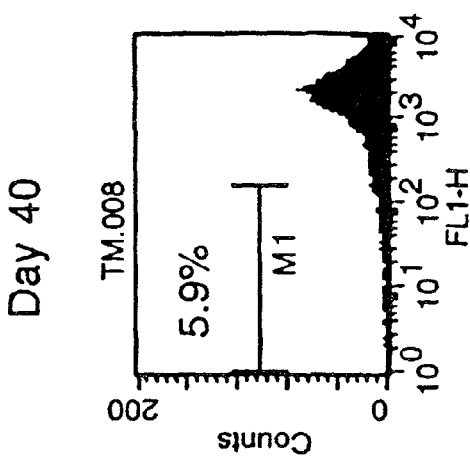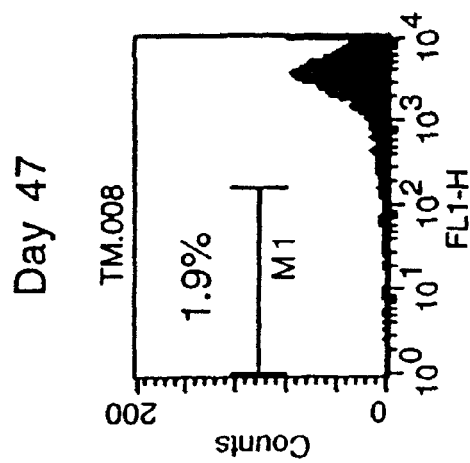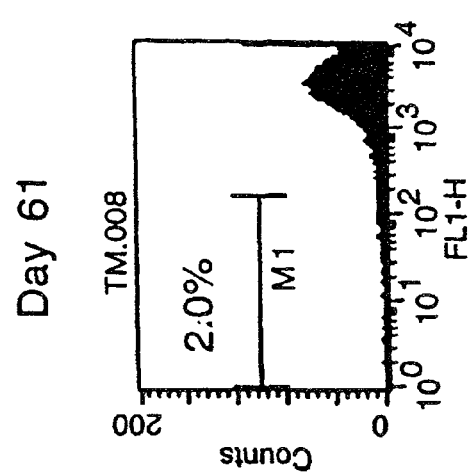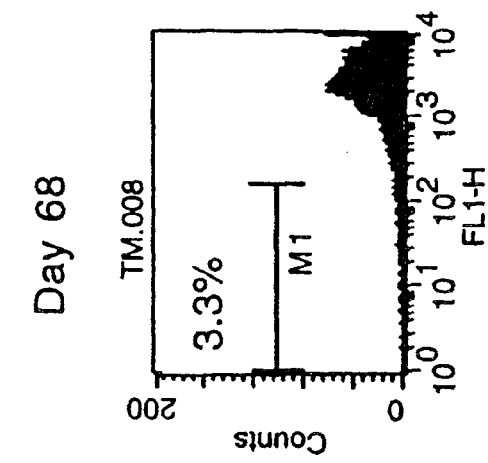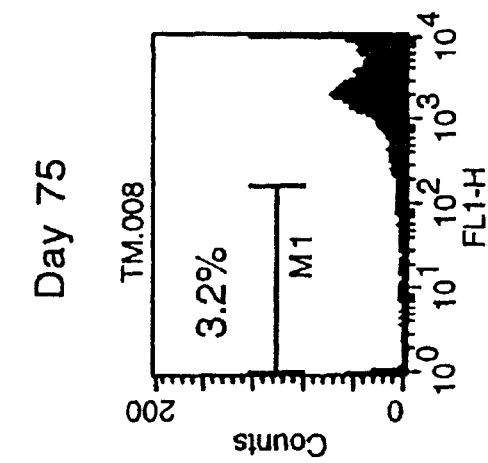
FIG. 28

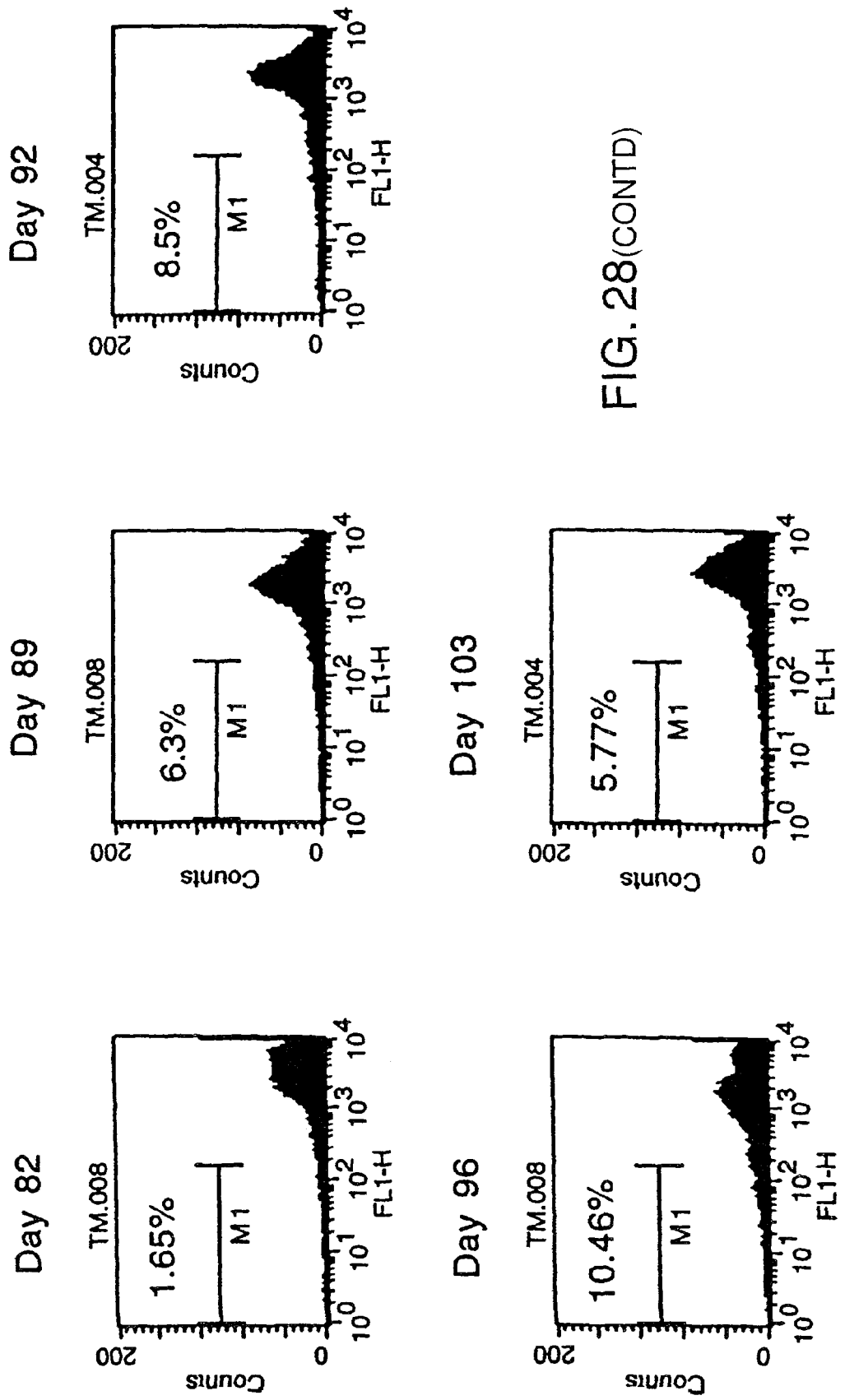
FIG. 28 (CONTD)

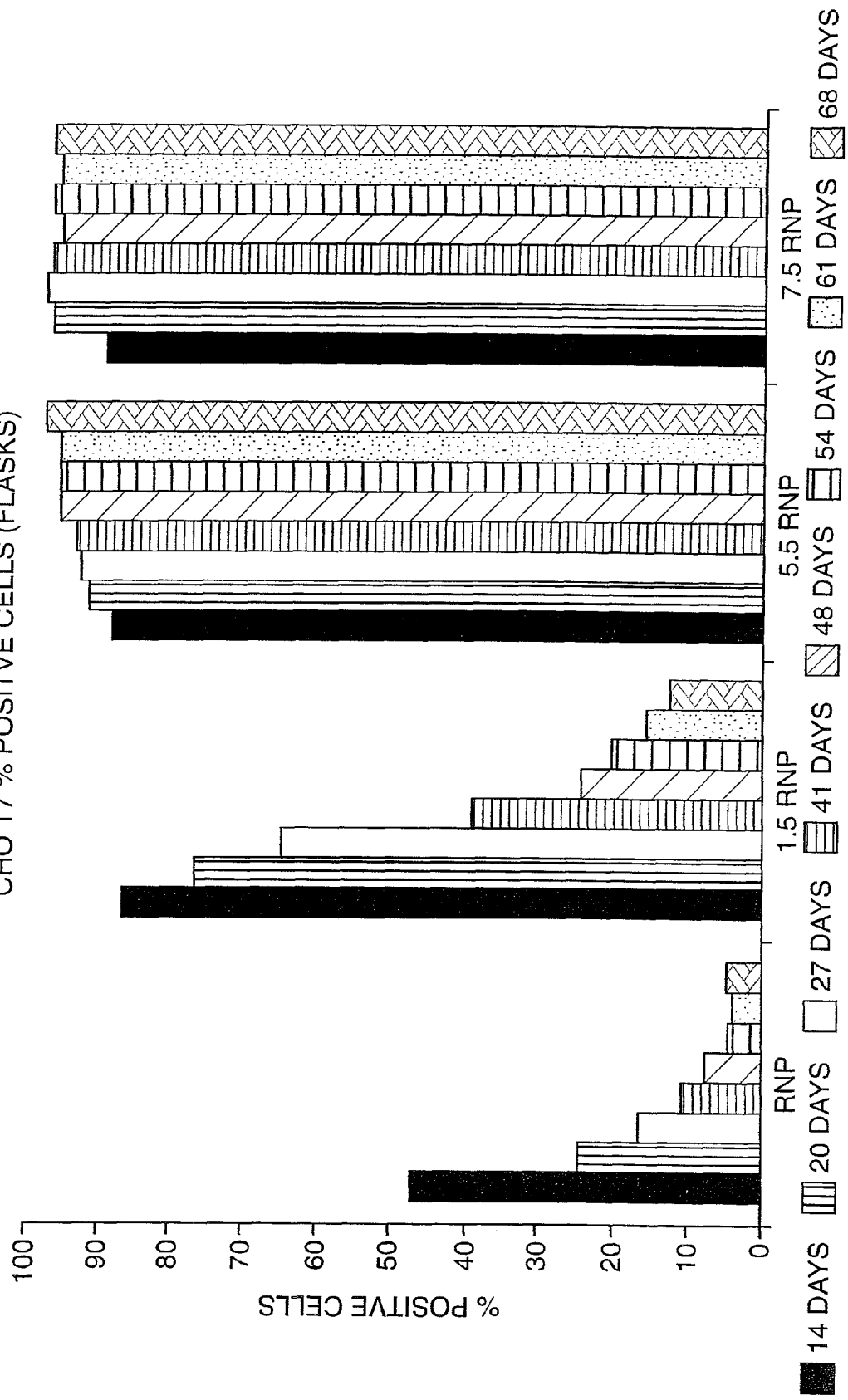

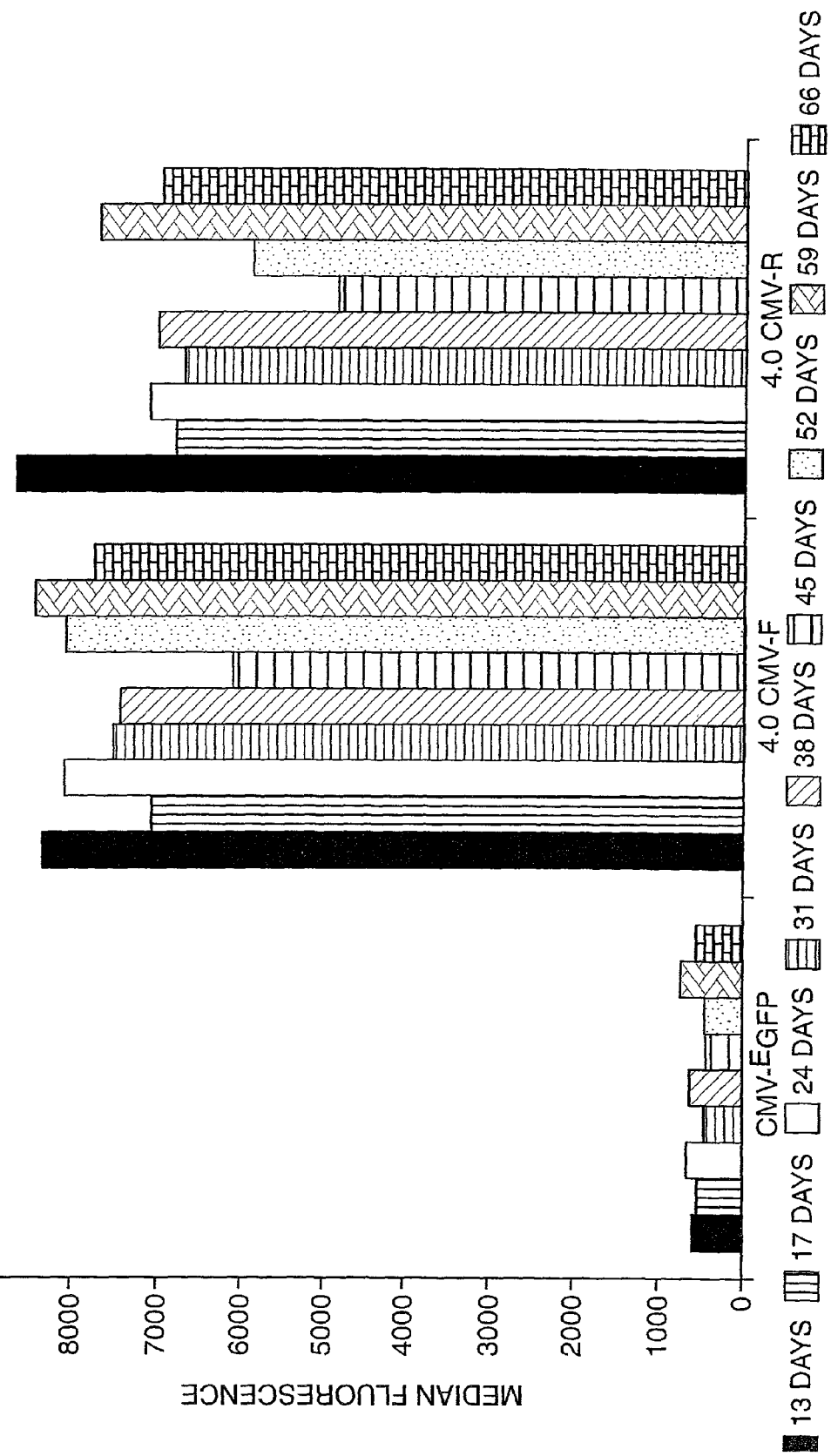

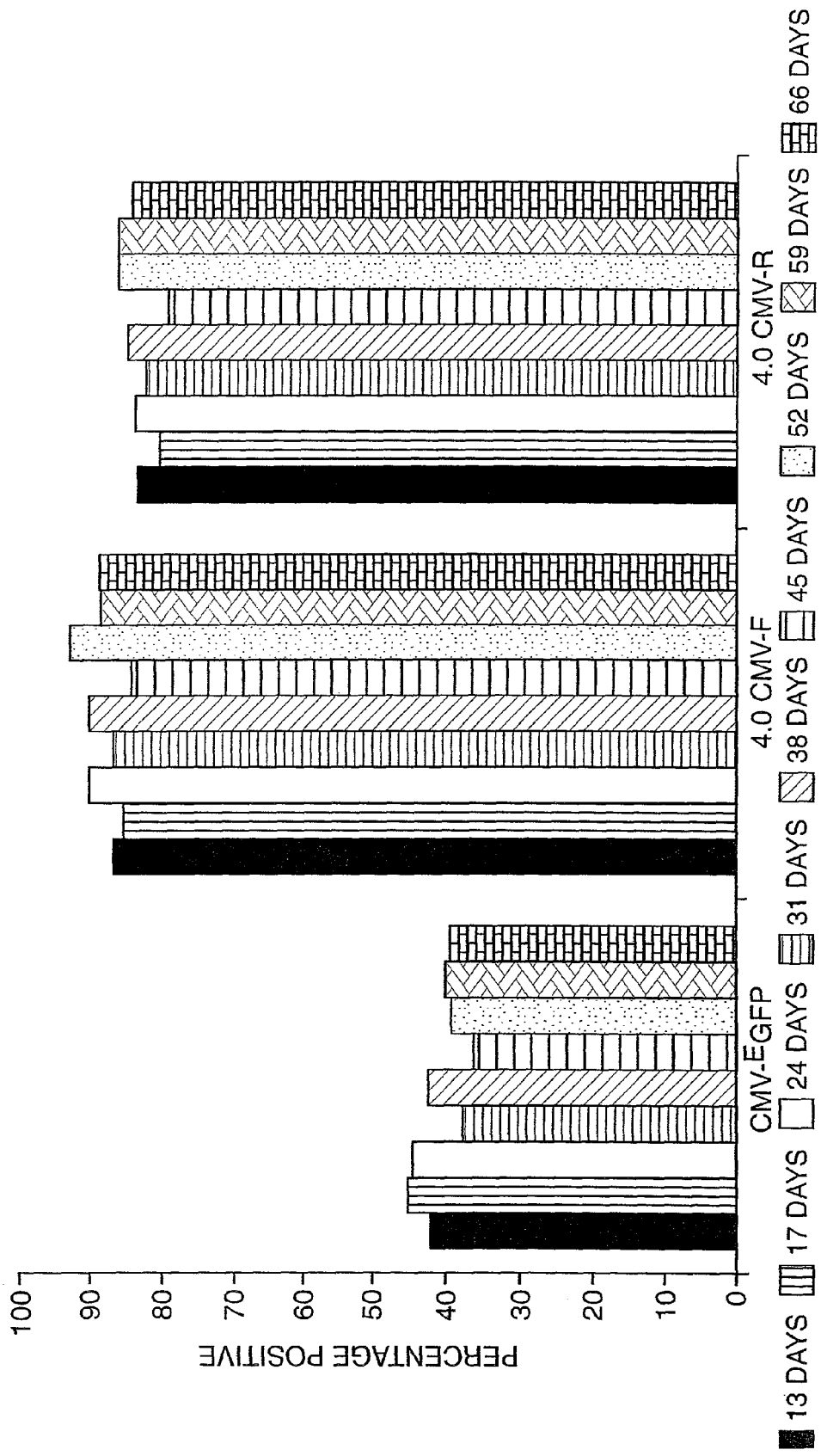

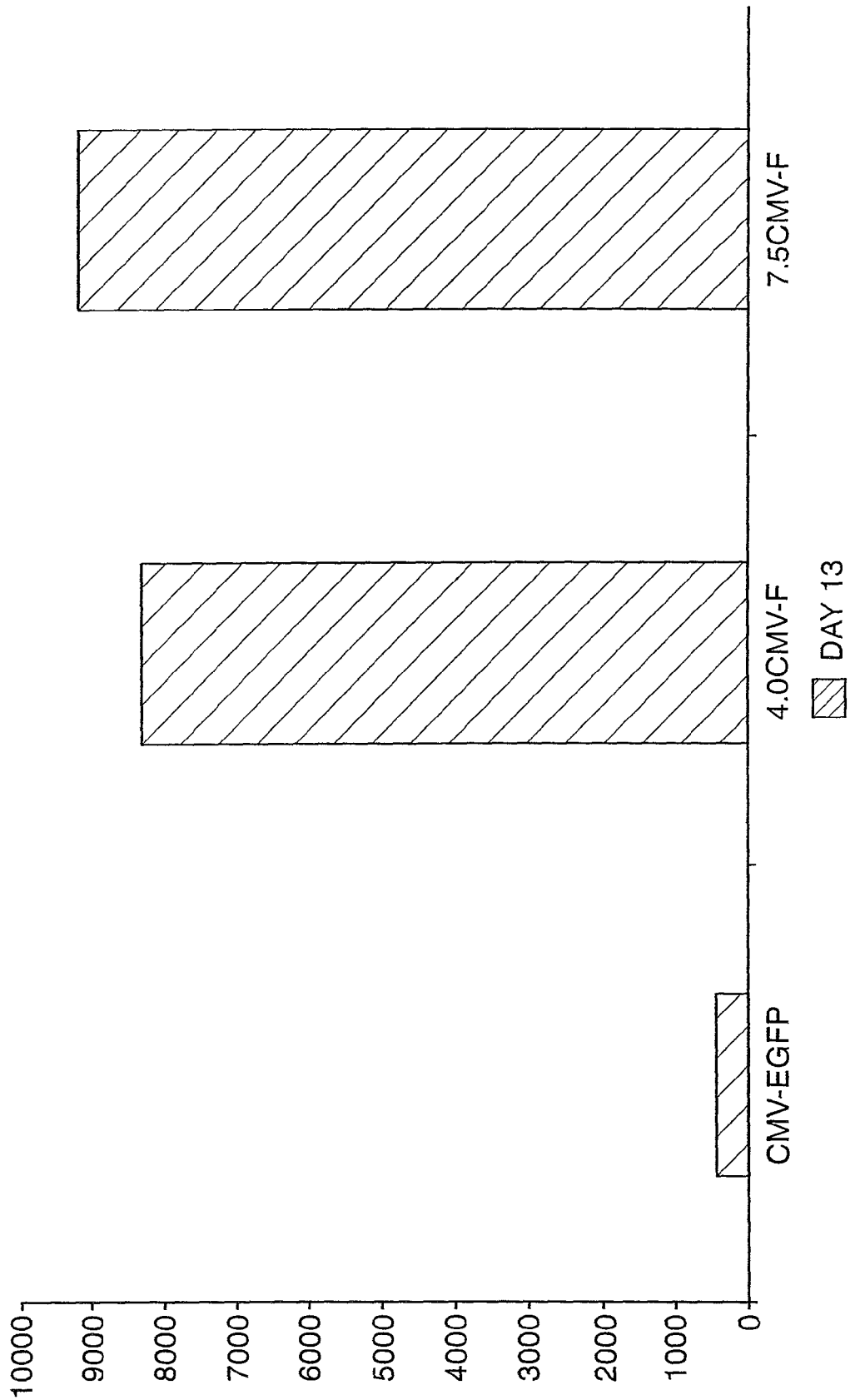

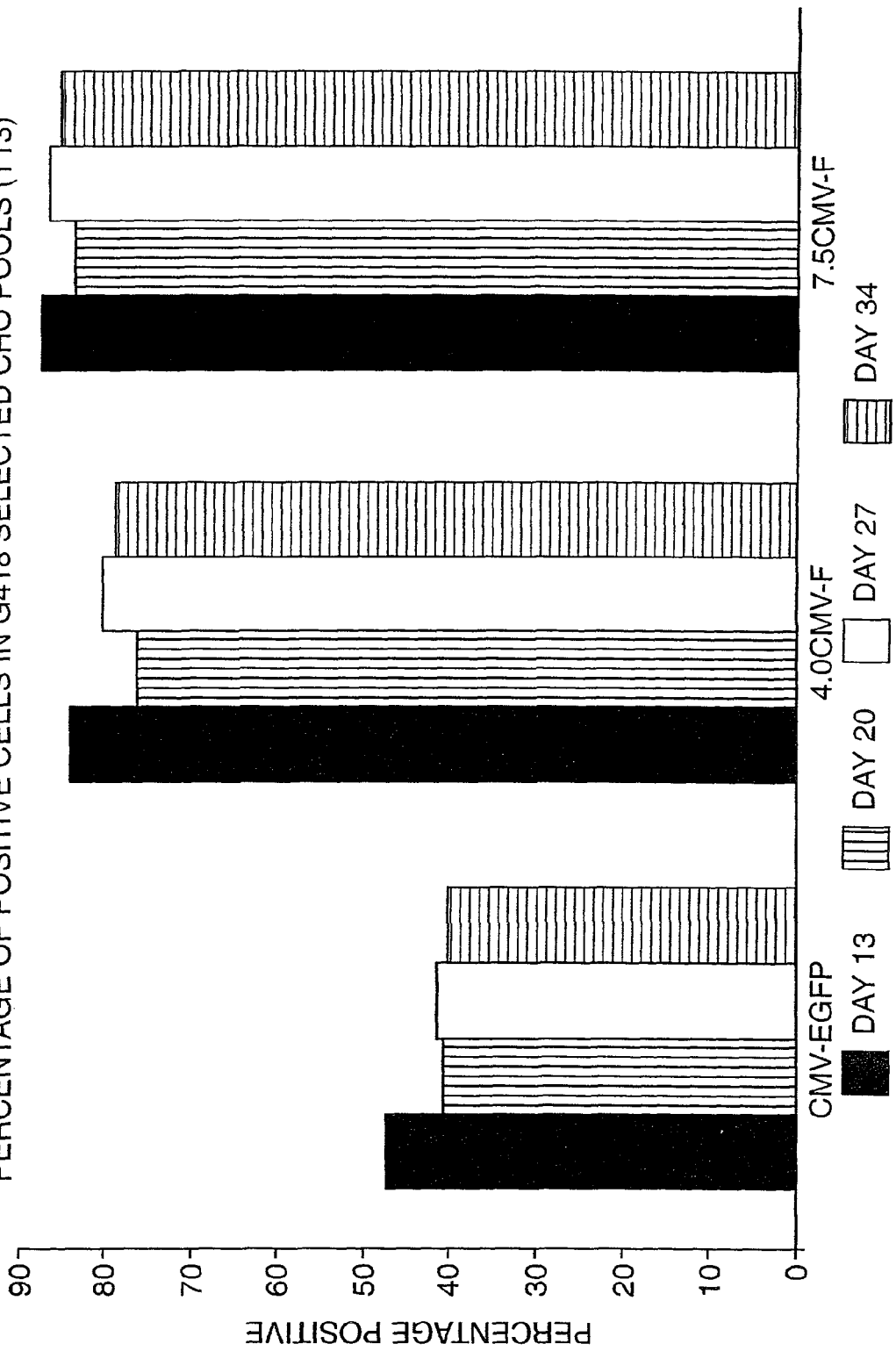

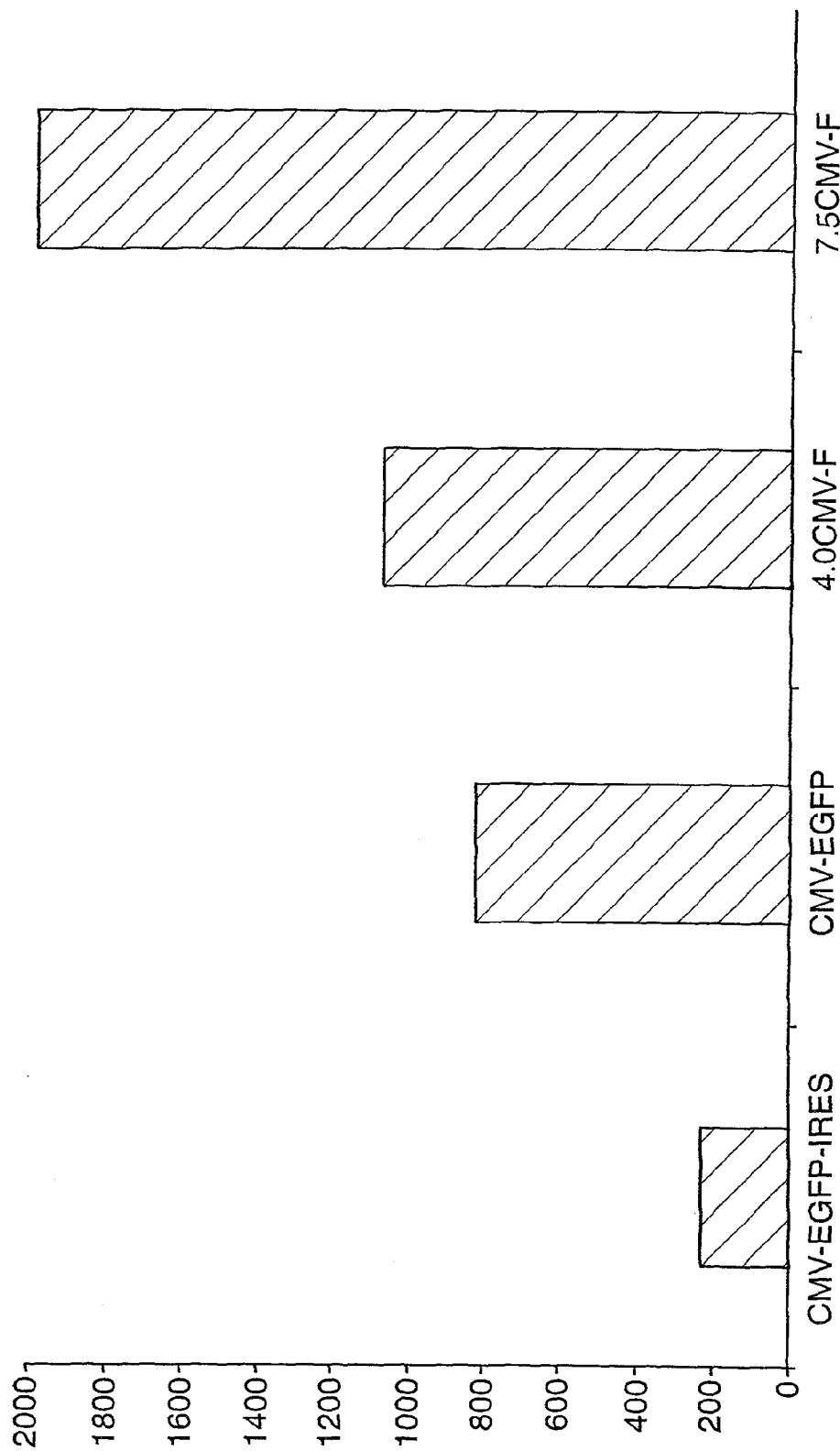

FIG. 35(A)

| | 1 | 2 | 3 | 4 | 5 | 6 | 7 | 8 |
|---|---|---|---|---|---|---|---|---|
| A | | AMYGDALA<br>135 | CAUDATE NUCLEUS<br>161 | CERRE-BELLUM<br>109 | CEREBREL CORTEX<br>99 | FRONTAL LOBE<br>89 | HIPPO-CAMPUS<br>118 | MEDULLA OBLONGATA<br>124 |
| B | | PUTAMEN<br>202 | SUBSTANTIA NIGRA<br>132 | TEMPORAL LOBE<br>117 | THALAMUS<br>125 | SUB-THALAMIC NUCLEUS<br>127 | SPINAL CORD<br>169 | |
| C | HEART<br>410 | AORTA<br>106 | SKELETAL MUSCLE<br>210 | COLON<br>177 | BLADDER<br>100 | UTERUS<br>114 | PROSTATE<br>190 | STOMACH<br>293 |
| D | TESTIS<br>213 | OVARY<br>205 | PANCREAS<br>514 | PITUITARY GLAND<br>331 | ADRENAL GLAND<br>349 | THYROID GLAND<br>169 | SALIVARY GLAND<br>393 | MAMMARY GLAND<br>93 |
| E | KIDNEY<br>213 | LIVER<br>429 | SMALL INTESTINE<br>275 | SPLEEN<br>175 | THYMUS<br>209 | PERIPHERAL LEUKOCYTE<br>94 | LYMPH NODE<br>164 | BONE MARROW<br>147 |
| F | APPENDIX<br>152 | LUNG<br>243 | TRACHEA<br>235 | PLACENTA<br>361 | | | | |
| G | FETAL BRAIN<br>137 | FETAL HEART<br>135 | FETAL KIDNEY<br>210 | FETAL LIVER<br>243 | FETAL SPLEEN<br>149 | FETAL THYMUS<br>104 | FETAL LUNG<br>245 | |
| H | YEAST TOTAL RNA<br>100 ng | YEAST tRNA<br>100 ng | E.coli rRNA<br>100 ng | E.coli DNA<br>100 ng | POLY r(A)<br>100 ng | HUMAN $C_{o}t$ 1 DNA<br>100 ng | HUMAN DNA<br>100 ng | HUMAN DNA<br>500 ng |

FIG. 35(B) (PSMB1)
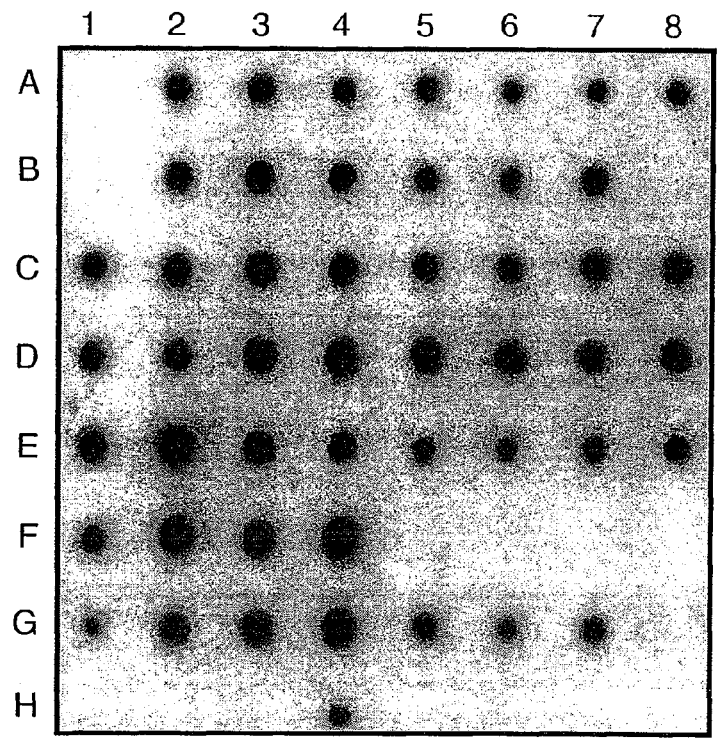
FIG. 35(C) (PDCD2)
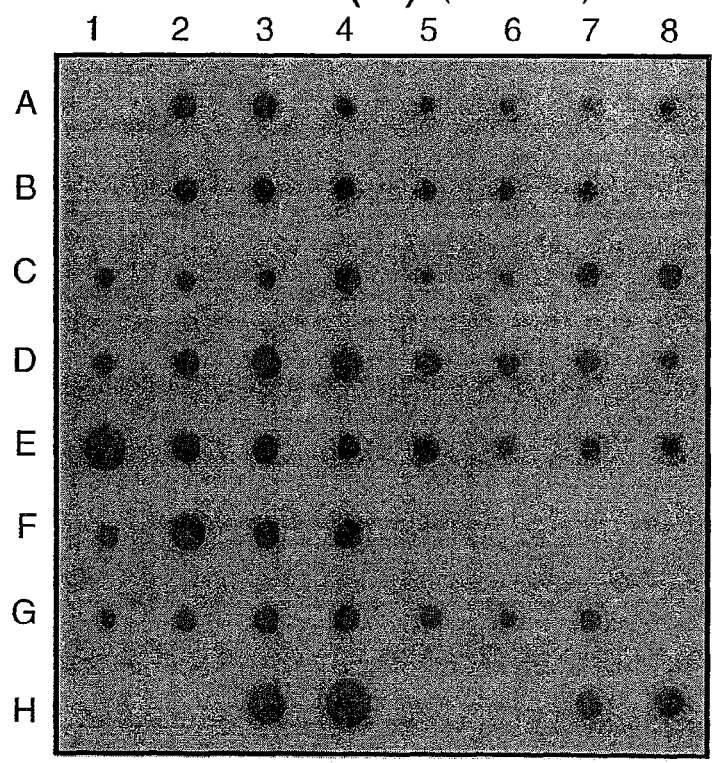

FIG. 35(D) (TBP)
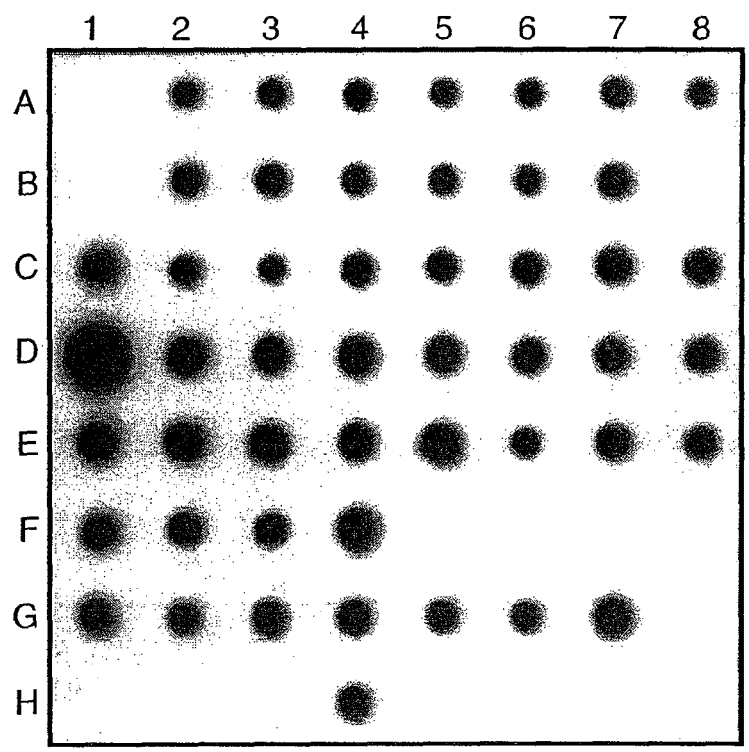
FIG. 35(E) (UBIQUITIN)
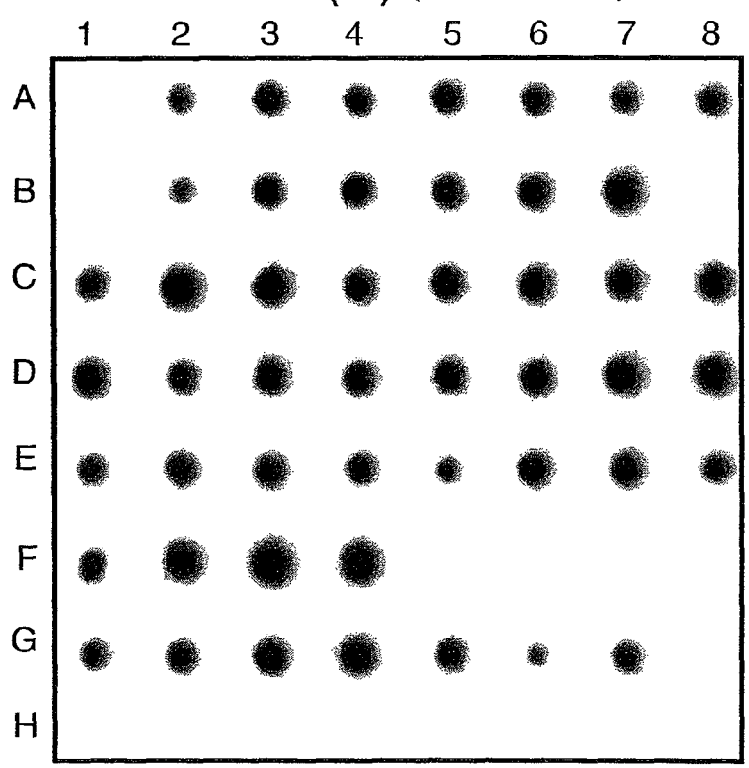

FIG. 38(A)

|   | 1 | 2 | 3 | 4 | 5 | 6 | 7 | 8 |
|---|---|---|---|---|---|---|---|---|
| A | WHOLE BRAIN<br>100 | AMYGDALA<br>135 | CAUDATE NUCLEUS<br>161 | CERRE-BELLUM<br>109 | CEREBRAL CORTEX<br>99 | FRONTAL LOBE<br>89 | HIPPO-CAMPUS<br>118 | MEDULLA OBLONGATA<br>124 |
| B | OCCIPIGAL LOBE<br>100 | PUTAMEN<br>202 | SUBSTANTIA NIGRA<br>132 | TEMPORAL LOBE<br>117 | THALAMUS<br>125 | SUB-THALAMIC NUCLEUS<br>127 | SPINAL CORD<br>169 | |
| C | HEART<br>410 | AORTA<br>106 | SKELETAL MUSCLE<br>210 | COLON<br>177 | BLADDER<br>100 | UTERUS<br>114 | PROSTATE<br>190 | STOMACH<br>293 |
| D | TESTIS<br>213 | OVARY<br>205 | PANCREAS<br>514 | PITUITARY GLAND<br>331 | ADRENAL GLAND<br>349 | THYROID GLAND<br>169 | SALIVARY GLAND<br>393 | MAMMARY GLAND<br>93 |
| E | KIDNEY<br>213 | LIVER<br>429 | SMALL INTESTINE<br>275 | SPLEEN<br>175 | THYMUS<br>209 | PERIPHERAL LEUKOCYTE<br>94 | LYMPH NODE<br>164 | BONE MARROW<br>147 |
| F | APPENDIX<br>152 | LUNG<br>243 | TRACHEA<br>235 | PLACENTA<br>361 | | | | |
| G | FETAL BRAIN<br>137 | FETAL HEART<br>135 | FETAL KIDNEY<br>210 | FETAL LIVER<br>243 | FETAL SPLEEN<br>149 | FETAL THYMUS<br>104 | FETAL LUNG<br>245 | |
| H | YEAST TOTAL RNA<br>100 ng | YEAST tRNA<br>100 ng | E.coli rRNA<br>100 ng | E.coli DNA<br>100 ng | POLY r(A)<br>100 ng | HUMAN Cot 1 DNA<br>100 ng | HUMAN DNA<br>100 ng | HUMAN DNA<br>500 ng |

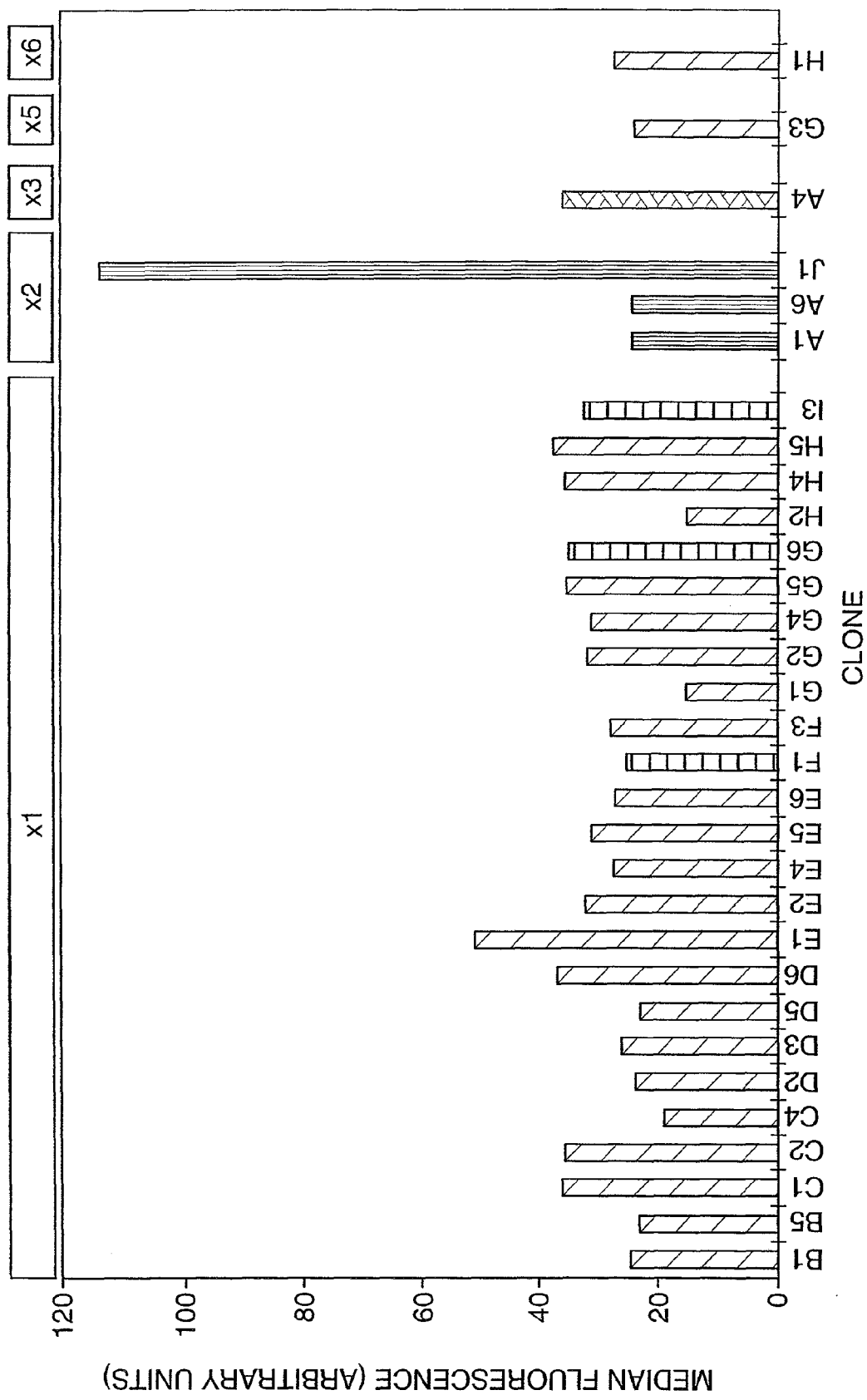

FIG. 43
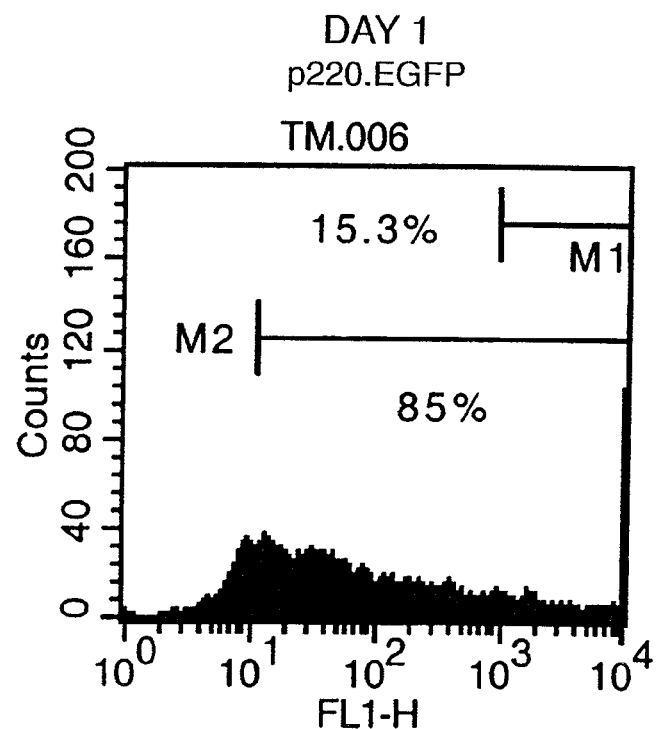
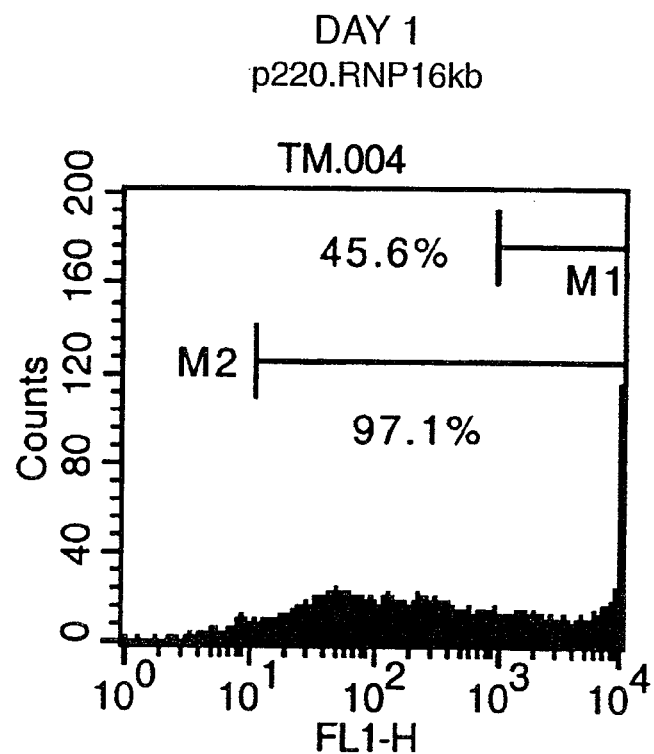

FIG. 43(I)
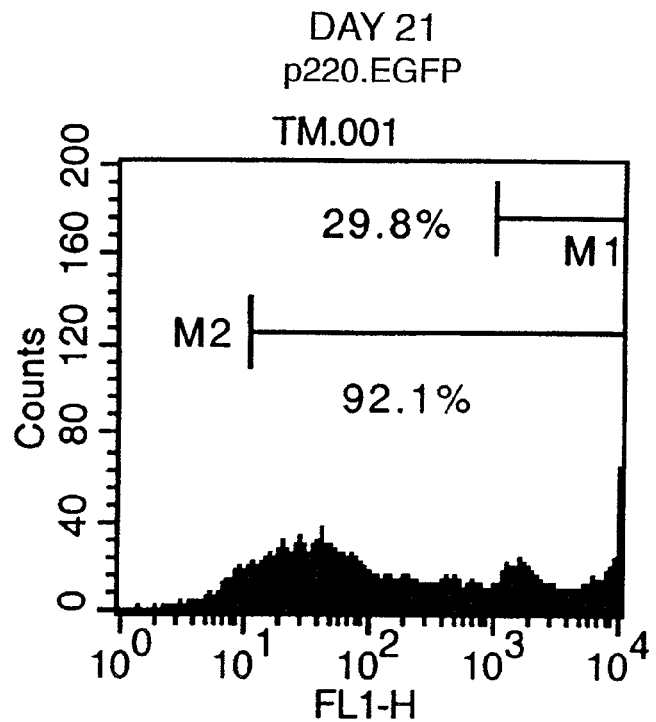
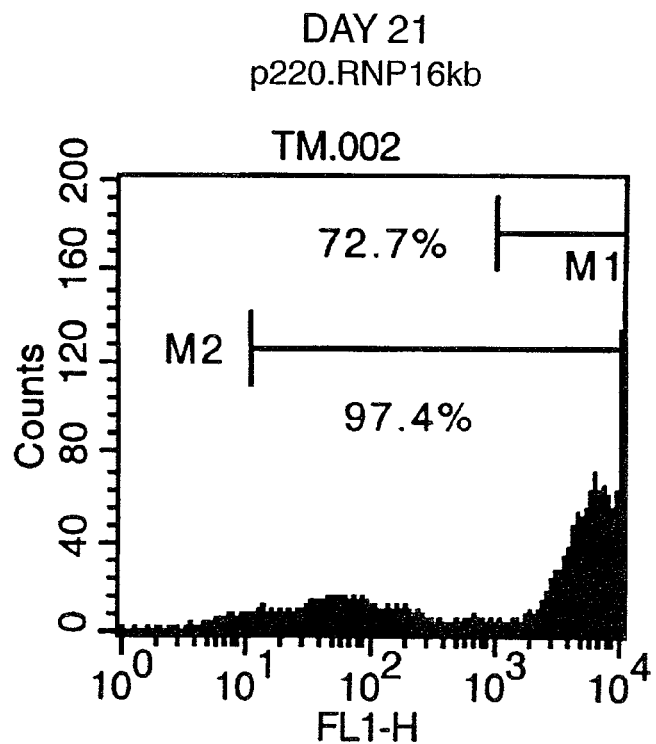

FIG. 43(II)
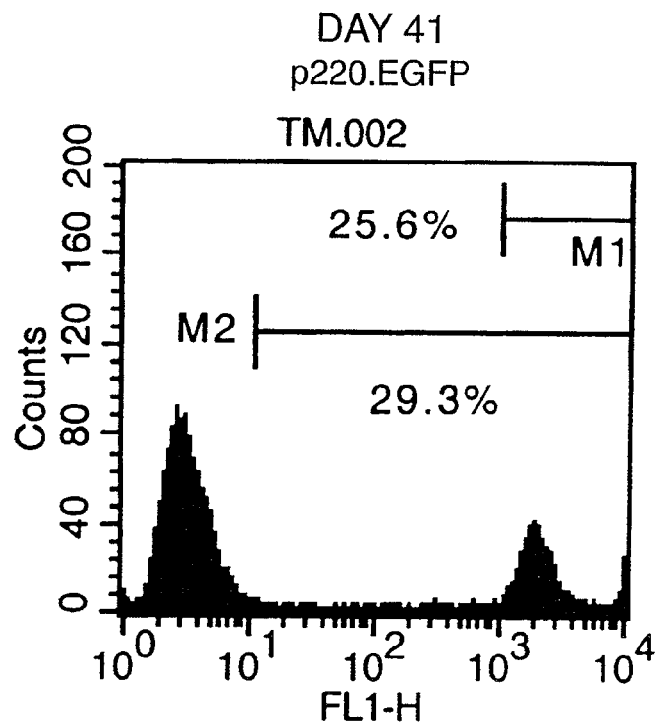
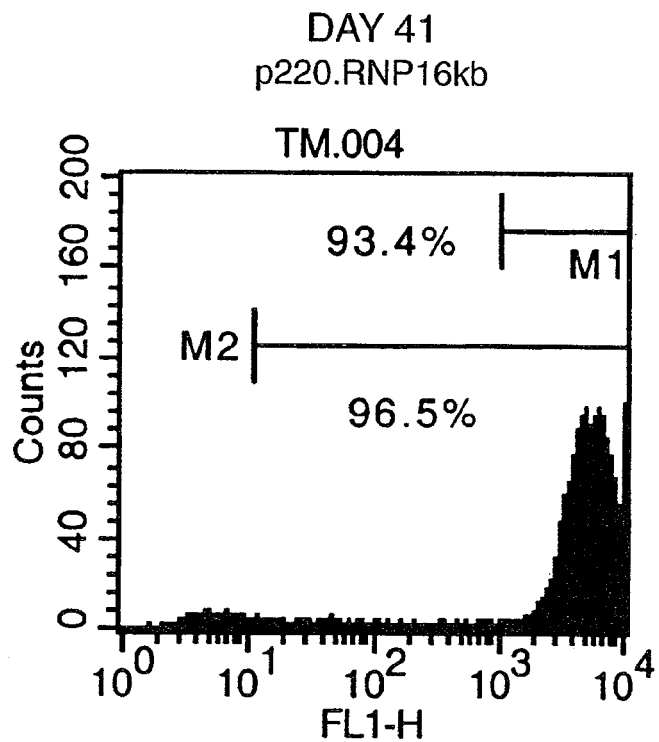

EPO PRODUCTION IN TRANSIENT TRANSFECTION

FIG. 47

| | TUMOUR (%) | LIVER (%) |
|---|---|---|
| _CTL102; 7.5E+9_ | | |
| MOUSE 1 | + | 1 |
| MOUSE 2 | 5 | + |
| MOUSE 3 | 15 | 0 |
| MOUSE 4 | 20 | +/- |
| MOUSE 5 | 25 | + |
| MOUSE 6 | 60 | + |
| _CTL208; 7.5E+9_ | | |
| MOUSE 7 | 0 | 0 |
| MOUSE 8 | 10 | 0 |
| MOUSE 9 | 30 | 0 |
| MOUSE 10 | 40 | 0 |
| MOUSE 11 | 80 | 0 |

+/- FEW CELLS (AVERAGE OF 3/SECTION)

+ AVERAGE OF 30-50 CELLS/SECTION

* UNIQUE RESTRICTION SITE

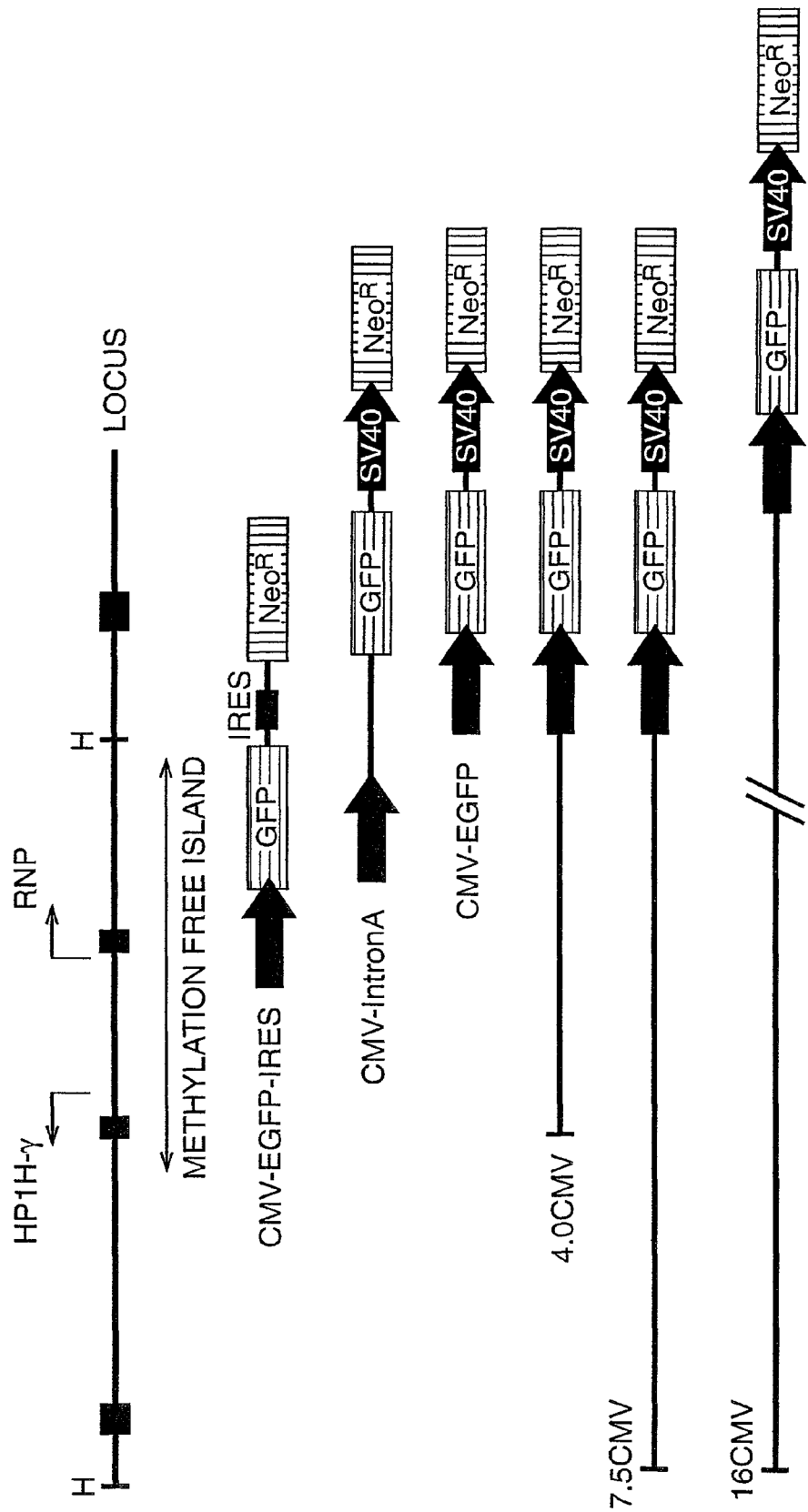

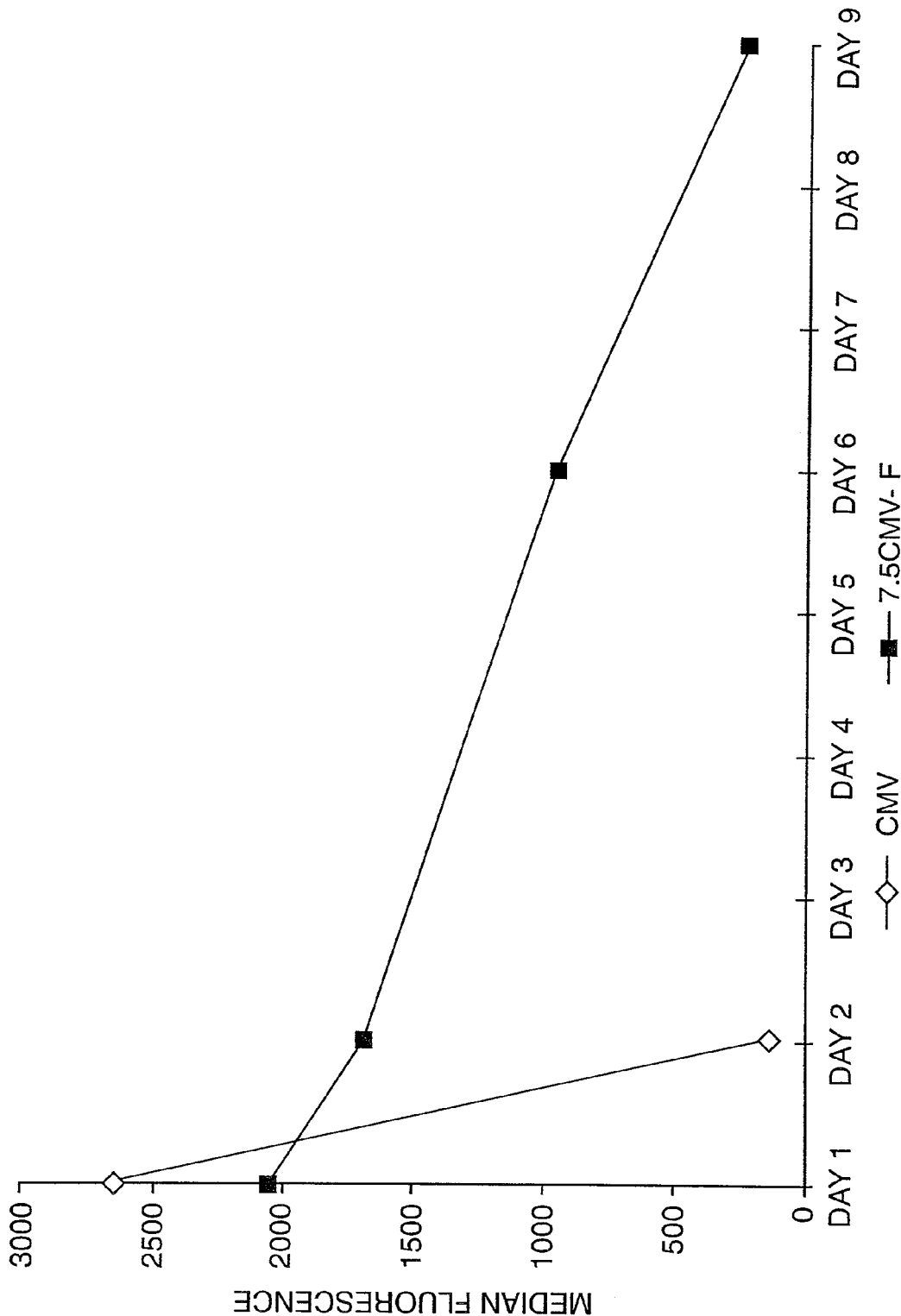

7.5 CMV 24 hrs p-t

CMV-EGFP 24 hrs p-t 7.5 CMV 6 days p-t

CMV-EGFP 6 days p-t

SEQUENCE LISTING

```
<160> NUMBER OF SEQ ID NOS: 29

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 1
gctgaagcga ctgagtccat g                                              21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: PCR primer
```

-continued

<400> SEQUENCE: 2
ccaatccatt gacaaaatgg gc                                          22

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 3
atgtgacaac agtgcatgaa ctgggagtgg                                  30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 4
cacttcctgt gtttccatag gtaaggaggg                                  30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 5
ggtggtgttg tgagaagatg gatgttgagg                                  30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 6
gcaatactgg agaggtggaa tgtgtctggc                                  30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 7
atttcaaact gcgcgacgtt tctcaccgc                                   29

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 8
cattgatttc aaacccgtta cctcc                                       25

<210> SEQ ID NO 9
<211> LENGTH: 28
<212> TYPE: DNA

```
<213> ORGANISM: Artificial Sequence
<220> FEATURE:
<223> OTHER INFORMATION: Description of Artificial Sequence: PCR primer

<400> SEQUENCE: 9
ggaaactttg gtggtagcag gaacatgg                                          28

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 10
atccatccag tcttttaaac aagcag                                            26

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 11
tgcggccgct aatacgactc actatagg                                          28

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: PCR primer

<400> SEQUENCE: 12
ggccaggcgg ccgccaggcc tacccactag tcaattcggg a                           41

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: PCR primer

<400> SEQUENCE: 13
ctccaccata tggtcccc                                                     18

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 14
accggttctc tctgcaaagg aaaatacc                                          28

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 15
ggtaccctct gccagcaggt cacctc                                            26
```

```
<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: PCR primer

<400> SEQUENCE: 16
accggttctc tctgcaaagg aaaatacc                                          28

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: PCR primer

<400> SEQUENCE: 17
ggtaccgagc atgcgaatgg agggagagct ccg                                    33

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 18
ctagcgttcg aagtttaaac gc                                                22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 19
ggccgcgttt aaacttcgaa cg                                                22

<210> SEQ ID NO 20
<211> LENGTH: 35
<212> TYPE: PRT
<213> ORGANISM: Artificial Sequence
<220> FEATURE:
<223> OTHER INFORMATION: Description of Artificial Sequence: CL22
      peptide

<400> SEQUENCE: 20

Lys Lys Lys Lys Lys Lys Gly Gly Phe Leu Gly Phe Trp Arg Gly Glu
 1               5                  10                  15

Asn Gly Arg Lys Thr Arg Ser Ala Tyr Glu Arg Met Cys Asn Ile Leu
            20                  25                  30

Lys Gly Lys
        35

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: PCR primer

<400> SEQUENCE: 21
caggtcgctg agggac                                                       16
```

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: PCR primer

<400> SEQUENCE: 22
ctcgacgggg ttcagg                                                     16

<210> SEQ ID NO 23
<211> LENGTH: 351
<212> TYPE: DNA
<213> ORGANISM: Homo sapiens

<400> SEQUENCE: 23
attgctgcaa tgctgtctac aatcctgtat tcaaggcgct tctttccata ctatgtttac     60
aacatcatcg gtggacttga tgaagaagga aaggggctg tatacagctt tgatccagta    120
gggtcttacc agagagactc cttcaaggct ggaggctcag caagtgccat gctacagccc    180
ctgcttgaca accaggttgg ttttaagaac atgcagaatg tggagcatgt tccgctgtcc    240
ttggacagag ccatgcggct ggtgaaagat gtcttcattt ctgcggctga gagagatgtg    300
tacactgggg acgcactccg gatctgcata gtgaccaaag agggcatcag g             351

<210> SEQ ID NO 24
<211> LENGTH: 351
<212> TYPE: DNA
<213> ORGANISM: Murinae gen. sp.

<400> SEQUENCE: 24
attgctgcaa tgctgtctac catcctgtac tcacggcgct tcttcccctta ctatgtttac   60 aacatcattg gaggacttga tgaagaagga aagggagctg tgtacagctt tgacccagtg    120
ggctcttacc agagagactc tttcaaggcg ggaggctcag caagtgccat gctgcagcct    180
ctgctcgaca accaggttgg cttcaaaaat atgcagaatg tggagcacgt cccctgacg     240 ctggacagag ccatgaggct ggtgaaagat gtcttcattt ctgcagccga gagggatgtg    300
tatactggag atgctctcag gatctgcatc gtgaccaaag agggcatcag g             351

<210> SEQ ID NO 25
<211> LENGTH: 289
<212> TYPE: DNA
<213> ORGANISM: Homo sapiens

<400> SEQUENCE: 25
atggtgtgca caggagccaa gagtgaagaa cagtccagac tggcagcaag aaaatatgct    60
agagttgtac agaagttggg ttttccagct aagttcttgg acttcaagat tcagaacatg    120
gtggggagct gtgatgtgaa gtttcctata aggttagaag gccttgtgct cacccaccaa    180
caatttcgta gttatgagcc agagttattt cctggtttaa tctacagaat gatcaaaccc    240
agaattgttc tccttatttt tgtttctgga aaagttgtat taacaggtg                289

<210> SEQ ID NO 26
<211> LENGTH: 289
<212> TYPE: DNA
<213> ORGANISM: Murinae gen. sp.

<400> SEQUENCE: 26
atggtgtgca caggagccaa gagtgaagaa caatccagac tagcagcaag aaaatatgct    60

| | |
|---|---:|
| agagttgtgc agaagttggg cttcccagct aagttcttag acttcaagat ccagaacatg | 120 |
| gtggggagct gtgatgtgaa gttccccata aggctgaaag gccttgtgct gacccaccag | 180 |
| cagttccgta gctatgagcc agaattattt cctggattaa tctacagaat gatcaaaccc | 240 |
| agaattgttc tccttatttt tgtttctgga aaagttgtat taacaggtg | 289 |

<210> SEQ ID NO 27
<211> LENGTH: 1200
<212> TYPE: DNA
<213> ORGANISM: Homo sapiens

<400> SEQUENCE: 27

| | |
|---|---:|
| gaagtggaaa ttacaatgat tttggaaatt ataaccagca accttctaac tacggtccaa | 60 |
| tgaagagtgg aaactttggt ggtagcagga catgggggg accatatggt ggaggtaatt | 120 |
| tataaaaatt gaggttattc agattttttgt gattaaagga ttagcctttt gtgacttaaa | 180 |
| gggaagataa catactaagt agtttgtact gtgggcagtg ctccatgtac ggtcttagtg | 240 |
| aaaataaaga aattttgcat aaatctccac agaagtactc agcaagcagt tatgacatca | 300 |
| aattgggatt aggtagttgg aggtgggtgt cagtagttta atttctggtg ggactcataa | 360 |
| acagctaaat acagttgcaa cccacattgc aagtggtata cattggaatg agggtctttg | 420 |
| aagttaaatc cttaaaccat gattcaaacc attgcttagc ttattttga ggttttagc | 480 |
| taggagtaaa ctagctttgt cttgggcttg atgtactttt aaaaaaatcc cttactcagt | 540 |
| ccaaatgagg atgagagggt gaaggaccc tttatttaaa agaatagggt cagccacgaa | 600 |
| ataaaaatgt ctatgaaccc gagtaattta tctcctgagt aattctgcta actggctgca | 660 |
| aaggattagg atctgcttgt ttaaaagact ggatggatat aaaatagaat caactgtagt | 720 |
| gttaggctga tcatgggaaa tcaaagtaag tttgttttct cttgctgttc caacaattat | 780 |
| aggaaactat ggtccaggag gcagtggagg aagtgggggt tatggtggga ggagccgata | 840 |
| ctgagcttct tcctatttgc catgggtaag tagcttttga gttttacaat tattattatc | 900 |
| ttgggagaca tagctgcagg agtaaaagct ttttaggatc atggttatct ttccttaaaa | 960 |
| tctggttaga tggataattt cataacccat ttttttttta ccctttactt ctgttgaaac | 1020 |
| aggcttcact gtataaatag gagaggatga gagcccagag gtaacagaac agcttcaggt | 1080 |
| tatcgaaata acaatgttaa ggaaactctt atctcagtca tgcataaata tgcagtgata | 1140 |
| tggcagaaga caccagagca gatgcagaga gccatttgt gaatggattg gattatttaa | 1200 |

<210> SEQ ID NO 28
<211> LENGTH: 9098
<212> TYPE: DNA
<213> ORGANISM: Homo sapiens

<400> SEQUENCE: 28

| | |
|---|---:|
| aagcttagtt ctaggtcagc cccacaggac gtgggatgag ggatatatac aggcattcgt | 60 |
| taatgctgca ttgttcttat tctctatctc tatatctgac gtgtttcaca aaaaaaaaa | 120 |
| aaaaaaaaaa aagtgctcac ttcaccagca aacgtaacta agcaatatt taaaagatga | 180 |
| gtaaaagcta gtacaaggat ggtatccata aagttgtttt aaaatcttat ttctaatatt | 240 |
| tactactttc aagttgtaca agtgtcgtcc ttgaggagaa aaaaggtaa cacaagagca | 300 |
| ccataaacag aaagcagaaa gggggtatca aaagatgcaa gtggagagaa acagaactgg | 360 |
| gaagacgaaa acaaacttca ttgctttta agatgtgggc catccctagg agcaggaaag | 420 |
| acaacgtatc ttttcttctg tacctacttc ctacaataca aggagggtcc atccaaagga | 480 |

```
cctaaacctc gtaagtccca ttcctattac aattcaagtt taattaaccc aggaattcat      540
gaccatttat aagcatttcc aaaactggta aatacagacc actgccaatc tgcagtatgt      600
attcagtatt tatgcaggct ttttgttttt ttaagttttg gctttatttt catgttttag      660
gaaaaacata gctagcctat taaaactgag ctgtggacat aattgcttag gatatttcta      720
aaacgaatgt ttcaggtaaa aaaaaaagt gtggggaggc agatttaaaa aaaatatcat       780
ttaatggatt aatggtgctg tggtttgaat attcccttca aaactcatgt tgaaatttaa      840
ttgccattgt gatggtactg ggagttggga ccaggtgttt aggtcctagg gctcagcttt      900
catgaatgga cattatcaca gcagtgggtt cgcttgctct tctttctttc tctggccttc      960
caccatgtta agacacagca ggaaattttt catggtaaaa tgctggggtg aacacattta     1020
ggttaccgaa agcacttttg gtaccctgaa tacagcaaat attattaaga ctgcacatta     1080
aattattagg aaacattaac ttagaaaatg gttttctaat aaaaatgctc ccaacagcaa     1140
cttaaaaact catgaaacaa atcatttaga agtagaaact ctcacaacat taaatcatta     1200
caaaggcatt gtgaaatgtc tttagaaata tttacttaca atttgtaaca tttggggcta     1260
tcccgcgtat gaattgaaaa cccttcactc aatcgagtat cagaagcaac aattgcaaaa     1320
tcttctccag caattgccag tatagtactg aggaaaaaag aaaaaaatta attctccagg     1380
gtggtaatcc tatccctaca aatagaagaa tgctccatag tacataatgg gataaaatac     1440
tctagatgtc aacaaaaaca tgattcaaat gggaagagga aagatgagcg ggaagagaat     1500
gaacgcctgg ctacgagttg tctgggaaaa aaaaattatt aataagccaa atcagggcaa     1560
agtctccttg gcagagttaa cagaaaagcc aatgaattat catcaccaac acattaaata     1620
cttactcgcg caaggtacta ctaatacaga acaactaaat accccatctg tgcccttgag     1680
gatcaggtat agacagtggt actacaacgc aagctctatg agtttagaga gatgagatt      1740 tttttttctt gcttcatttc tttatatcca agtcctata taacgcctat ataatgctta      1800
tttctttata cccaatccct tatataatga caaatagatg gacaaacagt aaattttttcc    1860 ctctgtggct gtacaatttg acagcttatc aaagagactt acagtagaat tccaaaagca     1920
gactgcctgg gttctaattc tggctttccc gtttcgcaga tatgagactg tgggtaagtt     1980
acttctcaaa gcgtcaattt catcatatat acaacagaga tcactgcagt tgctacctca     2040
ttagggtgtt caaaggatca aatatgtaag cccttatagc agtccctgac atgtaactgg     2100
tcctctagta agtgttagct ataagtgcta tggcactgga gtatgactaa gcacctgggc     2160
tctggaatta catgagacag agacccactc ttgctactta ctaggtatgt gatcttggac     2220
aaatcctcca aatgcaagtt gatgataaca gtacctgtgt cacaaggtgt gtatatatat     2280
ttgggtgtgt atatttttaat gtacaaggct tgactgataa ctataaccac tgcttcaatg    2340
caatagtgga aattaaaggc atggtgcctc acagacgtaa gcactcagga aacttaagcc     2400 actatttta ctgaggaggg atttgtgcta agctctcaa gaagaaaagg atggcattcc       2460
aggtaatata aacagcaagc aatggcaaac aggtaattat tcaaatagta catacattca     2520
agcaactcat tcaggcagcc cttttttgcat aagcacatgt agtgacgtta aggtttatgt    2580
gatggacagg gttcctactg tagaaaatcc caaatgccaa gctaaagatt ttggaatttt     2640
agcaagaaat catgaaggta ttctgagcaa gaatgatctg tagttgtaac tactcaagag     2700
gctgaggtgg gaggactgct tgagcccagg tgttcaaggc tgcagtgagc tatgatcgtg     2760
cctgggcatt agagtgagac ctggtcttta aaaaggaat gcaagagaga gaaaagttcc      2820
atttacaaag tggggtttta ggaagactgc tctgacaaca acatagtatg tgaaatggga     2880
```

```
cagaaacact gttctaatac tactaatgca atagtaaggt agcagggtga acagtaaatc    2940
caaaatcatc acaaacacac aaaatagaca aattttttata tctacgcaaa tgttttagga   3000
actgggaaaa ccaattatga catccaagat ttagaactta gatgagcaga atgatggcat    3060
aattataagt attttaaagg agaggaggcc gggcacggtg gctcacacct gtaatcccaa    3120
cactttggga ggctgagggg ggggggggtc aattgcctga gatcaggagt tcgagaccag    3180
cctggccaac atggtgaaac ccatctctac taaaaataca aaaattagcc aggcgtggtg    3240
gcaggcacct gtaatcccag ctactcggga ggctgaggca gaaatgcgtg aacccaggag    3300
ttggaggttg cagtgagctg agatcgcacc gctgcactcc ggcctgggtg acagagtgag    3360
actctgtctc aaaaaataag aagaaaggag aagaggagat gaagggaat aattagcttg     3420 cttttttgttt tgctagctgt cttgagttgc cctgagagca gaaaaaccag ttaaaaatgt   3480
tttactgaag aagccgaatc gagggactca tgagaggcag aactggaaaa ccagatttgg    3540
gagtaatcct cccagcaatg agacatgaaa gagtgctgag cgataaacaa ggcggtaatg    3600
acttaactac atttaaagac aagtaggaaa agagaatgag gcctcatttt gcggaagcga    3660
aggctgcctg agagccagct gcagtaatca ctaaagaaaa agaacaatga ctgagaaaaa    3720
gtaatcagaa agatctaagt aattttttagg gcagtaatgg cttaaactgg attacaagga   3780
ttaaaaagtg agtaacgagt agggcatact gaacactgaa aattcttatt tatagagaat    3840
agccttacga aacgggtcca ataaccctcc ctacaatata caacttaatt agtcatcaca    3900
ggaagtgtta aggtgtataa tggaaaagca tccataaact cagtggtgaa atagctatga    3960
attaagtcct ggctcaactt cacaccagct ctctgacccct gacagtttaa cgtctaatat   4020
aaccctagga tgctaatatc atctaacatt cacttttcat gaggattaaa taagatgaca    4080
gcttgcaatt tacaaaatgc atctctcttg attctcacca aaaactatga agctactaag    4140
gaagataagg aaatttaggt tcaagaagtt cagaagtacc caaagtgtcc tttagtggca    4200
gaaccaaggc taaaatcaga ctttcgttat cttttctaaca cactcccaaa atgtgcattt    4260
atatttcaaa tttatgagga accaattaac attttttgctt tgttttttaaa atttatttt    4320 gtagagatgg ggtcttgcta tgctgcgcag gctggtcttc aactcctggc tcaagcgat     4380 gatcctcctg ccttggcttc ccaaagtcct gggattacag gtgcgagcca cactgcccag    4440
ccaatatttt ctgttttaag aaccatcggt tcgttcaaat tgcgtgtgta tattttaatg    4500
tacaaggctt gattggtaac tataaccact gtttcaattt acagctcttc cctgtcaaga    4560
gtcttaaaca gagcatcttt ctataaccct aaatctctgg cgtgccacca cggaaaatta    4620
tactactcaa gataaagctg gtaattaaaa taaaaaccaa aacttgaaca taacatacaa    4680
gaacacacat actaaaaggt ccatcttctg agtattttgt tttcctgaac ttaagctaaa    4740
cgttaaaaaa aaaagcactt atctatgaaa ctaagtttgc tcagccaatc ccaccttcta    4800
tttgaaataa acaaaatga ttaaaactgct acaattacaa ataacagaaa tcaggcggct     4860
acaattagac atctcggcta ccaacccagc tatgcatcta acaacacaga ccaaacaacc    4920 ctaacttttta gtttcagac gctaaccctc taccctcgcc ggctggcata agaaacgtgt    4980
acatgaggtc cagttttaat ggtcttccac agagcagagg ctatgtttca atttctactt    5040
tactgtctta cagcagcaag gagcacggag tggcggtcca cataaaaact caaatgacat    5100
gactgtaatg ggaaacccta aaaccaagg ctgtatcgca atcaccaagt aaacttgagc      5160
aaagcgagcc tgaagaggga acacagcgcg atgagaggac ggcagggaga ccggccttgt    5220
gcggaccccc tcagctcagg gttctgaggc ctgcaggagc ccggggcagc gccatcacgg    5280
```

-continued

```
cggtgactcc taaataggct tcagcagatg ggggaagggc gaaagtgaaa gccgcagctc    5340
tctgggtttt ttaccctccg ttgaaaacgt agggcgaaaa tcgcagcttg caaagggccc    5400
gcggctctgt gcggttccat ccccaagtct ctgccagcag cccgaataca tggcttgtag    5460
aggacaacat cgcacggctt gcgcctgcgg atccgacact tgctgtctca cggcgagatg    5520
gctgccttga ccggacgtta cgccacttcc ggcttctcct gaagttcgct tcccggcctc    5580
tctatctcac gctagtcgtt gctcctggag gcttgcacgg cggcttgtcc tttggtaagt    5640
gaatcccgcc cattccaaaa agcgctgaca gggatgtaaa gggttttttt tgtttgtttt    5700
ttgttttttt ccccctcgaa gaaaacattg gaattcaccc caatggacaa aaatttaagt    5760
ctgaccatac aaaaaaattg tcagaactat ggcgcaacgg caactcgaat aacggtggga    5820
acgttaattg tcctggctaa taaaaaatgt atataacatt tcctatcctt aaagagctca    5880
caacctcact gataataaaa agtacaaaga aaacaagcag tataacatat gattacgcca    5940
caatgaacta cagaagggaa aatcaaggcg tgctgaagtc ccactaagaa acaactgcgg    6000
aaagagccat gtgacaacag tgcatgaact gggagtggca gaactgaata taaatgcatg    6060
tgtaaacaca agctgtttgt tttgcttagt gttccttgtc attctacacg cttgaagatc    6120
agctagcgtt cttgctgaca ggtaaggagg acgcgcttac tgagtgccaa gcactgctca    6180
ggcactgatt ctgtcaatct ctgtcaatcc cccgacagcc caagggtaag cactgttatc    6240
attattcaat tttacagaaa aaaatgcgg gggagaggtc aggtaacttg tcgaaggtaa    6300
cgccgctagt tgctttaaac aacaacaaca acaacaacaa aacacactca cacatataca    6360
cacacacgcc atttaaaaat cgatctttcc tacgtccagc aagggccaat tagagatggc    6420
tgtggcacgg cggccccgcc ccggaactcc tcaagagctt ccgcccctcc ttacctatgg    6480
aaacacagga agtgacctat gctcacactt ctcacggcct cggccctagt gggagcaact    6540
cgctgaagcc gagggcagaa ctggcggaag tgacattatc aacgcgcgcc aggggttcag    6600
tgaggtcggg caggttcgct gtggcgggcg cctgggccgc cggctgttta acttcgcttc    6660
cgctggccca tagtgatctt tgcagtgacc caggtaacag attgtactct tttctgacgg    6720
ttcgggcgaa ggccaccact gcactgaggc ctggggcaa tggtgggaa gagactagga    6780
attggcgcgc gtgcaggccc ctcggggac gttcctccct tttcgtgctg ccgccgttcc    6840
ggcctgtaac ggccactcgg ccgccactcc cgcctggtgc cctactctgc tgtgtttcgc    6900
aggcagcttc ccatcgtacg attgtgggc tcagggtact actggctggc tgggcggcgg    6960
caggcgggac aggacagtcc cttgcatcga agaccctaag tttaccctgc cctgtcctgc    7020
catccgcttc ttctccatgt tagaagcaga ttcacccaga tctgtgcccg cctgttttgc    7080
tgccaacatt gagacttaaa tattttgtca gaagcctgag acagcgggca cggtagcgct    7140
taagatataa tacacaccac tttatttgca gggtctcccg tctctcggtt caggccatca    7200
tggttttcca aatctctagg gtagactttt ctgtgaaaag actgtgcttc atttagttat    7260
acagacacta gaaggctatg cagaattaat ttgattgcct ccaaaaaata tcggatttga    7320
tgtttcaatt tccaggagat gaagataccc agcaaacaac tcttttctga ggataaatta    7380
gtgcagtaat cactgtgcgt ttcttctgta gacttacttg caaaaagtgg cctgaagcca    7440
ccgaagtccc tggataaatc tctaatcata cttataatgg ctttaaatcc tgccgtcatt    7500
atctcttgcc tcaaccttag attcctgaaa cgaaacttcc gtcctccagt tttactcctc    7560
tcaaattcat ctagtcttgc caaattagat ctgttcatac tgcacttcca aaattccata    7620
actgttatta ttgcctatgc aataacattg aaaactcctg atagtatgag cccaccaata    7680
```

```
tgtgctgtct catctgctgc agtgaccttc tatacagtca tactaagctt gtcgcctgca    7740
tactgcatgc tttttcaatc tgtctctttc tgcttgattt ctcttttgtc tgaagccctg    7800
atgtgtaaat tcctactcac cttgtgagac ccaagttaga tggtccctgc tttgtgaaaa    7860
cactgcgcca cagtgattgg ctgttagtct atattgtctt ctcttccagg ggtgtatatg    7920
ggctcattca tgatcacata ctgtattcca ggcatagtgc tagatgcaga gatcacaaag    7980
acatgtaggc tggtttctgc attcaaggaa cttagcttag accatacctg ctgttataat    8040
actatgtttt acagtagtta tttgcatacc cttcatattg aacactttga tgccaaggac    8100
tatatcctcc tatctttata tcctcatctg caggacttct gttattgtta ttataggata    8160
actgtcaaaa aaaagtata ttttaaaaaa tatctctgat atatttattt ccagaagcag    8220
agcttgcttt cttttttggt ctgttttca gtgatgagta tgtaggatag atagtctttg    8280
ggggcatttg cccttttcaaa gtgatcgtca gagtctttca tacattcagc aaatatctga    8340
gtgtctgttc tgtaccagca catgcttgaa gtgcatatgc ctgaaggatc tttggacata    8400
taatttgtaa ctttgagacc tctaagttct atgtgagaat atgttgttat aaatcatttc    8460
agatgtgtag tgagtaaagc gatgtgattt agaaaagtca gataacaggc acagtttgca    8520
ttaatgtgtt ctaaagaggt aaggttatta catttataaa aattcagggc tttatctttg    8580
tgcggctttt tttttttaca gtttcattac agtaggagct tgataaatga tcactctgaa    8640
gtatattgga ttgaatttga tatttactta attttttgcc caagacattg tagaggatgt    8700
aaaattggaa tatttaaaga tctaaacttt gcctaacagt gctgtgtata cagtgcttag    8760
tgaatattct gctctgatat tacattttgc ttaggaatta ttttctcta ggtgtttttc    8820 ctcaaaagtt tttaatgctg gttatgacag ctcgattttg agcattttcc gattatttaa    8880
acatgtaaca aaatgatttt tgttttgttg gcgatttac atgcaatcgc cggaaacatg    8940
gaaggaataa aacttagga ttataaggta aaaacaaatg tattccaaaa tagcttcatt    9000
ggttttcatg tttgtgtttt gtatagccat agaactggct tataggactg tacaggttac    9060
ctggatcctt aaattaaact ttagactttt ttccaaag                           9098
```

<210> SEQ ID NO 29
<211> LENGTH: 15071
<212> TYPE: DNA
<213> ORGANISM: Homo sapiens

<400> SEQUENCE: 29

```
aagcttcaat gtttttagca ccctctgtgt ggaggaaaat aatgcagatt attctaatta     60
gtgtaatatc taaccacatt aaaatatatt acatagtaaa ctacactcca taattttata    120
aatttgactc cccagggtaa taaactagtc tctagtctgc tcaccttcaa ctgtacaata    180
aagtcttggt tcttttgaaa tagacctcaa atgagacacc taaaattcaa agtgtcttta    240
catttaaaga cacctacagg aaagcaggta aaagagccag gttaaaaaca aattctaaaa    300
ccacttagct gcagttaaac atatagtaaa gatgcactaa agtttcttac tctgtaaatc    360
ccttccactt caggaaatat tccactttcc cattcactac acgtcgatct agtacttttt    420
ccacgacaaa ttcttcaggc tctgcctctt caactttttt actctttcca ttctgttttt    480
ttcccatttt ttgctaaaat aaaacaaaag agaaattaag aaatattcct cttgaatttt    540
gagcacattt tcaaggctca attgcttata ttattatcac attcgacata aattttact     600 tctatatccc aggcagaca ccttctggaa agattaaaag tcaacagaca ataaaataaa    660
agaatgcttt atcttgttca tttagttcaa acttacaacc caccaccaaa ataatacaat    720
```

```
aaaaaaacac tatctggaaa cagttatttt tttccagtct ttttttttga gacagggtct    780
cacactcttg tcgcccaggc tggagtgcag tggcgtgatc tcagctcact gcaacctccg    840
cctccccagg ttcaagcagt tctcatgcct cagcctccag agtagctggg attataggcg    900
gatgccacca tgccgggcta attttttttg tgttttatt agaaacaggg tttcaccatg     960
ttgaccaggc tggtctcaaa ctcctgacct gaagtgattc accagcctgg cctcccaaa    1020 gtgctggcat tacaggcgtg agccactgcg cccggccctg tagtcttaaa agaccaagtt   1080
tactaatttt cactcatttt aacaacactg caacaaacaa ctatgcagga agtacctaaa   1140
gggtgatcca gagaagcaag tagtagtgac aggtcttagg tgaacctatg acagaccttg   1200
tatccacccc cagatggtaa aagccccagc ccccttctca attcaaatat taatgtcaaa   1260
agcatcaatg atacagagaa aagataaatg cagaatgaaa acatggttca aaatcctgat   1320
accaactgca gggtcaacta tagagaccac taggaggttc aattaaagga caagattatt   1380
tttccataat ctctgtagat aatatttcct accacttaga acaaaactat aaagctatca   1440
cttcaagaga ccaacattac aaatttattt taattcccta aggtgaaaaa aatccttcct   1500
tcctggtttc tcaagagaaa gtctatactg gtaaccaaat tcactttaaa caggcatttt   1560
ctttggtatg acactattta agagaagcag gaaaccaacg tgaaccagct ctttccaatg   1620
gctcaagatt tcctatgaga ggactaaaaa tggggaaaat ttttatgaga ggattaaaaa   1680
tgggggaaaa aaaaccctga aatggttaat cagaagatcc tatgggctga aaggaatcc    1740 atcttaacat ttcatcttaa agcaaatgct attgccgggg gcagtggctc atgcctgtaa   1800
tcccagcact ttgggaggcc gaggtgggca gatcatctga ggtcaggagt ttgagaccag   1860
cctgaccaac atgagaaac cccgtttcta ctaaaaatac aaaattagcc aggcatagtg     1920
gtgcatgcct gtaatcccag ctacttggga ggctgaggca ggagaactgc ttgaacccag   1980
gaggcttaag ttgcggtgag ccaagatcac gccattgcac tctagcctgg acaacaagag   2040
aaaaactctg tctcaaaaaa acacaaaaac aaaaaaccca aatactattt aaaaaagata   2100
aaccttaatt gctcaatcat taaagccatc ccacaagtaa agcagcaagc agaaaaaagt   2160
taagaacacc tcaaggctac agaaggacat ttcaagctat gcaggcatat gaagtgtgca   2220
gacagatatg taagaaaggc ctcaagactg caaaagggca tttcaagcta tgcaagcata   2280
taggtaacac atacacacac acaaaataaa atcccctgaa atacaaaaac atgcagcaaa   2340
cacctgacgt ttttggatac catttctaag tcaggtgtta tgattctcat tagtcaagat   2400
acttgagtac tgggcccaaa cagctttctg ccactgtaca gtacaagaag gtaggaataa   2460
tggtgggagg agcaaagaca aactgtaata gacagaagtg tatcagatac ctatactaca   2520
tgaaaaacaa aacagctact gccacaaagg gagaaggcta acaaaataaa gtcaacaata   2580
aatacagaaa atgaaaagga tacacactaa ggtttacaaa aaaaaaaagg cagacaaaat   2640
gccatacagt attcattcac tactatggca ttcataagct agtttcaaat gctcactatt   2700
ttcttttata gtatatattt gccttaaccc agcactttt tccaaaagtg atgagtcaa    2760 aataaatttc ccattattta agtgaaatta acagcacaca tatctcacaa cactaatgaa   2820
tttttaaaat ggaaagttaa gaactttaa agtggccaac ctgtgatcct tcacaaaata    2880
aactaaatac aataacagac cccaaaggct atcaattgcg tgcaaaaaca acttctgttt   2940
tccagggtaa acagaatcta atgcagaatc taatgcaggg taaacagact taatgcagaa   3000
tctaatgatg gcacaaatta aaaatcacta acgtgccctt tttagtgtga acccagaga    3060 gagcacatac aagccaaaaa caaatgcttt attttaccta ggagacatta acattcacct   3120
```

```
ttacgtgttt aagattaatg caatgttaaa tattgtgaaa actgtaactt tgaatttcat    3180
gatttttatg tgaatattcc agggtttaaa aaaacttgta acatgacatg gctgaataag    3240
ataaaaaaaa aatctagcct tttctcccct ctggctcata tttgcgattt cgatcatttt    3300
gtttaaaaaa caaacactg caatgaatta aacttaatat tcttctatgt tttagagtaa    3360
gttaaaacaa gataaagtga ccaaagtaat ttgaaagatt caatgacttt tgctccaacc    3420
taggtgcaca aggtaccttg ttctttaaat tgggctttaa tgaaaatact tctccagaat    3480
tctggggatt taagaaaaat tatgccaacc aacaagggct ttaccatttt atgtaacatt    3540
tttcaacgct gcaaaaatgt gtgtatttct atttgaagat aaaaatcctc agcaaaatcc    3600
acattgcact gtccttcaaa gattagcctt ctttgaacta gttaagacac tattaagcca    3660
agccagtatc tccctgtaat gaattcgttt ttctcttaat tttcccctgt aatttacact    3720
gggagagctg ggaaatatgt ggatgtaaat ttctcagcca cagagatgca aagttatact    3780
gtggggaaaa aaaacttgag ttaaatcctt acatatttta ggttttcatt aacttaccaa    3840
tgtagttttg ttggaggcca ttttttttat tgcagacttg aagagctatt actagaaaaa    3900
tgcatgacag ttaaggtaag tttgcatgac acaaaaaagg taactaaata caaattctgt    3960
ttggattcca accccaagt agagagcgca cactttcaaa cgtgaataca aatccagagt    4020
agatctgcgc tcctacctac attgcttatg atgtacttaa gtacgtgtcc taaccatgtg    4080
agtctagaaa gactttactg gggatcctgg tacctaaaac agcttacat ggcttaaaat    4140 aggggaccaa tgtcttttcc aatctaagtc ccatttataa taaagtccat gttccatttt    4200
taaaggacaa tcctttcggt ttaaaaccag gcacgattac ccaacaact cacaacggta    4260 aagcactgtg aatcttctct gttctgcaat cccaacttgg tttctgctca gaaaccctcc    4320
ctctttccaa tcggtaatta aataacaaaa ggaaaaaact taagatgctt caaccccgtt    4380
tcgtgacact ttgaaaaaag aatcacctct tgcaaacacc cgctcccgac ccccgccgct    4440
gaagcccggc gtccagaggc ctaagcgcgg gtgcccgccc ccacccggga gcgcgggcct    4500
cgtggtcagc gcatccgcgg ggagaaacaa aggccgcggc acggggctc aagggcactg    4560 cgccacaccg cacgcgccta ccccgcgcg gccacgttaa ctggcggtcg ccgcagcctc    4620
gggacagccg ccgcgcgcc gccaggctcg cggacgcggg accacgcgcc gccctccggg    4680
aggcccaagt ctcgacccag ccccgcgtgg cgctggggga gggggcgcct ccgccggaac    4740
gcgggtgggg gaggggaggg ggaaatgcgc tttgtctcga aatggggcaa ccgtcgccac    4800
agctccctac cccctcgagg gcagagcagt ccccccacta actaccgggc tggccgcgcg    4860
ccaggccagc cgcgaggcca ccgcccgacc ctccactcct tcccgcagct cccggcgcgg    4920
ggtccggcga aagggagg ggaggggagc ggagaaccgg gccccggga cgcgtgtggc    4980 atctgaagca ccaccagcga gcgagagcta gagagaagga aagccaccga cttcaccgcc    5040
tccgagctgc tccgggtcgc gggtctgcag cgtctccggc cctccgcgcc tacagctcaa    5100
gccacatccg aagggggagg gagccgggag ctgcgcgcgg ggccgccggg ggagggggtg    5160
gcaccgccca cgccgggcgg ccacgaaggg cgggcagcg ggcgcgcgcg cggcgggggg    5220
aggggccggc gccgcgcccg ctgggaattg gggccctagg gggagggcgg aggcgccgac    5280
gaccgcggca cttaccgttc gcggcgtggc gcccggtggt ccccaagggg agggaagggg    5340
gaggcggggc gaggacagtg accggagtct cctcagcggt ggcttttctg cttggcagcc    5400
tcagcggctg gcgccaaaac cggactccgc ccacttcctc gcccgccggt gcgagggtgt    5460
ggaatcctcc agacgctggg ggaggggag ttgggagctt aaaaactagt accccttggg    5520
```

```
gaccactttc agcagcgaac tctcctgtac accaggggtc agttccacag acgcgggcca    5580 gggggtgggtc attgcggcgt gaacaataat ttgactagaa gttgattcgg gtgtttccgg    5640
aaggggccga gtcaatccgc cgagttgggg cacggaaaac aaaaagggaa ggctactaag    5700
atttttctgg cggggggttat cattggcgta actgcaggga ccacctcccg ggttgagggg    5760
gctggatctc caggctgcgg attaagcccc tcccgtcggc gttaatttca aactgcgcga    5820
cgtttctcac ctgccttcgc caaggcaggg gccgggaccc tattccaaga ggtagtaact    5880
agcaggactc tagccttccg caattcattg agcgcattta cggaagtaac gtcgggtact    5940
gtctctggcc gcaagggtgg gaggagtacg catttggcgt aaggtggggc gtagagcctt    6000
cccgccattg gcggcggata gggcgtttac gcgacggcct gacgtagcgg aagacgcgtt    6060 agtgggggggg aaggttctag aaaagcggcg gcagcggctc tagcggcagt agcagcagcg    6120
ccgggtcccg tgcggaggtg ctcctcgcag agttgtttct cgagcagcgg cagttctcac    6180
tacagcgcca ggacgagtcc ggttcgtgtt cgtccgcgga gatctctctc atctcgctcg    6240
gctgcgggaa atcgggctga agcgactgag tccgcgatgg aggtaacggg tttgaaatca    6300
atgagttatt gaaagggca tggcgaggcc gttggcgcct cagtggaagt cggccagccg    6360
cctccgtggg agagaggcag gaaatcggac caattcagta gcagtggggc ttaaggttta    6420 tgaacgggc cttgagcgga ggcctgagcg tacaaacagc ttccccaccc tcagcctccc    6480
ggcgccattt cccttcactg ggggtggggg atggggagct ttcacatggc ggacgctgcc    6540 ccgctgggggt gaaagtgggg gcgcggaggcg ggaattctta ttccctttct aaagcacgct    6600
gcttcggggg ccacggcgtc tcctcggcga gcgtttcggc gggcagcagg tcctcgtgag    6660
cgaggctgcg gagcttcccc tccccctctc tcccgggaac cgatttggcg gccgccattt    6720
tcatggctcg ccttcctctc agcgttttcc ttataactct tttattttct tagtgtgctt    6780
tctctatcaa gaagtagaag tggttaacta ttttttttt cttctcgggc tgttttcata    6840
tcgtttcgag gtggatttgg agtgttttgt gagcttggat ctttagagtc ctgcgcacct    6900
cattaaaggc gctcagcctt ccctcgatg aaatggcgcc attgcgttcg gaagccacac    6960
cgaagagcgg ggaggggggg tgctccgggt ttgcgggccc ggtttcagag aagatatcac    7020
cacccagggc gtcgggccgg gttcaatgcg agccgtagga caaagaaacc attttatgtt    7080
tttcctgtct ttttttttcct ttgagtaacg gttttatctg ggtctgcagt cagtaaaacg    7140
acagatgaac cgcggcaaaa taaacataaa ttggaagcca tcggccacga ggggcaggga    7200
cgaaggtggt tttctgggcg ggggagggat attcgcgtca gaatccttta ctgttcttaa    7260
ggattccgtt taagttgtag agctgactca ttttaagtaa tgttgttact gagaagttta    7320
acccttacgg gacagatcca tggaccttta tagatgatta cgaggaaagt gaaataacga    7380
ttttgtcctt agttatactt cgattaaaac atggcttcag aggctccttc ctgtaatgcg    7440 tatgattga tgtgcaaaac tgttttgggc ctggccgct ctgtatttga actttgttac    7500
ttttctcatt ttgtttgcaa tcttggttga acattacatt gataagcata aggtctcaag    7560 cgaaggggt ctacctggtt attttttctttt gaccctaagc acgtttataa aataacattg    7620
tttaaaatcg atagtggaca tcgggtaagt ttggataaat tgtgaggtaa gtaatgagtt    7680 tttgctttttt gttagtgatt tgtaaaactt gttataaatg tacattatcc gtaatttcag    7740
tttagagata acctatgtgc tgacgacaat taagaataaa aactagctga aaaaatgaaa    7800
ataactatcg tgacaagtaa ccatttcaaa agactgcttt gtgtctcata ggagctagtt    7860
tgatcatttc agttaatttt ttctttaatt tttacgagtc atgaaaacta caggaaaaaa    7920
```

```
aatctgaact gggttttacc actactttt aggagttggg agcatgcgaa tggagggaga    7980
gctccgtaga actgggatga gagcagcaat taatgctgct tgctaggaac aaaaaataat    8040
tgattgaaaa ttacgtgtga ctttttagtt tgcattatgc gtttgtagca gttggtcctg    8100
gatatcactt tctctcgttt gaggtttttt aacctagtta acttttaaga caggtttcct    8160
taacattcat aagtgcccag aatacagctg tgtagtacag catataaaga tttcagctct    8220
gaggttttc ctattgactt ggaaaattgt tttgtgcctg tcgcttgcca catggccaat     8280
caagtaagct tcagctttca gtaattgtta tcttagagat tatgccacgt gaatgtattt    8340
tattgtacat atggttaagc tgagtaattc atattctgta ttgtcatata tcaaatatag    8400
acatgtccac caaaaattaa actttttaag cttcgagtgc tgctggtcat aaaaattaat    8460
ttgtcctggt tataagagta atttttaagg ttatttctaa tgcatatctt taaatatttt    8520
cgtaactgag agtcatatgg agaaacttag tgtttgttgt aaaaagttgt gttttttgg     8580
ctgagatact tagaatcacc accagagggg gcagttaagg gaaataaat gatacttttc     8640
agatattgaa tagtgaaata aaaactttgg gtcataagta atgaaccaag agttattttc    8700
tgatgtttaa aaatagaaat ttgcgttttt aggttgtagg gttgaaattt ttggtaaaga    8760
ttctttaata atcctttgat aatcacggtc tacatttgtt tattttcct tagaaagttt     8820
ttttttaat taataattta agataattta atgttgagta aatttatatc aagcattaat     8880
gactttgaaa cttgtgtaga tcagctgagg caatttttg gtgtaacaca actaatatgc     8940
agtttaacat atggtttaaa tttgatgtaa gttttttttt ccccccagaa aactttagaa    9000
actgttcctt tggagaggaa aaaggtactc tgccagcagg tcacctcata tttaagaatt    9060
taatttcctg catacaaaga ggaaaatgta aataaaaatt gaaatggtat tttcctttgc    9120
agagagaaaa ggaacagttc cgtaagctct ttattggtgg cttaagcttt gaaaccacag    9180
aagaaagttt gaggaactac tacgaacaat ggggaaagct tacagactgt gtggtatgta    9240
aattactgaa ttgttactgg atattagtct tttagctgta tgttaagtga atcatggagg    9300
aataactatc agcatagtaa aaaattctat tatgacttca cttataagct ataatgagat    9360
taaatgctaa agtttacccct ttggttttgaa aggtaatgag ggatcctgca agcaaaagat   9420
caagaggatt tggttttgta acttttttcat ccatggctga ggttgatgct gccatggctg    9480
caagacctca ttcaattgat gggagagtag ttgagccaaa acgtgctgta gcaagagagg    9540
taagcaaaca atgactgtct tgtgcattaa catgaagaac gctgccctgc tgaaaatcag    9600
aaactatttc tgaatttagt tttaactcaa gattttttct cttattaaag gtgtgttggg    9660
tttctggacc attttcttaa gctagcttat tttcaaaag ctaggtccct aaaagctatt     9720
ttatatctgg tagttttaag gtggatacaa gcgaagtatg gtactacggt tgggtgcttt    9780
gaattatgct tgtgttttt tctgtttgga tgacttttac cccaccacta ttttaggaat    9840
ctggaaaacc aggggctcat gtaactgtga agaagctgtt tgttggcgga attaaagaag    9900
atactgagga acatcacctt agagattact ttgaggaata tggaaaaatt gataccattg    9960
agataattac tgataggcag tctggaaaga aaagaggctt tggctttgtt acttttgatg   10020
accatgatcc tgtggataaa atcgtatgta agtgtctaac cacaaatgta ctgttttttt    10080
ccagtgtatc aattttgtgt atgttaacat ctgtaacttt attgaaaggt aaacttttga   10140
agctgcttaa tattgttgat ttaatttaaa aggagtctga attttcatt ccagtgcaga    10200
aataccatac catcaatggt cataatgcag aagtaagaaa ggctttgtct agacaagaaa   10260
tgcaggaagt tcagagttct aggagtggaa gaggaggtaa tttaattctg ttctctttat   10320
```

```
ttttgttcat atataagggc ttgcttctaa ctggggcatt tattgtaggc aactttggct    10380
ttggggattc acgtggtggc ggtggaaatt tcggaccagg accaggaagt aactttagag    10440
gaggatctgg tgagtttcaa gttctacgtg tttaaaggat gagtgtgctt ttattttaaa    10500
tatgattagg ttttcattag tagaatcaag aaatccaacc taagtcaatt ttcctaagac    10560
ttcaaataga ttgtatcctg gcaagctctt gtgatttggc cagacaagaa gttaatagag    10620
ttgtattaat aacagttgta tttatctgga ttaataatgt aacatgaagt gtcatccgaa    10680
aagctttgac ccccatcaag tgtcattctt acgtataaat aggatggaat ctctaagatt    10740
gagacttgtt aagagagccc aaaattagct ggagattaat tatatgcttc atgttttgtg    10800
ggtaaactgg tagcactggt gtgtcctttt ctgcggttct taattattgt gctgaggtag    10860
taagagaact gaaaatgaat attagcaata atgctgaaca gtttatagta aacgtaatct    10920
ttttttggcc cctaacagat ggatatggca gtggacgtgg atttggggat ggctataatg    10980
ggtatggagg aggacctgga ggtcagtttt cctctacgtt ttggtttgtt tatgtgacta    11040
atacttaact atatcgtata tttacttcat ttatattttg agttttttaaa catttatat    11100 tagtgtctat aaatggcttg ggtgatagtg gtccagttat ttctaagtag ttttgccatc    11160
ttagctgtta tagcctaagg aatagagtgc cattttaaat gaaaatgtaa agataaccat    11220
cagagtatct catcttttct caagcaaaat gattggatct agatatatct ttgtacgtgc    11280
cttctctgga aaagtacaga atactggatt taacagagta aaacctaagg gggtggtata    11340
tgtaggaaaa aatatgaaat atgtctaaac ccgtaactag atgggaagca tcccaggata    11400
actttcaaaa agcgtaacct acggaaatgt tccaaaatgt ttagtgtgct cctggctgca    11460
gataaggttg tgaactacca ttaaacatga agtgtgatat atcattggcg tacagaaaag    11520
gctgatacac actgacagat tttgtaacaa gggacattta aaactgagct ggtaatagac    11580
ttgatttctg gtgttgccac tcaataggca tgactaaata gtgtatctca ctgttctact    11640
ttttataatt aaaattttag aggaagctga gttcttgtat ttaactacaa gttagagact    11700
cagcccacaa gctttttttt ttttttttaat atggtttctt ttttttttttt tttttttgaga    11760 cggagccttg ctctgtcacc caggctggag tgtagtggcg cgtctctgct cactgcaatc    11820
tctgccttcc cggtccaagt gattctcctg cctcagcctc ctgagtagct gggattaccg    11880
gcgtgcacca ccacgccagc taattttagt attttttagta gagacgggtt tcccatgttg    11940
gtcaggctgg tcttgaactc ctgacctcgt gaactgccca ccttggcctc ccaaaaacgc    12000 tgggggttaca ggcgtgagca accatgccca gccttttttt ttttttttatt tttgttttgc    12060 agtatgtgaa tgtgtaaatt tttgtttatg tccgcacttc tatttacagt aaagaacata    12120
ctgtgtggag tgttgggtct gttttttttc tttgaaatgg ggtctggctt tgttgctcag    12180
actggagtgc agtggtgtga tcttggctta ctgcaatctt agtctcaagc catcctccca    12240
cctcagcctc ctgggtagct ggaactacgg ggtgtgccac catgaccggc taattttgtg    12300 ttttttttgta gaggtgtggg ggttttgctg tgttgccctg gctggtcttg aattcctggg    12360
ctcaagcaat ccaccgcct caacttcccg tactgctggg attacaggtg tgagctgctg    12420
cgcccagcca agaacattgt ttcgtttttt gagagggagt ctctctctgt cgcccaggct    12480
ggagtgcagt ggtgtgatct cagctcactg caacctctgc ctcccgggtt cacgccattc    12540
tcctgcctca gcctccagag tagctagtac tacaggttgc tgccaccatg tccggctaat    12600
gttttgtatt tttagtagag atgggggttc accgtgttag ccagggtggt ctcaatctct    12660
tgacctcgtg atccgtccgc ctcggccttc ccaaagtgct gggattacag gcatgagcca    12720
```

```
ctgtgcccaa ccgagaacat tgttttaaga tatgtaattc gtagagagac ataatagaaa   12780
ctttatcttt tgggccagta ggaggaagtg ctcttttact ttccctctag cccacactac   12840
tagtctagcc tcacagtcct tacccacaat atacatgaag tatttcaaga tacttaagat   12900
ttttagtttt gagggaaagc tgtggaatta caggtattta actgtgtgca catggtgtta   12960
tccatttggc tgagtaaccc cagccaccaa atgtttacca aggatagtta ttcagtcctt   13020
gaagctattt tagaggaatt tcattaaata tttcacatgg aaacttggaa agctggaaat   13080
ggatgtgagg agacagttca aaatggtatt gaaaatatta agtgattact taaaggctta   13140
ttttataata ggtggcaatt ttggaggtag ccccggttat ggaggaggaa gaggaggata   13200
tggtggtgga ggacctggat atggcaacca gggtgggggc tacggaggtg gttatgacaa   13260
ctatggagga ggtaataaat tcacctgcaa cctttatgtg ggaatttgga attaatgtct   13320
ttgtaacact tgatcttttg tttccatgtt tgtcactaga tgcccataaa atttgtggat   13380
aagtgtttgc ttttatttgt ttttatggga gctttgtcct aagtccttgg tttaatgttt   13440
gtattgttct gagtattcca atttttaat  aggaaattat ggaagtggaa attacaatga   13500
ttttggaaat tataaccagc aaccttctaa ctacggtcca atgaagagtg gaaactttgg   13560
tggtagcagg aacatggggg gaccatatgg tggaggtaat ttataaaaat tgaggttatt   13620
cagatttttg tgattaaagg attagccttt tgtgacttaa agggaagata acatactaag   13680
tagtttgtac tgtgggcagt gctccatgta cggtcttagt gaaaataaag aaattttgca   13740
taaatctcca cagaagtact cagcaagcag ttatgacatc aaattgggat taggtagttg   13800
gaggtgggtg tcagtagttt aatttctggt gggactcata aacagctaaa tacagttgca   13860
acccacattg caagtggtat acattggaat gagggtcttt gaagttaaat ccttaaacca   13920
tgattcaaac cattgcttag cttattttg  aggttttag  ctaggagtaa actagctttg   13980
tcttgggctt gatgtacttt taaaaaaatc ccttactcag tccaaatgag gatgagaggg   14040
tgaaaggacc cttatttaa  aagaatagg  tcagccacga aataaaaatg tctatgaacc   14100
cgagtaattt atctcctgag taattctgct aactggctgc aaaggattag gatctgcttg   14160
tttaaaagac tggatggata taaaatagaa tcaactgtag tgttaggctg atcatgggaa   14220
atcaaagtaa gtttgttttc tcttgctgtt ccaacaatta taggaaacta tggtccagga   14280
ggcagtggag gaagtggggg ttatggtggg aggagccgat actgagcttc ttcctatttg   14340
ccatgggtaa gtagcttttg agttttacaa ttattattat cttgggagac atagctgcag   14400
gagtaaaagc ttttaggat catggttatc tttccttaaa atctggttag atggataatt   14460
tcataaccca ttttttttt  accctttact tctgttgaaa caggcttcac tgtataaata   14520
ggagaggatg agagcccaga ggtaacagaa cagcttcagg ttatcgaaat aacaatgtta   14580
aggaaactct tatctcagtc atgcataaat atgcagtgat atggcagaag acaccagagc   14640
agatgcagag agccattttg tgaatggatt ggattattta ataacattac ttactgtgg   14700
aggaaggatt gtaaaaaaaa atgcctttga gacagtttct tagcttttta attgttgttt   14760
ctttctagtg gtctttgtaa gagtgtagaa gcattccttc tttgataatg ttaaatttgt   14820
aagtttcagg tgacatgtga aaccttttt  aagattttc  tcaaagtttt gaaaagctat   14880
tagccaggat catggtgtaa taagacataa cgttttcct  ttaaaaaaat ttaagtgcgt   14940
gtgtagagtt aagaagctgt tgtacattta tgatttaata aaataattct aaaggaaatt   15000
gtgtaattat agctttttta ttttttaaata agttaaggag tgggtagtat aattaaggtc   15060
gttcaaagct g                                                      15071
```

POLYNUCLEOTIDE

CROSS REFERENCE TO RELATED APPLICATIONS

The present application is a Divisional of application Ser. No. 11/087,052, Filed: Mar. 22, 2005, which is a Continuation of application Ser. No. 10/225,418, Filed: Aug. 21, 2002, which is a Divisional of application Ser. No. 09/358,082, Filed: Jul. 21, 1999, now U.S. Pat. No. 6,689,606, Issued: Feb. 10, 2004, which claims priority under 35 U.S.C. §119(e) to Provisional Application Ser. Nos. 60/107,688, Filed: Nov. 9, 1998; 60/127,410, Filed: Apr. 1, 1999, and 60/134,016, filed May 12, 1999 and under 35 U.S.C. §119(a) to United Kingdom Patent Application Nos. 9815879.3, Filed: Jul. 21, 1998, 9906712.6, Filed: Mar. 23, 1999, and 9909494.8, Filed: Apr. 23, 1999. All applications are hereby incorporated by reference in their entireties.

DETAILED DESCRIPTION

The present invention relates to a polynucleotide comprising a ubiquitous chromatin opening element (UCOE) which is not derived from an LCR. The present invention also relates to a vector comprising the polynucleotide sequence, a host cell comprising the vector, use of the polynucleotide, vector or host cell in therapy and in an assay, and a method of identifying UCOEs.

The current model of chromatin structure in higher eukaryotes postulates that genes are organised in "domains" (Dillon and Grosveld, 1994). Chromatin domains can consist of groups of genes that are expressed in a strictly tissue-specific manner such as the human β-globin family (Grosveld et al., 1993), genes that are expressed ubiquitously such as the human TBP/C5 locus (Trachtulec, Z. et al., 1997), or a mixture of tissue-specific and ubiquitously expressed genes such as murine γ/β TCR/dad-1 locus, (Hong et al., 1997; Ortiz et al., 1997) and the human α-globin locus, (Vyas et al., 1992). Genes with two different tissue-specificities may also be closely linked. For example, the human growth hormone and chorionic somatornammotropin genes (Jones et al., 1995). Chromatin domains are envisaged to exist in either a closed, "condensed", transcriptionally silent state or in a "de-condensed", open and transcriptionally competent configuration. The establishment of an open chromatin structure characterised by DNase I sensitivity, DNA hypomethylation and histone hyperacetylation, is seen as a pre-requisite to the commencement of gene expression.

The discovery of tissue-specific transcriptional regulatory elements known as locus control regions (LCRs) has provided novel insights into the mechanisms by which a transcriptionally competent, open chromatin domain is established and maintained in certain cases. LCRs are defined by their ability to confer on a gene linked in cis host cell type restricted, integration site-independent, copy-number-dependent expression of the gene (Grosveld et al., 1987: Lang et al., 1988; Greaves et al., 1989; Diaz et al., 1994; Carson and Wiles, 1993; Bonifer et al., 1990; Montoliu et al., 1996; Raguz et al., 1998; EP-A-0 332 667) especially as single copy transgenes (Ellis et al., 1996; Raguz et al., 1998). LCRs are able to obstruct the spread of heterochromatin and prevent position effect variegation (Festenstein et al., 1996; Milot et al., 1996). This pattern of expression conferred by LCRs suggests that these elements possess a powerful chromatin remodelling capability and are able to establish and maintain a transcriptionally competent, open chromatin domain. In addition, LCRs have been found to possess an inherent transcriptional activating capability that allows them to confer tissue-specific gene expression independent of their cognate promoter (Blom van Assendelft et al., 1989; Collis et al., 1990; Antoniou and Grosveld, 1990; Greaves et al., 1989).

All LCRs are associated with gene domains with a prominent tissue-specific or tissue restricted component and are associated with a series of DNase I hypersensitive sites which can be located either 5' (Grosveld et al., 1987; Carson and Wiles, 1993; Bonifer et al., 1994; Jones et al., 1995; Montoliu et al., 1996) or 3' (Greaves et al., 1989) of genes which they regulate. In addition, LCR elements have recently been found to exist between closely spaced genes (Hong et al., 1997; Ortiz et al., 1997). An LCR-like element has also been reported to have an intronic location within a gene (Aronow et al., 1995). In the few cases that have been investigated, these elements correspond to large clusters of tissue-specific and ubiquitous transcription factor binding sites (Talbot et al., 1990; Philipsen et al., 1990; Pruzina et al., 1991; Lake et al., 1990; Jarman et al., 1991; Aronow et al., 1995).

The discovery of LCRs suggests that the regulatory elements that control tissue-specific gene expression from a given chromatin domain are organised in a hierarchical fashion. The LCR would appear to act as a master switch wherein its activation results in the establishment of an open chromatin structure that has to precede any gene expression. Transcription at the physiologically required level can then be achieved through a direct chromatin interaction between the LCR and the local promoter and enhancer elements of an individual gene via looping out of the intervening DNA (Hanscombe et al., 1991; Wijgerde et al., 1995; Dillon et al., 1997).

As indicated above, an essential feature of an LCR is its tissue-specificity. The tissue-specificity of an LCR has been investigated by Ortiz et al., (1997), wherein a number of DNase I hypersensitive sites of the T-cell receptor alpha (TCR α) LCR were deleted and an LCR derived element, which opens chromatin in a number of tissues identified. Talbot et al., (1994, NAR, 22, 756 766) describe an LCR-like element that is considered to allow expression of a linked gene in a number of tissues. However, reproducible expression of the linked gene is not obtained. The levels of expression are indicated as having a standard deviation of between 74% from the average value on a per-gene-copy basis where the gene is expressed where transgene copy-number is 3 or more. When the copy-number is 1 or 2, the gene expression levels are 10 times lower and have a standard deviation of 49% from the average value on a per-gene-copy basis where the gene is expressed. The element disclosed by Talbot et al., does not give reproducible expression of a linked gene. This and the high variability of the system clearly limits the use of this system.

The long-term correction of genetically inherited disorders by gene therapy requires the maintenance and sustained expression of the transcription unit at sufficiently high levels to be of therapeutic value. This, may be achieved by one of two approaches. Firstly, transcription units can be stably integrated into the host cell genome using, for example, retroviral (Miller, 1992; Miller et al., 1993) or adeno-associated viral (AAV) vectors (Muzyczka, 1992; Kotin, 1994; Flotte and Carter, 1995). Alternatively, therapeutic genes can be incorporated within self-replicating episomal vectors comprising viral origins of replication such as those from EBV (Yates et al., 1985), human papovavirus BK (De Benedetti and Rhoads, 1991; Cooper and Miron, 1993) and BPV-1 (Piirsoo et al., 1996).

Unfortunately, the level of expression that is normally seen from genes that are integrated into the genome is too low or short in duration to be of therapeutic value in most cases. This is due to what are generally known as "position effects". The transcription of the introduced gene is dependent upon its site of integration where it comes under the influence of either competing activating (promoters/enhancers) or more frequently, repressing (chromatin silencing) elements. Position effects continue to impose substantial constraints on the therapeutic efficacy of integrating virus based vectors of retroviral and adeno-associated viral (AAV) origin. Viral transcriptional regulatory elements are notoriously susceptible to silencing by chromatin elements in the vicinity of integration sites. The inclusion of classical promoter and enhancer elements from highly expressed genes as part of the viral constructs has not solved this major problem (Dai et al., 1992; Lee et al., 1993).

The inclusion of a fully functional LCR as part of the transcription unit overcomes this deficiency since this element can be used to drive a predictable, physiological and sustained level of expression of the desired gene in a specific cell type (see Yeoman and Mellor, 1992; Brines and Klaus, 1993; Needham et al. 1992 and 1993; Tewari et al., 1998; Zhumabekov et al., 1995). This degree of predictability of expression is vital for a safe and successful gene therapy strategy.

The use of replicating episomal vectors (REVs) offers an attractive alternative to integrating viral vectors for producing long-term gene expression. Firstly, REVs do not pose the same size limitations on the therapeutic transcription unit as do viral vectors, with inserts in excess of 300 kb being a possibility (Sun et al., 1994). Secondly, being episomal, REVs do not suffer from potential hazards associated with insertional mutagenesis that is an inherent problem with integrating viral vectors. Lastly, REVs are introduced into the target cells using non-viral delivery systems that can be produced more cheaply at scale than with viral vectors.

It has been demonstrated that both non-replicating, transiently transfected plasmids (Reeves et al., 1985; Archer et al., 1992) and REVs (Reeves et al., 1985; Smith et al., 1993) assemble nucleosomes. Assembly on REVs is more organised and resembles native chromatin whereas nucleosomes on transient plasmids are less well ordered and may allow some access of transcription factors to target sequences although gene expression can be inhibited (Archer et al., 1992). It has recently been demonstrated that LCRs are able to confer long-term, tissue-specific gene expression from within REVs (International Patent Application WO 98/07876). The generation of cultured mammalian cell lines producing high levels of a therapeutic protein product is a major developing industry. Chromatin position effects make this a difficult, time consuming and expensive process. The most commonly used approach to the production of such mammalian "cell factories" relies on gene amplification induced by a combination of a drug resistance gene (e.g., DHFR, glutamine synthetase (Kaufman, 1990)) and high toxic drug concentrations which have to be maintained at all times. The use of vectors possessing LCRs from highly expressed gene domains, greatly simplifies the generation of these cell lines (Needham et al., 1992; Needham et al., 1995).

A problem with the use of LCRs is that they are tissue-specific and reproducible expression is only obtained in the specific cell type. Accordingly, one could not obtain reproducible expression in a tissue type or a number of tissue types for which there is no LCR. Accordingly, there is a need for a UCOE, which is not derived from an LCR.

As indicated above, Ortiz et al., (1997) discloses an LCR derived element, which opens chromatin in number of tissues. There are a number of problems with the LCR derived element of Ortiz et al., (1997). In particular, the element has to be carefully constructed using recombinant DNA techniques to contain the necessary regions of the LCR and also the element does not give reproducible levels of expression of a linked gene in cells of different tissues types, especially when the element is at single or low (less than 3) trans gene copy-number.

Elements comprising bi-directional promoters and methylation-free CpG-islands have been disclosed; however, there is no disclosure or indication that the elements opens chromatin or maintain chromatin in an open state and facilitate reproducible expression of an operably-linked gene in cells of at least two different tissue types.

The human Surfeit locus spans approximately 60 kb and is located on 9q34.2. The locus comprises bi-directional promoters between the SURF5 and SURF3 genes and between the SURF1 and SURF2 genes (Huxley et al., Mol. Cell. Biol., 10, 605-614, 1990; Duhig et al., Genomics, 52, 72-78, 1998; Williams et al., Mol. Cell. Biol., 6, 4558-4569, 1986). There is no indication that these regions open chromatin or maintain chromatin in an open state and facilitate reproducible expression of an operably-linked gene in cells of at least two different tissue types.

A bi-directional promoter is also disclosed by Brayton et al., (J. Biol. Chem., 269, 5313-5321, 1994) between the avian GPAT and AIRC genes. Again there is no indication that the region opens chromatin or maintain chromatin in an open state and facilitate reproducible expression of an operably-linked gene in cells of at least two different tissue types.

A bi-directional promoter is disclosed by Ryan et al. (Gene, 196, 9-17, 1997) between the mitochondrial chaperonin 60 and chaperonin 10 genes. Again there is no indication that the region opens chromatin or maintain chromatin in an open state and facilitate reproducible expression of an operably-linked gene in cells of at least two different tissue types.

A bi-directional promoter is also disclosed associated with the murine HTF9 gene. Again there is no indication that the region opens chromatin or maintain chromatin in an open state and facilitate reproducible expression of an operably-linked gene in cells of at least two different tissue types.

Palmiter et al., (PNAS, USA, 95, 8428-8430, 1998) and International Patent Application WO 94/13273 disclose an element associated with the metallothionein genes. The element comprises DNase I hypersensitive sites which are not associated with promoters. Furthermore, there is no evidence demonstrating that the element opens chromatin or maintain chromatin in an open state and facilitate reproducible expression of an operably-linked gene in cells of at least two different tissue types.

The use of non-replicating, transiently transfected plasmids to achieve gene expression by transfecting cells is well-known. It is also known that only short term expression (generally less than 72 hours) is achieved using non-replicating, transiently transfected plasmids. The short term of expression is generally considered to be due to the breakdown of the plasmid or loss of the plasmid from the cell. In view of this drawback, the use of such plasmids is limited.

The present invention provides isolated polynucleotides comprising a UCOE which opens chromatin or maintains chromatin in an open state and facilitates reproducible expression of an operably-linked gene in cells of at least two different tissue types, wherein the polynucleotide is not derived from a locus control region. The isolated polynucleotides according to the invention are preferably greater than about 1.5 kb in length, more preferably greater than about 4 kb in length, when composed of endogenous genomic UCOE sequences. Functional composites of UCOE sequences, however, can be constructed from the endogenous genomic UCOE. Such composites can be less than 1.5 kb in length and are within the scope of the present invention.

A "locus control region" (LCR) is defined as a genetic element which is obtained from a tissue-specific locus of a eukaryotic host cell and which, when linked to a gene of interest and integrated into a chromosome of a host cell, confers tissue-specific, integration site-independent, copy-number-dependent expression on the gene of interest. A polynucleotide derived from an LCR can be any part or parts of an LCR. Preferably, a polynucleotide derived from an LCR is any part of an LCR that functions to open chromatin. An LCR is associated with one or more DNase I hypersensitive (HS) sites that are not associated with a promoter and it is preferred that the UCOE does not comprise HS sites that are not associated with a promoter. HS sites are well-known to those skilled in the art and can be identified based on the standard techniques, which are described herein.

The term "facilitates reproducible expression" refers to the capability of the UCOE to facilitate reproducible activation of transcription of the operably-linked gene. The process is believed to involve the ability of the UCOE to render the region of the chromatin encompassing the gene (or at least the transcription factor binding sites) accessible to transcription factors. Reproducible expression preferably means that the polynucleotide when operably-linked to an expressible gene gives substantially the same level of expression of the operably-linked gene irrespective of its chromatin environment and preferably irrespective of the cell tissue type. Preferably, substantially the same level of expression means a level of expression which has a standard deviation from an average value of less than 48%, more preferably less than 40% and most preferably, less than 25% on a per-gene-copy basis. Alternatively, substantially the same level of expression preferably means that the level of expression varies by less than 10 fold, more preferably less than 5 fold and most preferably less than 3 fold on a per-gene-copy basis. The level of expression is preferably the level of expression measured in a transgenic animal. It is especially preferred that the UCOE facilitates reproducible expression of an operably-linked gene when present at a single or low (less than 3) copy-number.

As used herein, "linked" refers to a cis-linkage in which the gene and the UCOE are present in a cis relationship on the same nucleic acid molecule. The term "operatively linked" refers to a cis-linkage in which the gene is subject to expression facilitated by the UCOE.

Open chromatin or chromatin in an open state refers to chromatin in a de-condensed state and is also referred to as euchromatin. Condensed chromatin is also referred to as heterochromatin. As indicated above, chromatin in a closed (condensed) state is transcriptionally silent. Chromatin in an open (de condensed) state is transcriptionally competent. The establishment of an open chromatin structure is characterised by DNase I sensitivity, DNA hypomethylation and histone hyperacetylation. Standard methods for identifying open chromatin are well-known to those skilled in the art and are described in Wu, 1989, Meth. Enzymol., 170, 269-289; Crane-Robinson et al., 1997, Methods, 12, 48-56; Rein et al., 1998, N.A.R., 26, 2255-2264.

The term "cells of two or more tissue types" refers to cells of at least two, preferably at least 4 and more preferably all of the following different tissue types: heart, kidney, lung, liver, gut, skeletal muscle, gonads, spleen, brain and thymus tissue. Preferably, the polynucleotide facilitates reproducible expression non-tissue-specifically, i.e. with no tissue-specificity. It is further preferred that the polynucleotide of the present invention facilitates reproducible expression in at least 50% and more preferably in all tissue types where active gene expression occurs.

Preferably, the polynucleotide of the present invention facilitates reproducible expression of an operably-linked gene at a physiological level. By physiological level, it is meant a level of gene expression at which expression in a cell, population of cells or a patient exhibits a physiological effect. Preferably, the physiological level is an optimal physiological level depending on the desired result. Preferably, the physiological level is equivalent to the level of expression of an equivalent endogenous gene.

The UCOE of the present invention can be any element, which opens chromatin or maintains chromatin in an open state and facilitates reproducible expression of an operably-linked gene in cells of at least two different tissue types provided it is not derived from an LCR. In a preferred embodiment, the UCOE comprises an extended methylation-free, CpG-island. CpG-islands have an average GC content of approximately 60%, compared with a 40% average in bulk DNA. One skilled in the art can easily identify CpG-islands using standard techniques such as using restriction enzymes specific for C and G sequences. Such techniques are described in Larsen et al., 1992 and Kolsto et al., 1986. An extended methylation-free CpG-island is a methylation-free CpG-island that extends across a region encompassing more than one transcriptional start site and/or extends for more than 300 bp and preferably more than 500 bp.

Preferably, the UCOE is derived from a sequence that in its natural enclogenous position is associated with, more preferably, located adjacent to, a ubiquitously expressed gene. It is further preferred that the UCOE comprises at least one transcription factor binding site. Transcription factor binding sites include promoter sequences and enhancer sequences. Preferably, the UCOE comprises dual or bi-directional promoters that are divergently transcribed. Dual promoters are defined herein as two or more promoters which are independent from each other so that one of the promoters can be activated or deactivated without effecting the other promoter or promoters. A bi-directional promoter is defined herein as a region that can act as a promoter in both directions but cannot be activated or deactivated in one direction only. Preferably, the UCOE comprises dual promoters. Preferably, the UCOE comprises dual or bi-directional promoters that transcribe divergently (i.e. can lead to transcription in opposite directions) and which in their natural endogenous positions are associated with ubiquitously expressed genes. Preferably, the UCOE comprises dual promoters that are transcribe divergently. The UCOE may comprise a heterologous promoter, i.e. a promoter that is not naturally associated with the other sequences of the UCOE. For example, it is possible to use the CMV promoter with the UCOE associated with the hnRNP A2 and the HP1H-γ, promoters, which is discussed further below. The present invention therefore also provides a UCOE comprising one or more heterologous promoters. The heterologous promoter or promoters can replace of one or more of the endogenous promoters of the UCOE or can be used in addition to the one or more endogenous promoters of the UCOE. The heterologous promoter may be any promoter including tissue-specific promoters such as tumour-specific promoters and ubiquitous promoters. Preferably the heterologous promoter is a substantially ubiquitous promoter and most preferably is the CMV promoter.

Preferably, the UCOE is not the 3725 bp Eco RI fragments comprising the bi-directional promoter of the Hpa II tiny fragment (HTF) island HTF9 as described in Lavia at al., EMBO J., 6, 2773 2779, (1987).

Preferably, the UCOE is not the 149 bp MES-1 element located within a 800 bp Bam HI genomic fragment located between the murine SURF1 and SURF2 genes of the Surfeit locus (Williams et al., Mol. Cell. Biol, 13, 4784-4792, 1993). Preferably, the UCOE is not the bi-directional promoter located between the SURF5 and the SURF3 genes of the Surfeit locus (Williams at al., Mol. Cell. Biol, 13, 4784 4792, 1993). It is further preferred that the UCOE is not derived from the human surfeit gene locus which spans 60 kb and is located on chromosome 9q34.2 as defined in Duhig et al., Genomics, 52, 72-78, (1998) or the corresponding murine locus (Huxley et al., Mol. Cell. Biol., 10, 605-614, 1990).

Preferably, the UCOE is not the bi-directional promoter region located between avian GPAT and AIRC genes contained in the 1350 bp Sma I fragment deposited in the GenBank database (accession no. L-12533) (Gavalas et al., Mol. Cell. Biol, 13, 4784-4792, 1993) or the corresponding human equivalent (Brayton et al., J. Biol. Chem., 269, 5313-5321, 1994).

Preferably, the UCOE is not the 13894 bp genomic DNA fragment (GenBank accession no. U68562) comprising the rat mitochondrial chaperonin 60 and chaperonin 10 genes. It is also preferred that the UCOE is not the 581 bp fragment containing the bi-directional promoter located in the intergenic region between the rat mitochondrial chaperonin 60 and chaperonin 10 genes (Ryan et al., Gene, 196, 9-17, 1997).

In a preferred embodiment of the present invention, the UCOE is a 44 kb DNA fragment spanning the human TATA binding protein (TBP) gene and 12 kb each of the 5' and 3' flanking sequence, or a functional homologue or fragment thereof.

A further preferred embodiment of the present invention, the UCOE is a 60 kb DNA fragment spanning the human hnRNP A2 gene with 30 kb 5' flanking sequence and 20 kb 3' flanking sequence, or a functional homologue or fragment thereof. In a further preferred embodiment, the UCOE comprises the sequence of FIG. 21 between nucleotides 1 to 6264 or a functional homologue or fragment thereof. This sequence encompasses the hnRNP A2 promoter (nucleotides 5636 to 6264) and 5.5 kb 5' flanking sequence comprising the HP1H-γ promoter.

In a further preferred embodiment of the present invention, the UCOE is a 25 kb DNA fragment spanning the human TBP gene with 1 kb 5' and 5 kb 3' flanking sequence, or a functional homologue or fragment thereof.

In a further preferred embodiment, the UCOE is a 16 kb DNA fragment spanning the human hnRNP A2 gene with 5 kb 5' and 1.5 kb 3' flanking sequence, or a functional homologue or fragment thereof.

In a further preferred embodiment, the UCOE comprises the sequence of FIG. 21 between nucleotides 1 and 5636 (the 5.5 kb 5' flanking sequence of the hnRNP A2 promoter) and the CMV promoter or a functional homologue or fragment thereof.

In a further preferred embodiment, the UCOE comprises the sequence of FIG. 21 between nucleotides 1 and 9127 or a functional homologue or fragment thereof. This sequence encompasses both the hnRNP A2 and HP1H-γ promoters and the 3' flanking sequence of the hnRNP A2 promoter up to but not including exon 2 of the hnRNP A2 gene.

It is further preferred that the UCOE of the present invention has the nucleotide sequence of FIG. 20 or FIG. 21, or a functional fragment or homologue thereof.

The term "functional homologues or fragments" as used herein means homologues or fragments, which open chromatin or maintain chromatin in an open state and facilitate reproducible expression of an operably-linked gene. Preferably, the homologues are species homologues corresponding to the identified UCOEs or are homologues associated with other ubiquitously expressed genes. Sequence comparisons can be made between UCOEs in order to identify conserved sequence motifs enabling the identification or synthesis of other UCOEs. Suitable software packages for performing such sequence comparisons are well-known to those skilled in the art. A preferred software package for performing sequence comparisons is PCGENE (Intelligenetics, Inc. USA). Functional fragments can be easily identified by methodically generating fragments of known UCOEs and testing for function. The identification of conserved sequence motifs will also assist in the identification of functional fragments, as fragments comprising the conserved sequence motifs will be likely to be functional. Functional homologues also encompass modified UCOEs wherein elements of the UCOE have been replaced by similar elements, such as replacing one or more promoters of a UCOE with different heterologous promoters. As indicated above, the heterologous promoter may be any promoter including tissue-specific promoters such as tumour-specific promoters and ubiquitous promoters. Preferably the heterologous promoter is a strong and/or substantially ubiquitous promoter and most preferably is the CMV promoter.

In another embodiment of the present invention, there is provided a method for identifying a UCOE which facilitates reproducible expression of an operably-linked gene in cells of at least two different tissue types, comprising: 1. testing a candidate UCOE by transfecting cells of at least two different tissue types with a vector containing the candidate UCOE operably-linked to a marker gene; and 2. determining if reproducible expression of the marker gene is obtained in the cells of two or more different tissue types.

Preferably, the method for identifying a UCOE of the present invention comprises the additional step of selecting candidate UCOEs that are associated with one or more of: a ubiquitously expressed gene, a dual or bi-directional promoter and an extended methylation-free CpG-island.

Preferably, reproducible expression of the marker gene is determined in cells containing a single copy of the UCOE linked to the marker gene.

The present invention further provides the method of the present invention wherein the candidate UCOE is tested by generating a non-human transgenic animal containing cells comprising a vector containing the candidate UCOE operably-linked to a marker gene and determining if reproducible expression of the marker gene is obtained in the cells of two or more different tissue types. Preferably, the non-human transgenic animal is a F1, or greater, generation non-human transgenic animal. Preferably the non-human transgenic animal is a rodent, more preferably a mouse.

The present invention provides a UCOE derivable from a nucleic acid sequence associated with or adjacent to a ubiquitously expressed gene. Preferably, the nucleic acid sequence comprises an extended methylation-free, CpG-island. It is further preferred that the nucleic acid sequence comprises at least one transcription factor binding site. Preferably, the nucleic acid sequence comprises dual or bi-directional promoters that are divergently transcribed. Preferably, the nucleic acid sequence comprises dual promoters that are divergently transcribed. Preferably, the nucleic acid sequence comprises dual or bi-directional promoters that are divergently transcribed and which are associated with ubiquitously expressed genes. Preferably, the nucleic acid sequence comprises dual promoters that are divergently transcribed and which are associated with ubiquitously expressed genes.

The present invention also provides the use of the polynucleotide of the present invention, or a fragment thereof, in an assay for identifying other UCOEs. Preferably, a fragment of the polynucleotide is used which encompasses a conserved sequence or structural motif. Methods for performing such an assay are well-known to those skilled in the art.

The present invention provides a vector comprising the polynucleotide of the present invention. The vector preferably comprises an expressible gene operably-linked to the polynucleotide. The expressible gene comprises the necessary elements enabling gene expression such as suitable promoters, enhancers, splice acceptor sequences, internal ribosome entry site sequences (IRES) and transcription stop sites. Suitable elements for enabling gene expression are well-known to those skilled in the art. The suitable elements for enabling gene expression can be the natural endogenous elements associated with the gene or may be heterologous elements used in order to obtain a different level or tissue distribution of gene expression compared to the endogenous gene. Preferably, the vector comprises a promoter operably associated with the expressible gene and the polynucleotide. The promoter may be a natural endogenous promoter of the expressible gene or may be a heterologous promoter. The heterologous promoter may be any promoter including tissue-specific promoters such as tumour specific promoters and ubiquitous promoters. Preferably the heterologous promoter is a strong and/or a substantially ubiquitous promoter and most preferably is the CMV promoter.

The vector may be any vector capable of transferring DNA to a cell. Preferably, the vector is an integrating vector or an episomal vector.

Preferred integrating vectors include recombinant retroviral vectors. A recombinant retroviral vector will include DNA of at least a portion of a retroviral genome which portion is capable of infecting the target cells. The term "infection" is used to mean the process by which a virus transfers genetic material to its host or target cell. Preferably, the retrovirus used in the construction of a vector of the invention is also rendered replication-defective to remove the effect of viral replication of the target cells. In such cases, the replication-defective viral genome can be packaged by a helper virus in accordance with conventional techniques. Generally, any retrovirus meeting the above criteria of infectiousness and capability of functional gene transfer can be employed in the practice of the invention.

Suitable retroviral vectors include but are not limited to pLJ, pZip, pWe and pEM, well-known to those of skill in the art. Suitable packaging virus lines for replication-defective retroviruses include, for example, ψ Crip, ψ Cre, ψ 2 and ψ Am.

Other vectors useful in the present invention include adenovirus, adeno-associated virus, SV40 virus, vaccinia virus, HSV and pox virusvectors. A preferred vector is the adenovirus. Adenovirus vectors are well-known to those skilled in the art and have been used to deliver genes to numerous cell types, including airway epithelium, skeletal muscle, liver, brain and skin (Hitt, M M, Addison C L and Graham, Fla. (1997) Human adenovirus vectors for gene transfer into mammalian cells. *Advances in Pharmacology*, 40: 137B3206; and Anderson WF (1998) Human gene therapy, *Nature* 392 (6679 (Suppl): 25B30).

A further preferred vector is the adeno-associated (AAV) vector. AAV vectors are well-known to those skilled in the art and have been used to stably transducer human T-lymphocytes, fibroblasts, nasal polyp, skeletal muscle, brain, erythroid and heamopoietic stem cells for gene therapy applications (Philip et al., 1994, Mol. Cell. Biol., 14, 2411-2418; Russell et al., 1994, PNAS USA, 91, 8915-8919; Flotte et al., 1993, PNAS USA, 90, 10613-10617; Walsh et al., 1994, PNAS, USA, 89, 7257-7261; Miller et al., 1994, PNAS USA, 91, 10183-10187; Emerson, 1996, Blood, 87, 3082-3088). International Patent Application WO 91/18088 describes specific AAV based vectors.

Preferred episomal vectors include transient non-replicating episomal vectors and self-replicating episomal vectors with functions derived from viral origins of replication such as those from EBV, human papovavirus (BK) and BPV-1. Such integrating and episomal vectors are well-known to those skilled in the art and are fully described in the body of literature well-known to those skilled in the art. In particular, suitable episomal vectors are described in WO 98/07876.

Mammalian artificial chromosomes are also preferred vectors for use in the present invention. The use of mammalian artificial chromosomes is discussed by Calos (1996, TIG, 12, 463-466).

In a preferred embodiment, the vector of the present invention is a plasmid. It is further preferred that the plasmid is a non-replicating, non-integrating plasmid.

The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures.

A non-replicating, non-integrating plasmid is a nucleic acid which when transfected into a host cell does not replicate and does not specifically integrate into the host cell's genome (i.e. does not integrate at high frequencies and does not integrate at specific sites).

Replicating plasmids can be identified using standard assays including the standard replication assay of Ustav et al., EMBO J., 10, 449-457, 1991.

Preferably, a non-replicating, non-integrating plasmid is a plasmid that cannot be stably maintained in cells, independently of genomic DNA replication, and which does not persist in progeny cells for three or more cell divisions without a significant loss in copy-number of the plasmid in the cells, i.e., with a loss of greater than an average of about 50% of the plasmid molecules in progeny cells between a given cell division. Generally, in self-replicating vectors, the self-replicating function is provided by using a viral origin of replication and providing one or more viral replication factors that are required for replication mediated by that particular viral origin. Self-replicating vectors are described in WO 98/07876. The term "transiently transfecting, non-integrating plasmid" herein means the same as the term "non-replicating, non-integrating plasmid" as defined above.

Preferably the plasmid is a naked nucleic acid. As used herein, the term "naked" refers to a nucleic acid molecule that is free of direct physical associations with proteins, lipids, carbohydrates or proteoglycans, whether covalently or through hydrogen bonding. The term does not refer to the presence or absence of modified nucleotides or ribonucleotides, or chemical modification of the all or a portion of a nucleic acid molecule by such means as methylation or the inclusion of protecting groups or cap- or tail structures.

Preferably, the vector of the present invention comprises the sequence of FIG. 21 between nucleotides 1 and 7627 (encompassing both the hnRNP A2 and HP1H-γ promoters), the CMV promoter, a multiple cloning site, a polyadenylation sequence and genes encoding selectable markers under suitable control elements. Preferably the vector of the present invention is the CET200 or the CET210 vector schematically shown in FIG. 49.

The present invention also provides a host cell transfected with the vector of the present invention. The host cell may be any cell such as yeast cells, insect cells, bacterial cells and mammalian cells. Preferably the host cell is a mammalian cell and may be derived from mammalian cell lines such as the CHO cell line, the 293 cell line and NSO cells.

Preferably, the operably-linked gene is a therapeutic nucleic acid sequence. Therapeutically useful nucleic acid sequences, which may be used in the present invention, include sequences encoding receptors, enzymes, ligands, regulatory factors, hormones, antibodies or antibody fragments and structural proteins. Therapeutic nucleic acid sequences also include sequences encoding nuclear proteins, cytoplasmic proteins, mitochondrial proteins, secreted proteins, membrane-associated proteins, serum proteins, viral antigens, bacterial antigens, protozoal antigens and parasitic antigens. Nucleic acid sequences useful according to the invention also include sequences encoding proteins, peptides, lipoproteins, glycoproteins, phosphoproteins and nucleic acid (e.g., RNAs or antisense nucleic acids). Proteins or polypeptides which can be encoded by the therapeutic nucleic acid sequence include hormones, growth factors, enzymes, clotting factors, apolipoproteins, receptors, erythropoietin, therapeutic antibodies or fragments thereof, drugs, oncogenes, tumor antigens, tumor suppressors, viral antigens, parasitic antigens and bacterial antigens. Specific examples of these compounds include proinsulin, growth hormone, androgen receptors, insulin-like growth factor I, insulin-like growth factor II, insulin-like growth factor binding proteins, epidermal growth factor, transforming growth factor α transforming growth factor-β, plate let-derived growth factor, angiogenesis factors (acidic fibroblast growth factor, basic fibroblast growth factor, vascular endothelial growth factor and angiogenin), matrix proteins (Type IV collagen, Type VII collagen, laminin), phenylalanine hydroxylase, tyrosine hydroxylase, oncoproteins (for example, those encoded by ras, fos, myc, erb, src, neu, sis, jun), HPV E6 or E7 oncoproteins, p53 protein, Rb protein, cytokine receptors, IL-1, IL-6, IL-8, and proteins from viral, bacterial and parasitic organisms which can be used to induce an immunological response, and other proteins of useful significance in the body. The choice of gene, to be incorporated, is only limited by the availability of the nucleic acid sequence encoding it. One skilled in the art will readily recognise that as more proteins and polypeptides become identified they can be integrated into the polynucleotide of the present invention and expressed.

When the polynucleotide of the present invention is comprised in a plasmid, it is preferred that the plasmid be used in monogenic gene therapy such as in the treatment of Duchenne muscular dystrophy and in DNA vaccination and immunisation methods.

The polynucleotide of the invention also may be used to express genes that are already expressed in a host cell (i.e., a native or homologous gene), for example, to increase the dosage of the gene product. It should be noted, however, that expression of a homologous gene might result in deregulated expression, which may not be subject to control by the UCOE due to its over expression in the cell.

The polynucleotide of the invention may be inserted into the genome of a cell in a position operably associated with an endogenous (native) gene and thereby lead to increased expression of the endogenous gene. Methods for inserting elements into the genome at specific sites are well-known to those skilled in the art and are described in U.S. Pat. No. 5,578,461 and U.S. Pat. No. 5,641,670. Alternatively, the polynucleotide of the present invention in its endogenous (native) position on the genome may have a gene inserted in an operably associated position so that expression of the gene occurs. Again, methods for inserting genes into the genome at specific sites are well-known to those skilled in the art and are described in U.S. Pat. No. 5,578,461 and U.S. Pat. No. 5,641,670.

The present invention provides the use of the polynucleotide of the present invention to increase the expression of an endogenous gene comprising inserting the polynucleotide into the genome of a cell in a position operably associated with the endogenous gene thereby increasing the level of expression of the gene.

Numerous techniques are known and are useful according to the invention for delivering the vectors described herein to cells, including the use of nucleic acid condensing agents, electroporation, complexation with asbestos, polybrene, DEAE cellulose, Dextran, liposomes, cationic liposomes, lipopolyarnines, polyornithine, particle bombardment and direct microinjection (reviewed by Kucherlapati and Skoultchi, Crit. Rev, Biochem. 16:349-379 (1984); Keown et al., Methods Enzymol. 185:527 (1990)).

A vector of the invention may be delivered to a host cell non-specifically or specifically (i.e., to a designated subset of host cells) via a viral or non-viral means of delivery. Preferred delivery methods of viral origin include viral particle packaging cell lines as transfection recipients for the vector of the present invention into which viral packaging signals have been engineered, such as those of adenovirus, herpes viruses and papovaviruses. Preferred non-viral based gene delivery means and methods may also be used in the invention and include direct naked nucleic acid injection, nucleic acid condensing peptides and non-peptides, cationic liposomes and encapsulation in liposomes.

The direct delivery of vector into tissue has been described and some short term gene expression has been achieved. Direct delivery of vector into muscle (Wolff et al., Science, 247, 1465-1468, 1990) thyroid (Sykes et al., Human Gene Ther., 5, 837-844, 1994) melanoma (Vile et al., Cancer Res., 53, 962-967, 1993), skin (Hengge et al., Nature Genet, 10, 161-166, 1995), liver (Hickman et al., Human Gene Therapy, 5, 1477-1483, 1994) and after exposure of airway epithelium (Meyer et al., Gene Therapy, 2, 450-460, 1995) is clearly described in the prior art.

Various peptides derived from the amino acid sequences of viral envelope proteins have been used in gene transfer when co-administered with polylysine DNA complexes (Plank et al., J. Biol. Chem. 269:12918-12924 (1994)); Trubetskoy et al., Bibconjugate Chem. 3:323 (1992); WO 91/17773; WO 92/19287; and Mack et al., Am. J. Med. Sci. 307:138-143 (1994)) suggest that co-condensation of polylysine conjugates with cationic lipids can lead to improvement in gene transfer efficiency. International Patent Application WO 95/02698 discloses the use of viral components to attempt to increase the efficiency of cationic lipid gene transfer.

Nucleic acid condensing agents useful in the invention include spermine, spermine derivatives, histones, cationic peptides, cationic non-peptides such as polyethyleneimine (PEI) and polylysine. Spermine derivatives refers to analogues and derivatives of spermine and include compounds as set forth in International Patent Application No. WO 93/18759 (published Sep. 30, 1993).

Disulphide bonds have been used to link the peptidic components of a delivery vehicle (Cotten et al., Meth. Enzymol. 217:618-644 (1992)); see also, Trubetskoy et al., (supra).

Delivery vehicles for delivery of DNA constructs to cells are known in the art and include DNA/poly-cation complexes which are specific for a cell surface receptor, as described in, for example, Wu and Wu, J. Biol. Chem. 263:14621 (1988); Wilson et al., J. Biol. Chem. 267:963 (1992); and U.S. Pat. No. 5,166,320).

Delivery of a vector according to the invention is contemplated using nucleic acid condensing peptides. Nucleic acid condensing peptides, which are particularly useful for condensing the vector and delivering the vector to a cell, are described in WO 96/41606. Functional groups may be bound to peptides useful for delivery of a vector according to the invention, as described in WO 96/41606. These functional groups may include a ligand that targets a specific cell-type such as a monoclonal antibody, insulin, transferrin, asialoglycoprotein, or a sugar. The ligand thus may target cells in a non-specific manner or in a specific manner that is restricted with respect to cell type.

The functional groups also may comprise a lipid, such as palmitoyl, oleyl, or stearoyl; a neutral hydrophilic polymer such as polyethylene glycol (PEG), or polyvinylpyrrolidine (PVP); a fusogenic peptide such as the HA peptide of influenza virus; or a recombinase or an integrase. The functional group also may comprise an intracellular trafficking protein such as a nuclear localisation sequence (NILS) and endosome escape signal or a signal directing a protein directly to the cytoplasm.

The present invention also provides the polynucleotide, vector or host cell of the present invention for use in therapy. Preferably, the polynucleotide, vector or host cell is used in gene therapy.

The present invention also provides the use of the polynucleotide, vector or host cell of the present invention in the manufacture of a composition for use in gene therapy.

The present invention also provides a method of treatment, comprising administering to a patient in need of such treatment an effective dose of the polynucleotide, vector or host cell of the present invention. Preferably, the patient is suffering from a disease treatable by gene therapy.

The present invention also provides a pharmaceutical composition comprising the polynucleotide, vector or host cell of the present invention in combination with a pharmaceutically acceptable recipient.

The present invention also provides use of a polynucleotide, vector or host cell of the present invention in a cell culture system in order to obtain the desired gene product. Suitable cell culture systems are well-known to those skilled in the art and are fully described in the body of literature known to those skilled in the art.

The present invention also provides the use of the polynucleotide of the present invention in producing transgenic plant genetics. The generation of transgenic plants which have increased yield, resistance, etc., are well-known to those skilled in the art. The present invention also provides a transgenic plant containing cells which contain the polynucleotide of the present invention.

The present invention also provides a transgenic non-human animal containing cells, which contain the polynucleotide of the present invention.

The pharmaceutical compositions of the present invention may compromise the polynucleotide, vector or host cell of the present invention, if desired, in admixture with a pharmaceutically acceptable carrier or diluent, for therapy to treat a disease or provide the cells of a particular tissue with an advantageous protein or function.

The polynucleotide, vector or host cell of the invention or the pharmaceutical composition may be administered via a route which includes systemic intramuscular, intravenous, aerosol, oral (solid or liquid form), topical, ocular, as a suppository, intraperitoneal and/or intrathecal and local direct injection.

The exact dosage regime will, of course, need to be determined by individual clinicians for individual patients and this, in turn, will be controlled by the exact nature of the protein expressed by the gene of interest and the type of tissue that is being targeted for treatment.

The dosage also will depend upon the disease indication and the route of administration. Advantageously, the duration of treatment will generally be continuous or until the cells die. The number of doses will depend upon the disease, and efficacy data from clinical trials.

The amount of polynucleoticle or vector DNA delivered for effective gene therapy according to the invention will preferably be in the range of between about 50 ng-1000μ of vector DNA/kg body weight; and more preferably in the range of between about 1-100 μg vector DNA/kg.

Although it is preferred according to the invention to administer the polynucleotide, vector or host cell to a mammal for in vivo cell uptake, an ex vivo approach may be utilized whereby cells are removed from an animal, transduced with the polynucleotide or vector, and then re implanted into the animal. The liver, for example, can be accessed by an ex vivo approach by removing hepatocytes from an animal, transducing the hepatocytes in vitro and re-implanting the transduced hepatocytes into the animal (e.g., as described for rabbits by Chowdhury et al., Science 264:1802-1805, 1991, or in humans by Wilson, Hum. Gene Ther. 3:179-222, 1992). Such methods also may be effective for delivery to various populations of cells in the circulatory or lymphatic systems, such as erythrocytes, T-cells, B cells and haematopoietic stem cells.

In another embodiment of the invention, there is provided a mammalian model for determining the tissue-specificity and/or efficacy of gene therapy using the polynucleotide, vector or host cell of the invention. The mammalian model comprises a transgenic animal whose cells contain the vector of the present invention. Methods of making transgenic mice (Gordon et al., Proc, Natl. Acad. Sci. USA, 77:7380 (1980); Harbers et al., Nature 293:540 (1981); Wagner et al., Proc. Natl. Acad. Sci. USA, 78:5016 (1981); and Wagner et al., Proc, Natl. Acad. Sci. USA, 78:6376 (1981), sheep, pigs, chickens (see Hammer et al., Nature 315:680 (1985)), etc., are well-known in the art and are contemplated for use according to the invention. Such animals permit testing prior to clinical trials in humans.

Transgenic animals containing the polynucleotide of the invention also may be used for long-term production of a protein of interest.

The present invention also relates to the use of the polynucleotide of the present invention in functional genomics applications. Functional genomics relates principally to the sequencing of genes specifically expressed in particular cell types or disease states and now provides thousands of novel gene sequences of potential interest for drug discovery or gene therapy purposes. The major problem in using this information for the development of novel therapies lies in how to determine the functions of these genes. UCOEs can be used in a number of functional genomic applications in order to determine the function of gene sequences. The functional genomic applications of the present invention include, but are not limited to:

(1) Using the polynucleotide of the present invention to achieve sustained expression of anti-sense versions of the gene sequences or ribozyme knockdown libraries, thereby determining the effects of inactivating the gene on cell phenotype.

(2) Using the polynucleotide of the present invention to prepare expression libraries for the gene sequences, such that delivery into cells will result in reliable, reproducible, sustained expression of the gene sequences. The resulting cells, expressing the gene sequences can be used in a variety of approaches to function determination and drug discovery. For example, raising antibodies to the gene product for neutralisation of its activity; rapid purification of the protein product of the gene itself for use in structural, functional or drug screening studies; or in cell-based drug screening.

(3) Using the polynucleotide of the present invention in approaches involving mouse embryonic stem (ES) cells and transgenic mice. One of the most powerful functional genomics approaches involves random insertion into genes in mouse ES cells of constructs which only allow drug selection following insertion into expressed genes, and which can readily be rescued for sequencing (G. Hicks et al., 1997, Nature Genetics, 16: 338-344). Transgenic mice with knockout mutations in genes with novel sequences can then readily be made to probe their function. At present this technology works well for the "10% of mouse genes which are well expressed in mouse ES cells." Incorporation of UCOEs into the integrating constructs will enable this technique to be extended to identify all genes expressed in mice.

The following examples, with reference to the figures, are offered by way of illustration and are not intended to limit the invention in any manner. The preparation, testing and analysis of several representative polynucleotides of the invention are described in detail below. One of skill in the art may adapt these procedures for preparation and testing of other polynucleotides of the invention.

The figures show:

FIG. 1 shows the human TBP gene locus.

A: Schematic representation of the pCYPAC-2 clones containing the human TBP gene used in this study. The positions of NotI and Sac II restriction sites that may indicate the positions of unidentified genes are marked.

B: Illustration of the CpG-island spanning the 5=TBP/C5 regions. The density of CpG di-nucleotide residues implies that the methylation-free island is 3.4 kb in length and extends between the FspI site within intron I of C5, and the HindIII site within the first intron of TBP.

C: Is a further schematic representation of the clones from the TBP/C5 region. The arrangement of the genes has been reversed from that given in FIG. 1A. Please note, the C5 gene is also referred to as the PSMBI gene. A 257 kb contiguous region from the telomere of chromosome 6q with positions of the 3 closely linked genes and relevant restriction sites is shown (B, Bss HII; N, NotI; S, Sac II). PAC clones with their designated names are indicated. The subclone pBL-3-TPO-puro is also shown. The distance between the NotI site within the first exon of PDCD2 and the beginning of the telomeric repeat is approximately 150 kb.

FIG. 2 shows end-fragment analysis of TLN:3 and TLN:8 transgenic mice. Southern blot analysis of transgenic mouse tail biopsy DNA samples were probed with small DNA fragments located at (a) the 3' end of the transgene, (b) the 5' end, (c) the promoter, (d) −7.7 kb from TBP mRNA CAP site, (e) −12 kb from TBP mRNA CAP site. The results for TLN:3 (a,b) show that there is only one hybridising band with both end-probes, which does not match the predicted size for any head-to-head, head to tail, or tail-to-tail concatamer. Thus it would appear that there is only one transgene copy in this line. However, panel (c) shows that with a promoter probe, two bands are seen indicating that there must also be a second, deleted copy of the transgene present in this line. TLN:8 analysis in (a) shows a transgene concatamer band at 6 kb and an end-fragment band at 7.8 kb. As the concatamer band is twice the intensity of the end-fragment, this indicates a copy-number of three for this line. The lack of hybridisation in (b) suggests a deletion at the 5' end of all three copies has occurred and work is in progress to map this. Panels (d) and (e) indicate that the transgenes appear to be intact up to 12 kb 5' to the TBP gene.

FIG. 3A shows the analysis of TLN:28 mice. Southern blots of TILN:28 DNA were hybridised to a probe located at the very 3' end of the transgene locus. Multiple bands were seen to hybridise to this probe, suggesting multiple integration events. However, an intense concatamer band is seen in the position expected for a head-to-tail integration event. Comparison of the signal intensities between this and the end-fragments suggested a copy-number of approximately 4 in this line.

FIG. 3B shows a summary of transgene organisation in TILN mouse lines. TLN:3: contains two copies of the transgene in a head-to-tail arrangement. A deletion has occurred at both the 5' and 3' ends of this array. The 5' deletion extends into the 5' flanking region of TBP, completely deleting the C5 gene in this copy. At the 3' end, the deletion extends into the 3' UTR of TBP, leaving the C5 gene intact. This animal, therefore, possesses a single copy of the C5 gene and a single functional copy of the TBP gene. TLN:8: contains a head-to-tail arrangement of three copies. Each copy would seem to possess a deletion at the very 5' region, although the extent of this deletion is not known at present. It does not extend to the C5 gene as human C5 mRNA is detected in this line. TLN:28: contain 5 copies in a head-to-tail configuration, but there are also a number of additional fragments seen, indicating that this array may be more complex. FIG. 3C shows an updated summary of the transgene organisation in the TLN mouse lines. The figure shows the predicted organisations of the TLN transgene arrays in each of the mouse lines. Only functional genes are shown and only one of the 3 possible arrangements of the TLN:3 mice is indicated.

FIG. 4 shows analysis of the deletion in TLN:3 mice. A series of probes were hybridized to Southern blots of TLN:3 DNA. Only the furthest 5' probe gave a single band, indicating that the deleted copy did not contain this sequence. The deletion maps to a region upstream of the major TBP mRNA CAP sites, Ets factor binding site and DNase I hypersensitive site. It is currently unknown if the entire 5' region is deleted in this copy or a small internal deletion has occurred.

FIG. 5 shows the comparison of TBP and C5 mRNA sequences from human and mouse. (a) The human CS mIRNA sequence (SEQ. ID NO:23) from nt. 358 to 708 (Genbank accession no. D00761) exhibits significant homology to the mouse sequence (SEQ. ID NO:24) (indicated by a vertical bar) from nt. 355 to 705 (Genbank accession no. X80686). RT-PCR amplification of both human and mouse mRNAs produces a mixture of 350 bp DNA molecules from both species. The primer locations (highlighted, 5' primer C5RTF, 3' primer C5R) are positioned so as to span a number of exons, eliminating error from PCR amplification from contaminating genomic DNA. Although the intron/exon structure of either the human or mouse gene is limited, the distance between the primers is such that they are positioned in different exons. Mouse and human PCR products can be distinguished by incubation with Pst I that will only cut the mouse sequence. Radiolabelling of the C5RTF primer gives a product of 173 nt when resolved on a denaturing polyacrylamide gel. (b) Similar analysis for human TBP mRNA sequence (SEQ. ID NO:25) from nt. 901 in exon 5 to nt. 1185 in exon 7 (Genbank accession no. M55654) and mouse TBP mRNA (SEQ. ID NO:26) from positions 655 to 939 (Genbank accession no. D01034). The last nucleotide from an exon and the first nucleotide from the next exon are shown in red. The primers used (highlighted) were 5' TB-22 and BTB-14. The size of the amplified product from both species with the primers shown (boxed) is 284 bp. The Bsp 14071 site 63 nt from the 5' end of the PCR products allows human and mouse transcripts to be distinguished. The size of the human specific product on a polyacrylamide gel with radiolabelled TB-14 is 221 nt.

FIG. 6 shows expression analysis of human TBP expression in the TLN transgenic mice. Total RNA (I μg) from various mouse tissues was used in a reverse transcription reaction using Avian Myeloblastosis Virus reverse transcriptase. As a control, human RNA from K562 cells and non-transgenic mouse RNA were also used. (a) Location of the recognition site for the human specific restriction enclonucleases within the T822/14 RT-PCR products. (b) Analysis of TLN:3 expression in various tissues. As can be seen, the level of human expression is physiological in all tissues. (c) Similar analysis for TLN:8. (d) Analysis of TLN:28 indicates levels of human TBP mRNA are again expressed at comparable levels to the enclogenous gene.

FIG. 7 shows expression analysis of human C5 expression in the TLN transgenic mice. Analysis was performed as in FIG. 6. The upper panel (a) shows the location of the recognition site for the mouse specific restriction enclonucleases within the C5RTF/CSR RT-PCR products. (b) Analysis of C5 expression in various tissues of TLN transgenics can be seen, the level of human expression is physiological in all tissues tested.

FIG. 9 shows a schematic representation of the pWE-TSN cosmid.

FIG. 10 shows transgene copy-number determination of pWE-TSN L-cell clones. Mouse L-cells were transfected with the pWE-TSN cosmid, DNA isolated and used to generate Southern blots. Blots were probed with a DNA fragment from the two copy murine vavlocus and a probe located –7 kb from the TBP gene. Copy numbers were determined from the ratio of the three copy TLN:8 control and are given underneath each lane. Copy numbers ranged from 1 to 60.

Figure 11:
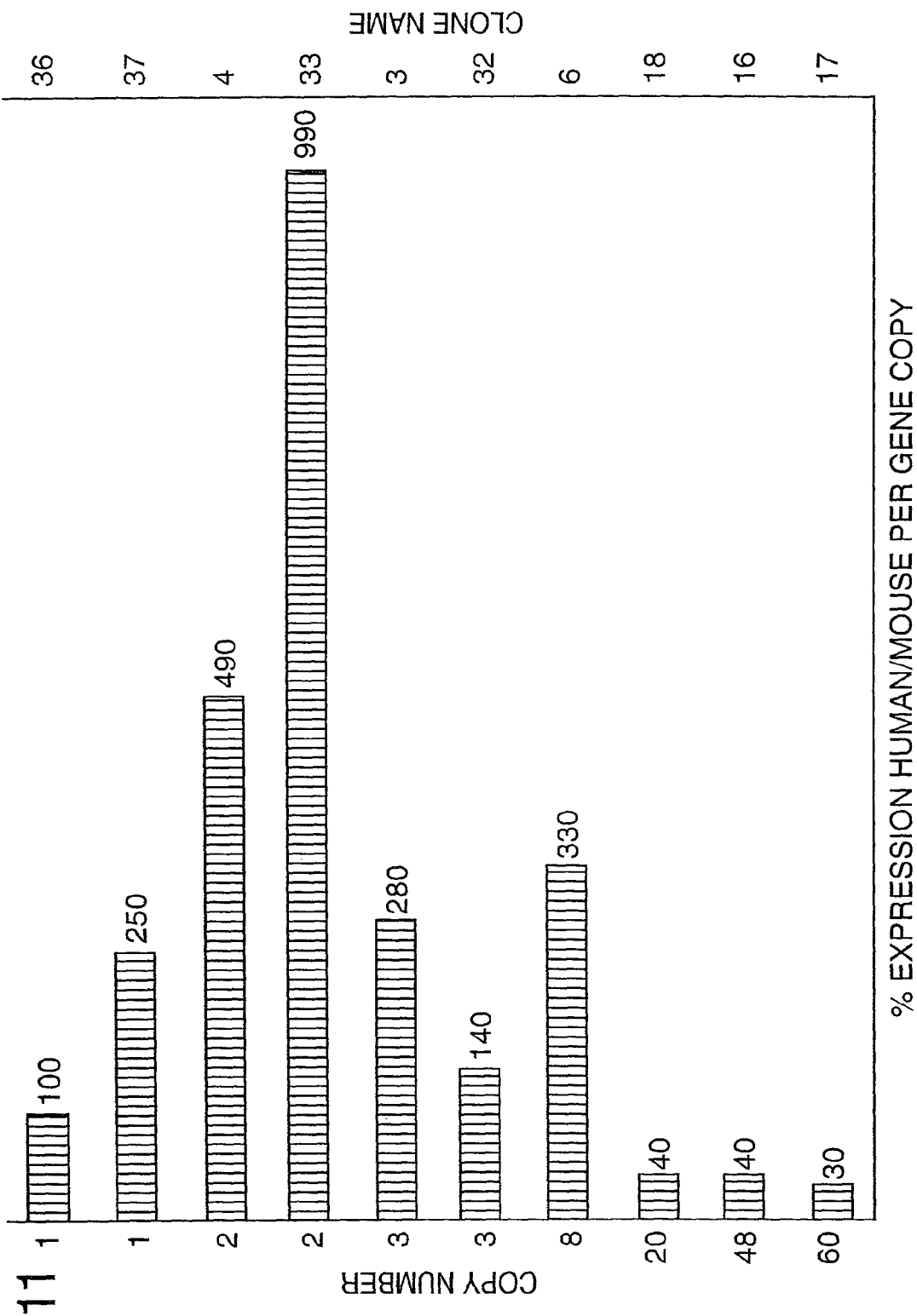

FIG. 11 shows a summary of expression of pWE-TSN cosmid clones in mouse L-cells.

Figure 12:
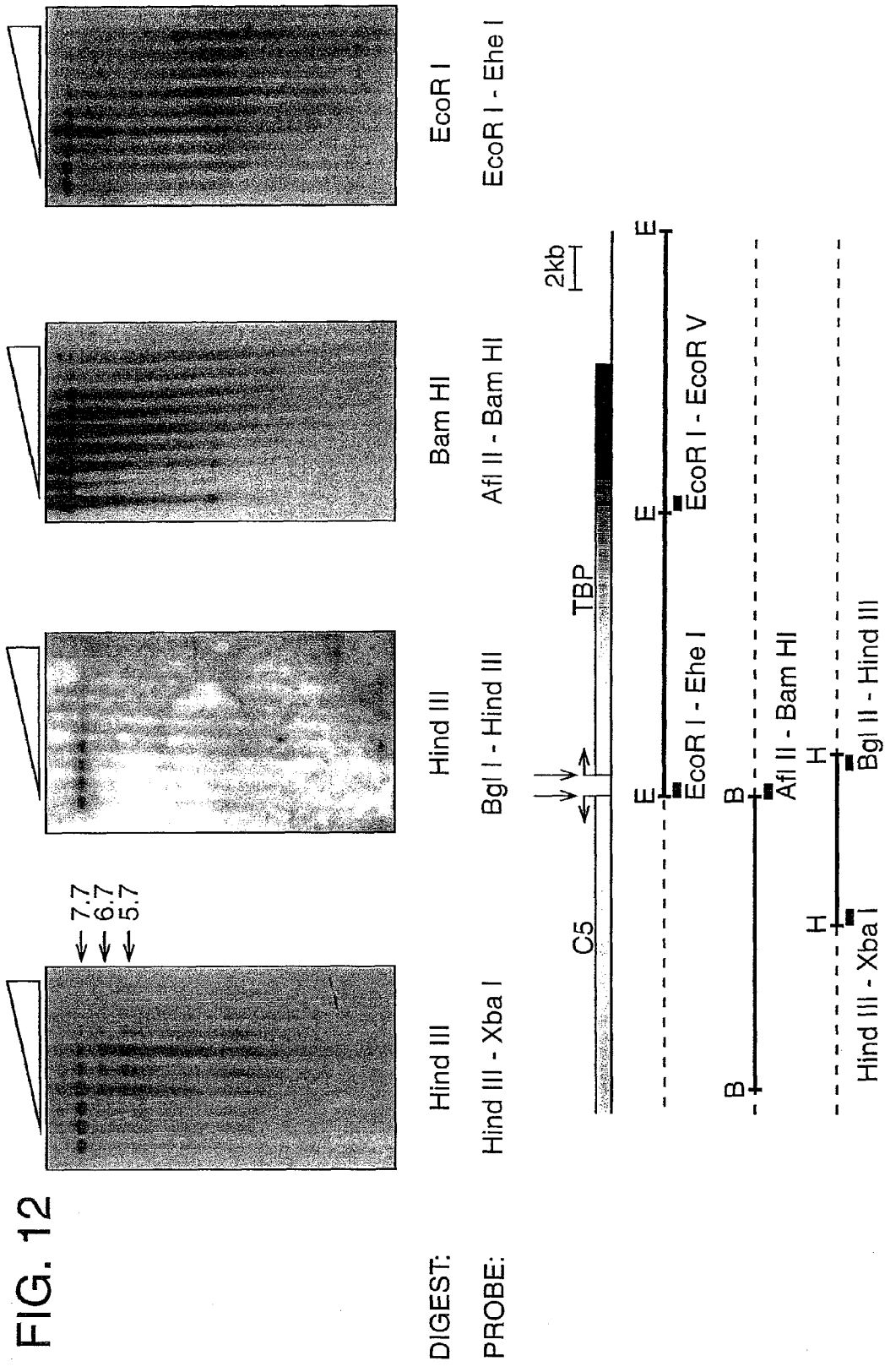

FIG. 12 shows DNase I hypersensitive site analysis of the human TBP locus. Probes located over a 40 kb region surrounding the TBP gene were used to probe Southern blots of K562 nuclei digested with increasing concentrations of DNase I. Only two hypersensitive sites were found, at the promoters of the PSMBI and the TBP gene. Increased DNase I concentration is shown from left to right in all cases.

FIG. 13A shows a schematic representation of the human hnRNP A2 gene locus showing the large 160 kb pCYPAC derived clone MA1 60. The reverse arrow denotes the HP1H γ gene. The two Sac II sites, which may represent the presence of methylation-free islands are boxed.

FIG. 13B shows the 60 kb Aat II sub-fragment derived from MA160. Both of these have been used for generation of transgenic mice.

Figure 13C:
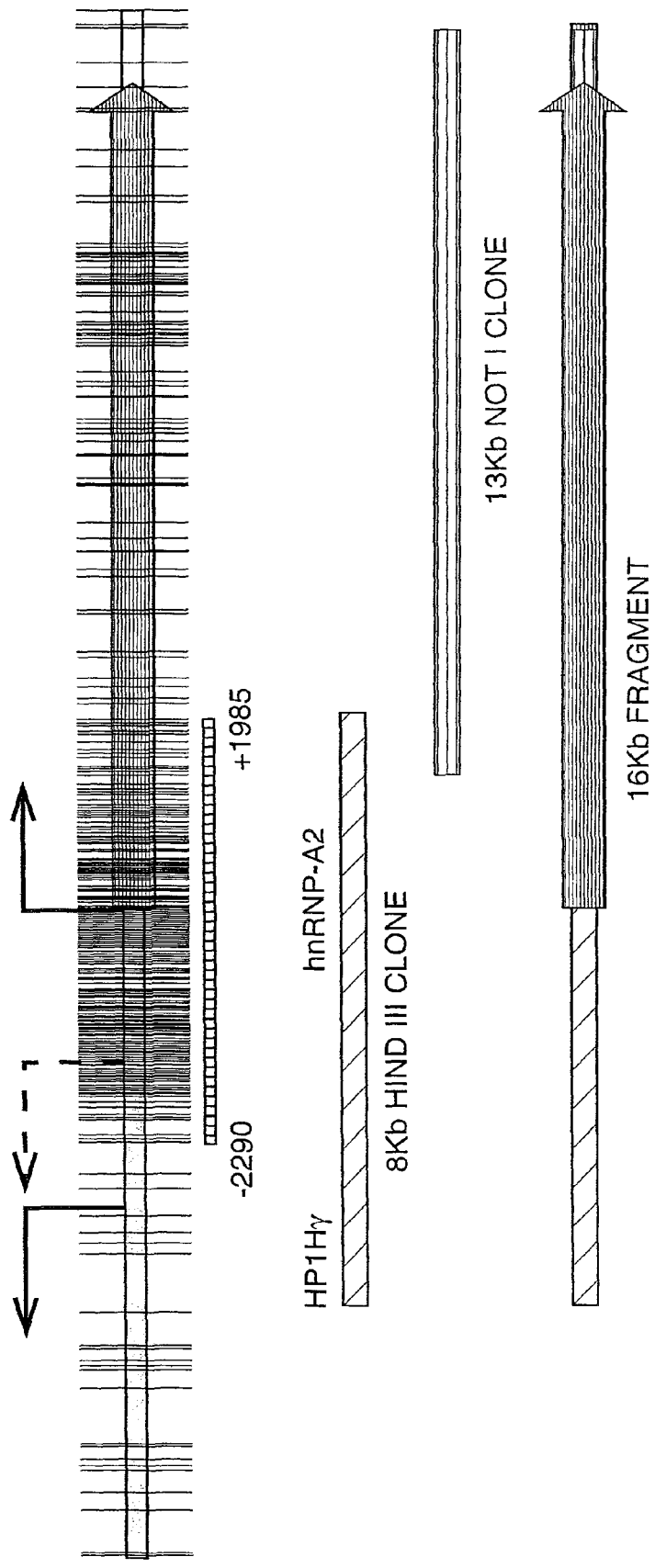

FIG. 13C shows the extent of the CpG-island (red bar) spanning the 5' end of the hnRNP A2 gene. The CpG residues are denoted as vertical lines. The numbers are in relation to the transcriptional start site (+1) of the hnRNP A2 gene (solid arrow). The broken arrow denotes the position of the divergently transcribed HP1H-γ gene. The 16 kb sub-fragment that contains the intact hnRNP A2 gene is also shown.

Figure 14B:
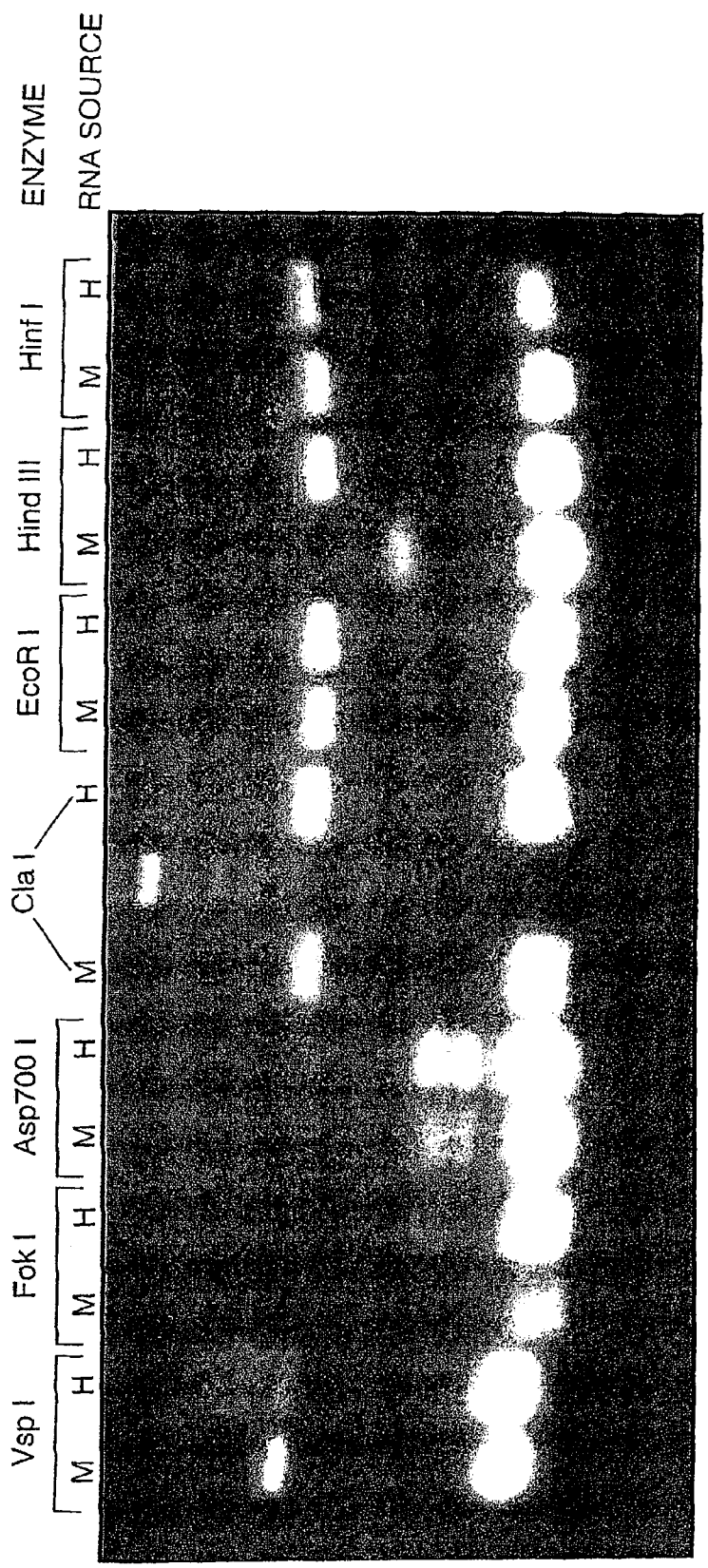

FIG. 14A shows exons 10 to 12 of the human hnRNP A2 cDNA (SEQ ID NO:27), and FIG. 14B shows quantification of human and mouse hnRNP A2 gene expression. Human (K562) and mouse RNA was reverse transcribed with a primer to exon 12 of the hnRNPA2 gene. Samples were subsequently amplified by PCR with primers Hn9 and Hn11 spanning exons 10 to 12. The product produced was then digested with random enzymes to find a cut site unique to each species. The mouse product can be seen to contain a Hind III that is not present in the human product.

FIG. 15 shows the analysis of human hnRNP A2 expression in transgenic mice microinjected with the Aa60 fragment (FIG. 13B). Total RNA from various tissues was analysed as described in FIG. 15. After RT-PCR, samples were either untreated (–) or digested with Hind III (+) and then separated on a polyacrylamide gel to resolve the human (H) and mouse (M) products. Intensity of the bands was measured by Phosphorimager analysis.

FIG. 16 shows the analysis of human hnRNP A2 expression by transgenic mice microinjected with the 160 kb Nru I fragment (FIG. 13A). A transgenic mouse was dissected and total RNA extracted from tissues. The RNA was reverse transcribed by Hn11 and then amplified by PCR using primers Hn9 and Hn11 of which Hn9 was radioactively end-labelled with $^{32}$P. Samples were either untreated (–) or digested with Hind III (+) and then separated on a 5% polyacrylamide gel in the presence of 8M urea as denaturant to resolve the human (H) and mouse (M) products. Intensity of the bands was measured by PhosphorImager analysis.

FIG. 17 shows the quantification of hnRNP A2 transgene expression. The RT-PCR analysis of human hnRNP A2 transgene expression in various mouse tissues was quantified by PhosphorImager. Levels are depicted as a percentage of murine hnRNP A2 expression on a transgene copy-number basis. A: Mice harbouring MA160 (see FIG. 15). B: Mice harbouring Aa60 (see FIG. 16).

FIG. 18 shows DNase I hypersensitive site mapping of the human hnRNP A2 gene locus. Nuclei from K562 cells were digested with increasing concentrations of DNase I. DNA from these nuclei was subsequently digested with a combination of Aat II and Nco I restriction endonucleases and Southern blotted. The blot was then probed with a 766 bp Eco RI/Nco I fragment from exon II of the hnRNP A2 gene. Three hypersensitive sites were identified corresponding to positions B1. 1, –0.7 and BO.1 kb 5' of the hnRNP A2 transcriptional start site.

Figure 19:
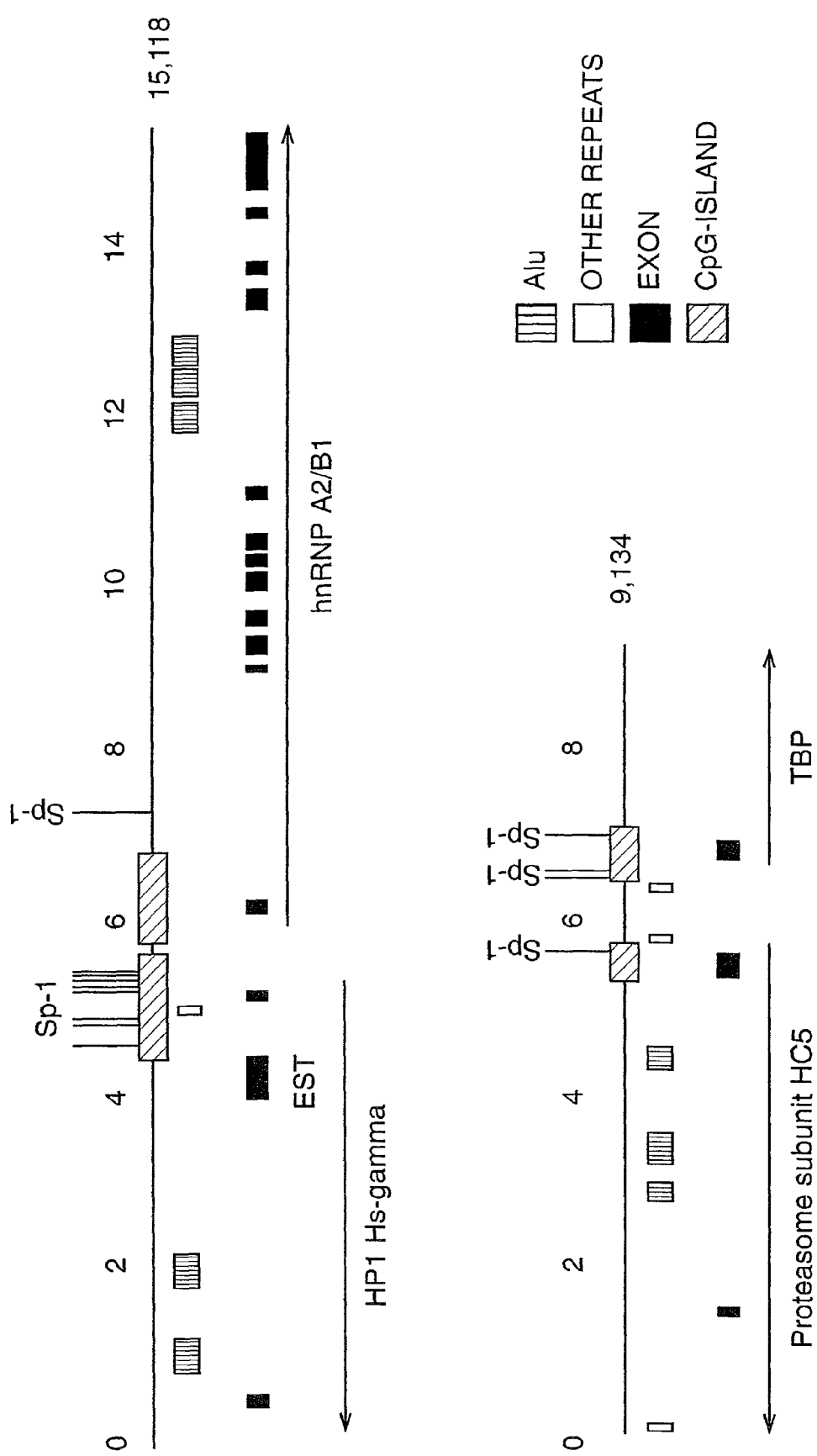

FIG. 19 shows the bioinformatic analysis and sequence comparisons between the hnRNP A2 and the TBP loci.

Figure 20:
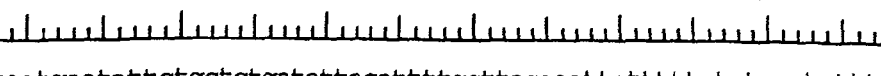

FIG. 20 shows the nucleotide sequence of a genomic clone of the TBP focus (SEQ. ID NO:28) beginning at the 5' HindIII site (nucleotides 1 to 9098).

FIG. 21 shows the nucleotide sequence of a genomic clone of the hnRNP A2 locus (SEQ. ID NO:29) beginning at the 5' Hind III site shown in FIG. 22 (nucleotides 1 to 15071).

FIG. 22 shows the expression vectors containing sub-fragments located in the dual promoter region between RNP and HPIH-γ which were designed using both GFP and a Neo$^R$ reporter genes. The vectors are: a control vector with the RNP promoter (RNP) driving GFP/Neo expression; a vector comprising the 5.5 kb fragment upstream of the RNP promoter region and the RNP promoter (5.5RNP); vectors constructed using a splice acceptor strategy wherein the splice acceptor/ branch concensus sequences (derived from exon 2 of the RNP gene) were cloned in front of the GFP gene, resulting in exon 1/part of intron 1 upstream of GFP (7.5RNP, carrying approximately 7.5 kb of the RNP gene preceding the GFP gene; and a vector comprising the 1.5 kb fragment upstream of the RNP promoter region and the RNP promoter (1.5RNP).

Figure 23:
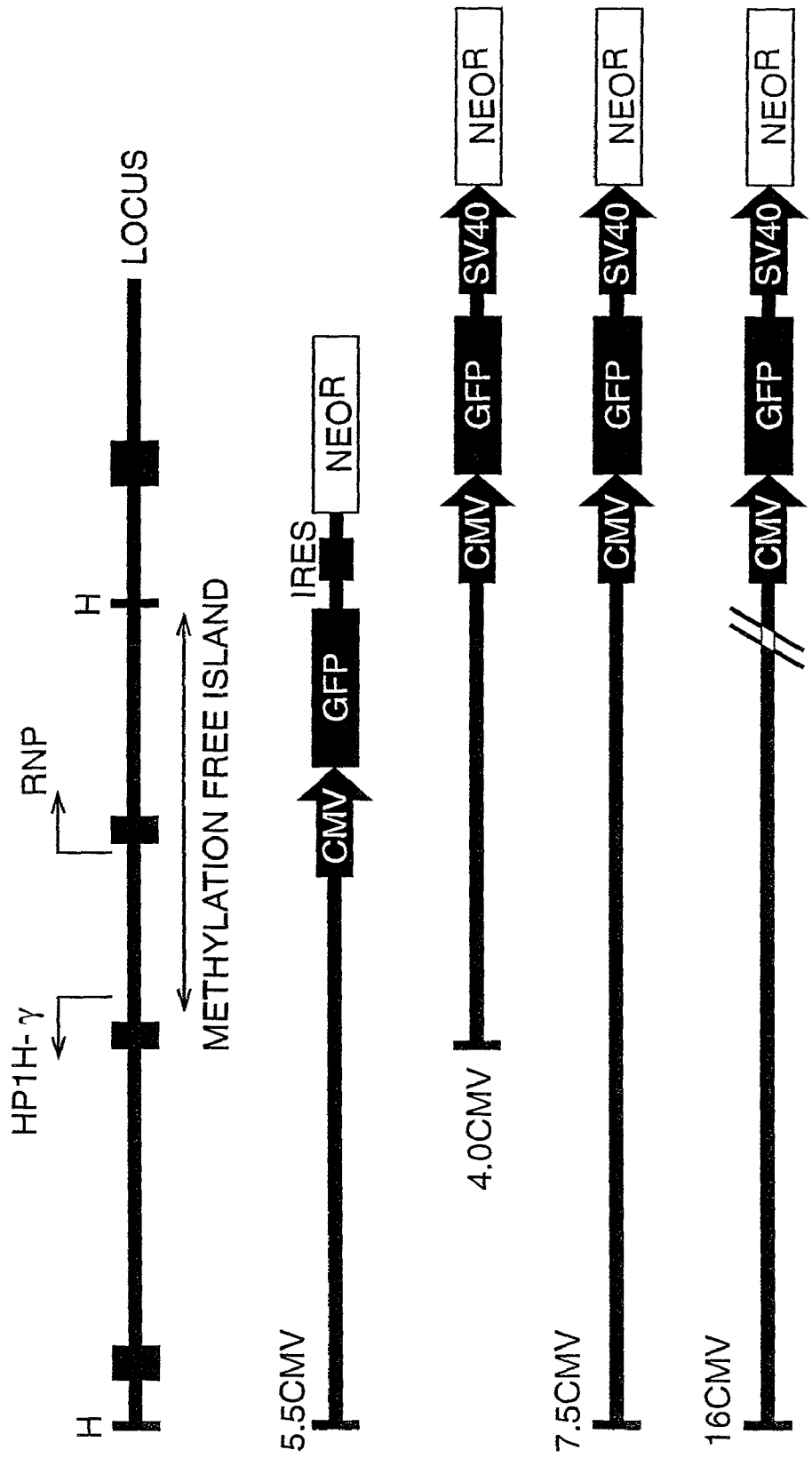

FIG. 23 shows expression vectors containing sub-fragments located in the dual promoter region between RNP and HPIH-γ which were designed using both GFP and a Neo$^R$ reporter genes. The vectors comprise the heterologous CMV promoter. The vectors are: control vectors with the CMV promoter driving GFP/Neo expression with (a) internal ribosome entry site sequences (CMV-EGFP-IRES) and (b) with out internal ribosome entry site sequences and an SV40 promoter upstream of the Neo reporter gene (CMV-EGFP); a vector comprising the 5.5 kb fragment upstream of the RNP, promoter region and the CMV promoter driving GFP/Neo expression with internal ribosome entry site sequences (5.5CMV); a vector comprising 4.Okb sequence encompassing the RNP and the HPI H-γ promoters and the CMV promoter driving GFP/Neo expression with an SV40 promoter upstream of the Neo$^R$ reporter gene (4.OCMV); and a vector comprising 7.5 kb sequences of the RNP gene including exon 1 and part of intron 1, and the CMV promoter driving GFP Neo$^R$ expression with an SV40 promoter upstream of the Neo$^R$ reporter gene (7.5CMV).

Figure 24:
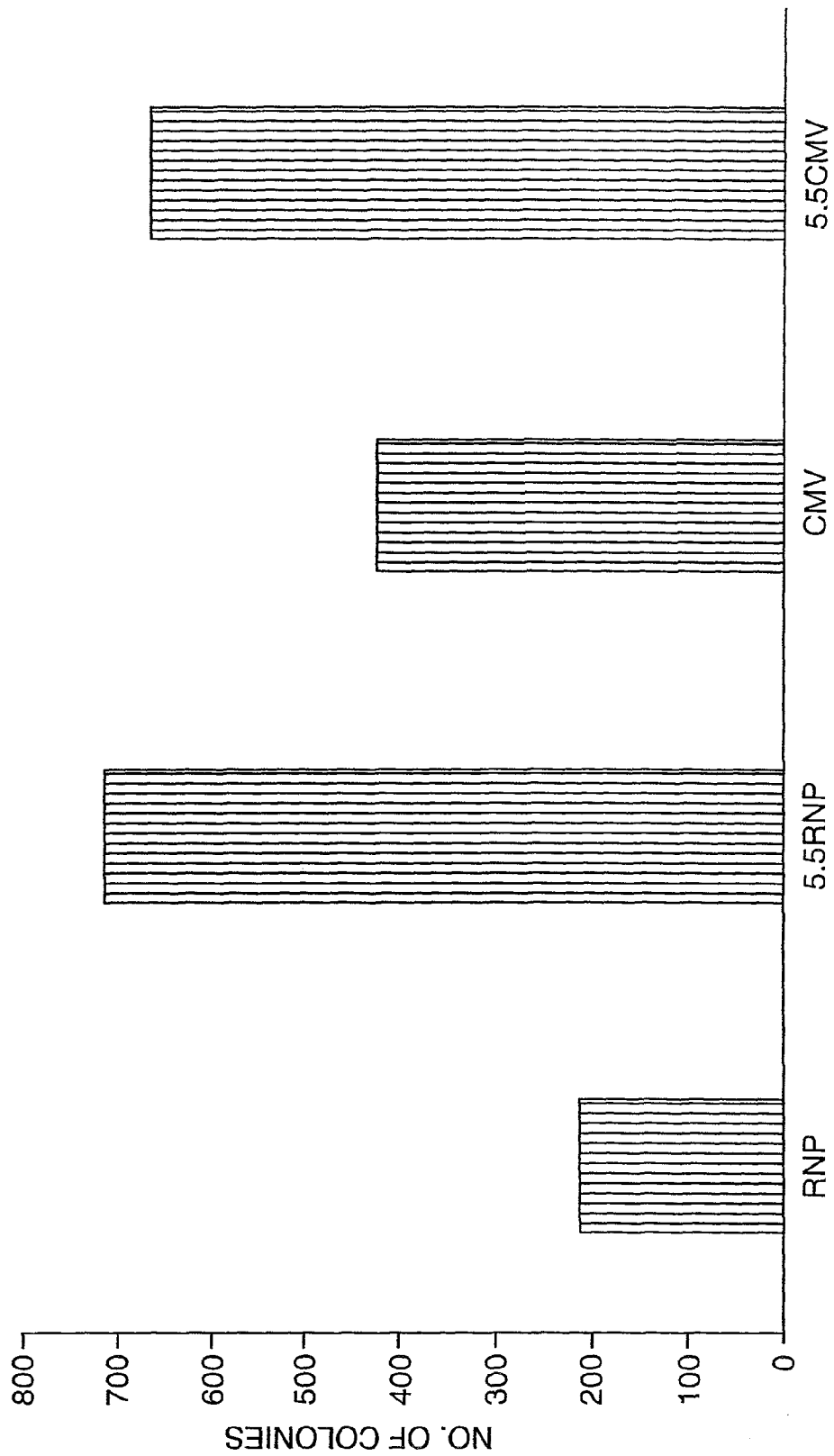

FIG. 24 shows the number of G418$^R$ colonies produced by transfecting the RNP- and CMV-constructs into CHO cells.

Figure 25:
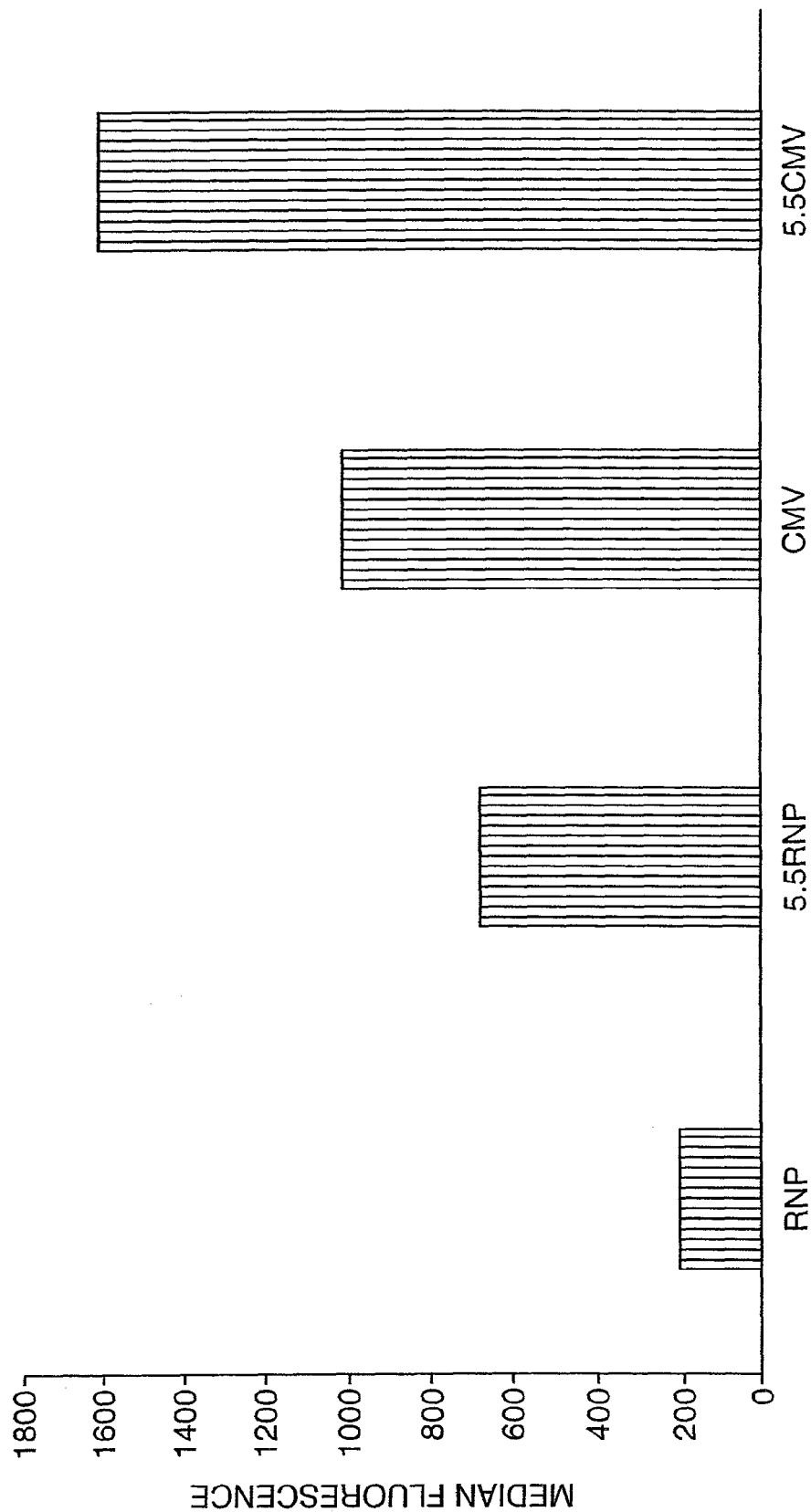

FIG. 25 shows the comparison of GFP expression in G418-selected CHO clones transfected with RNP- and CMV-constructs with and without upstream elements.

Figure 26:
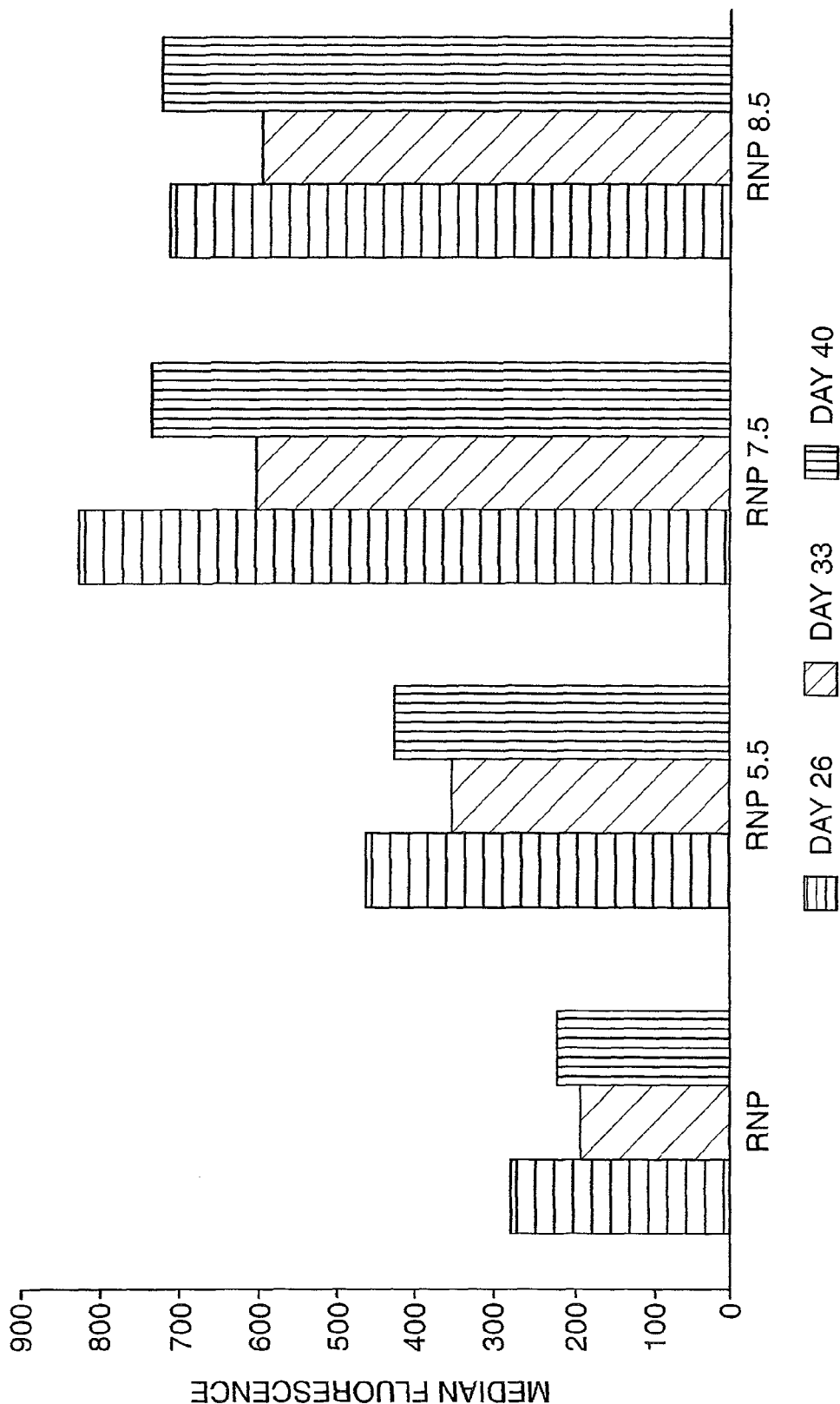

FIG. 26 shows the average median GFP fluorescence levels in G418-selected CHO clones transfected with RNP constructs with and without upstream elements over a period of 40 days.

Figure 27:
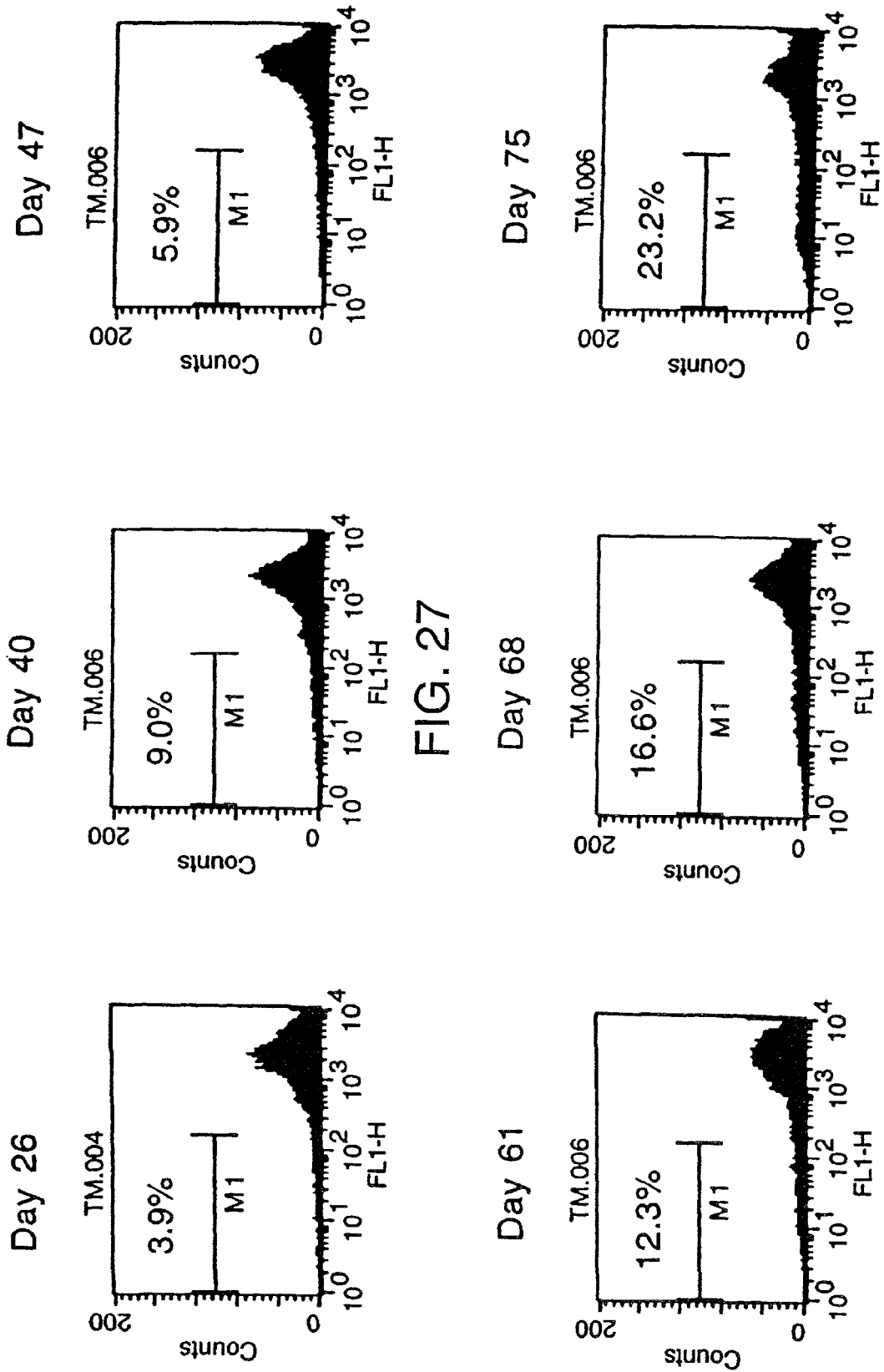

FIG. 27 shows FACS profiles of GFP expression of CMV GFP pools cultured in the absence of G418 followed over a period of 103 days.

FIG. 28 shows FACS profiles of GFP expression of 5.5 CMV-GFP pools cultured in the absence of G418 followed over a period of 103 days.

FIG. 29 shows the percentage of transfected cells expressing GFP reducing over a 68 day time-course.

FIG. 30 shows the median fluorescence of G418 selected cells transfected with CMV-constructs over a 66 day time-course.

FIG. 31 shows the percentage of positive G418 selected cells transfected with CMV-constructs over a 66 day time-course.

FIG. 32 shows the median fluorescence of G418 selected cells transfected with CMV-constructs on day 13 after transfection.

FIG. 33 shows the percentage of positive G418 selected cells transfected with CMV-constructs over a 27 day time-course.

FIG. 34 shows the colony numbers after transfection of CHO cells with various CMV-constructs.

FIG. 35 shows the dot-blot analysis of human PSMB1, PDCD2 and TBP mRNAs. The tissue distribution of mRNAs from genes within the TBP cluster using a human multiple-tissue mRNA dotBblot: each segment is loaded with a given amount of poly(A)$^+$RNA (A, shown in ng below each tissue). The dot-blot was hybridized with (B) PSMB1 cDNA, (C) a 4.7 kb genomic fragment (MA445) containing a partial PDCD2 gene and (D) TBP cDNA. A ubiquitin control probe (E) demonstrated the normalisation process had been successful and that the RNA was intact.

Figure 36A:
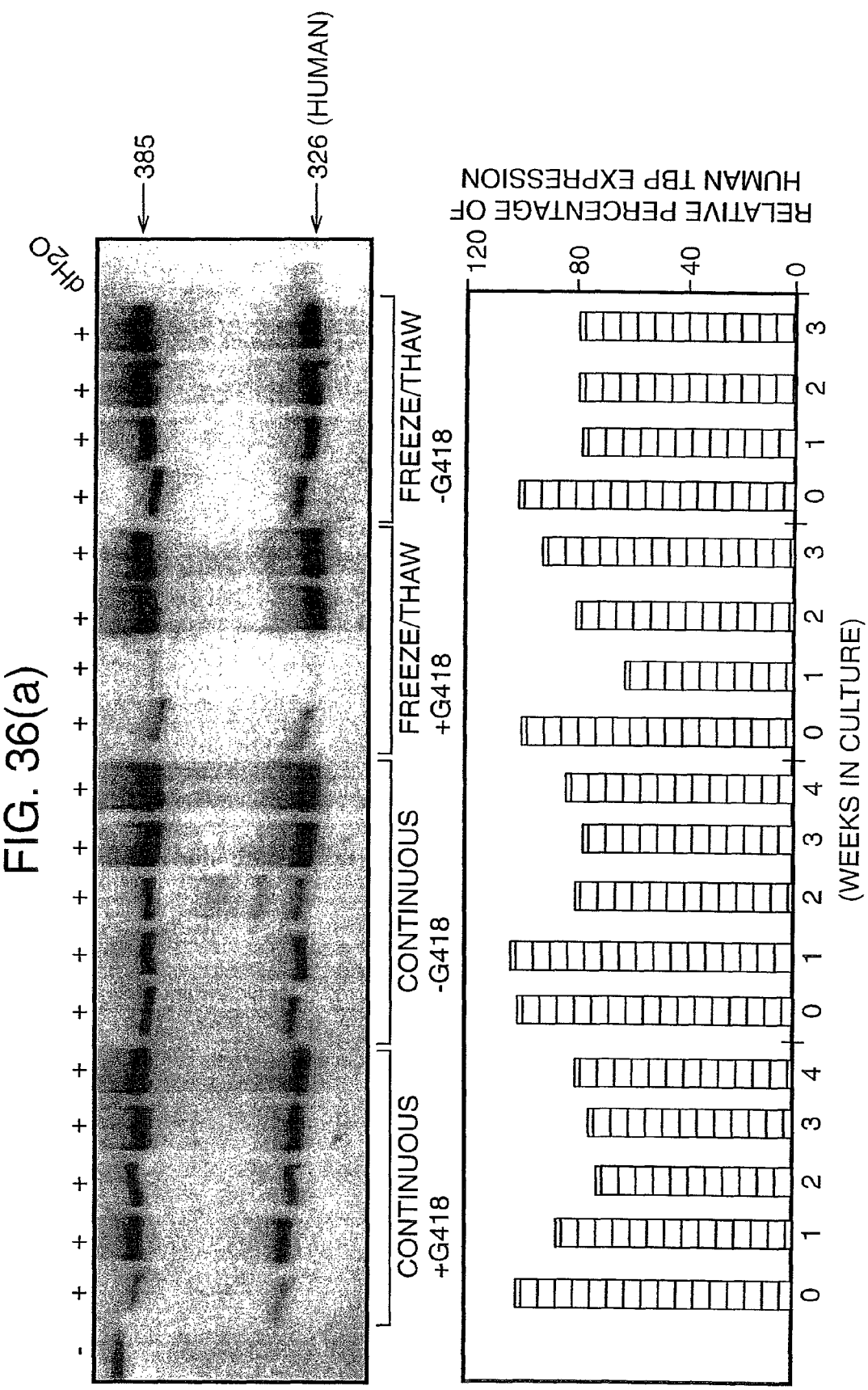
Figure 36B:
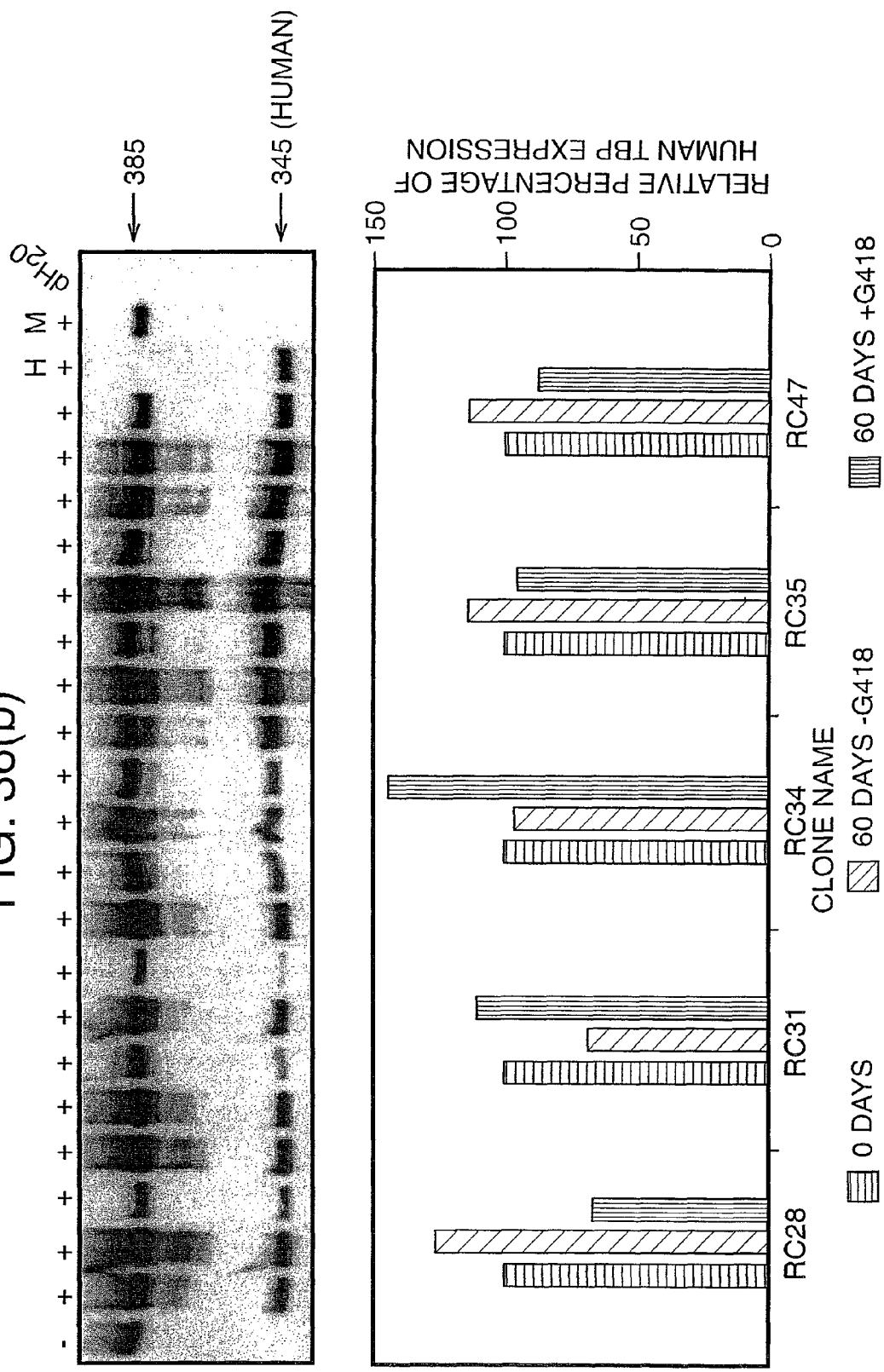

FIG. 36 shows the effect of long-term culturing on pWE-TSN clones. A number of pWE-TSN mouse L-cell clones were grown continuously for 60 generations. For freeze/thaw, clones were stored in liquid nitrogen for at least 2 days, defrosted and cultured for 1 week before RNA was harvested and the cells frozen for the next cycle. Experiments were performed with and without G418 present in the medium. TBP expression was assayed by using TB14 oligonucleotides and a human specific restriction endonuclease (as indicted by +) as described herein. All samples were analysed without the enzyme and were identical. A representative (−) sample is also shown.

Figure 37:
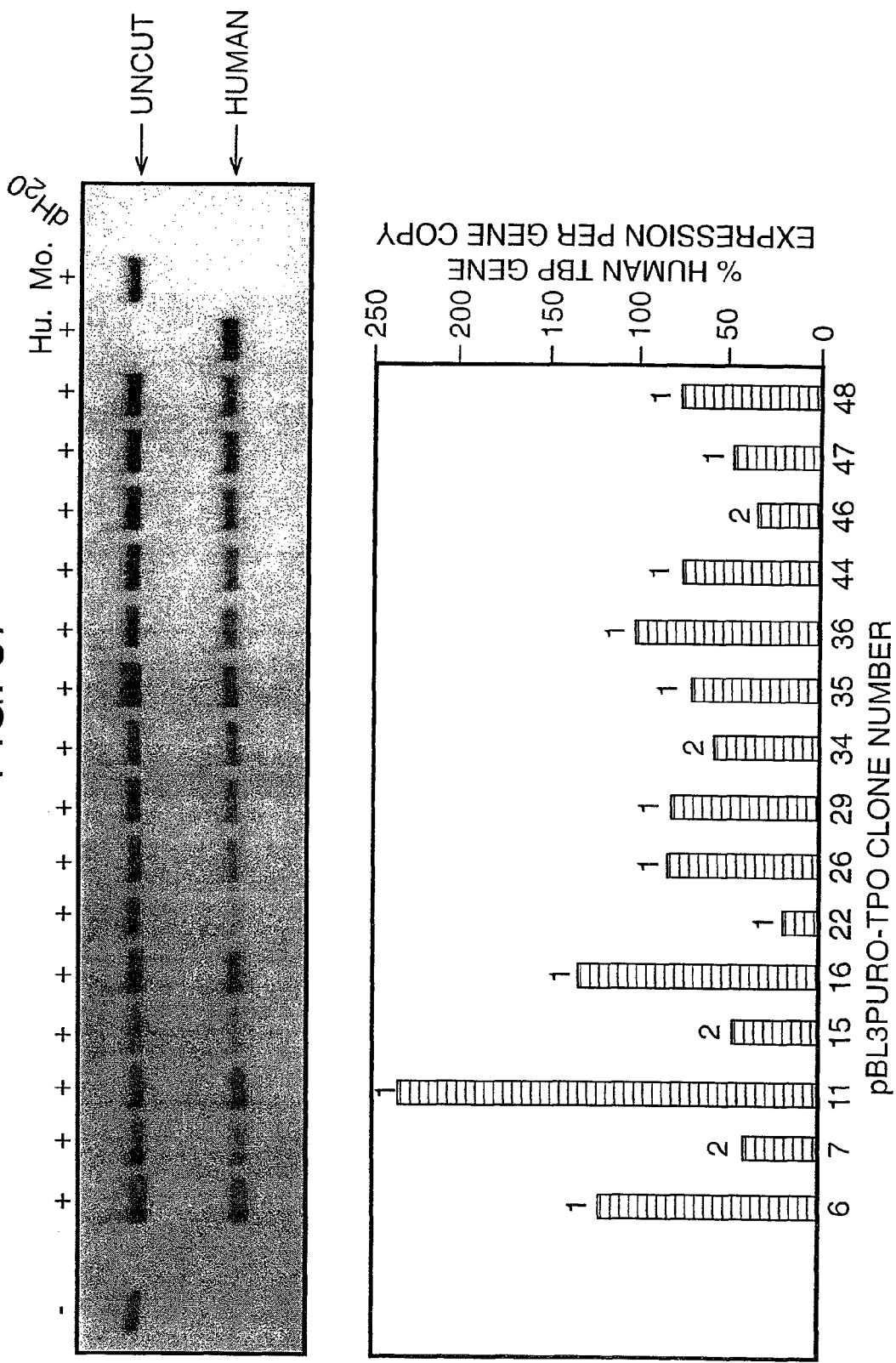

FIG. 37 shows analysis of TBP gene expression in pBL3-TPO-puro clones. The analysis for TBP gene expression was performed using the TB14 primers with total RNA isolated from mouse L-cells transfected with the pBL3-TPO-puro construct as described herein. A (+) above a lane indicates that the PCR product has been digested with a human specific enzyme, (−) indicates no digestion (control). Human (K562) and mouse (non-transgenic lung) RNA controls are also shown as well as a no-RNA control (dH$_2$0). Arrows indicate the positions of the uncut (human and mouse or mouse) and human specific products. Expression values are corrected for copy-number such that 100% expression means that a single copy of the transgene is expressing at the same level as one of the two enclogenous mouse genes. All copy-numbers varied from 1-2 and are indicated above each bar.

Figure 38B:
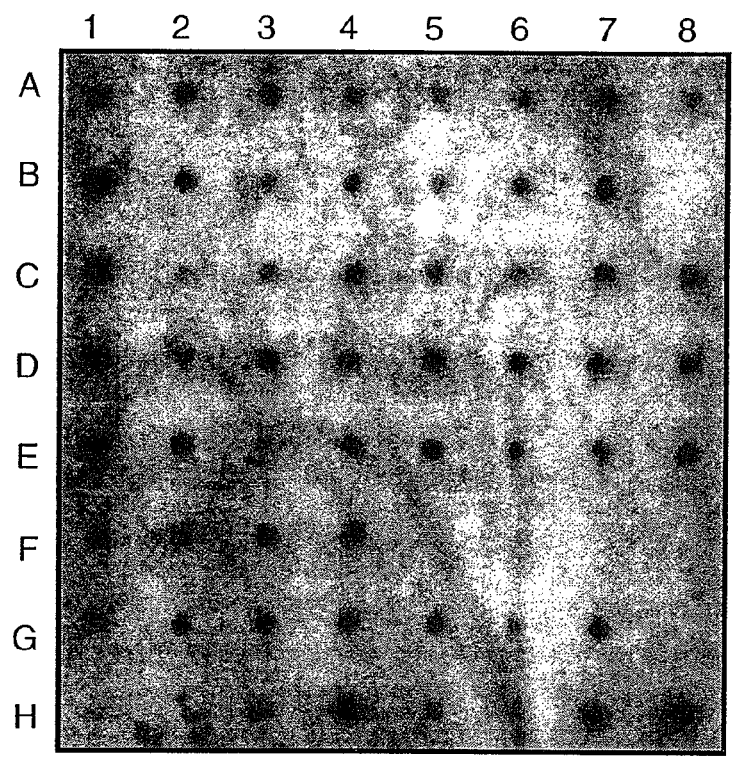
Figure 38C:
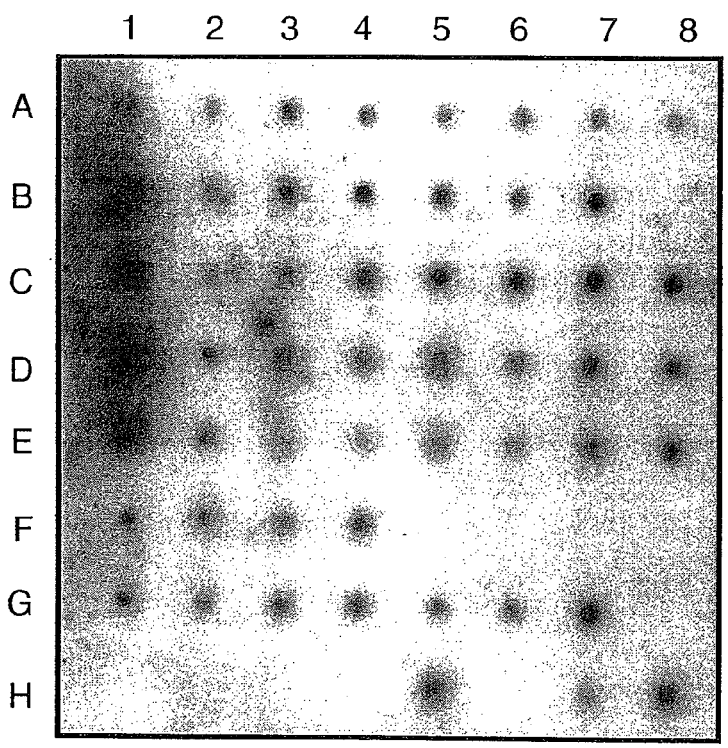

FIG. 38 shows dot-blot analysis of (B) human HPIγ mRNA expression and (C) human hnRNP A2 mRNA. Tissue distribution of HPI γ mRNA and hnRNP A2 mRNA from within the hnRNP A2 cluster using a human multiple-tissue mRNA dot-blot: each segment is loaded with a given amount of poly(A)$^+$RNA (A, shown in ng below each tissue). The blot was hybridized with (B) a 717 nt PCR fragment from the HPI γ cDNA sequence and with (C) a 1237 nt PCR probe generated by using PCR primers 5' GCTAAGCGACTGAGTC-CATG 3' (SEQ ID NO:1) and 5' CCAATCCATTGA-CAAAATGGGC 3' (SEQ ID NO:2) for the expression of hnRNP A2.

Figure 39A:
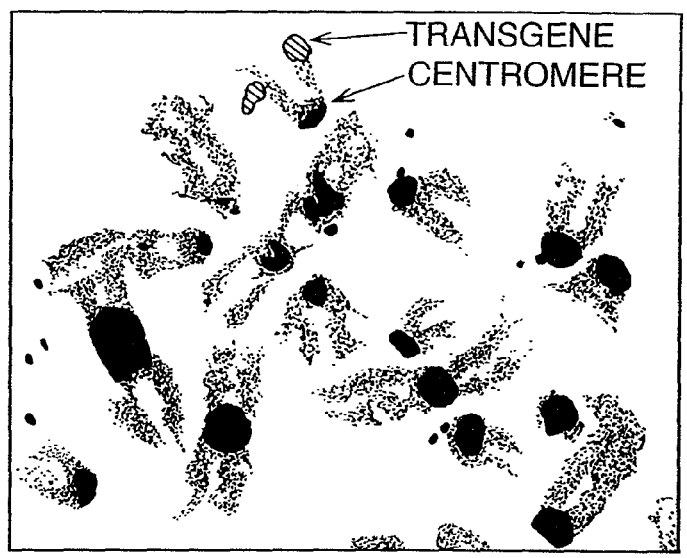
Figure 39B:
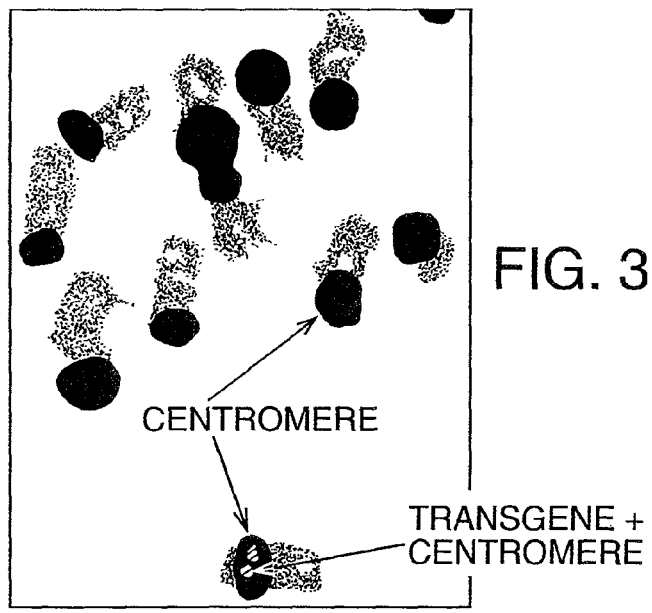
Figure 39C:
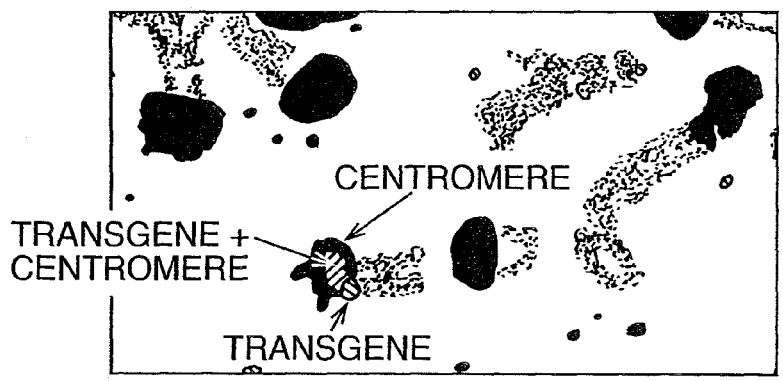

FIG. 39 shows the results of the FISH analysis of TBP transgene integrated into mouse Ltk cells demonstrating integration onto centromeric heterochromatin. (A) shows a non-centromeric integration, (B) and (C) show two separate centromeric integrations.

Figure 40:
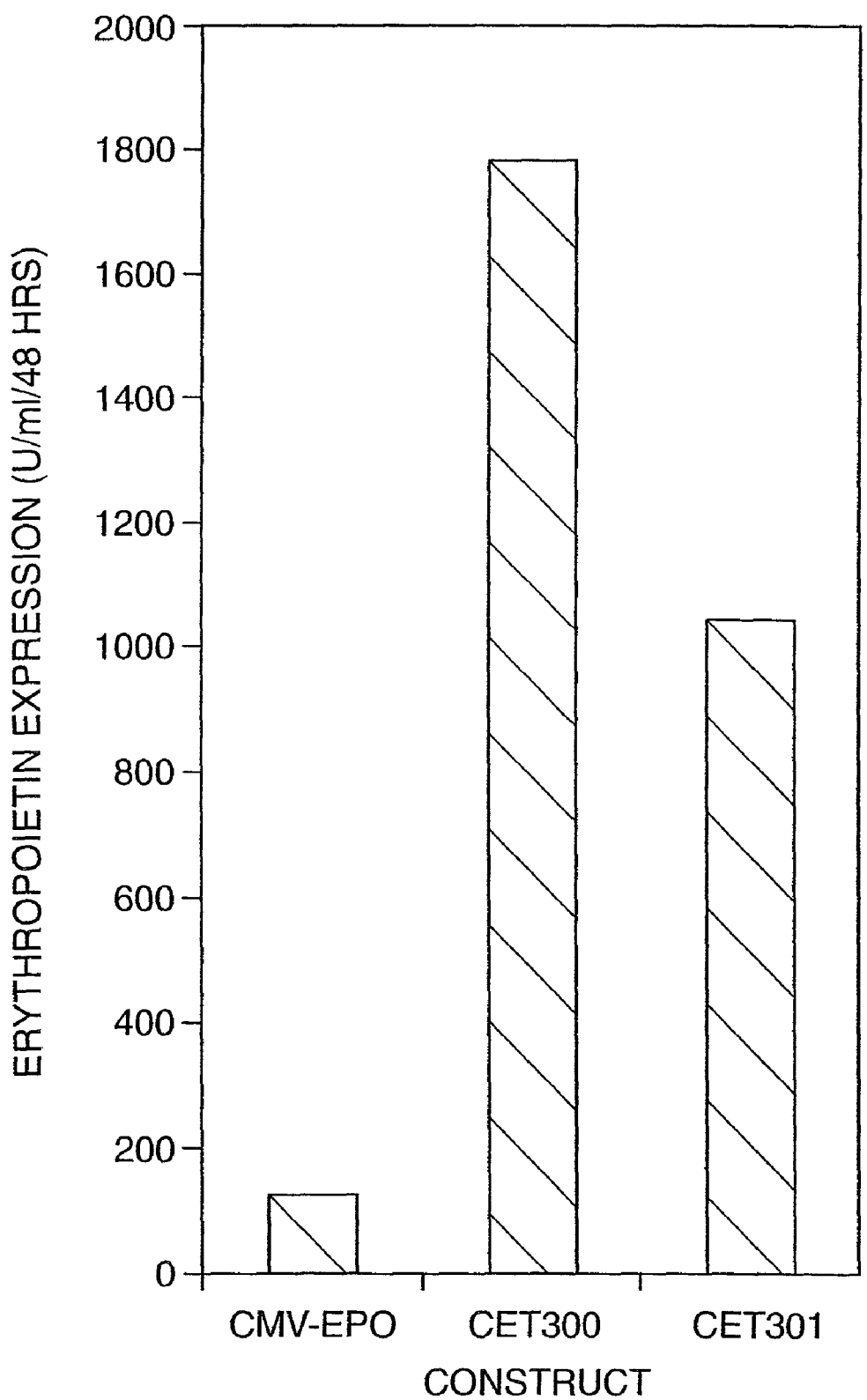
Figure 42B:
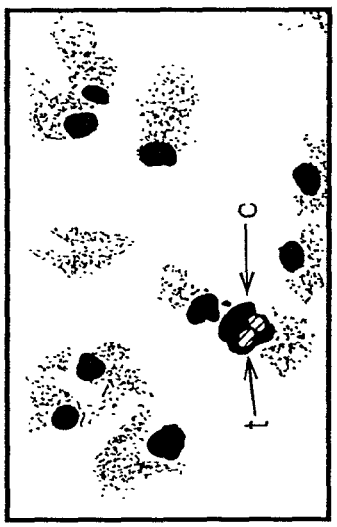
Figure 42D:
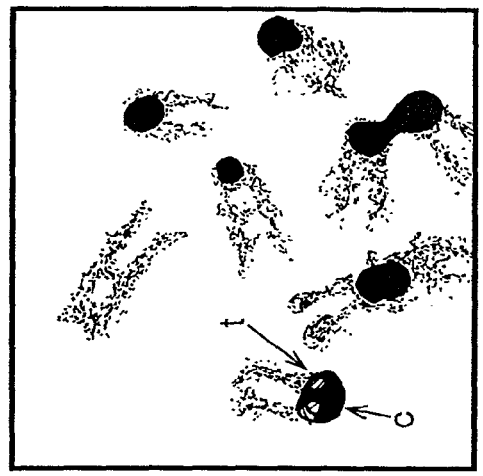
Figure 42A:
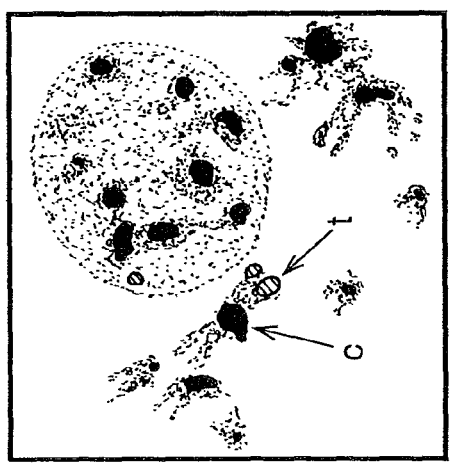
Figure 42C:
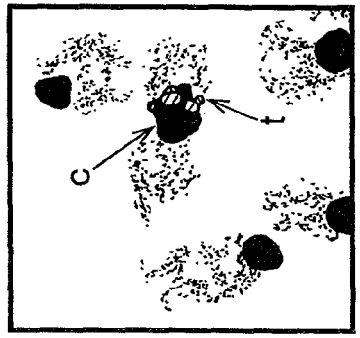

FIG. 40 shows erythropoietin (EPO) expression in CHO cell pools stably transfected with CET300 and CET301 constructs comprising the 7.5 kb sub-fragment located in the dual promoter regions between RNP and HP1H-γ, the CMV promoter and the gene encoding EPO.

FIG. 41 shows fluorescent EGFP expression of mouse Ltk cell clones transfected with 16RNP-EGFP and its relationship to copy-number. Clones F1, G6 and 13 have 16RNP-EGFP co-localized with the murine centromeric heterochromatin.

FIG. 42 shows the FISH analysis of mouse Ltk cells transfected with 16RNP-EGFP. (A) shows clone H4 having a non-centromeric integration. (B, C, & D) show clones G6, F1 and 13 having centromeric integrations, respectively, t is the 16RNP-EGFP and c is the mouse centromere.

FIG. 43 shows FACS profiles of EGFP expression of HeLa cells transfected with EBV comprising 16RNP cultured in the presence of Hygromycin B over a period of 41 days.

Figure 44:
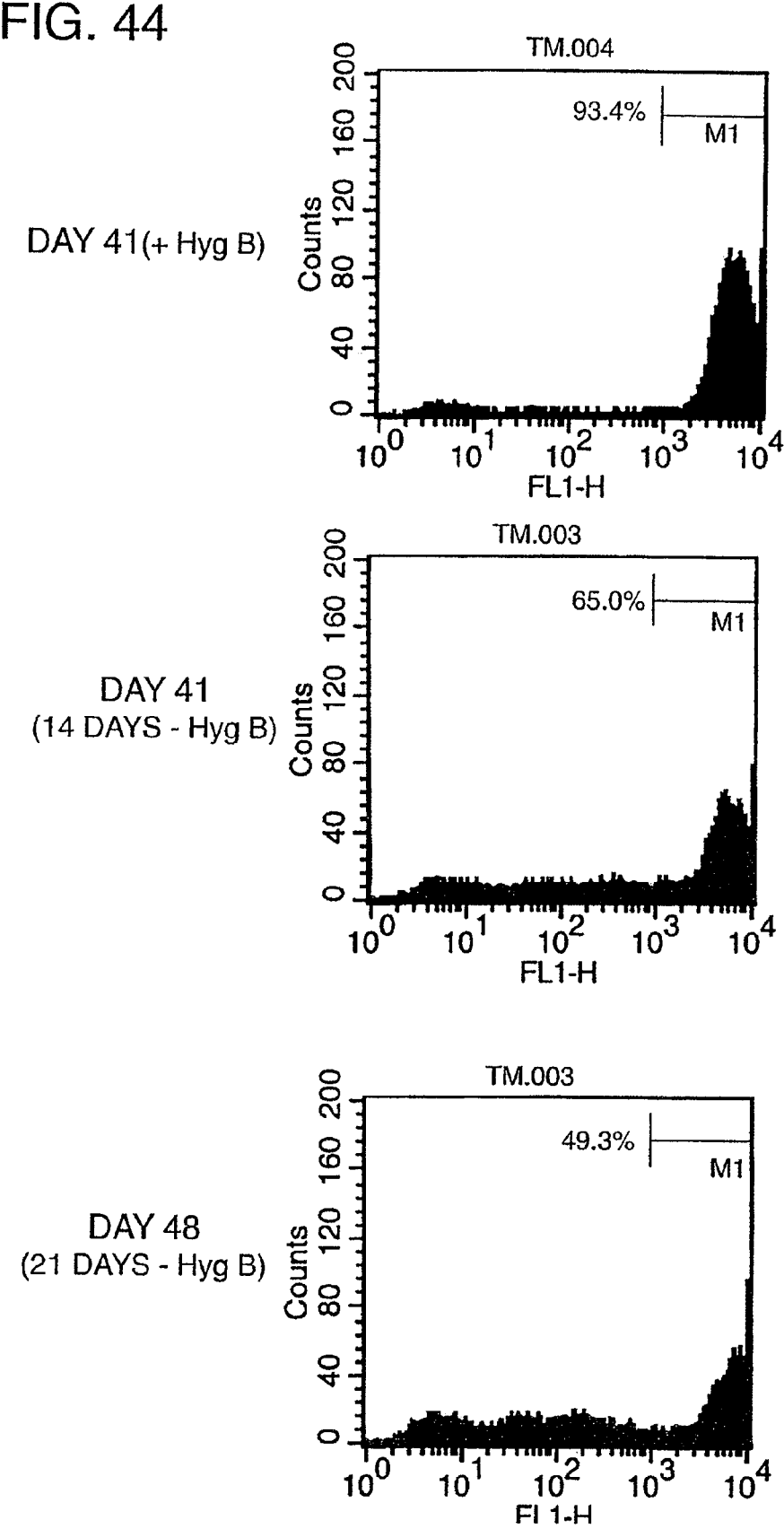

FIG. 44 shows FACS profiles of EGFP expression of HeLa cells transfected with EBV comprising 16RNP cultured in the presence of Hygromycin B throughout and when Hygromycin B is removed from day 27.

Figure 45:
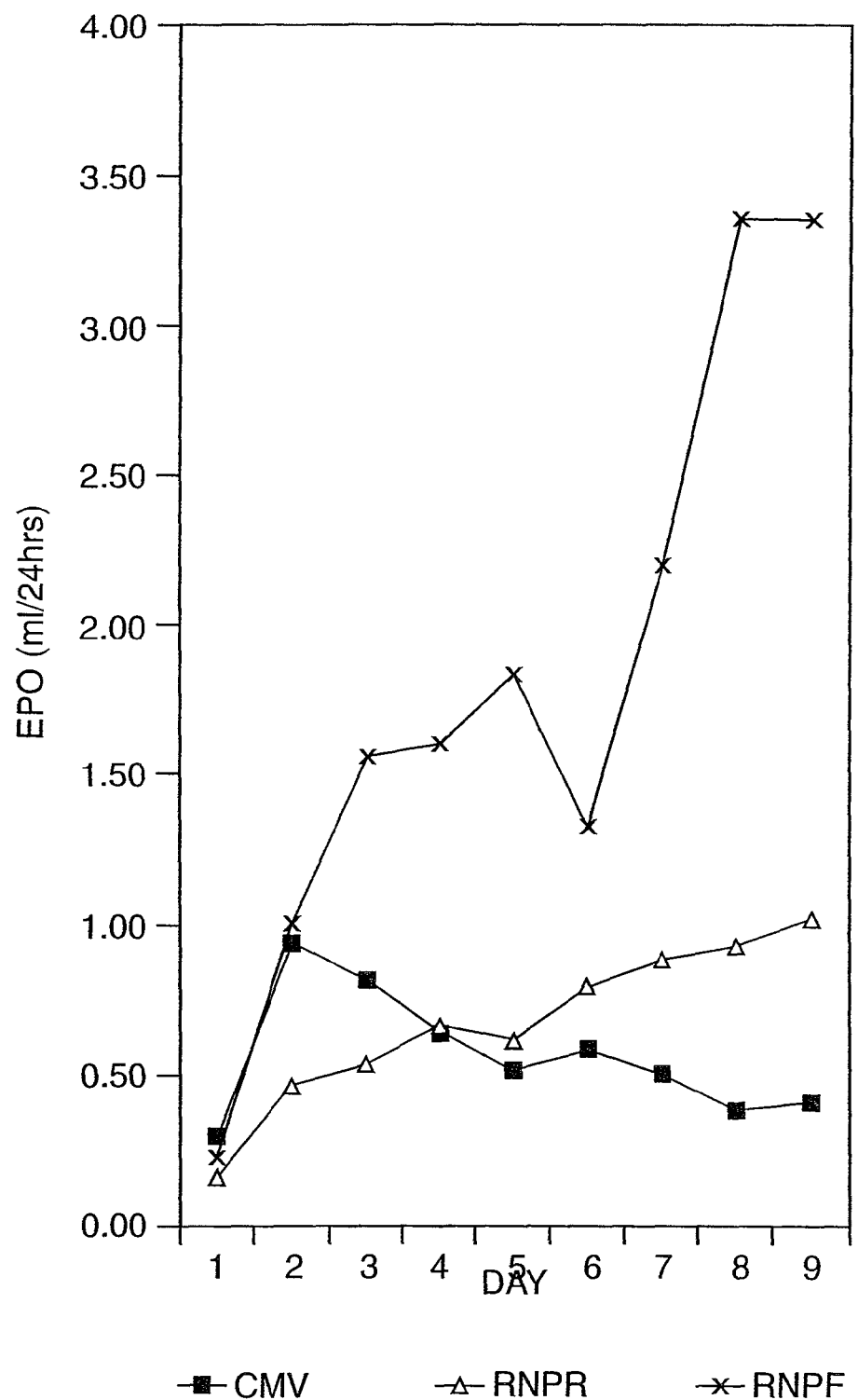

FIG. 45 shows EPO production in cells transiently transfected with CET300, CET301 and CMV-EPO.

Figure 46:
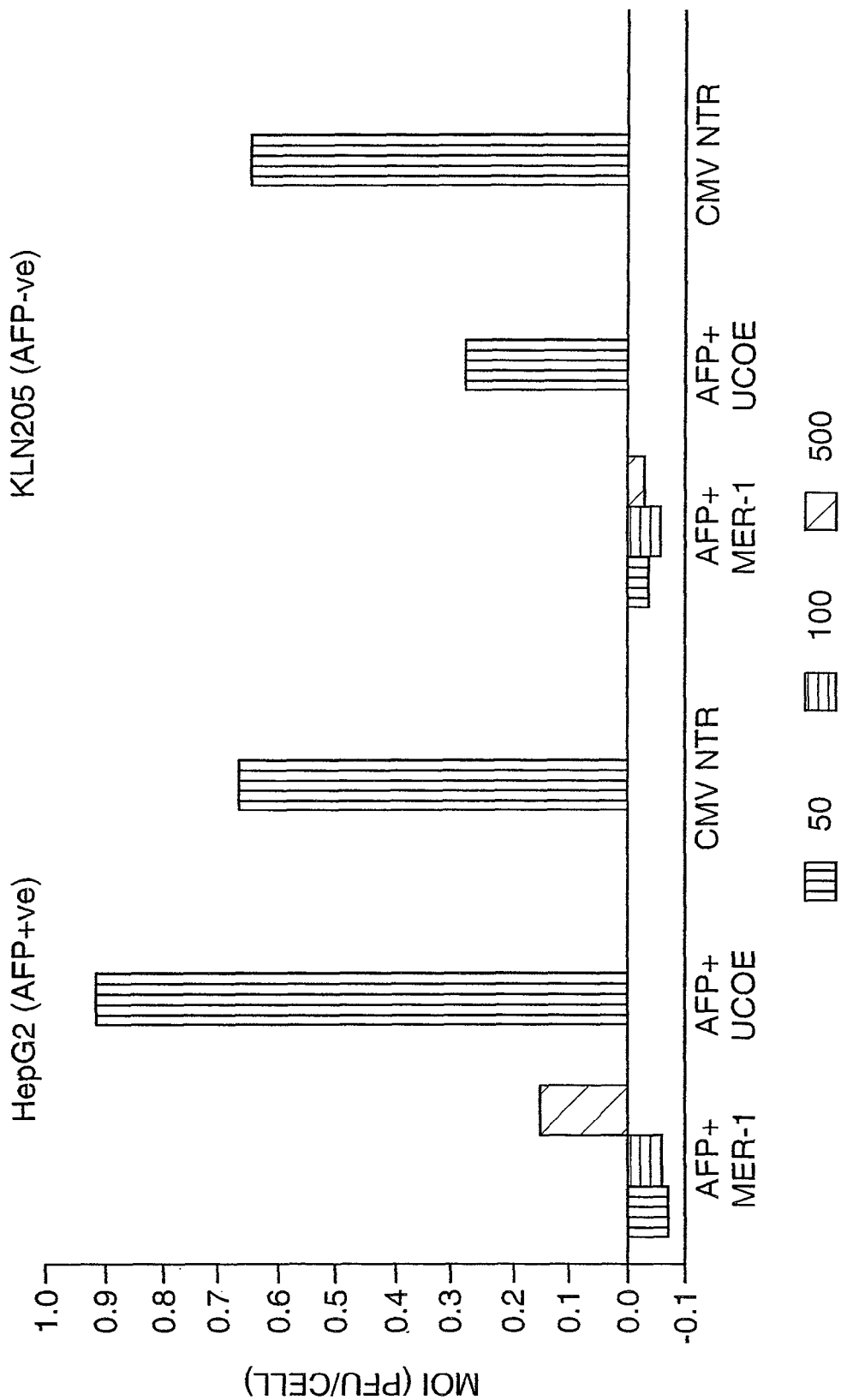

FIG. 46 shows results of ELISA detecting NTR expression for various AFP constructs in HepG2 (AFP+ve) and KLN20S (AFP-ve) cells.

FIG. 47 shows NTR expression in HepG2 tumours and host mouse livers following intratumoural injection with CTL102/CTL208.

Figure 48:
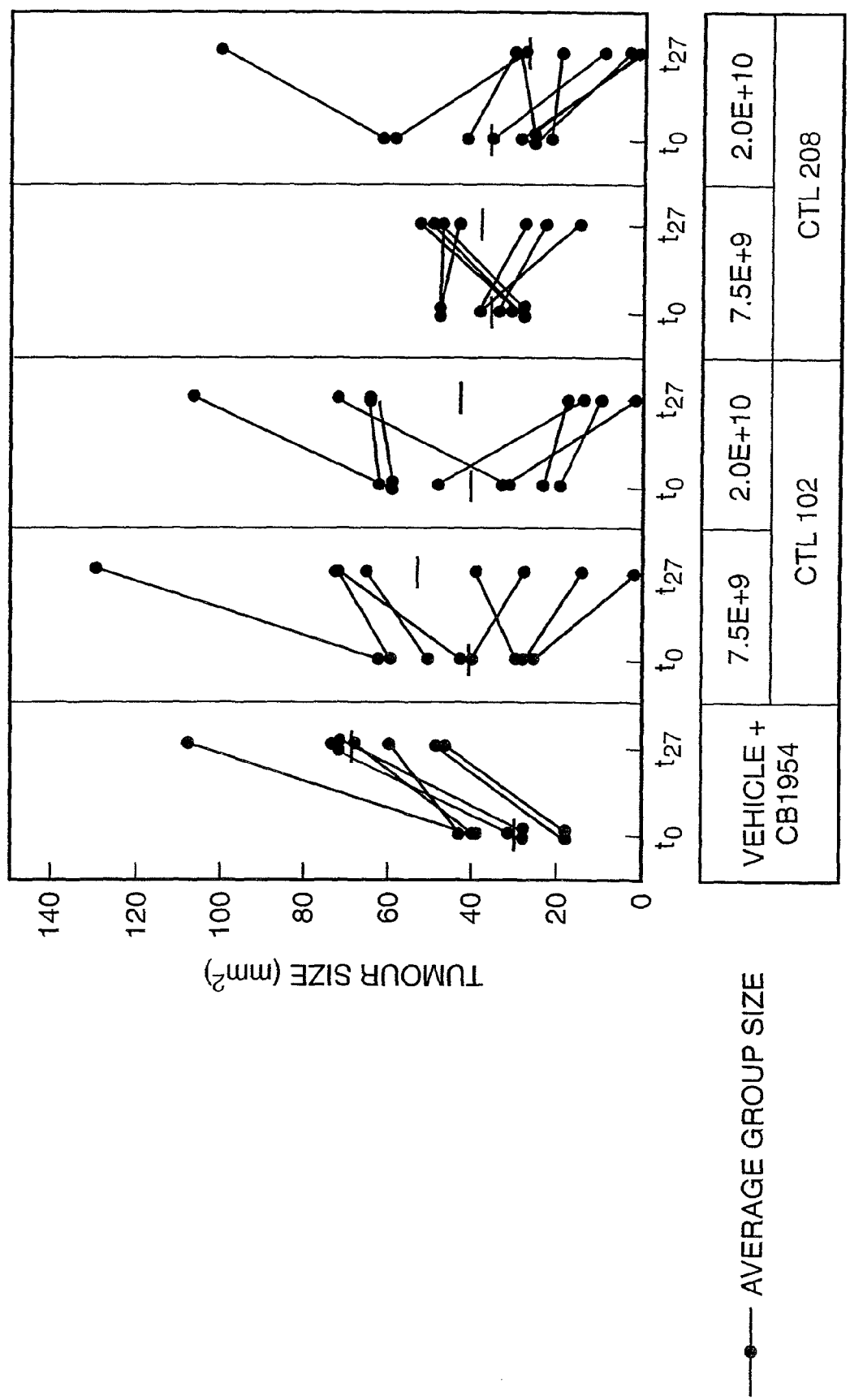

FIG. 48 shows growth inhibition of HepG2 tumours following intratumoural injection with CTL102/CTL208 and CB1954 administration.

Figure 49:
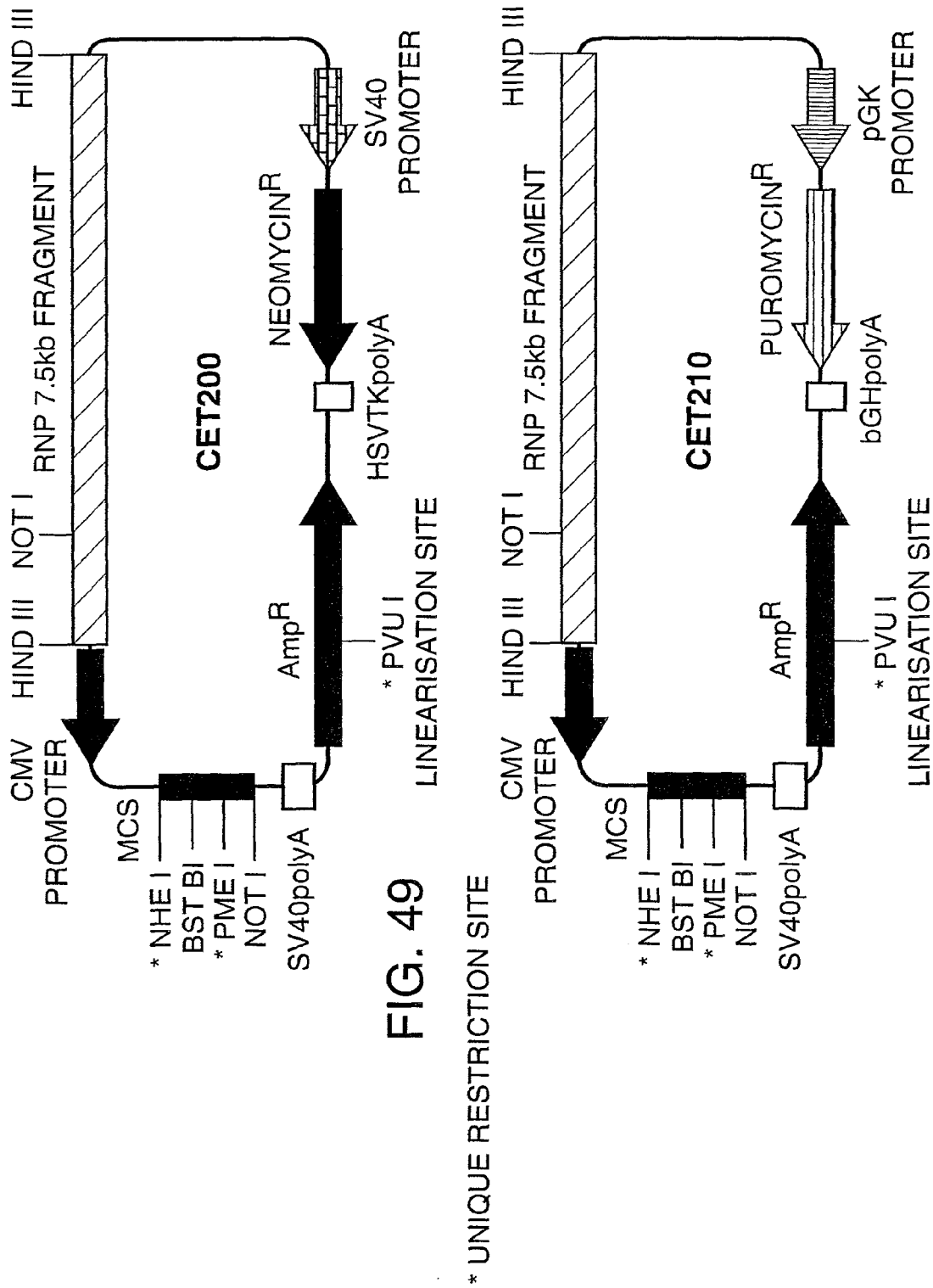
Figure 52B:
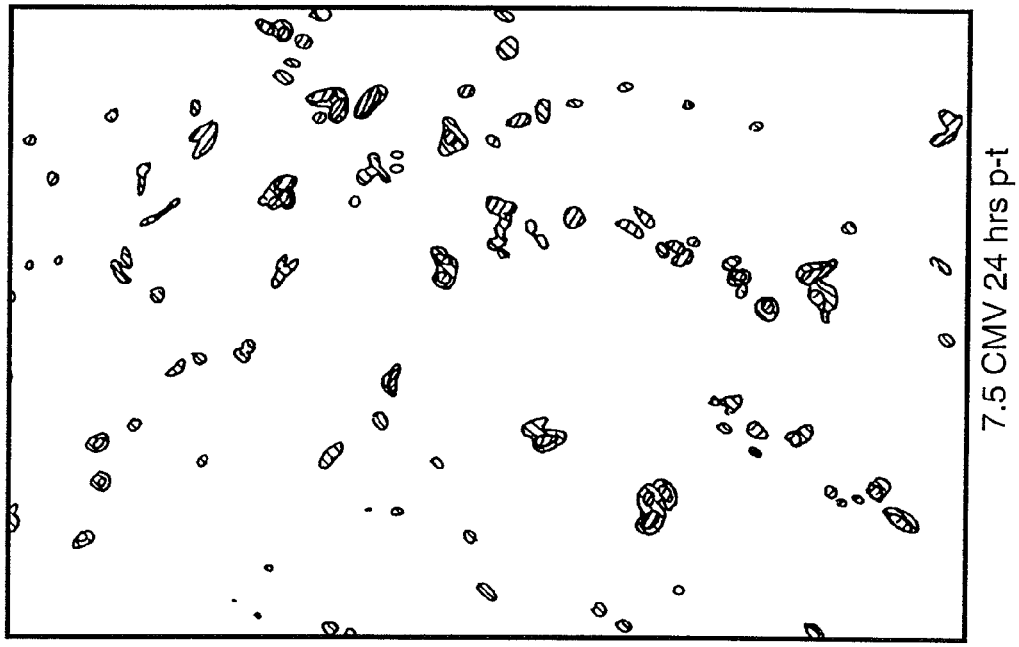
Figure 52A:
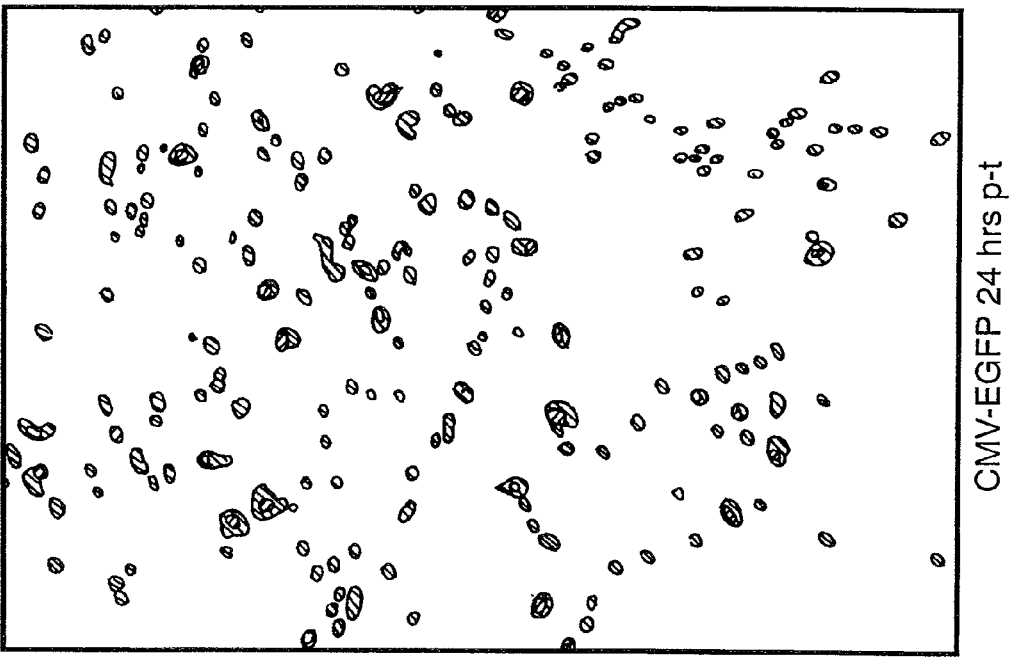
Figure 52D:
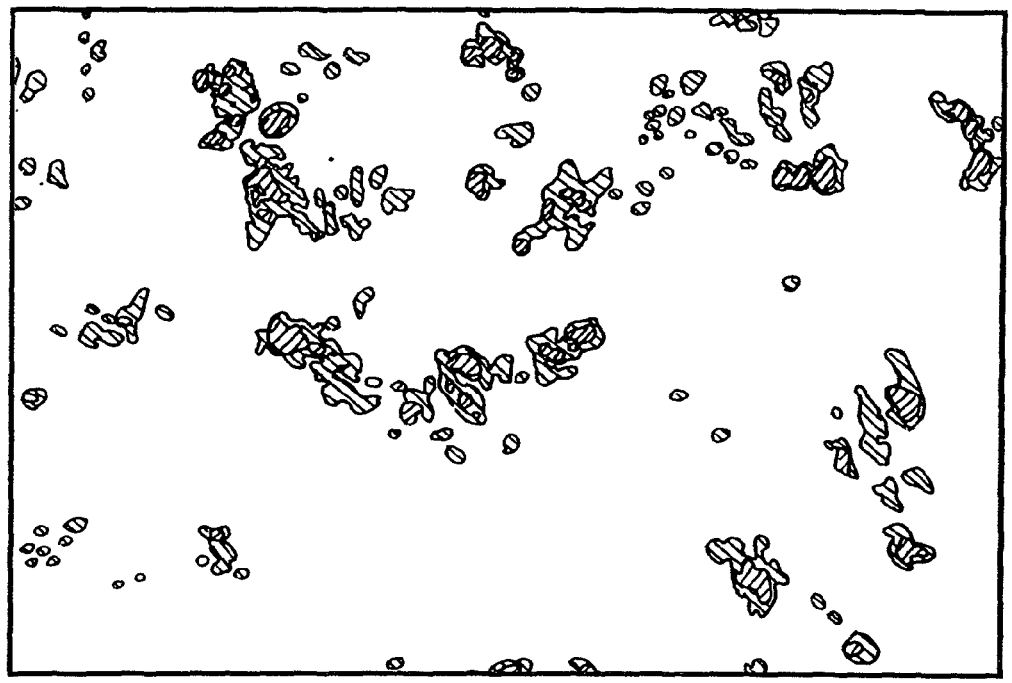
Figure 52C:
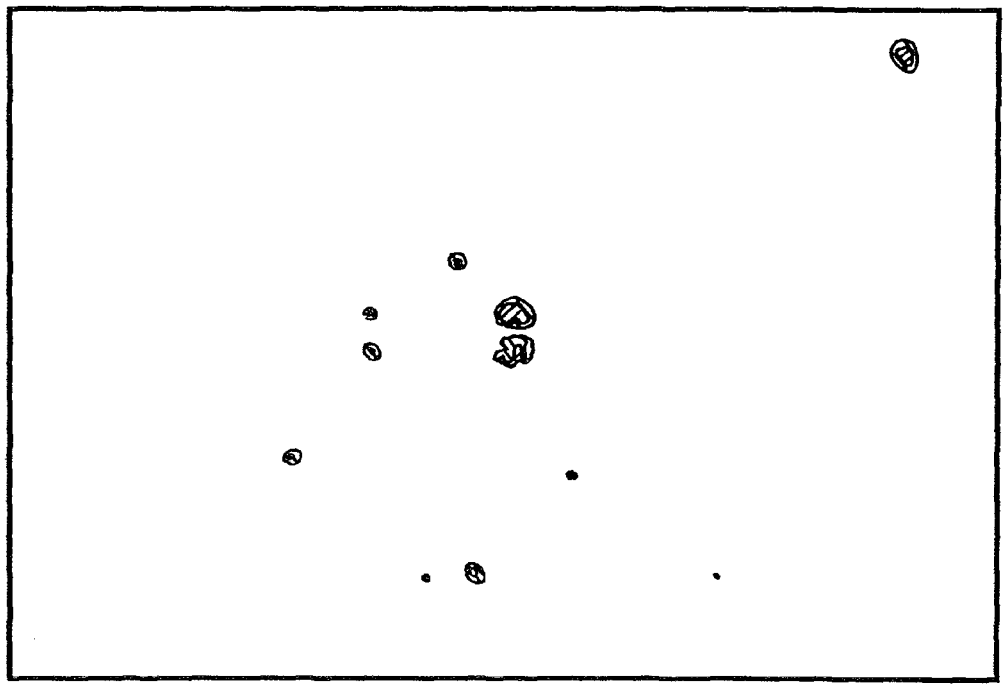

FIG. 49 shows schematically the structure of vectors CET200 and CET210.

FIG. 50 shows the constructs generated and fragments used in comparison to the hnRNP A2 endogenous genomic locus.

FIG. 51 shows a graph of the FACS analysis with median fluorescence of HeLa populations transiently transfected with non-replicating plasmid.

FIG. 52 shows representative low magnification field of views of HeLa cell populations transiently transfected with non-replicating plasmid.

EXAMPLES

Materials and Methods

Library Screening

Genomic clones spanning the human TBP and hnRNPA2 loci were isolated from a P1-derived artificial chromosome (pCYPAC 2) library (CING-1; Ioannou et al., 1994). Screening was by polymerase chain reaction (PCR) of bacterial lysates.

Primers for TBP

Primers were designed using the partial genomic sequence described by Chalutet et al., (1995) and were as follows: TB3 [5'ATGTGACAACAGTGCATGAACTGGGAGTGG3'] (SEQ ID NO:3) (−605) and TB4 [5'CACTTCCTGTGTTTC-CATAGGTAAGGAGGG3'] (SEQ ID NOA) (119) hybridise to the 5' region (5'UTR) of the TBP gene and give rise to a 486 bp PCR product from the human gene only (see results). The numbers in parenthesis are with respect to the mRNA CAP site defined by Peterson et al., (1990).

T85 [5'GGTGGTGTTGTGAGAAGATGGATGT-TGAGG3'] (SEQ ID NO:5) (1343) and TB6 [5'GCAATACTGGAGAGGTGGAATGTGTCTGGC3'] (SEQ ID NO:6) (1785) amplify a region from the 3'UTR and produce a 415 bp product from both human and mouse DNA due to significant sequence homology in this region. The numbers in parenthesis are with respect to the cDNA sequence defined by Peterson et al., (1990).

Primers for hnRNP A2

Primers for hnRNP A2 were designed from the genomic sequence described by Biamonti et al., (1994).

Hn1 [5'ATTTCAAACTGCGCGACGTTTCTCAC-CGC3'] (SEQ ID NO:7) (−309) and Hn2 [5'CAT-TGATTTCAAACCCGTTACCTCC3'] (SEQ ID NO:8) (199) in the 5' UTR to give a PCR product of 508 bp. Hn3 [5' GGAAACTTTGGTGGTAGCAGGAACATGG3'] (SEQ ID NO:9) (7568) and Hn4 [5'ATCCATCCAGTCTTTTAAAA-CAAGCAG3'] (SEQ ID NO: 10) (8176) amplify a region in the penultimate exon (number 10) to give a PCR product of 607 bp. The numbers in parentheses are with respect to the transcription start point defined by Biamonti et al. (1994).

PCR Protocol

PCR was carried out using 1 μl pooled clone material in a reaction containing 25 mM each dATP, dGTP, dCTP, dTTP, 1× reaction buffer (50 mM Tris-HCl [pH 16 mM $(NH_4)_2SO_4$' 3.5 mM$_2$, 150 μg/ml bovine serum albumin), 2.5 units Taq Supreme polymerase (Fermentas) and 1 μM each primer in a total reaction volume of 25 μl. Cycling conditions were: 4 cycles of 94° C. for 1 minute, 62° C. for 1 minute, 72° C. for 1 minute, followed by 30 cycles of 94° C. for 1 minute, 58° C. for 1 minute, 72° C. for 1 minute. Positively identified clones were grown in T-Broth (12 g tryptone, 24 g yeast extract (both Difco), 23.1 g $KH_2PO_4$ 125.4 g $K_2HPO_4$, 0.4% glycerol per 1 liter distilled water; Tartof and Hobbs, 1987) containing 30 μ/ml kanamycin. Permanent stocks of the bacteria were prepared by freezing individual suspensions in 1× storage, buffer (3.6 mM $K_2HPO_4$, 1.3 mM 2 $PO_4$, 2.0 sodium citrate, 1 mM $MgSO_4$, 4.4% glycerol) at −80° C.

CYPAC 2 DNA Isolation

Plasmid DNA was isolated using a modified alkaline lysis method (Birnboirn and Doly, 1979), as follows. Baffled 2 liter glass flasks containing 1 liter T-broth were inoculated with a single bacterial colony and incubated at 37° C. for 16 hours with constant agitation. Bacteria were harvested by centrifugation in a Beckman 16 centrifuge at 4200 rpm (5020× g, similarly for all subsequent steps) for 10 minutes. Pellets were vortexed, re suspended in 15 mM Tris[pH 8.0], 10 mM EDTA, 10 [μg/ml RNaseA (200 ml) and incubated at room temperature for 15 minutes. Lysis solution (0.2M NaOH, 1% SDS; 200 ml) was added with gentle mixing for 2 minutes, followed by the addition of 200 ml neutralisation solution QM potassium acetate [pH 5.5] with gentle mixing for a further 5 minutes. Bacterial debris was allowed to precipitate for 1 hour at 4° C. and then removed by centrifugation for 15 and filtration of the supernatant through sterile gauze. Isopropanol (400 ml; 40% final concentration) was added to precipitate the plasmid DNA at room temperature for 1 hour. After centrifugation for 15 minutes and washing of the pellet in 70% ethanol, the DNA was re suspended in a 4 ml solution of 1×THE (50 mM Tris-HCl [pH 7.5], 5 mM EDTA, 100 mM NaCl), 0.1% SDS and 0.5 mg/ml Proteinase-K (Cambio) to remove residual proteins. Following incubation at 55° C. for 1 hour and subsequent phenol:chloroform (1:1 v/v) extraction, the DNA was precipitated with 1 volume of 100% ethanol or isopropanol and spooled into 2 ml TE buffer (10 mM Tris-HCl [pH8.0], 1 mM EDTA). Yields of 50 p μg/ml were routinely obtained.

Restriction Enzyme Mapping

Restriction enzyme mapping was carried out by hybridising oligonucleotides derived from both pCYPAC-2 and TBP gene sequences to Southern blots (Southern, 1975) of restriction enzyme digested cloned DNA as described above. Oligonucleotides which hybridise to pCYPAC-2 sequences just proximal to the Bam HI site into which genomic fragments are cloned were used, the sequences of which were: EY2:[5'-TGCGGCCGCTAATACGACTCACTATAGG-3'] (SEQ ID NO:11) 189:[5'(-GGCCAGGCGGCCGCCAGGCCTAC-CCACTAGTCAATTCGGGA 3'(SEQ ID NO: 12) Excision of any genomic insert from pCYPAC-2 with NotI means that the released fragment will retain a small amount of plasmid sequence on each side. On the EY2 side this will be 30 bp with the majority of the EY2 sequence within the excised fragment. Hybridisation of this oligonucleoticle to NotI digested pCYPAC-2 clones should therefore, highlight the released genomic band on Southern blot analysis. At the 189 side, the excised fragment will contain 39 bp of plasmid sequence and the majority of the 189 oligonucleoticle sequence is 3' to the NotI site, within pCYPAC-2. Therefore, this oligonucleotide will hybridise to the vector on NotI digests of pCYPAC-2 clones. Approximately 100 ng plasmid DNA was subjected to restriction endonuclease digestion using manufacturers recommended conditions (Fermentas), and subsequently electrophoresed on 0.7% agarose gels in 0.5×TAE buffer (20 mM Tris Acetate (PH 8.0], 1 mM EDTA, 0.5 μg/ml ethidium bromide) or on pulsed field gels. Pulsed Field Gel Electrophoresis (PFGE) was carried out on a CHEF-DRII system (Biorad) on 1% PFGE agarose (FMC)/0.5×TAE gels at 6V/cm for 14 hours with switch times from 1 second to 30 seconds. Identical conditions were used for all PFCE analysis throughout this study. Gels were stained in 1 µg/ml ethidium bromide solution before being photographed under ultraviolet light.

In preparation for Southern blot analysis, the DNA was depurinated by first exposing the agarose gels to 254 nm ultraviolet light (180,000 µJ/cm$^2$ in a UVP crosslinker, UVP) and then subsequently denaturing by soaking in 0.5M NaOH, 1.5M NaCl for 40 minutes with a change of solution after 20 minutes. The DNA was transferred to HYBOND-N nylon membrane (Amersham) by capillary action in a fresh volume of denaturation solution for 16 hours. Cros slinking of the nucleic acids to the nylon was achieved by exposure to 254 nm ultraviolet light at 120,000 µJ/cm$^2$. Membranes were neutralised in 0.5M Tris-HCl [pH 7.5], 1.5M NaCl for 20 minutes and rinsed in 2×SSC before use. (1×SSC is 150 mM NaCl, 15 mM sodium citrate, [pH7.0]).

Oligonucleoticle probes were 5' end-labelled with T4 polynucleotide kinase and $^{32}$P-γ ATP to enable detection of specific fragments on Southern blots. Each experiment employed 100 ng of oligonucleotide labelled in a reaction containing 2µ$^{32}$P-γ ATP (>4000 Ci/mmol; 10 mCi/ml, Amersham) and 10 units T4 polynucleotide kinase (Fermentas) in the manufacturers specified buffer. After incubation at 37° C. for 2 unincorporated nucleotides were removed by chromatography on Sephadex G50 columns (Pharmacia) equilibrated with water. End-labelled probes were typically labelled to a specific activity >1×10$^8$ dpm/µg.

Hybridisation was carried with membranes sandwiched between nylon meshes inside glass bottles (Hybaid) containing 25 ml pre-warmed hybridisation mix (1 mM [pH8.0], 0.25M Na$_2$HPO$_4$[PH 7.2], 7% SDS; Church and Gilbert, 1984) and 100 µg/ml denatured sheared salmon testis DNA. After pre-hybridisation at 65° C. for 1 hour, the solution was decanted and replaced with an identical solution containing the labelled probe. Optimal hybridisation temperature was determined experimentally and found to be 20° C. below the $T_m$ for the oligonucleotide in TE buffer, calculated as $T_m$ 59.9+41 [% GC]−[675/primer length]). After 16 hours hybridisation membranes were removed and washed with three, 2 minutes washes of 6×SSC, 0.1% SDS followed by exposure to x-ray film (BioMAX, Kodak).

DNA Constructs

A 44 kb genomic DNA region spanning the TBP gene with 12 kb of both 5' and 3' flanking sequences, was derived from the pCP2pCYPAC-2 clone (see FIG. 9) as a NotI fragment. This was cloned into the cosmid vector pWE15 (Clontech) to generate pWE-TSN (FIG. 9). The vector exchange was necessary as the pCYPAC-2 plasmid does not contain a selectable marker for eukaryotic cell transfection studies. Digestion of pCP2-TNN with NotI liberates a 44 kb fragment extending from the 5' end of the genomic insert to the NotI site present in the genomic sequence located 12 kb downstream of the last exon of TBP (see FIG. 9). In addition, fragments containing the remaining 20 kb of 3' flanking sequence in this clone and the pCYPAC-2 vector are produced. The ligation reaction was performed using approximately 1 µg of NotI digested pCP2-TNN and 200 ng similarly cut pWE15 in a 10 µl reaction using conditions as described above. After heat inactivation of the T4 DNA ligase, the complete ligation mix was packaged into infectious lambda>phage particles with Gigapack Gold III (Stratagene). Recombinant bacteriophage were stored in SM buffer (500µ of 50 mM Tris-HCl, 100 mM NaCl, 8 mM MgSO$_4$ 0.01% (w/v) gelatine, 2% chloroform). Infection was carried out as follows: 5 ml of an overnight culture of E. coli DH a was centrifuged (3000×g, 5 minutes) and the bacteria resuspended in 2.5 ml of 10 mM MgCl$_2$. Equal volumes of packaged material and E. coli were mixed and incubated at 25° C. for 15 minutes after which time 200 µl was added and the mixture incubated at 37° C. for a further 45 minutes. The suspension was plated on LB ampicillin agar plates and single colonies analysed as mini preparations the following day. Large amounts of pWE were prepared from 1 liter cultures as for pCYPAC-2 clones.

PCYPAC-2 DNA Sub-Cloning Methods

The following procedure was used in order to sub-clone small (less than 10 kb) restriction enzyme fragments derived from pCYPAC-2 clones. DNA was restriction enzyme digested and electrophoresed on 0.6% low melting point agarose gels (FMC) with all ultraviolet photography carried out at a wavelength of 365 nm to minimise nicking of ethidium bromide stained DNA (Hartman, 1991). The gel area containing fragments of the desired range of sizes was excised from the gel, melted at 68° C. for 10 minutes and allowed to equilibrate to 37° C. for a further 5 minutes. The plasmid vector pBluescriptKS(+) (Stratagene) was similarly restriction enzyme digested to give compatible termini with the pCYPAC-2 derived DNA, treated with 10 units calf intestinal phosphatase (Fermentas) for 1 hour to minimise self and purified by phenol:chloroform (1:1 v/v) extraction followed by ethanol precipitation. Molten gel slices were mixed with 50 ng of this vector preparation giving a molar excess of 4:1 fragment to vector molecules. T4 DNA Ligase (10 units; Fermentas) was added along with the specified buffer and the mixture incubated at 16° C. for 16 hours after which time the enzyme was heat inactivated (65° C. for 20 minutes) to improve transformation efficiency (Michelsen, 1995). Preparation of calcium chloride competent DH5 oc E. coli and subsequent transformation was performed using established procedures (Sambrook et al., 1989). Transformation was achieved by melting and equilibrating the ligation mixture to 37° C. before the addition of 100 µl competent cells maintaining a final agarose concentration of no more than 0.02%. Bacteria were incubated on ice for 2 hours followed by heat shock at 37° C. for 5 minutes and subsequent addition of 1 ml SOC media (20 g tryptone; 5 g yeast extract; 0.5 g NaCl; 20 mM glucose, [pH 7.0] per 1 distilled water; Sambrook et al., 1989). After a further hour at 37° C., cells were mixed with 50 µl selection solution (36 mg/ml Xgal, 0.1 M IPTG) and plated on the appropriate LB-antibiotic plates (10 g NaCl [pH 7.0], 10 g tryptone, 5 g yeast extract, 20 g agar per liter distilled water) containing 20 µg/ml ampicillin After incubation at 37° C. for 16 hours, bacterial colonies containing recombinant plasmids were identified by their white (as opposed to blue) colour due to disruption of β-galactosidase gene activity. Selected colonies were analysed by restriction digestion of DNA isolated from single colony mini preparations. Using this procedure it was possible to sub-clone fragments of up to 20 kb in size into the pBluescriptKS(+) vector.

FPCR amplified products were cloned using the following procedure. After a standard PCR reaction using 1 ng of the pCYPAC-2 derived clone DNA as a template in a 50 µl volume, 10 units T4 DNA polymerase (Fermentas) were added to the reaction and incubated for 30 minutes at 37° C. After inactivation of the polymerase enzyme (96° C., 20 minutes), 7 µl of the PCR product were ligated to 50 ng Eco RV digested pBluescriptKS(+) vector in a final volume of 10 µl. Use of the T4 DNA polymerase to blunt the ends of the PCR products resulted in a high proportion of recombinant clones (data not shown).

Generation of pBL3-TPO-puro pBL3-TPO-puro contains the entire 19 kb TBP gene with approximately 1.2 kb 5= and 4.5 kb 3=flanking sequences and a puromycin resistance gene cassette, sub-cloned into the pBL3 vector. This was achieved by 3 consecutive cloning steps.

Firstly, the 4.5 kb of sequence flanking the 3' end of the human TBP gene in the pCP2-TLN plasmid was sub-cloned from pCP2-TLN as a NotI B SacII fragment. This fragment extends from the SacII site in the 3' UTR of the TBP gene to the OL1 89-proximal NotI site within the pCYPAC-2 vector. This fragment was cloned into SacII and NotI digested pBL3 and designated MA426. The remaining TBP gene sequences reside on a 19 kb SacII fragment extending from approximately 1.2 kb upstream of the mRNA cap site to the SacII site in the 3'-UTR. This fragment was ligated in to MA426 which was linearised with SacII, and clones screened for the correct orientation.

DNA Sequencing and Computer Sequence Analysis

DNA was prepared using the Flexi-Prep system (Pharmacia) and automated fluorescent sequencing provided as a service from BaseClear (Netherlands). dBEST and non-redundant Genbank databases were queried using previously described search tools (Altschul et al., 1997). All expressed sequence tag clones used in this study were obtained through the I.M.A.G.E. consortium (Lennon et al., 1996). Multiple sequence alignments and prediction of restriction enzyme digestion patterns of known DNA sequences was performed using the program PCGENE (Intelligenetics Inc., USA). Plots of CpG di-nucleotide frequency were produced using Vector NTI software (Informax Inc., USA).

Generation of Transgenic Animals

Preparation of TSP Fragments for Microinjection

The 90 kb genomic fragment (TLN) encompassing the TBP/PSMB1 gene region was isolated by NotI digestion of the pCP2-TLN clone and prepared for microinjection using a modified sodium chloride gradient method (Dillon and Grosveld, 1993). Initially, bacterial lipopolysaccharide (LPS) was removed from a standard pCP2-TLN maxi preparation using an LPS removal kit (Quiagen) according to the manufacturer's instructions. Approximately 50 µg of DNA was then digested for 1 hour with 70 units of NotI (Fermentas) and a small aliquot analysed by PFGE to check for complete digestion. A 14 ml 5-30% sodium chloride gradient in the presence of 3 mM EDTA was prepared in ultra-clear centrifuge tubes (Beckman) using a commercial gradient former (Life Technologies). The digested DNA was layered on the top of the gradient using wide bore pipette tips to minimise shearing and the gradient centrifuged at 37,000 rpm for 5.5 hours (at 251 C) in a SW41 Ti swing out rotor (Beckman). Fractions of approximately 300 µl were removed starting from the bottom of the gradient (highest density) into individual microcentrifuge tubes containing 1 ml 80% ethanol followed by incubation at −20° C. for 1 hour. DNA precipitates were collected by centrifugation at (14900×g, 15 minutes). Pellets were washed in 70% ethanol, dissolved in 20 µl transgenic microinjection buffer (10 mM Tris-HCI [pH 7.4], 0.1 mM EDTA) and 5 µl aliquots from alternate fractions analysed by gel electrophoresis to assess contamination of vector and chromosomal DNA. Those fractions, which appeared to be free of such contaminants, were pooled and the DNA concentration assessed by absorbance at 260 nm.

The 40 kb genomic fragment (TSN) was isolated from pWE-TSN by NotI digestion and purification using electro-elution as previously described (Sambrook et al., 1989). After electro elution, DNA was purified by sequential extraction with TE buffer-saturated phenol, phenol:chloroform (1:1 v/v) and twice with water saturated n butanol to remove residual ethidium bromide. DNA was precipitated with 2 volumes of 100% ethanol and resuspended in microinjection buffer. Fragment integrity was assessed by PFGE and concentration determined by absorbance at 260 nm. The 25 kb genomic fragment (TPO) was isolated from pBL3-TPO using an identical procedure except the insert was liberated from the vector by digestion with SalI.

Preparation of hnRNPA2 Fragments for Microinjection

The 160 kb genomic fragment (MA160) encompassing the hnRNP A2 gene region as isolated and prepared form microinjection by NruI digestion of pCP2-HLN (FIG. 3A) and sodium chloride gradient ultracentrifugation as described above.

The 60 kb genomic fragment (HSN; FIG. 13b) was isolated from MA160 by Aat II digestion and purification by PFGE as described above. The 60 kb band was excised from the gel and cut into slices. Each slice was melted at 65° C. and 30 µl analysed by PFGE. The fraction showing the purest sample of the 60 kb fragment was retained. The melted gel volume was measured, made 1× with Gelase buffer, equilibrated at 42° C. for 10 minutes and 1 unit Gelase enzyme (Epicentre Technologies) added per 500 µl. Samples were incubated overnight at 42° C. and then centrifuged for 30 minutes at 4° C. The supernatant was decanted with a wide bore tip and drop-dialysed against 15 ml of transgenic microinjection buffer on a 0.25 µm filter in a 10 cm Petri dish for 4 hours. The dialysed solution was transferred into a microcentrifuge tube and spun for 30 minutes at 4° C. Fragment integrity was assessed by PFGE and concentration determined by absorbance at 260 nm.

Generation of Transgenic Mice

Transgenic mice were produced by pronuclear injection of fertilised eggs of C57/B16 mice. Each DNA fragment was injected at a concentration of 1 ng/µ in transgenic buffer.

This was performed as a service by the UMDS Transgenic Unit (St Thomas's Hospital, London) using standard technology. Transgenic founders were identified using PCR screening of tail biopsy DNA isolated as follows. Approximately 0.5 cm tail biopsies from 10-15 day old mice were incubated at 37° C. for 16 hours in 500 µl tail buffer (50 mM Tris-HCI [pH 8.01], 0.1M EDTA, 0.1M NaCl, 1% SDS, 0.5 mg/ml Proteinase-K). The hydrosylate was extracted by gentle inversion with an equal volume phenol:chloroform (1:1.v/v) followed by centrifugation (14900×g, 15 minutes). The DNA was precipitated from the aqueous phase by the addition of 2 volumes of 100% ethanol and washed in 70% ethanol. DNA was spooled and dissolved in 100 I TE buffer. Typically, 50-200 µg DNA was obtained as determined by absorbance measurements at 260 nm. The conditions for the PCR reactions were as described for the screening of the pCYPAC-2 library using 100 ng tail biopsy DNA as template and the TB3/TB4 primer set. Positive founders were bred by back-crossing to wild type C57/816 mice to generate fully transgenic F1 offspring.

Transgene Integrity and Copy-Number Integrity and Copy-Number

Transgene copy-number and integrity was assessed by Southern blot analysis of Bam HI, BgIII, Eco RI, and Hind III digested tail biopsy DNA. Approximately 10 µWg DNA was digested with 20-30 units of the specific restriction endonuclease and electrophoresed on 0.7% agarose/0.5×TBE (45 mM Tris borate, [pH 8.0], 1 mM EDTA,) gels for 16 hours at 1.5V/cm. Staining and transfer of DNA onto nylon membranes was as for plasmid Southern blots except a positively charged matrix (HYBOND N+, Amersham) was used.

DNA probes were prepared by restriction enzyme digestion to remove any cloning vector sequences and purified from low melting point agarose using the Gene-Clean system (Bio 101, USA). Radioactive labelling of 100 samples of the probes was performed by nick translation using a commercially available kit (Amersham) and 200 pmol each of dCTP, dGTP, dTTP and 3 μl α-$P^{32}$-dATP (specific activity >3000 Ci/mmol, 10 mCi/ml, Arnersham). The enzyme solution consisting of 0.5 units DNA polymerase 1/10 pg DNase I in a standard buffer, was added and the reaction incubated at 15° C. for 2.5 hours. Probes were purified by Sephadex G-50 chromatography and boiled for 5 immediately prior to their use. Typically, specific activities of $>1\times10^8$ cpm/μg were obtained.

Hybridisation was performed as for plasmid Southern blots described above. Membranes were incubated in 15 ml pre-hybridisation solution (3×SSC, 0.1% SDS, 5×Denhardt's solution [100×Denhardt's solution is 2% Ficoll (Type 400, Pharmacia), 2% polyvinyl pyrolliclone, 2% bovine serum albumin (Fraction V, Sigma) per liter distilled water]), containing 100 μg/ml denatured salmon testis DNA at 65° C. for 1 hour. The solution was then replaced by 15 ml hybridisation solution (as pre-hybridisation solution with the addition of dextran sulphate to 10%) containing 100 μg/ml denatured salmon testis DNA and the heat denatured radio labelled probe. After hybridisation at 65° C. for 16 hours membranes were washed three times in 2×SSC/0.1% SDS for 30 minutes each and exposed to Phosphorimager (Molecular Dynamics) screens or x-ray film at 80° C. Those blots which were to be re-analysed, bound probe was removed by soaking in 0.2M NaOH for 20 minutes followed by neutralisation as described above.

The majority of the probes used in this study were derived from regions of the genomic clones where no sequence information was available (e.g., pCP2-TLN end-fragment probes and those derived from the TBP intronic regions). A number of probes hybridized non-specifically to human genomic DNA suggesting the presence of repetitive sequence elements. In order to circumvent this problem, aliquots of probe DNA were individually digested with a number of restriction enzymes, electrophoresed and Southern blotted. Enzymes with short recognition sites (which should occur very frequently within the DNA), were chosen so as to digest the probe into a number of smaller fragments. Radiolabelled human $C_0$ t–1 DNA was used as a probe to indicate those fragments that contained repetitive sequences. Using this procedure, it was possible to obtain fragments >500 bp that did not hybridise to the $C_0$ t–1 probe, for all probes which contained repetitive elements.

Preparation of Cosmid DNA and Generation of Single Copy L-Cell Clones pWE-TSN DNA was prepared by alkaline lysis of 1 liter cultures as described above until the isopropanol precipitation stage. After incubation at 25° C. for 1 hour, the pellet was resuspended in 300 μl TE and then added with continuous mixing to 10 ml Sephaglas FP DNA binding matrix (Pharmacia). The solution was constantly inverted for 10 minutes and the martix-bound DNA collected by centrifugation (280×g, 1 minute). The pellet was washed firstly with WS buffer (20 mM Tris-HCl [pH 7.5], 2 mM EDTA, 60% ethanol), collected by centrifugation, washed with 70% ethanol and re-centrifuged. DNA was eluted from the matrix by resuspending the pellet in 2 ml TE buffer and incubation at 70° C. for 10 minutes with periodic mixing. The solution was centrifuged 0 100×g, 2 minutes) and the DNA containing supernatant split equally into two microfuge tubes. Residual Sephaglass was removed by centrifugation (14950×g, 15 minutes), the supernatants pooled and DNA precipitated with 2 volumes of ethanol. The spooled DNA was washed once in 70% ethanol and resuspended at 1 μg/μl in sterile water. Approximately 75-100 μg of pure cosmid DNA was obtained using this procedure, which represents a yield of 60-80% of DNA obtained without Sephaglas purification.

Transfection of adherent mouse L-cells (Earle et al., 1943) was performed as follows. Approximately $1\times10^7$ cells grown in DMEM containing 10% heat inactivated foetal calf serum (PAA laboratories), 2 mM L-glutamine, were mixed with 1 μg pWE-TSN DNA linearised with SalI and incubated on ice for 10 minutes. DNA was introduced into the cells by electroporation (Chu et al., 1987) with settings of 960 μF, 250V in a Biorad Gene-Pulser. Transfected cells were selected for and maintained in the same medium including 400 μg/ml geneticin sulphate (G418; Life Technologies Inc.). Individual clones were isolated using cloning rings (Freshney, 1994). Thick-walled stainless steel cloning rings (Life Technologies Inc.) were autoclaved in silicon grease and transferred to the tissue culture plate such that the colony was isolated. A solution of trypsin (300 μl of 0.25% trypsin [pH 7.6] (Difco), 0.25M Tris-HCl [pH 80], 0.4% EDTA [pH 7.61, 0.12M NaCl, 5 mM glucose, 2.4 mM $KH_2PO_4$ 0.84 mM $Na_2HPO_4.12H_2O$, 1% phenol red) was added and the plate incubated at 37° C. for 5 minutes. Cells were transferred to 24-well plates and clonal cell lines established. Clones were preserved as follows. Approximately $1\times10^7$ cells were harvested by centrifugation, resuspended in 0.75 ml freezing mix (70% standard growth media but including 20% foetal calf serum and 10% DMSO) and snap frozen on dry ice for 1 hour before to liquid nitrogen storage.

Genomic DNA was prepared from these L-cell clones using standard procedures (Sambrook et al., 1989). Cells in T75 flasks were grown to confluency (approximately $4\times10^7$), the media removed and the flask washed with PBS (2.68 mM KCl, 1.47 mM $KH_2PO_4$ 0.51 mM $MgCl_2$, 136.89 mM NaCl, 8.1 mM $N8_2HPO_4$ [pH 7.3]) and 2 ml lysis buffer (10 mM Tris-HCl [pH 7.5], 10 mM EDTA, 10 mM NaCl, 0.5% SDS, 1 mg/ml Proteinase-K) added. Cells were dislodged from the culture flask by scraping and transferred to a 15 ml centrifuge tube using a wide bore pipette tip. Lysis was allowed to proceed at 68° C. for 16 hours after which the solution was extracted once with phenol:chloroform (1:1 v/v) and the DNA precipitated with an equal volume of isopropanol. After washing in 70% ethanol, the DNA was resuspended in 1 ml TE buffer and concentration assessed by absorbance at 260 nm Transfected gene copy-numbers were determined by Southern Blot analysis of Bgl II II digested genomic DNA. Human TBP was detected using a specific probe (1.4HX) located in the C5 gene, 4 kb 5' of the TBP transcription initiation region and which detects a 4.2 kb fragment (see FIG. 10). In addition, blots were simultaneously probed with a 1 Nco I fragment derived from the endogenous murine vav locus (Ogilvy et al., 1998) that gives a 5.2 kb band and that acts as a single copy reference standard. Human TBP transgene copy-number was ascertained by comparing the ratio of the TBP to vav signal obtained with the 3 copy transgenic mouse line TLN:8 after analysis of blots by PhosphorImager.

Total RNA was prepared from approximately $4\times10^7$ cells by selective precipitation in 1 ml of 3M LiCl, 6M urea (Auffrey and Rougeon, 1980; see Antoniou, 1991).

Dnase I Hypersensitive Site Analysis

This was performed as previously described (Forrester et al., 1987; Reitmann et al., at 1993). Nuclei were prepared from approximately $1\times10^9$ K562 cells (Lozzio and Lozzio, 1975). Harvested cells were washed in PBS and resuspended in 4 ml ice-cold RSB 10 mM Tris-HCl [pH7.5], 10 mM NaCl, 3 mM$M_2$) and placed in a glass dounce homogeniser fitted with a loose pestle. After the addition of 1 ml of 0.5% NP40/RSB cells were homogenised slowly for 10-20 strokes and nuclei recovered by the addition of 50 ml RSB and centrifugation at 4° C. (640×g, 5 minutes). The supernatant was discarded and nuclei were resuspended in 1 ml RSB with 1 mM $CaCl_2$. Immediately, a 100 µl aliquot (representing approximately $1×10^8$ nuclei) was taken and DNA purified as described below, to control for endogenous nuclease activity during the isolation procedure.

The DNase I digestion was performed as follows. A range of aliquots (0, 0.5, 1, 2, 3, 4, 5, 6, 8, 10 µl) of 0.2 mg/ml DNase I (Worthington) was added to individual microfuge tubes containing 100 µl of nuclei and incubated at 37° C. for 4 minutes. The digestion was stopped by the addition of 100 µl 2× stop mix (20 mM[pH 8.0], 10 mM EDTA, 600 mM NaCl, 1% SDS), 10 µl Proteinase-K (10 mg/ml concentration) and incubation at 55° C. for 60 minutes. DNA was purified by phenol:chloroform (1:1 v/v) extraction and ethanol precipitation. Samples were electrophoresed on 0.7% agarose/0.5× TBE gels and Southern blotted for analysis using $^{32}$P-radiolabelled probes.

RNA Preparation

Adult mice aged 10-40 weeks were sacrificed by cervical dislocation and whole tissues isolated, snap frozen, in liquid nitrogen and stored at −80° C. until required. Total RNA was prepared by selective precipitation in 3M LiCl, 6M urea (Auffray and Rougeon, 1980). Tissues were transferred to 14 ml tubes containing 1 ml of the LiClsolution and homogenised for 30 seconds with an Ultra Turrax T25 (Janke & Kunkel). Samples were then subjected to three, 30 second pulses of sonication (Cole Parmer Instrument Co., USA), the homogenate transferred to sterile microfuge tubes and RNA allowed to precipitate at 4° C. for 16 hours. The RNA was collected by centrifugation (4° C., 14900×g, 20 minutes) washed in 500 µl LiClsolution and resuspended in 500 µp I TES (10 mM Tris HCl [pH 7.5], 1 mM EDTA, 0.5% SDS). After extraction with phenol:chloroform, samples were made 0.3M with sodium acetate and RNA precipitated by the addition of 1 ml 100% ethanol and storage at −20° C. for at least 1 hour. The RNA was collected by centrifugation and re-suspended in 20 µl sterile water and concentration assessed by absorbance at 260 nm.

Competitive RT PCR Based Assay

Analysis of Human TBP Expression

A modified competitive RT-PCR approach (Gilliland et al., 1990) was used to accurately quantify human TBP and PSMB1 gene expression in a mouse background. Total RNA (1 µg) from transgenic mouse tissues or cell lines was reversed transcribed in a 25 µl reaction consisting of 10 units Avian Myeloblastosis Virus (AMV) reverse transcriptase (Promega), 10 mM DTT, 2.5 mM each dNTP, 25 units ribonuclease inhibitor (Fermentas) with 1 µM reverse primer (TB14 or C5R) in 1×RT buffer (25 mM Tris-HCl [pH 8.3], 25 mM KCl, 5 mM $MgCl_2$ 5 mM DTT, 0.25 mM spermidine). Synthesis of cDNA was allowed to proceed at 42° C. for 1 hour followed by a further hour at 52° C. and heat inactivation of the enzyme at 95° C. for 5 minutes. PCR reactions contained 1 µl cDNA amplified using the reaction mix described for tail biopsy screening and containing specific primer sets for the sequence in question (as detailed above, one of which was end-labelled using the protocol described above. Primers were purified with two rounds of Sephadex-G25 chromatography (Pharmacia) and an 80% recovery was assumed. PCR conditions were 94° C. for 1 minute, 58° C. for 1 minute and 72° C. for 1 minute with cycle numbers between 5 and 30.

In order to distinguish between human and mouse PCR products, 2-10 µl of each sample was incubated with 5 units of the appropriate restriction enzyme at 37° C. for 2 hours. This reaction was carried out in a large (250 µl) volume to dilute salts and detergents from the PCR buffer to prevent inhibition of restriction enzyme activity. (Control experiments demonstrated that this was indeed the case). Digested and undigested samples were ethanol precipitated in the presence of 25 µg yeast tRNA (Sigma) as co-precipitant, collected by centrifugation and resuspended in 5 µl gel loading buffer (5 mM Tris-Borate [pH 8.3], 1 mM EDTA, 7M Urea, 0.1% xylene cyanol, 0.1% bromophenol blue). Samples were analysed on pre-run, 5% polyacrylamide gels in the presence of 7M Urea. (National Diagnostics) as denaturant and 0.5× TBE buffer. After electrophoresis at 40V/cm for 1 hour, the gel was cut to remove residual unincorporated nucleotide running below the xylene cyanol dye front, dried and exposed to x-ray film or PhosphorImager screens.

Analysis of Human hnRNPA2 Expression

A similar competitive RT-PCR approach (Gilliland et al., 1990) was used to accurately quantify human hnRNP A2 gene expression in a mouse background. After reverse transcription, cDNA samples were amplified by PCR using primer sets Hn9 and Hn12 [5' CTCCACCATATGGTCCCC 3'] (SEQ ID NO: 13), one of which was end-labelled using the protocol described above. In order to distinguish between human and mouse hnRNP A2 PCR products, 2-10 µl of each sample was digested with 5 units HindIII at 37° C. for 2 hours, purified, resolved on 5% denaturing polyacrylamide gels and results quantified as described above.

Sequencing and Bidinformatic Analyses of Clones

HindIII genomic clones of both TBP (nucleotides 1-9098, FIG. 20) and hnRNPA2 (nucleotides 1-15071, FIG. 21) loci were sequenced by Baseclear, Leiden, N L. Using a primer-walking strategy starting with primers made to known sequence, regions of unknown sequence were generated; TBP nucleotides 1-5642 and hnRNPA2 nucleotides 1-3686.

These sequences were spliced together with previously known sequence data and were then used in bioinformatic analyses.

Direct comparisons were made between TBP and hnRNPA2 sequences using standard Smith-Waterman searching. This showed no obvious regions of homology other than several Alu repeats as shown in FIG. 19. Masking these repeats and performing a comparison using the GCG bestfit program resulted in two short regions of homology as follows:

RNP 3868-3836: TBP 8971-9003 length=33% identity=75.758

RNP 3425-3459: TBP 9049-9083 length=35% identity=74.286

CpG-islands were also identified and are shown in FIG. 19. Nucleotide positions are as follows:

RNP 4399-5491, 5749-6731

TBP 5285-5648, 6390-6966

Sequencing studies were performed as described above so as to provide more sequence data from the region immediately upstream of the RNP and TBP genes.

The sequence data given in FIGS. 20 and 21 begins at the 5' HindIII site and includes the Baseclear generated sequence and the already published sequence data spliced together. In the case of the TBP sequence the Baseclear sequence is denoted in capitals.

Analysis of these sequences demonstrated the existence of a previously characterized gene, HP1H-γ, or heterochromatin associated protein H-gamma upstream of the RNP gene (FIGS. 19 and 22). This gene has also been shown to be ubiquitously expressed by human tissue dot-blot analysis (data not shown).

Bioinformatic analysis and sequence comparisons showed no obvious sequence homologies between the loci. However, a summary of the data is shown in FIG. 19. As can be seen, several putative Sp1 transcription factor binding sites are located in the bidirectional promoter regions of the two loci. The CpG methylation free islands are also indicated. Both loci show a bidirectional structure containing a cluster of ubiquitously expressed genes.

Construction of hnRNP A2 EGFP Reporter Constructs

CMV-EGFP-RES was constructed by digesting pEGFP-N1 (Clontech) with Kpn1 and NotI to liberate the EGFP sequence, this was then ligated into pIRESneo (Clontech) that had been partially digested with Kpn1 and then NotI. This created a vector with the EGFP gene 3' to the CMV promoter and 5' to IRESneo (CMV-EGFP-IRES).

The CMV promoter was exchanged for the RNP promoter to create the construct referred to in FIG. 22 as RNP. CMV EGFP-IRES was digested with AgeI, blunted with T4 DNA polymerase (50 mM Tris pH7.5, 0.05 mM MgCl$_2$, 0.05 mM DTT, 1 mM dNTP, 1 μT4 DNA polymerase/μg DNA) and then cut with NruI to release the CMV promoter to give EGFP-IRES. The RNP promoter was removed from an 8 kb hnRNPA2 HindIII clone (8 kb Hind BKS) which contained the promoters and first exons of the RNPA2 and HP1H-γ genes. 8 kb Hind BKS was cut with BspEI and Tth 111 I (to release the 630 bp promoter) blunted with T4 DNA polymerase, and the isolated RNP promoter ligated into EGFP-IRES.

5.5.RNP was constructed by inserting the EGFP-IRES cassette into 8 kb Hind BKS such that expression of EGFP was under the control of the RNP promoter. The latter was partially digested with Tth 111 I, blunted with T4 DNA polymerase and then digested with SalI, this removed all sequences 3' to the RNP promoter. The EGFP-RES cassette was removed from CMV-EGFP-IRES by digestion with AgeI and blunted prior to digestion with XhoI. This was then ligated into the restricted 8 kb Hind BKS.

5.5CMV was constructed by inserting the CMV-EGFP-IRES cassette into 8 kb Hind BKS with the subsequent removal of the RNP promoter. 8 kb Hind BKS was cut with BspEI, blunted and then digested with SalI removing the RNP promoter and all sequences 3' to the promoter. The CMV-EGFP-IRES cassette was removed from CMV-EGFP-IRES by digestion with NruI and XhoI and ligated into the digested 8 kb Hind BKS.

Approximately 4 kb of DNA was removed from 5.5 RNP to leave 1.5 kb 5' to the RNP promoter creating 1.5 RNP. This was achieved by digesting 5.5 RNP with BamHI which gave fragments of 4, 2.9 and 5 kb. The 2.9 and 5 kb fragments were then isolated and religated to create 1.5 RNP, when the 2.9 kb fragment was inserted in the correct orientation.

The 5.5RNP construct was extended to include hnRNPA2 sequences 3' to the RNP promoter (constructs 7.5RNP and 8.5RNP), this region included the first exon and intron of hnRNPA2. In order to include the EGFP-IRES reporter in these constructs it was necessary to place the hnRNPA2 splice acceptor sequence of exon 2 in frame with the EGFP gene such that the first exon of hnRNPA2 could splice to the EGFP gene and hence EGFP expression could be driven off the RNP promoter. Two constructs were made which included the hnRNPA2 splice acceptor, these contained 80 bp and approximately 1 kb of sequence 5' to the second exon, these sequences were obtained by PCR from MA160 which includes the whole hnRNPA2 genomic sequence. The 80 bp sequence was isolated by PCR (20 mM Tris HCl pH8.4, 50 mM KCl, 1 μM Primer, 2 mM MgCl$_2$, 0.2 mM dNTP 3.5 μg MA160 DNA, 5U Platinum Taq DNA Polymerase) using primers [5'ACCGGTTCTCTCTGCAAAGGAAAATACC 3'] (SEQ ID NO:14) and [5' GGTACCCTCTGCCAGCAG-GTCACCTC 3'] (SEQ ID NO: 15), the 1 kb fragment was isolated using the primers [5'ACCGGTTCTCTCTG-CAAAGGAAAATACC 3'] (SEQ ID NO:16) and [5'GGTAC-CGAGCATGCGAATGGAGGGAGAGCTCCG 3] (SEQ ID NO: 17). The primers were designed such that the PCR product contained Kpn1 and AgeI sites at the 5' and 3' ends respectively. PCR products were then cloned into the TA cloning vector pCR3.1 (Invitrogen).

The 80 bp and 1 kb fragments were isolated from pCR3.1 as Kpn1 AgeI fragments and ligated into CMV-EGFP-IRES that had been partially digested with Kpn1 and then cut with AgeI, this created inframe fusions of the splice acceptor (SA) with the EGFP gene.

7.5RNP was constructed by digesting 8 kb Hind BKS with ClaI, blunting with T4 DNA polymerase, then digesting with SalI. The 80 bp SA-EGFP-IRES cassette was isolated by a Kpn1 partial digest followed by blunting with T4 DNA polymerase and XhoI digestion. This was ligated into the ClaI-SalI digested 8 kb Hind BKS.

8.5RNP was constructed by an SphI partial digest of 8 kb Hind BKS followed by digestion with SalI, the 1 kb SA-EGFP-IRES cassette was similarly isolated by an SphI partial digest followed by restriction with XhoI. The cassette was ligated into 8 kb Hind BKS to create 8.5 RNP.

4.0CMV was constructed by excising a 4 kb fragment from 8 kb Hind BKS with BamHI/HindIII/BstEII digestion. The ends of the fragment were then end-filled with Klenow and T4 DNA polymerase.

Pegfp-N1 (Clontech) was linearised with AseI, the ends blunted as above and then treated with calf intestinal phosphatase (CIP). Both fragments were then ligated overnight.

p7.5CMV was constructed by excising the 8.3 kb fragment from p8 kb Hind BKS with HindIII digestion. The ends of the fragment were then end filled with Klenow and T4 DNA Polymerase pEGFP-N1 (Clontech) was linearised with AseI, the ends were blunted as above and then treated with calf intestinal phosphatase (CIP). Both fragments were then ligated overnight. The resultant clones were screened for both forward and reverse orientations of the 8.3 kb UCOE insert.

p16CMV was constructed by excising a 16 kb fragment from MA551 (hnRNPA2 genomic clone containing 5 kb 5' and 1.5 kb 3' sequence including the entire coding region (16 kb fragment shown in FIG. 13C) by SalI digestion. The ends of the fragment were then end filled with Klenow and T4 DNA Polymerase. pEGFP N1 (Clontech) was linearised with AseI, the ends were blunted as above and then treated with calf intestinal phosphatase (CIP). Both fragments were then ligated overnight. The resultant clones were screened for both forward and reverse orientations of the 16 kb UCOE insert.

CHO Transfection

CHO cells were harvested at $2 \times 10^7$ cells/ml in serum free medium. $1 \times 10^7$ cells (0.5 ml) were used per transfection, along with 1 μg (5 μl) of linear DNA and 50 μg (5 μl) of salmon sperm carrier DNA. The DNA and cells were mixed and left on ice for 10 minutes. Cells were electroporated using the BioRad Gene-Pulser II™ at 975 uF/250V and then left on ice for 10 minutes. The mix is then layered onto 10 mls of complete medium (HF10) and spun at 1400 rpm for 5 minutes. The supernatant is removed and the pellet resuspended in 5 mls of HF10. The cells were then plated out at $5 \times 10^4$ or $1 \times 10^4$ in 10 cm dishes and at $2 \times 10^6$ cells per T225 flask. After 24 hours the cells were placed under selection, initially at 300 μg/ml G418 and then after 4 days at 600 μg/ml G418. 10 days after transfection colonies were stained with methylene blue (2% solution made up in 50% ethanol) and counted. Duplicate plates were maintained in culture either as restricted pools or as single cell clones.

Analysis of GFP Expression in Transfected CHO Clones

The transfected cells were maintained on G418 selection at 600 µg/ml. Cells were stripped off 6-well plates for expression analysis of GFP. Cells were washed with phosphate buffered saline (PBS; Gibco) and incubated in Trypsin/EDTA (Sigma) until they had detached from the surface of the plates. An excess of Nutrient mixture F12 (HAM) medium (Gibco) supplemented with 10% foetal calf serum (FCS; Sigma) was added to the cells and the cells transferred to 5 ml polystyrene round-bottom tubes. The cells were then analysed on a Becton-Dickinson FACScan for the detection of GFP expression in comparison to the autofluorescence of the parental cell population. 19 RNP clones, 24 5.5RNP clones, 21 CMV clones and 12 5.5CMV clones were analysed and the average taken of the median fluorescence of all the positive clones.

Analysis of GFP Expression in Transfected CHO Pools

Colonies of transfected CHO cells, that had undergone selection on G418, were stripped from a T225 tissue culture flask and plated on 10 cm petri dishes to give approximately 100 colonies/plate. When the colonies had grown up, the cells were stripped and this limited pool of transfected cells was analysed for GFP expression. GFP expression was monitored on a regular basis, with the pools split 1:10 every 3-4 days. Cells were always split into 24-well plates the day before analysis, so that the cells were approximately 50% confluent on the day of analysis. The cells were then stripped from the 24-well plates and analysed in the same way as the previous section. For the expression time-course, a marker region (MI) was set which contained only a minor proportion of the positive population of cells and was used to investigate any loss of GFP expression from the initial level over time.

FISH Analysis of Single/Low Copy-Number Integrants
FISH Analysis Using the 40 kb TBP Cosmid pWE-TSN or the pBL3-TPO-puro.

FMouse Ltk-cells grown in DMEM –10% fetal calf serum were electroporated with the 40 kb TBP cosmid pWE-TSN (FIG. 9) or the 25 kb plasmid pBL3-TPO-puro. The transfectants were selected with either 200 mg/ml G418 (TSN) or 5 mg/ml puromycin (TPO) and single or low copy clones were generated as outlined previously. Logarithmically growing cells from the selected clones were treated with 0.4 mg/ml colchicine for 1 h prior to harvest. Cells were then hypotonically swollen in 0.056 M KCl, fixed in 3:1 methanol-acetic acid, and spread on microscope slides to obtain metaphase chromosomes. The slides were pretreated with 100 mg of RNaseA/ml in 2×SSC (1×SSC is 0.15 M NaCl, 0.0 15 M sodium citrate) for 1 h at 37° C., washed in 2×SSC, and put through an ethanol dehydration series (70, 90, and 100% ethanol). The chromosomes were denatured at 70° C. for 5 minutes in 70% formamide-2×SSC, plunged into ice-cold 70% ethanol, and dehydrated as before. One hundred nanograms of TBP probe (entire TPO plasmid carrying 25 kb of human genomic DNA comprising the TBP gene) and 50 nanograms of mouse gammasatellite probe (as described by Horz et al., Nucl. Acids Res. 9:683-696, 1981) were labelled with digoxigenin-11-dUTP and biotin-16-dUTP, respectively, by nick translation (Boehringer) following manufacturer's instructions. Labelled probes were precipitated with 1 mg of cot-1 DNA and 5 mg of herring sperm DNA, resuspended in 50% formamide-2×SSC-1% Tween 20-10% dextran sulfate, denatured at 75° C., the TBP probe preannealed for 30 min at 37° C. and pooled and applied to the slides. Hybridisation was carried out overnight at 37° C. The slides were washed four times for 3 minutes each time in 50% formamide-2×SSC at 45° C., four times for 3 minutes each time in 2×SSC at 45° C., and four times for 3 minutes each time in 0.1×SSC at 60° C. After being washed for 5 minutes in 4×SSC-0.1% Tween 20, the slides were blocked for 5 minutes in 4×SSC-5% low fat skimmed milk. The biotin labelled probe was detected by 30 minutes incubation at 37° C. with each of the following: avidin-conjugated Texas Red (Vector Laboratories Inc, USA) followed by biotinylated anti-avidin (Vector Laboratories Inc, USA) and avidin-conjugated Texas Red (Vector Laboratories Inc, USA). Digoxigenin labelled probe was detected at the same time as biotin detection with each of the following: anti-digoxigenin-fluorescein (FITC, Boehringer) followed by mouse anti FITC: (DAKO) and horse fluorescein-conjugated anti mouse IgG (Vector Laboratories Inc, USA). Between every two incubations, the slides were washed three times for 2 minutes each time in 4×SSC-0.1% Tween 20. The slides were counterstained with DAPI (4=–6-diamidino-2-phenylindole) and mounted in Vectashield (Vector Laboratories Inc, USA). Images were examined with an oil 100× objective on a fluorescence microscope. The images were capture using a Photometrics cooled charge couple device camera and Vysis Smartcapture software.

FISH Analysis Using the 16RNP-EGFP Construct.

The 6RNP EGFP vector was constructed by inserting the E Mouse Ltk-cells grown in DMEM-10% fetal calf serum were electroporated with the 40 kb TBP cosmid pWE-TSN (FIG. 9) or the 25 kb plasmid pBL3-TPO-puro. The transfectants were selected with either 200 mg/ml G418 (TSN) or 5 mg/ml puromycin (TPO) and single or low copy clones were generated as outlined previously. Logarithmically growing cells from the selected clones were treated with 0.4 mg/ml colchicine for 1 h prior to harvest. Cells were then hypotonically swollen in 0.056 M KCl, fixed in 3:1 methanol acetic acid, and spread on microscope slides to obtain metaphase chromosomes. The slides were pretreated with 100 mg of RNaseA/ml in 2×SSC (1×SSC is 0.15 M NaCl, 0.0 15 M sodium citrate) for 1 h at 37° C., washed in 2×SSC, and put through an ethanol dehydration series (70, 90, and 100% ethanol). The chromosomes were denatured at 70° C. for 5 minutes in 70% formamide-2×SSC, plunged into ice-cold 70% ethanol, and dehydrated as before. One hundred nanograms of TBP probe (entire TPO plasmid carrying 25 kb of human genomic DNA comprising the TBP gene) and 50 nanograms of mouse gamma satellite probe (as described by Horz et al., Nucl. Acids Res. 9:683-696, 1981) were labelled with digoxigenin-11-dUTP and biotin-16-dUTP, respectively, by nick translation (Boehringer) following manufacturer's instructions. Labelled probes were precipitated with 1 mg of cot-1 DNA and 5 mg of herring sperm DNA, resuspended in 50% formarn ide-2×SSC-1% Tween 20-10% dextran sulfate, denatured at 75° C., the TBP probe preannealed for 30 minutes at 37° C. and pooled and applied to the slides. Hybridisation was carried out overnight at 37° C. The slides were washed four times for 3 minutes each time in 50% formamide-2×SSC at 45° C. four times for 3 minutes each time in 2×SSC at 45° C. and four times for 3 minutes each time in 0.1×SSC at 60° C. After being washed for 5 minutes in 4×SSC-0.1% Tween 20, the slides were blocked for 5 minutes in 4×SSC-5% low fat skimmed milk. The biotin labelled probe was detected by 30 minutes incubation at 37° C. with each of the following: avidin-conjugated Texas Red (Vector Laboratories Inc, USA) followed by biotinylated anti-avidin (Vector Laboratories Inc, USA) and avid in conjugated Texas Red (Vector Laboratories Inc. USA). Digoxigenin labelled probe was detected at the same time as biotin detection with each of the following: anti-digoxigenin-fluorescein (FITC, Boehringer) followed by mouse anti FITC (DAKO) and horse fluorescein conjugated anti mouse IgC (Vector Laboratories Inc, USA). Between every two incubations, the slides were washed three times for 2 minutes each time in 4×SSC-0.1% Tween 20. The slides were counterstained with DAPI (4=6-diamidino-2-phenylindole) and mounted in Vectashield (Vector Laboratories Inc, USA). Images were examined with an oil 100× objective on a fluorescence microscope. The images were capture using a Photometrics cooled charge couple device camera and Vysis Smartcapture software. GFP IresNeo expression cassette and some RNP 5' sequences from 8.5RNP into MA551. 8.5 RNP was digested with Xho I, blunted with T4 DNA polymerase and then digested with Pac I, the resulting fragment was ligated into MA551 that had been cut with Nhe I, blunted and then digested with Pac I. As with 8.5RNP expression is driven off the RNP promoter resulting in an in-frame fusion of exon I of RNP with EGFP.

Clones of mouse LTK cells transfected with 16RNP-EGFP were grown in DMEM 10% fetal calf serum and 200 µg/ml G418. Logarithmically growing cells were treated with 0.4 g/ml colchicine for 1 h prior to harvest. Cells were hypotonically swollen in 0.056 M KCl, fixed in 3:1 methanol acetic acid, and spread on microscope slides to obtain metaphase chromosomes. The slides were pretreated with 100 µg of RNase A/ml in 2×SSC (1×SSC is 0.15 M NaCl, 0.015 M sodium citrate) for 1 h at 37° C., washed in 2×SSC, and put through an ethanol dehydration series (70, 90, and 100% ethanol). The chromosomes were denatured at 70° C. for 5 minutes in, 70% formamide-2×SSC, plunged into ice-cold 70% ethanol, and dehydrated as before. One hundred nanograms of 16RNP-EGFP and 50 nanograms of mouse gamma satellite (Horz et al., Nucl. Acids Res. 9, 683 696, 1981) were labelled with digoxigenin-11-dUTP and biotin-16-dUTP, respectively, by nick translation (Boehringer) following manufacturer's instructions. Labelled probes were ethanol precipitated with 5 µg of herring sperm DNA and the RNP probe with 1 µg of cot DNA; resuspended in 50% formamide-2×SSC-1% Tween 20-10% dextran sulfate; denatured at 75° C., the RNP probe preannealed for 30 minutes at 37° C.; pooled and applied to the slides. Hybridisation was carried out overnight at 37° C. The slides were washed four times for 3 minutes each time in 50% formamide-2×SSC at 45° C., four times for 3 minutes each time in 2×SSC at 45° C., and four times for 3 minutes each time in 0.1×SSC at 60° C. After being washed for 5 minutes in 4×SSC-0.1% Tween 20, the slides were blocked for 5 minutes in 4×SSC S % low fat skimmed milk. The biotin was detected by 30 minutes incubation at 37° C. with each of the following: avid in conjugated Texas Red (Vector Laboratories) followed by biotynylated anti-avidin (Vector Laboratories) and avid in conjugated Texas Red (Vector Laboratories). Digoxigenin was detected at the same time as biotin with each of the following: anti-digoxigenin-fluorescein (FITC, Boehringer) followed by mouse anti FITC (DAKO) and horse fluorescein conjugated anti mouse IgC (Vector Laboratories). Between every two incubations, the slides were washed three times for 2 minutes each time in 4×SSC-0.1% Tween 20. The slides were counterstained with DAPI (4'-6-diamidino-2-phenylindole) and mounted in Vectashield (Vector). Images were examined with an oil ×100 objective on a Olympus BX40 fluorescence microscope. The images were captured with a Photometrics cooled charge couple device camera and Vysis Smartcapture software.

Copy Number Determination

Genomic DNA was prepared from cell clones by standard procedures (Sambrook et al., 1989). Transfected gene copy-number was determined by Southern blot analysis of Hincil digested genomic DNA. The transgene was detected as a 2.5 kbp band by hybridisation to a 1 kpb fragment from 16RNP-EGFP, comprising the neomycin resistance gene, labelled with [$\alpha^{32}$ P] dCTP following manufacturer's instructions (Megaprime DNA labelling system, Amersham). For normalization, blots were simultaneously hybridized with a 1 kbp NcoI fragment, labelled as above, derived from the murine vav locus (Ogilvy et al., 1998) which gave a 1.4 kbp band. As copy-number standards, DNA from several pWE-TSN clones was digested with PstI and hybridized to the above probes. Hybridisation signal quantification was performed with a Cyclone PhorsphorImager (Packard).

Analysis of GFP Expression in Transfected Ltk Clones

The transfected cells were maintained on G418 selection at 200 µg/ml. Cells at 80-100% confluency were stripped off 6-well plates for expression analysis of GFP. Cells were washed with PBS and incubated in Trypsin/EDTA (Sigma) until they had detached from the surface of the plates. An excess of DMEM (Gibco) supplemented with 10% foetal calf serum (Sigma) was added to the cells and transferred to 5 ml polystyrene round-bottom tubes. The cells were then analysed on a Becton Dickinson FACScan for the measurement of GFP fluorescence in comparison to the autofluorescence of an untransfected control.

Production of EB V Receptor Construct

TA DNA fragment containing the cytomegalovirus (CMV) promoter, the enhanced green fluorescent protein (EGFP) and the simian virus 40 (SV40) polyadenylation sequence, was removed from the vector, pEGFP-NI (Clontech), by restriction endonuclease digestion with Ase I and Afl II using the manufacturers recommended conditions (NEB). The DNA was electrophoresed on a 0.5% agarose gel to separate the fragment from the vector backbone. The DNA fragment was cut out of the gel and purified from the gel slice using the standard glass milk purification technique. The fragment was blunted using T4 DNA polymerase (NEB) according to the manufacturers conditions and purified by 1:1 (v/v) extraction with phenol:chloroform:isoamylalcohol (25:24:1) followed by ethanol precipitation.

The reporter cassette was then cloned into the Epstein Barr virus (EBV) vector, p220.2 (described in International Patent Application WO 98/07876). P220.2 was restriction endonuclease digested with Hind III (a unique site in the multiple cloning sequence (MCS) of the vector), blunted and purified in the same way as described above. The reporter cassette was ligated into p220.2 using T4 DNA ligase (Promega). The ligation reaction was performed in a 10 µl volume using 200 ng of the linearised p220.2 and either a molar equivalent or 5 molar excess of the CMV-EGFP-SV4OpA fragment, in 1× ligation buffer (Promega). The reaction was incubated overnight at room temperature. 2.5 µl of the ligations were transformed into electrocompetent DH5 a E. coli cells by electroporation at 2.5 kV 400Ω, 2 5 µF followed by the addition. of 900 µl of SOB medium and incubation at 37° C. for 1 hour. 200 µl of each of the transformations were plated on LB ampicillin agar plates and incubated overnight at 37° C.

The resulting colonies were screened for the presence of the reporter cassette by colony polymerase chain reaction (PCR) with DNA primers in the CMV and EGFP sequence, using Taq polymerase (Advanced Biotechnologies) with the manufacturers standard conditions. Positive colonies were grown overnight in LB ampicillin medium and were analysed as alkaline lysis DNA minipreparations (Qiagen). The DNAs were screened for the correct orientation of the fragment using Bam HI restriction endonuclease digestion. The resultant construct was named p220.EGFP.

p220.EGFP was demonstrated to express EGFP by analysis on a Becton Dickinson FACScan, after electroporation into K562 cells, using essentially the same method as described below.

Production of EBV Reporter Constructs Containing the hnRNPA2 76 kb (RNP16) UCOE Fragment.

A SalI site was removed from p220.EGFP by partial restriction endonuclease digestion of the vector with SalI, followed by blunting and religation of the vector, thus leaving a unique SalI site in the multiple cloning site (MCS) of the vector which could be utilised for the cloning of the 16 kb RNP fragment. The resultant vector was restriction endonuclease digested with SalI, treated with calf Intestinal phosphatase (to prevent recircularisation of the vector during the ligation) and purified by phenol: chloroform extraction and ethanol precipitation.

The 16 kb RNP fragment was removed from the vector, MA551, using the restriction endonuclease, SalI, and was blunted, purified by electroelution and ligated into the linearised vector. The ligation reactions were set up in the same way as previously described (using a molar equivalent amount of the fragment), followed by transformation and screening of the colonies for the presence of the fragments. Colonies were screened as DNA minipreparations, with positive colonies being confirmed by agarose gel electrophoresis analysis. The correct orientation of the 16 kb RNP fragment was determined by restriction endonuclease analysis using NotI. The resultant construct was named p220.RNP16.

Transfection of EB V Reporter Constructs into HeLa Cells.

HeLa cells were transfected in 6-well plates with p220.EGFP and p220.RNP16, using the CL22 peptide mediated delivery system described in International Patent Application WO 98/35984 and described below. After culture for 24 hours, hygromycin B (Calbiochem) selection was added to a final concentration of 400 µg/ml. Hygromycin B resistant colonies of cells were maintained in culture and analysed periodically for GFP expression on a Becton Dickinson FACScan. Cells were routinely split into 24-well plates the day before analysis so that they were approximately 50% confluent on the day of analysis. For the expression time-course, a marker region was set which contained the GFP expressing population of cells and this marker was used to investigate the stability of GFP expression over time. Transfected HeLa cells were also taken off hygromycin B selectin to investigate the stability of GFP expression, in the absence/presence of the UCOE, without selection pressure.

P Cloning of CET200

EGFPN1 was restricted with NheI/NotII and the following oligos were annealed and inserted to create the multiple cloning site (MCS):

```
5'CTAGCGTTCGAAGTrTAAACGC 3'''      (SEQ ID NO: 18)

5'GGCCGCGMAAACTTCGAACG 3'''        (SEQ ID NO: 19)
```

The resulting plasmid was restricted with AseI blunted and the 8.3 kb HindIII fragment blunted RNP A2 fragment inserted. The resulting orientation was then determined creating the final vector CET200 (see FIG. 49).

Cloning CET210 pUC 19 was restricted with EcoRI/ArI and blunted, removing one PvuI site thus creating a unique PvuI site for linearisation (pUC19 Δ). The MCS was removed from pEGFPN1 by digestion with NheI/AgeI and blunted. This creates the NheI site. The CMV EGFP SV40 cassette was removed as a AfiII blunt AseI fragment and inserted into pUC-A19 that had been restricted with PvuII and pGK puro bGH (from pGK puro BKS) was inserted with NdeI. The resulting vector was then restricted with NheI/NotI removing EGFP and the MCS inserted as described above. The MCS containing vector was then restricted with HindIII and the 8.3 kb RNP HindIII fragment inserted creating the final vector CET210 (see FIG. 49). 0278]

Preparation of Plasmid Containing a UCOE

Cloning of RNP UCOE Containing Reporter Constructs p8 kb Hind BKS contained a 8.3 kb HindIII genomic fragment of the RNP locus contained the promoters and first exons of RNPA2 and HPI H-γ genes.

pCMVEGFP-IRES was constructed by digesting pEGFP-NI (Clontech, same as CMV-EGFP FIG. 35) with Kpn1 and NotI to liberate the EGFP sequence, this was then ligated into pIRESneo (Clontech) that had been partially digested with Kpn1 and then NotI. This created a vector with the EGFP gene 3' to the CMV promoter and 5' to IRESneo.

IntronA CMV was cloned by taking the 1.5 kb IntronA-CMV fragment from pTX0350 (a pUC based CMV IntronA-MAGE1 plasmid) with NruI (blunt cutter) and HindIII. pEGFP N1 was digested with AseI and the ends of the fragment were then end filled with Klenow and T4 DNA Polymerase. This was then digested with HindIII to obtain a 4.2 Kb fragment. Both fragments were then ligated overnight.

p4.00MV was constructed by excising a 4 kb fragment from p8 kb Hind BKS with BamHI/HindIII/BstEII digestion. The ends of the fragment were then end filled with Klenow and T4 DNA polymerase.

pEGFP NI (Clontech) was linearised with AseI, the ends blunted as above and then treated with calf intestinal phosphatase (CIP). Both fragments were then ligated overnight. The resultant clones were screened for both forward and reverse orientations of the 4 kb UCOE insert.

p75CMV was constructed by excising the 8.3 kb fragment from p8 kb Hind BKS with HindIII digestion. The ends of the fragment were then end filled with Klenow and T4 DNA Polymerase. pEGFP-NI (Clontech) was linearised with AseI, the ends were blunted as above and then treated with calf intestinal phosphatase (CIP). Both fragments were then ligated overnight. The resultant clones were screened for both forward and reverse orientations of the 8.3 kb UCOE insert.

P16CMV was constructed by excising a 16 kb fragment from MA551 (hnRNPA2 genomic clone containing 5 kb 5' and 1.5 kb 3' sequence including the entire coding region) by SalI digestion. The ends of the fragment were then end filled with Klenow and T4 DNA Polymerase. pEGFP-NI (Clontech) was linearised with AseI, the ends were blunted as above and then treated with calf intestinal phosphatase (CIP). Both fragments were then ligated overnight. The resultant clones were screened for both forward and reverse orientations of the 16 kb UCOE insert.

Transfection, of HeLa cel/s Using the CL22 Peptide

The CL22 peptide has the amino acid sequence:

```
                                        (SEQ ID NO: 20)
NH 2-KKKKKKGGFLGFWRGENGRKTRSAYERMCNILKGK-COOH
```

The CL22 peptide was used as a transfecting agent in accordance with the methods described in WO 98/35984.

HeLa cells are routinely cultured in EF10 media, splitting a confluent flask 1:10 every 3 to 4 days. 24 Hours prior to transfection, cells were seeded at $5 \times 10^4$ per well (6-well plate). Complexes were formed 1 hour prior to transfection by mixing equal volumes of DNA:CL22, which are at concentrations of 40 µg/ml and 80 µ/ml respectively in Hepes buffered saline (10 mM Hepes pH7.4, 150 mM NaCl), and incubated at room temperature for 1 hour. Media was removed from cells, which were then washed with 1% phosphate buffered saline. 2.5 µg of DNA:complex (125 µl) was then added to the cells and the volume made up to 1 ml with RAQ (RPM1 media (Sigma), 0.1% human albumin, 137 p M chloroquine (added fresh)) which gives a final concentration of chloroquine of 120 µM. Cells and complex were incubated for 50 hours at 37° C. The complex was then removed and replaced with EF10 media (Minimal Essential medium (Sigma), 10% Foetal calf serum, 100 unit/ml penicillin/0.1 mg/ml streptomycin, 1× Non Essential amino acids (Sigma)).

Analysis of GFP Expression in Transfected HLta Cells

Cells were stripped off 6-well plates for expression analysis of GFP. Cells were washed with phosphate buffered saline (PBS; Gibco) and incubated in Trypsin/EDTA (Sigma) until they had detached from the surface of the plates. An excess of EF10 medium (Gibco) supplemented with 10% foetal calf serum (FCS; Sigma) was added to the cells and the cells transferred to 5 ml polystyrene round-bottom tubes. The cells were then analysed on a Becton Dickinson FACScan for the detection of GFP expression in comparison to the autofluorescence of the parental cell population.

Preparation of Total DNA Samples

In order to examine the episomal DNA content of the transfected populations, a total preparation of cellular DNA was made. The cells were washed with PBS and then lysed with lysis buffer [10 mM tris pH7.5, 10 mM EDTA pH 8.0, 10 mM NaCl and 0.5% Sarcosyl to which was added fresh Proteinase-K1 mg/ml F/C]. The cell lysate was scraped off the plate and transferred to an eppendorf tube with a wide bore pipette. Following overnight incubation at 65° C. the cell lysate was phenol/chloroform extracted and ethanol precipitated. The DNA pellet was resuspended in TE pH8.0.

Detection of Episomal DNA in Total Genomic DNA Samples

Total genomic DNAs, prepared from transfected cells, 7 days after transfection, were restriction endonuclease digested using an endonuclease that linearised the DNA constructs used in the transfection and therefore any episomal DNA present in the sample. Apa LI (NEB) was used for mock, CMV EGFP, lntronA CMV and 4.0CMV forward and reverse samples. BspLU1 1 1 (Boehringer) was used for 7.5CMV forward and reverse samples. 10 µl (20% of the sample) of total genomic DNA were digested with 30 units of restriction endonuclease, for 16 hours according to the manufacturers recommended conditions. The samples were electrophoresed for 400 volt/hours on a 0.6% agarose gel along with 100 pg or 4 ng of linearised plasmid controls. The gel was then transferred to Hybond-N Hybridisation transfer membrane (Amersham) by Southern blotting. Briefly, the gel was incubated in 0.25M HCI for I S minutes to depurinate the DNA, followed by denaturation in 1.5M NaCl/0.5M NaOH for 45 minutes and neutralisation in 1.5M NaCl/0.5M Tris Cl pH7.0, for 45 minutes. The DNA was then transferred from the gel to the membrane by capillary blotting in 20×SSC (3M NaCl, 0.3M $Na_3$ citrate $2H_20$, pH 7.0) for 16 hours. The filter was air-dried for 1 hour and cross-linked for 2 minutes using a UVP CL-100 ultraviolet crosslinker (GRI) an energy setting of 1200. The membrane was probed using a radioactive EGFP probe using "Church hybridisation conditions". The membrane was prehybridised in 0.5M NaPi pH7.2, 1% SDS at 65° C. for longer than 2 hours. An EGFP fragment of DNA was removed from pEGFP N1 (Clontech) by restriction endonuclease digestion with Bgl II/NotI (NEB), separated by electrophoresis and purified from the gel slice using a GFX TM PCR DNA and Gel Band Purification kit (Amersham Pharmacia Biotech). 50 ng of the EGFP fragment were labelled with $\alpha$-$^{32}$P dCTP 3000Ci/mmol; Amersham) using a Megaprime DNA labelling kit (Amersham). The labelled probe was mixed with 100 µl of 10 mg/ml salmon sperm DNA, incubated at 95° C. for 10 minutes and placed on ice followed by addition to the hybridisation. The membrane was hybridised for 16 hours at 65° C., followed by two 30 minute washes in 40 mM NaPi pH7.2, 1% SDS at 65° C. The radiolabelled membrane was then analysed on a Cyclone storage phosphor system (Packard) after exposure on a super resolution phosphor screen.

Fluorescence Microscopy

The transfected cells cultured in 6-well plates were viewed under fluorescence using a Zeiss Axiovert S1 00 inverted microscope. Photography was carried out at regular timepoints throughout using a Zeiss MC 100 camera and Fujichrome Provia 400ASA film.

Example 1

Analysis of the Human TBP Gene Locus

Mapping the TV Gene Domain

Figure 1B:
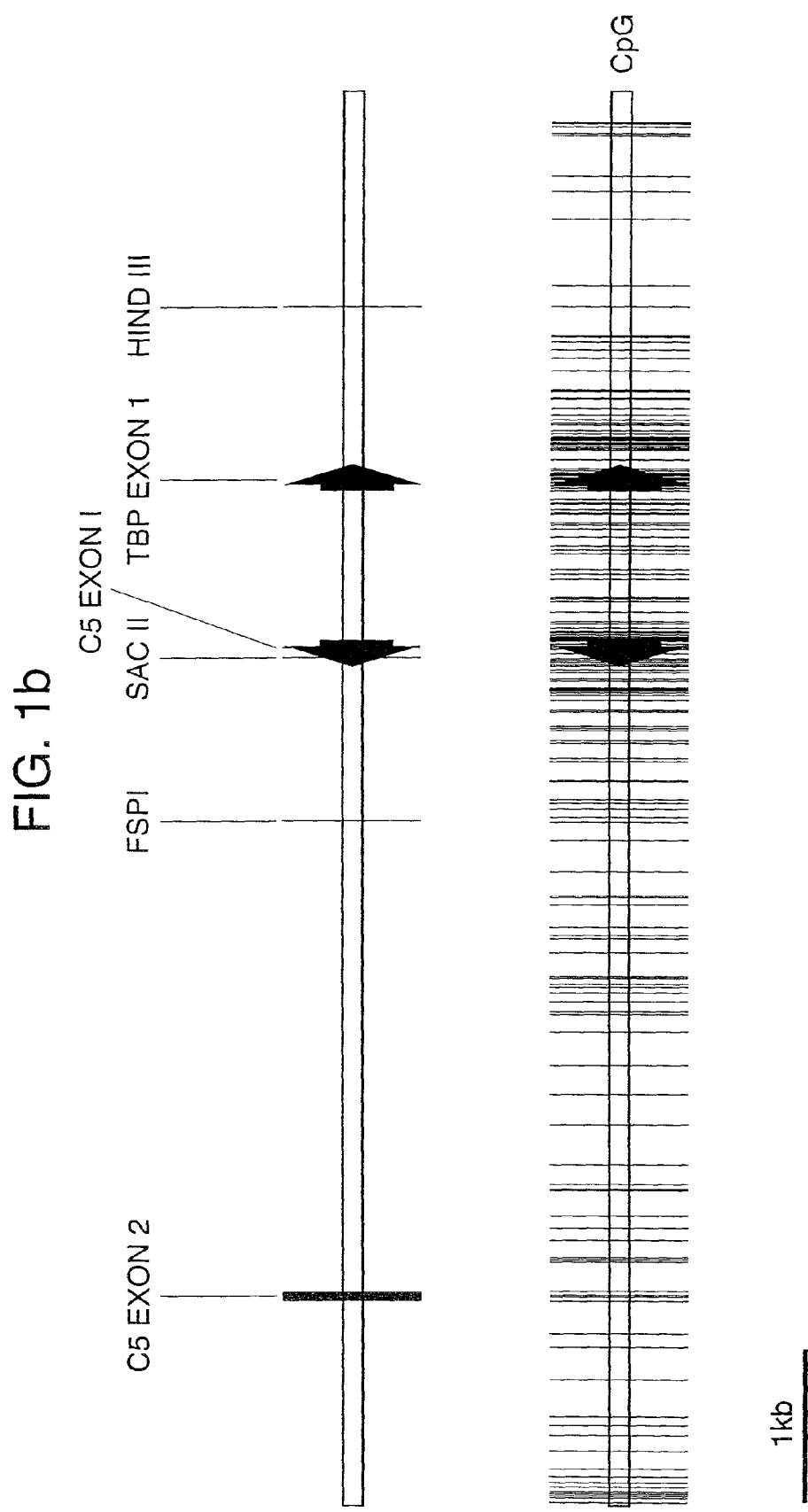

The human TBP gene is 20 kb in length (Chalut et al., 1995), located on chromosome 6q27-tel (Heng et al., 1994) and is closely linked to the gene encoding the protein C5 which forms part of a ubiquitous proteosome (FIGS. 1 A and C; Trachtulec, Z. et al., 1997). The CS gene is divergently transcribed from a position 1 kb upstream from the cap site of TBP. TBP and C5 may therefore comprise dual promoters. This has important ramifications with regards to the construction of expression vectors based on TBP since dual promoters do not necessarily function with equal efficiency in both directions (see Gavalas and Zalkin, 1995).

Sequence analysis has revealed that the TBP/CS promoter regions are contained within a methylation free, CpG-island of 3.4 kb. This extends from a Fsp I site within intron I of C5 and a HindIII site within intron 1 of TBP and encompasses the most 5' 1 kb sequences of the first intron of both genes as well as the 1.4 kb region between their transcriptional start sites (FIG. 1 B).

The human TBP gene locus consists of 3 closely linked genes. The PSMB 1 gene (also referred to herein as C5) is divergently transcribed from a position 1 kb upstream from the cap site of TBP. The 3' end of a recently identified gene, PDCD2 is located 5 kb downstream of TBP. These 3 transcription units span a total of 50 kb. Downstream of the PSM131 gene in the direction of the centromere, there is a region of at least 80 kb which consists of blocks of repeat sequence DNA with no identifiable structural genes. Upstream of the PDCD2 gene toward the telomere there is a 30 kb stretch of repeat, non coding sequences followed by a potential new transcription unit. The PDCD2 gene is approximately 150 kb from the start of the telomeric repeat region. This makes the TBP locus the first structural gene cluster from the telomere on the long arm of chromosome 6. Pa.

Pattern of Gene Expression from the TBP Domain

The tissue distribution of expression from within the TBP gene cluster was assessed using a commercially available dot-blot prepared with poly(A)⁺ RNA derived from a wide range of human tissues and cell types (FIG. 35A). Hybridisation of this dot-blot with appropriate probes showed that the PSM81 (FIG. 35B), PDCD2 (FIG. 35C) and TBP (FIG. 35D) genes are all ubiquitously expressed. These data confirm that the TBP locus consists exclusively of a ubiquitously expressed chromatin domain

Mapping Transgene Integrity in Mice Harbouring pCP2-TLN

The pCYPAC-2 derived clone pCP2 TLN (FIG. 1) which is 90 kb in length was used to generate transgenic mice. This clone starts at a position 46 kb downstream of the CS gene (65 kb 5' of TBP) and terminates 4.5 kb 3 of TBP. This clone therefore possesses both C5 and TBP genes in their entirety.

Figure 3A:
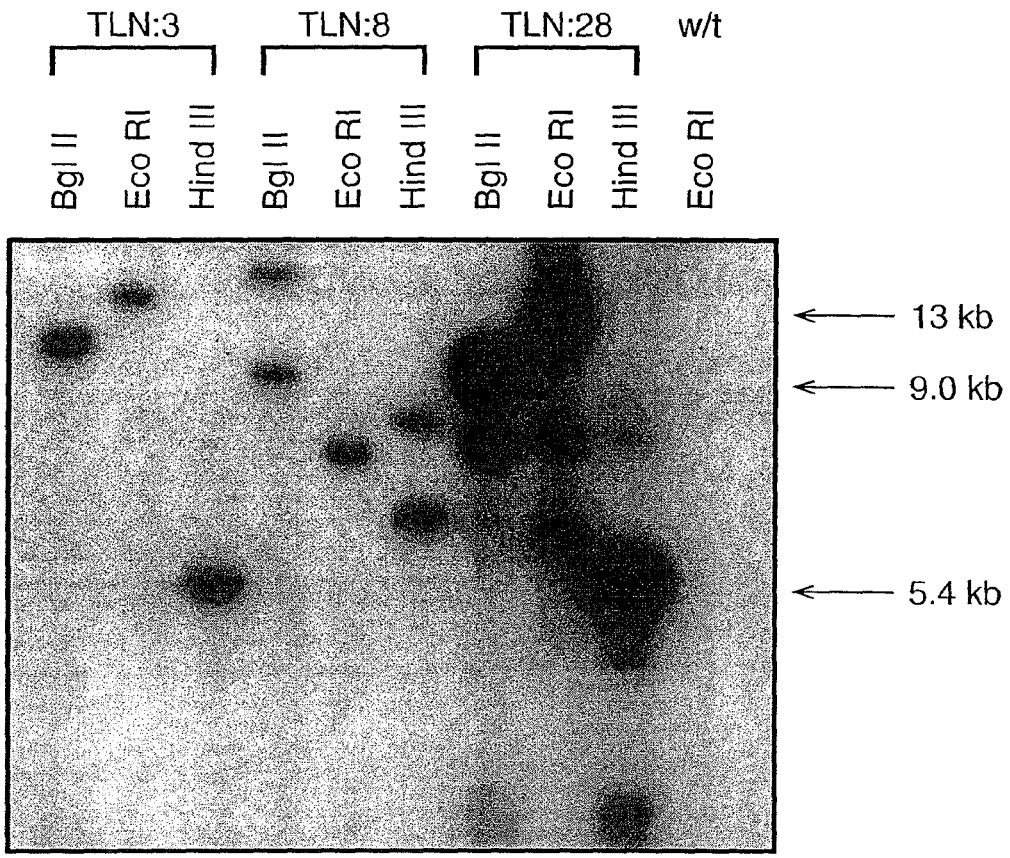
Figure 4:
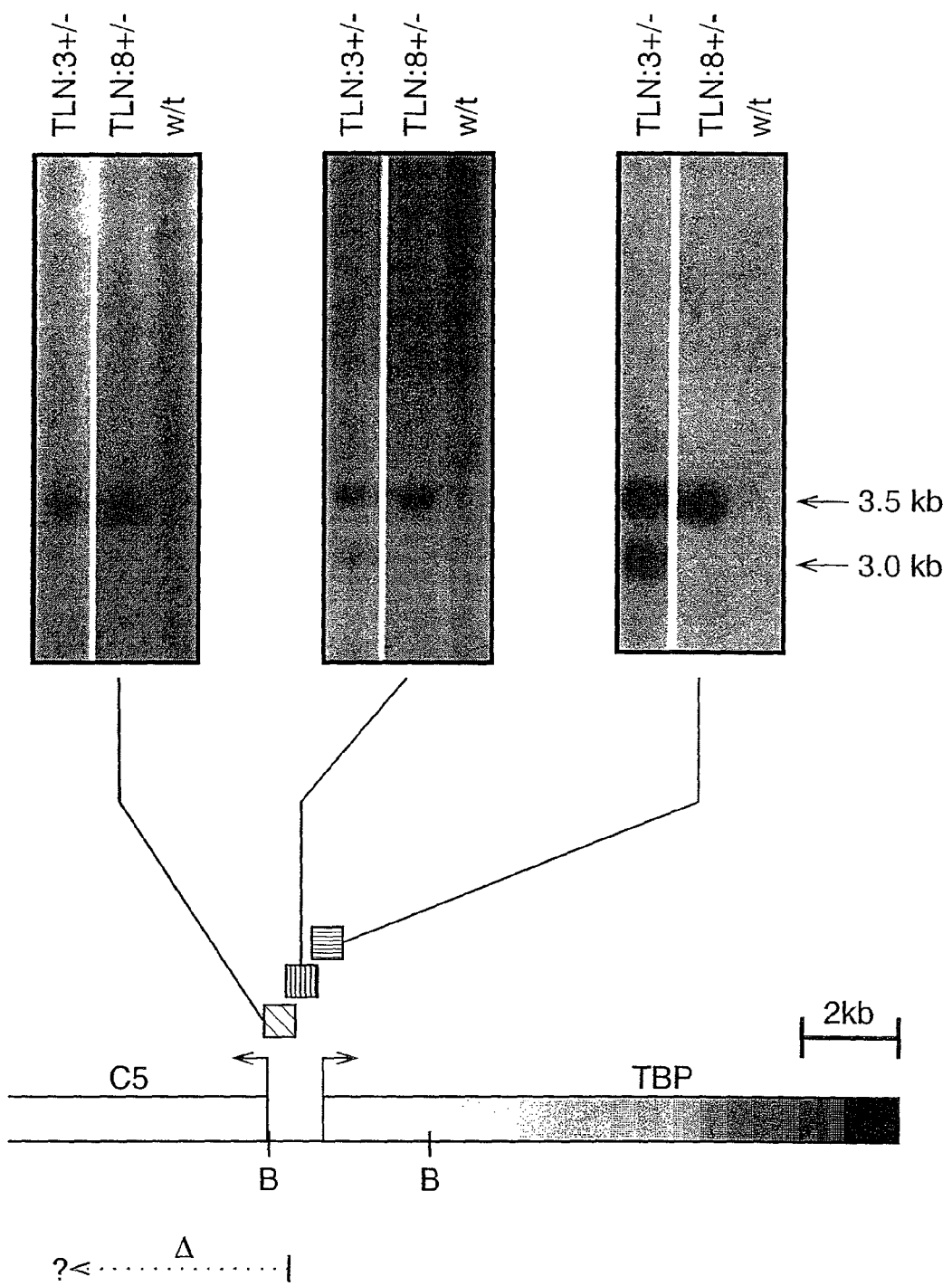

Three transgenic lines with pCP2 TLN have been produced. The initial Southern blot analysis with probes derived from the ends of pCP2 TLN showed that line TLN:3 possesses two copies of the transgene (FIG. 2a,b lanes TLN 3) in a head-to-tail configuration (FIG. 3a, lanes TLN:3). However, one copy appears to have suffered a 5' deletion, which extends into the TBP promoter (FIG. 4, lanes TLN:3). Line TLN:8 by end-fragment analysis appeared to harbour 3 copies of pCP2 TLN (FIG. 2a,b lanes TLN 8). Line TLN:28 appeared to harbour several copies at multiple integration sites (FIG. 3a, lanes TLN:28).

Figure 3B:
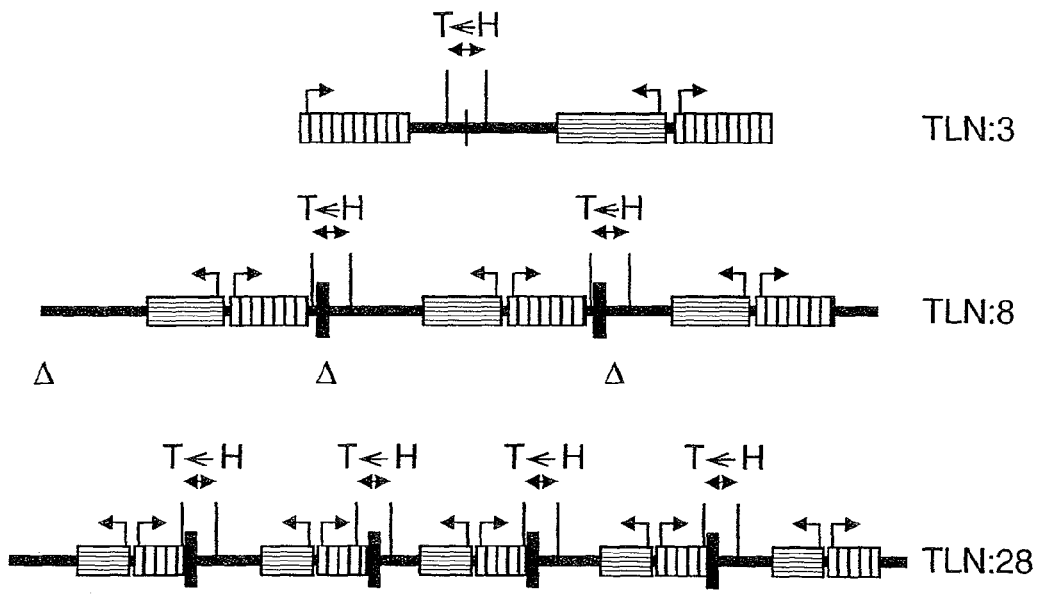

A summary of the initial analysis of transgene copy-number and integrity in these TLN mice is shown in FIG. 3B.

Figure 3C:
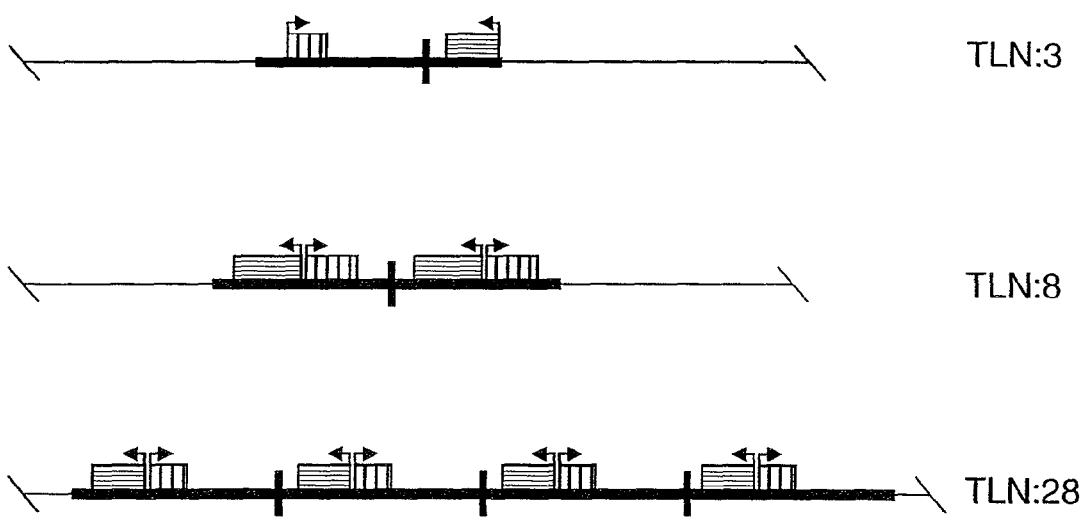

Further analysis of the transgenic lines produced with pCP2 TLN has now shown that line TLN:3 contains two deleted copies of pCP2 TLN such that a single functional copy of the TBP and PSMBI genes remains intact (FIG. 3C, TLN:3). Line TLN:8 harbours two, tandem integrated copies of pCP2 TLN (FIG. 3C, TLN:8). Line TLN:28 possesses 4 tandem arranged copies of pCP2 TLN (FIG. 4, TLN:28). The deletions at the 5' and 3' ends of the transgene tandem arrays in TLN:8 and TLN:28 still leave the PSM131 and TBP genes intact.

As expected the methylation free island of TBP/C5 is preserved in transgenic mice (data not shown) as has been observed for the S' region of other genes which harbour a CpG rich domain (e.g., murine Thy 1; Kolsto et al., 1986).

Expression Analysis of the TV and C5 Transgenes on pCP2 TLN in Mice.

Figure 6A:
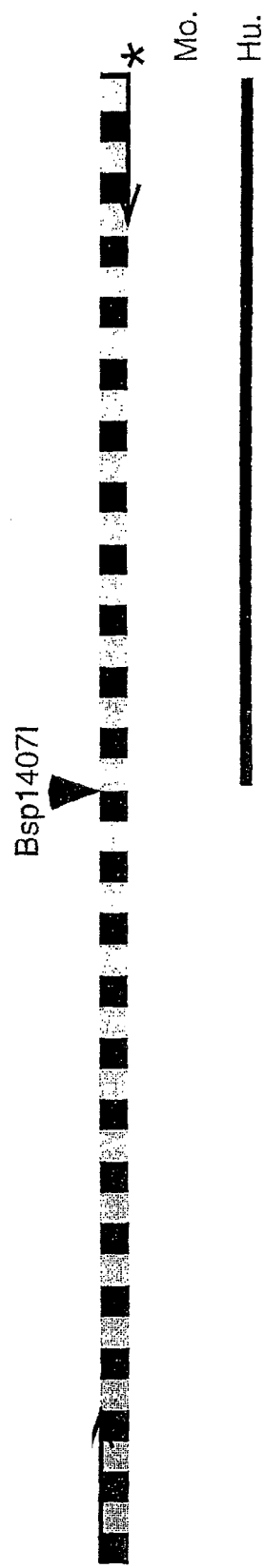
Figures 7A, 7B:
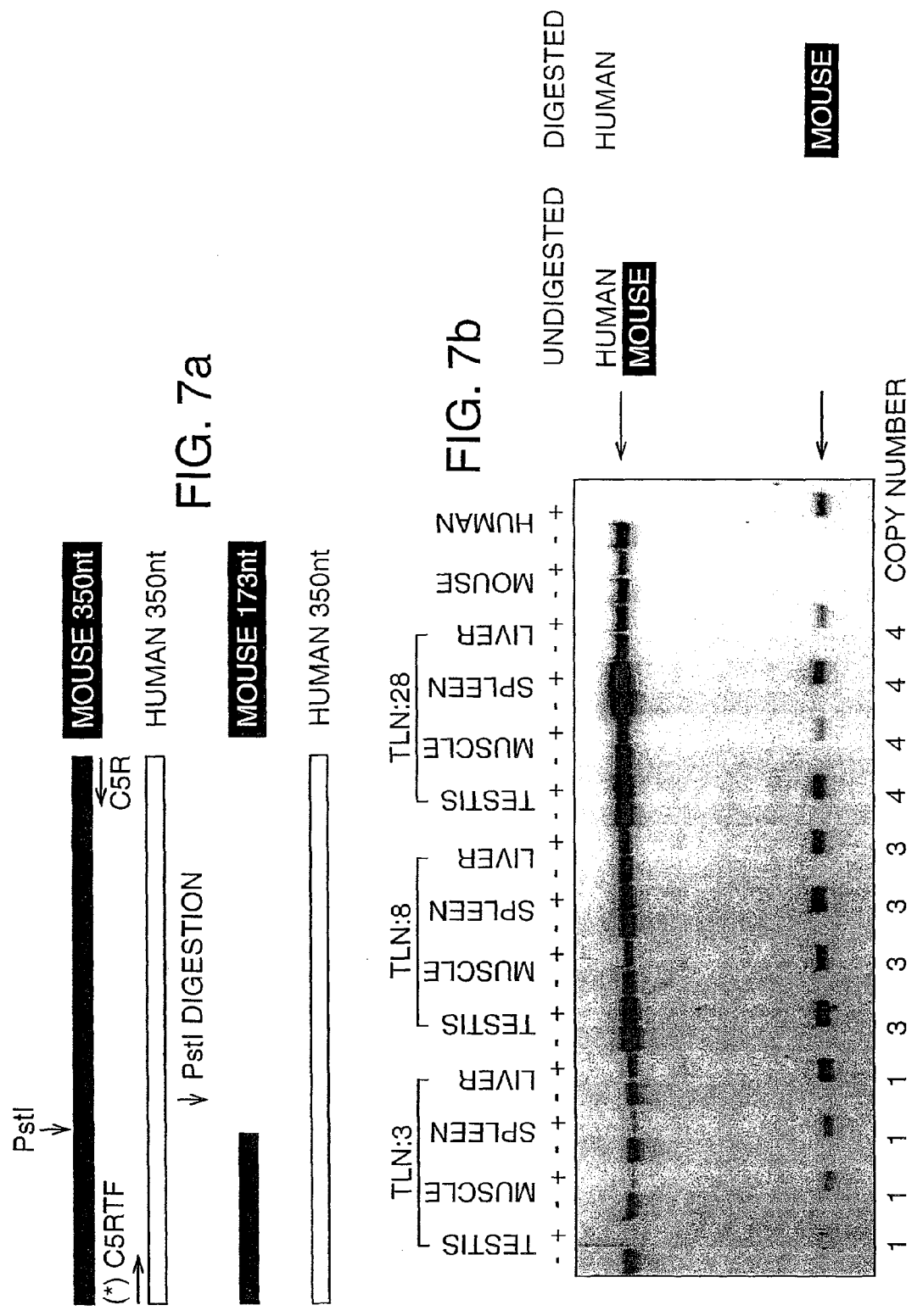

An RT PCR based assay that would simultaneously detect both the endogenous murine as well as the human transgene TBP and CS message was developed. Primers (TB 14 and TB 22) for the RT PCR reactions were selected from a region of homology between the human and mouse TBP cDNA sequence (FIG. 5b). This allows an RT PCR product of 284 bp to be produced from both mRNAs by a single pair of primers. In order to distinguish between the human and mouse TBP products, minor base differences resulting in changes in the presence of restriction enzyme sites are exploited. Digestion with Bsp 14071 cleaves the human PCR product, giving rise to a fragment of 221 nucleotides (nt) (FIG. 6a). Similarly, from a region of homology between the human and mouse C5 cDNA sequence (FIG. 5a), allowed the generation of an RT PCR product of 3SOnt from both sequences. Cleavage with Pst I reduced the size of the product derived from the murine C5 mRNA to 173 nt (FIG. 7a).

Figure 6B:
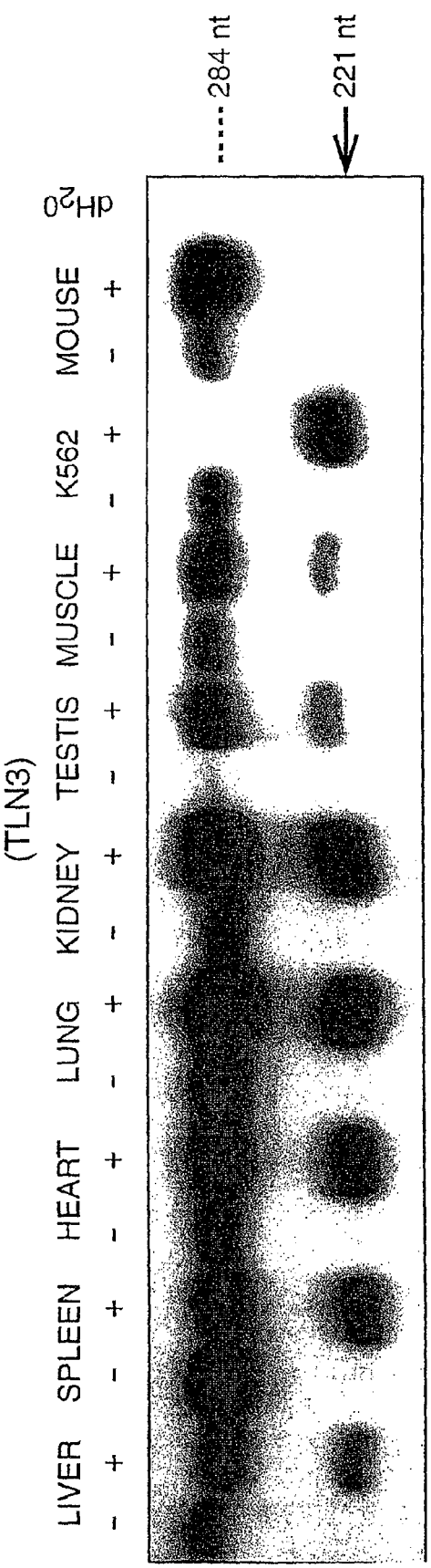

Primers TB14 (FIG. 5b) and C5RTF (FIG. 5a) were end-labelled with 32 P resulting in the generation of radioactive products after the PCR reaction. These products are finally resolved by electrophoresis on denaturing polyacrylamide gels (FIGS. 6b-c and 7b).

Figure 8A:
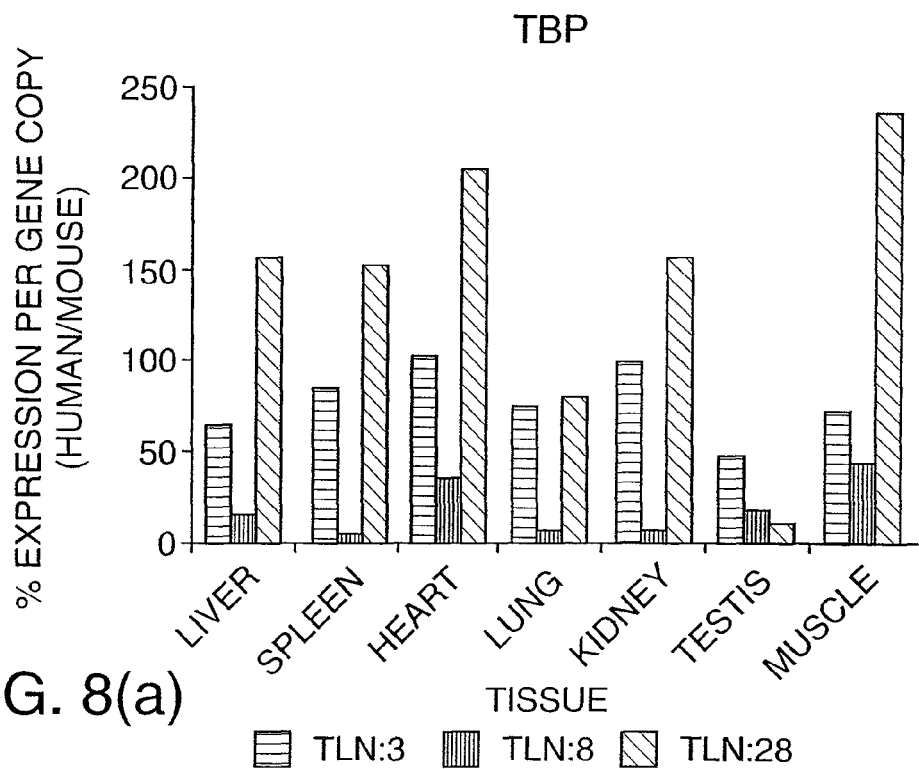
FIG. 8 shows a summary of quantification of (a) human TBP gene expression (b) human C5 gene expression in TLN transgenic mice.
Figure 8B:
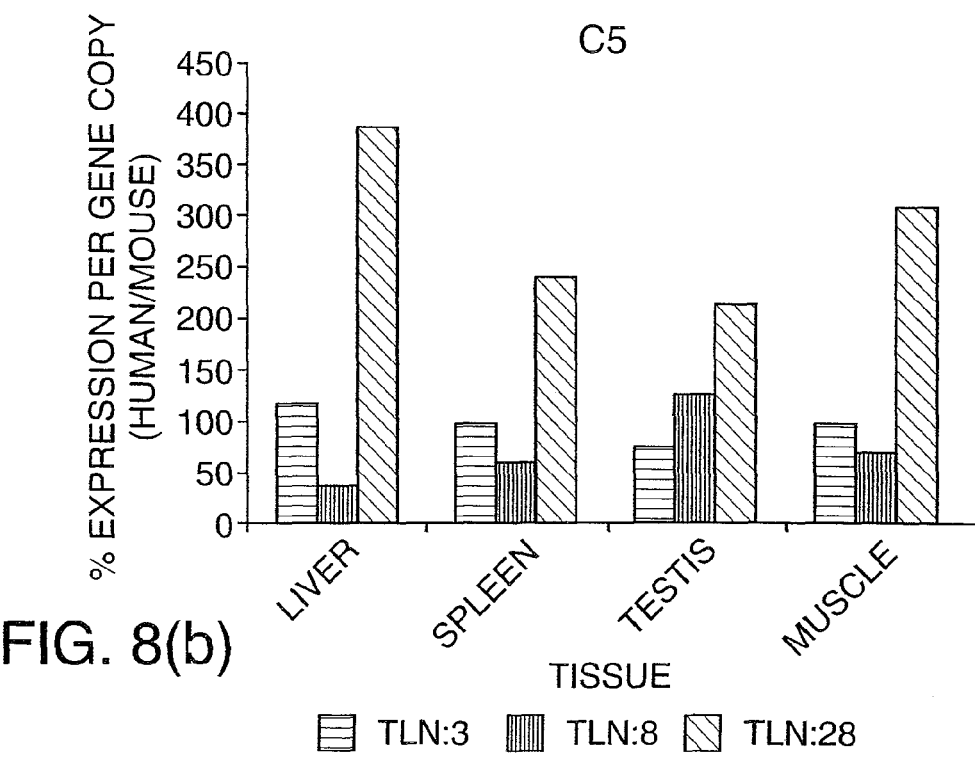

Total RNA (1 µg) from various tissues of transgenic mouse lines TLN:3, TLN:8, and TLN:28, were subjected to the above analytical procedure and quantified by Phosphorlmager analysis (FIG. 8). All mice showed significant levels of expression of both the human TBP and CS transgenes in all tissues analysed including TLN:3, which harbours a single intact copy of these two genes. Most importantly, a reproducible level of expression was observed between tissues in a given mouse line especially for CS. This indicates that the TLN clone in all likelihood possesses a ubiquitous chromatin opening capability. However, some variation in the level of expression per transgene copy-number was observed between mouse lines. In addition, expression of TBP in line TLN:8 between tissues also varied from 5.40%. These results suggest that although TLN possesses a chromatin opening capability, the C5 and especially the TBP promoters are prone to positive and negative transcriptional interference. This in turn implies that the inherent transcriptional activating potential of the TBP and CS regions on this clone are weak and therefore unable to always exert a dominant effect over position effects. This is in contrast to what seems to be a chromatin opening UCOE effect of this region, which is strong and appears to over ride such position effects. This hypothesis is supported by the observation that the weaker TBP promoter is more prone to variability; compare, for example, the ratio of TBP levels between spleen and muscle with that for CS in line TLN:8 (FIG. 8).

Transgene expression analysis as described previously, was carried out using tissues from mice that were between 2 and 6 months of age. The stability of transgene expression was also assessed in 23 month old mice from lines TLN:3 and TLN:8 by analysing PSMBI mRNA. Similar results were obtained in both lines compared to that obtained with the younger animals. The result further demonstrates that the transgenes are maintaining a transcriptionally competent open chromatin structure.

T Expression Analysis of a 40 kb Subc/One of the TBP Locvs

The reproducible, physiological levels of expression given by the pCP2-TLN clone in transgenic mice indicate that it possesses a ubiquitous chromatin opening capability. As a first step to fine mapping the region(s) of DNA responsible for this activity, we have begun to analyse a 40 kb subclone (pCP2 TSN; FIG. I a) of the human TBP locus. The pCP2 TSN clone possesses 12 kb of both 5' and 3' flanking sequences surrounding the TBP gene. As a result it only harbours a complete TBP and a 3' truncated mutant of C5.

Previous work with the human β-globin LCR demonstrated that an initial indication for the presence of LCR activity may be obtained by comparing expression levels between stable transfected tissue culture cell clones harbouring a single copy of the transgene. It has been found that the more complete the LCR element, the higher the degree of reproducibility of expression between independent clones. Expression analysis of pCP2-TSN was conducted using this strategy to assess for the presence of LCR-type activity.

pCP2-TSN was first cloned into the cosmid vector pWE1 S (Clontech) which possesses a neomycin resistance gene (FIG. 9). The resulting pWE-TBP construct was then used to generate stable transfected clones of murine fibroblast L-cells. The transgene copy-number of 23 clones was then determined by Southern blot analysis (FIG. 10). A number of clones representing a range of copy-numbers were then selected and analysed for transgene expression as described for the transgenic mice above. The results are summarised in FIG. 11 and show that expression at or above physiological levels are obtained per copy of the transgene up to a number of eight. With copy-numbers of 20 or more, expression levels per transgene are reduced to 30-40% of wild type.

These data demonstrate that reproducible, physiological levels of expression can be produced by pCP2-TSN at both single and multiple transgene copy-numbers. This strongly suggests that this genomic clone possess a ubiquitous chromatin opening capability. There are clearly a number of clones (e.g., number 4, 33 and 6), which show a pronounced "positive" position effect giving rise to expression levels that are markedly greater than physiological per transgene copy. This would be the anticipated outcome in certain cases where integration of the transgene had taken place within already open, active chromatin. The nearby Presence of a strong transcriptional enhancer under these circumstances would be expected to have a stimulatory effect on the inherently weak TBP promoter.

The stability of expression of the constructs was tested over a 60 day period. Expression levels were found to remain constant (FIG. 36). This was even the case when drug selective pressure was removed (FIG. 36, lanes marked BG418) in addition, expression remained stable through successive freeze and thaw cycles of the cells regardless of whether drug selective pressure was maintained.

Expression Analysis of a 25 kb Sub-Clone of the TBP Locus

The 25 kb genomic clone (TPO) spanning the TBP gene with 1 kb 5' and 5' kb 3' flanking sequences (FIG. 1C) was cloned into the polylinker region of a modified pBluescript vector harbouring a puromycin resistance gene to give pBL-TPO puro as described above. The construct was used to generate stable transfected clones of murine fibroblast L-cells.

The pBL-TPO puro construct gave similar results to those obtained using the TSN construct (FIG. 37). The data demonstrate that reproducible physiological levels of expression can be produced by both TSN and TPO at single and multiple transgene copy-numbers. The data is consistent with the genomic clones possessing a ubiquitous chromatin opening capability. This surmise is further enhanced by the finding that TPO clone numbers 7 (two copies), 29 (single copy) and 34 (two copies) are centromeric integration events (data shown below) demonstrating that the genomic fragment has the ability to express from within a heterochromatin environment.

There are clearly a number of clones (e.g., FIG. 37, clone 11), which show a pronounced "positive" position effect giving rise to expression levels that are greater than physiological per transgene copy. This would be the anticipated outcome in certain cases where integration of the transgene had taken place within already open, active chromatin. The nearby presence of a strong transcriptional enhancer under these circumstances would be expected to have a stimulatory effect on the inherently weak TBP promoter.

Similar results have also been obtained using HeLa cells instead of CHO cells (data not shown).

Mapping DNase I hypersensitive Sites All

All known LCR elements have been found to be regions of high, tissue-specific IDNase I hypersensitivity, indicative of the highly open chromatin configuration which these elements are thought to generate. We have therefore begun to analyse for the presence of DNase I hypersensitive (HS) sites both within and around the human TBP gene. FIG. 12 summaries a series of experiments using nuclei from the human myelogenous leukaemia cell line K562, which maps IDNase I HS sites over a 40 kb region starting from 12 kb 5' and extending 4.5 kb 3' of the TBP gene. The only HS sites that are evident throughout this region map to the immediate promoter regions of the C5 and TBP genes (FIG. 12, top panel, Hind III digest/Hind III-Xba I probe). These HS sites correlate well to previously identified promoter elements important for TBP and CS gene expression as determined by transient transfection assays (Tumara, T. et al., 1994; Foulds and Hawley, 1997). However, it would appear that if LCR-type elements are present within this locus, they are at a considerable distance from the transcriptional start sites of both the TBP and C5 genes. This places any LCR-type element outside of the 40 kb clone spanning the TBP gene that has given an initial indication of ubiquitous chromatin opening capability.

FISH Analysis

A total of 34 clones carrying 1-2 copies of the human TBP transgene were analysed by FISH. The TBP transgene and the heterochromatin component of the mouse centromere, the gamma or major satellite, were detected with Fluorescein and Texas Red, respectively. This produced green and red fluorescent signals in the clones in which the transgene had integrated into the chromosome arm (see FIG. 39A). However, in the case of centromeric integration both signals co localized and a mixture of both colours could be detected as a yellow fluorescent signal. Two clones, 344-6 and 344-37, out of the 18 generated with pWE-TSN, showed the transgenic signal in the centromeric region. In clone 344-6, the TBP transgene had integrated in the centromere of a Robertsonian chromosome, whereas, integration in clone 344-37 was in a typical mouse acrocentric chromosome.

Three clones, 440-7, 440-29, and 440-34, out of the 16 generated with pBl-3-TPO-puro, showed centromeric integration in typical acrocentric chromosomes. Clone 440-29, which carried a single copy of the TBP transgene, showed the TBP signal clearly surrounded by heterochromatic satellite sequences (see FIGS. 39B and C). It was further shown that these clones continued to express TBP at physiological levels for at least 12 to 14 weeks in the absence of selection (data not shown).

These results show that a single copy of the 25 kb fragment of the TBP locus (TPO) is capable of ensuring physiological expression even in the context of a heterochromatic location (i.e. centromeric integration), and thus provides formal proof of chromatin opening (Sabbattini P, Georgiou A, Sinclair C, Dillon N (1999) Analysis of mice with single and multiple copies of transgenes reveals a novel arrangement for the λ 5-$V_{preB1}$ locus control region. Molecular and Cellular Biology 19: 6718679).

Example 2

Analysis of the Human hnRNPA2 Gene Locus
Mapping the hnRNPA2 Gene Domain

The hnRNP A2 gene is composed of 12 exons spanning 10 kb and is highly homologous to the hnRNP-AI gene in its coding sequence and overall intron/exon structure indicating that it may have arisen by gene duplication (Biamonti et al, 1994). However, unlike the A1 gene no A2-specific pseudogenes have been found (Burd et al., 1989; Biamonti et al., 1994). In addition, the A1 and A2 genes are not genetically linked being on human chromosomes 12q13.1 (Saccone et al., 1992) and 7pI 5 (Biamonti et al., 1994) respectively. FIG. 13A depicts a genetic map of the human hnRNP A2 locus present on the 160 kb pCYPAC-2 derived clone MAI 60. This genomic fragment possesses 110 kb5' and 50 kb of 3' flanking sequences. The DNA sequence of the 4.5 kb region upstream of the known transcriptional start site of the hnRNP-A2 was determined. This identified the position of the gene for the heterochromatin associated protein HPI γ to be divergently transcribed from a position approximately 1-2 kb 5' of the hnRNP-A2 cap site (FIG. 13C). Southern blot analysis indicates that the entire HPI γ gene is contained within a region of 10 kb (data not shown).

Therefore the TBP and hnRNP A2 gene loci share the common feature of closely linked, divergently transcribed promoters.

The pattern of expression of the HP1 HPI γ ene within human tissues was assessed on a dot-blot prepared with poly (A)$^+$ RNA derived from a wide range of human tissues and cell types. The results (FIG. 38) show that the gene, like that for hnRNP A2 is also ubiquitously expressed. The two genes can therefore be seen to form a ubiquitously expressed gene domain similar to that of the TBP locus.

Functional Analysis of the hnRNP A2 Locus in Transgenic Mice

MAI 60 (FIG. 13A) was used to generate transgenic mice. Southern blot analysis of the two founders that have bred through to the F1 stage has shown that these lines possess 1-2 copies of the transgene (data not shown).

A similar RT PCR based assay to that used for TBP was used to analyse expression of the human hnRNP A2 transgene. The cDNA sequence of the murine hnRNP A2 is not known. Therefore, we could not select a region of homology between human and mouse hnRNP A2 by sequence comparison for RT-PCR amplification. We initially chose two primers Hn9 and Hn11, which correspond to sequences within exons 10 and 12 respectively of human hnRNP A2 (FIG. 114A) and gives rise to an RT-PCR product of 270 bp. However, we found that these two primers gave an identical sized product from both human and mouse RNA preparations (FIG. 148) indicating a region of homology between these two species. Tests with a range of restriction enzymes also revealed that Hind III is able to cut the murine (FIG. 148, lane HindIII M) but not the human (FIG. 14B, lane HindIII H) product to give a fragment of 170 bp.

Total RNA (1 µg) prepared from various tissues of an F1 transgenic mice of line Hn35 and Hn55, were then analysed using the above method with 32 P end-labelled 5' Hn9 (FIG. 16). PhosphorImager analysis was used to quantify the ratio of human to mouse RT PCR products. The results (FIG. 17A) show that reproducible, physiological levels of expression per transgene copy-number are obtained in all tissue types analysed.

Analysis of 600 Subclone of the hnRNPA2 Locus in Transgenic Mice

The data obtained with the MA160 pCYPAC derived clone indicate that this genomic fragment possesses a ubiquitous chromatin opening capability. In order to further define the location of the DNA region(s) responsible for this activity, transgenic mice were generated with a 60 kb Aat 11 subfragment (Aa60) obtained from MA160 (FIG. 1313). This fragment possesses 30 kb 5' and 20 kb Vlanking sequences around the hnRNPA-2 gene.

Three transgenic mice (Aa7, Aa23 and Aa31) have been generated to date with the Aa60 fragment, two of which (Aa23 and 31) have bred through to establish lines. Estimated transgene copy-numbers are: Aa7, 3; Aa23, 1 2; Aa31, 1 2).

Total RNA (1 µg) from a range of tissues was analysed for transgene expression as described above. The results are shown in FIG. 15 and quantified by PhosphorImager (FIG. 1713). These data show that all transgenic mice express at a reproducible level per transgene copy-number in all tissues analysed. This indicated that the ubiquitous chromatin opening capacity shown by MA160 is preserved on the Aa60 sub-fragment.

Mapping of DNase/Hypersensitive Sites

The results of preliminary experiments to map DNase I HS sites over a 20-25 kb region 5' of the transcriptional start point of the human hnRNP A2 gene are shown in FIG. 18. A 766 bp probe from exon 2 on a double restriction enzyme digest with Aat II and Cla I, gave a series of three HS sites (FIG. 18, upper panel) corresponding to positions −1.1, −0.7 and −0.1 kb 5 of the hnRNP A2 gene (FIG. 18, lower panel). We have also extended the analysis to 12-13 kb downstream of the transcriptional start of hnRNP-A2 and no further HS sites where identified.

As in the case of the TBP/C5 locus, these HS sites correspond to the 1-2 kb region between the promoter of hnRNP A2 and the HPI HHPI H-y e. No LCR-type HS sites were detected indicating that the chromatin opening capacity of this locus is not associated with this type of element.

The data presented clearly show we have been able to obtain reproducible, ubiquitous, physiological levels of expression with two different gene loci (TBP and hnRNP A2) in all tissues of transgenic mice. This indicates that genetic control elements, not derived from an LCR, with a ubiquitous chromatin opening capability do indeed exist.

It is important to note that the data herein presented demonstrate a totally different function to the previously published, results using promoter-enhancer combinations from other ubiquitously expressed genes such as human 0-actin (e.g., see Ray, P. et al., 1991; Yamashita et al., 1993; Deprimo et al., 1996), murine hydroxyl-methylglutaryl CoA reductase (Mehtali et al., 1990), murine adenosine deaminase (Winston et al., 1992 and 1996), human ornithine decarboxylase (Halmekyt ö et al., 1991) and murine phosphoglycerate kinase-1 (McBurney et al., 1994). In these earlier studies high levels of expression were observed in only a subset of tissues and a chromatin opening function was not demonstrated or tested for.

In the case of the TBP gene, expression data from tissue culture cells (FIG. 11) indicate that this ubiquitous chromatin opening capacity is contained within a 40 kb genomic fragment with 12 kb of 5' and 3' flanking sequences (pCP2-TSN, FIG. 1a).

Transgenic mouse data with a 60 kb fragment spanning the hnRNP A2 gene (Aa60; FIG. 13B), indicate that the region with a ubiquitous chromatin opening capacity is contained on this fragment (FIGS. 15-17).

The only DNase I HS sites that have been mapped to these regions to date correspond to classical promoter rather than LCR-type elements. Therefore, the regions of DNA which act as ubiquitous chromatin opening elements (UCOEs) do not meet the definition of LCR elements which are associated with genes that are expressed in a tissue-specific or restricted manner UCOEs and their activities can therefore clearly be distinguished from LCRs and LCR derived elements.

Expression Vector Development

Sub-fragments of the 60 kb RNP region are assayed for UCOE activity using reporter based assays.

Expression vectors containing sub-fragments located in the dual promoter region between RNP and HPI H-y were designed using both GFP and a Neo R reporter genes, as described above and as shown in FIG. 22. These include a control vector with the RNP promoter driving GFP/Neo expression (RNP), a vector comprising the 5.5 kb fragment upstream of the RNP promoter region and the RNP promoter (5.5RNP), vectors constructed using a splice acceptor strategy wherein the splice acceptor/branch consensus sequences (derived from exon 2 of the RNP gene) were cloned in front of the GFIR gene (ensuring that the entire CpG-island including sequences from RNP intron 1 can be tested in the same reporter based assay), resulting in exon 1/part of intron 1 upstream of GFP (7.5RNP), carrying 7.5 kb of the RNP gene preceding the GFP gene, and a vector comprising the 1.5 kb fragment upstream of the RNP promoter region and the RNP promoter (1.5RNP).

Expression vectors comprising the heterologous promoter CMV are also described above and are shown in FIG. 23. These include control vectors with the CMV promoter driving GFP/Neo expression with an internal ribosome binding site (CMV-EGFP-IRES) and without an internal binding site (CMV-EGFP), a vector comprising the 5.5 kb fragment upstream of the RNP promoter region and the CMV promoter driving GFP/Neo expression (5.5CMV), a vector comprising 4.0 kb sequence encompassing the RNP and the HP1 HHPI H-y promoters; and the CMV promoter driving GFP/Neo expression (4.0CMV), and a vector comprising 7.5 kb sequences of the RNP gene including exon I and part of intron 1, and the CMV promoter driving GFP-Neo expression.

These constructs were transfected into CHO cells by electroporation, as described above. Addition of the 5.5 kb region in front of the RNP promoter resulted in a 3.5-fold increase in number of G418$^R$ colonies, FIG. 24. Transfection of these same constructs into COST cells using a nucleic acid condensing peptide delivery strategy showed an increase in colony numbers closer to 7-fold (data not shown).

A 1.5-fold increase in colony numbers was also observed after transfection of the CMV-based vectors (i.e. CMV vs. 5.5CMV) into CHO cells, FIG. 24.

Ring cloning of colonies from these transfections resulted in stable G418 R cell lines which could then be analysed for GFP expression levels. The FACS data is shown in FIG. 25. Addition of the upstream sequences resulted in a 3.5-fold increase in GFP expression when assayed with the endogenous promoter (RNP vs 5.5 RNP). An increase in GFP expression is also seen with addition of the 5.5 kb sequence in front of the heterologous CMV promoter (CMV vs 5.5CMV).

Extension of the constructs to include the entire methylation-free island showed no increase in the number of G418$^R$ colonies as compared with 5.5RNP, but there was an increase in the average median GFP fluorescence (5.5RNP cf. 7.5RNP; see FIG. 26).

GFP expression of individual clones and restricted pools (approx. 100 colonies) were followed over time culturing the cells with/without G418 selection. Clones generated with the RNP promoter alone showed dramatic instability, with the percentage of GFP expressing cells rapidly decreasing over time. Clones expressing GFP from the 5.5RNP construct in comparison were stable for more than 3 months. Although CMV-GFP pools initially show better stability, after prolonged culturing in the absence of G418 a decrease in the number of GFP expressing cells was evident, in comparison to the 5.5CMV populations which remained completely stable. FIGS. 27 and 28 show FACS profiles of these populations clearly indicating a shift to the left i.e. an increasing proportion of non-fluorescent cells with the CMV-GFP construct. In contrast the 5.5CMV-GFP pools show a stable uniform peak of expression over time. The percentage of low or non expressing cells is estimated from a gated population M1.

The studies on the RNP locus have narrowed in on a 5.5 kb region covering the dual promoters of the RNP and HPI H-y genes. Extension of this fragment in the 3' direction (7.5RNP or 8.5RNP) shows an enhancement in the level of gene expression and may relate to maintaining the methylation-free islands intact. It has also been found that minimisation of the 5.5 kb sequences to a 1.5 kb region (1.5RNP, FIG. 23) does not dramatically affect the outcome of reporter transfection studies, in terms of both the numbers of G418R colonies and expression as determined by FACsSanalysis (FIG. 29). However, 1.5RNP does not confer the stability of gene expression as shown by 5.5RNP and 7.5RNP. FIG. 30 shows the percentage of GFP expressing cells rapidly reduces over 68 days.

The construct 4.0CMV was designed so that the entire 4 kb of sequence representing the CpG methylation-free island remained intact. In addition, the cassette was inserted in front of CMV-EGFP (4.00MV-EGFP-F (forward) and 4.0CMV-EGFP-R (reverse)) in both orientations. FIG. 31 shows a dramatic enhancement (greater than 10-fold) of GFP median fluorescence, as compared to the standard CMV-GFP construct, CMV-EGFP. It is also shown that this boost of GFP expression occurs when the 4 kb cassette is in both the forward and reverse orientations.

In terms of stability of gene expression, the vectors containing the upstream 5.5 kb RNP sequences when transfected into CHO cells and followed over time show a definite advantage. Most importantly this stability is not only limited to the endogenous promoter but also confers a stability advantage to the heterologous and widely used CMV promoter.

FIG. 32 shows CMV based constructs 4.0CMV and 7.5CMV with control vector CMV-EGFP transfected into CHO cells and analysed at day 13 post-transfection following G418 selection. A substantial increase (15-20 fold) in median fluorescence can be seen by adding the 4.0 or the 7.5 kb fragments from the RNP locus in front of the CMV promoter. This increase was independent of the orientation of the fragment (data not shown).

FIG. 33 shows the percentage of GFP expressing cells in the same G418 selected pools as in FIG. 32. It can be seen that inclusion of the 4.0 and the 7.5 kb fragments enhances the percentage of GFP positive cells in the G418 selected population. In addition, the populations appear relatively stable over time, although, from previous experiments it was evident that CMV-EGFP instability is only apparent after approximately 60 days in culture.

FIG. 34 shows colony numbers after transfection of CHO cells with equivalent molar amounts of various constructs. The 7.5CMV-constructs show approximately 2.5-fold more colonies than the control vector CMV-EGFP. These observations are consistent with 7.5CMV-F ensuring an enhanced number of productive integration events and therefore with there being a chromatin opening/maintaining capacity to the 7.5 kb fragment.

Adenovirus Vector Containing a UCOE

At the present time adenovirus (Ad) is the vector system giving the most efficient delivery of genes to many cell types of interest for gene therapy. Many of the most promising gene therapies in clinical development use this vector system, notably vectors derived from Ad subtype 5. The utility of Ad for human gene therapy could be substantially increased by improving expression of the therapeutic genes in two main ways. The first involves increasing the level of transgene expression in order to obtain the maximum effect with the minimum dose, and this applies whichever promoter is used. The second involves improving tissue-specific or tumour-specific promoters, such that they retain specificity but give stronger expression in the permissive cells. Although several promoters giving good specificity for particular tissues or tumour types are known, the level of expression they give in the permissive cells is generally too weak to be of real therapeutic benefit. An example of this is the promoter of the mouse alpha-fetoprotein (AFP) gene, which gives expression that is weak but very specific for hepatoma (liver cancer) cells (Bui et al., 1997, Human Gene Therapy, 8, 2173-2182). Such tumour-specific promoters are of particular interest for Gene-Directed Enzyme Prodrug Therapy (GDEPT) for cancer, which exploits gene delivery to accomplish targeted chemotherapy. In GDEPT a gene encoding a prodrug converting enzyme is delivered to tumour cells, for example by injecting the delivery vector into tumours. Subsequent administration of a relatively harmless prodrug converts this into a potent cytotoxic drug which kills the cells expressing the enzyme in situ. An example concerns the enzyme nitroreductase (NTR) and the prodrug CB 1954 (Bridgewater et al., 1995, Eur. J. Cancer, 31 A, 2362-2370). Adenovirus vectors give the most efficient delivery of genes encoding such enzymes, for example by direct injection into tumours.

Construction of an Ad Expressing NTR from the AFP Promoter and a UCOE

A recombinant type 5 adenovirus vector was made which expresses the NTR gene from the AFP promoter preceded by the 4 kb RNP UCOE (the sequence of FIG. 20 between nucleotides 4102 and 8286). The 4 kb UCOE was first cloned as a PmeI fragment into pTX0379, an intermediate vector which carries the NTR gene preceded by the AFP promoter (Bui et al., 1997, Human Gene Therapy, 8, 2173-2182) and flanked by Ad5 sequences (1-359, 352S-10589), by blunt end ligation into the ClaI site located 5' to the AFP promoter. Restriction digestion was used to confirm the presence of a single UCOE copy and to establish the orientation of the UCOE. A recombinant Ad construct was then generated using the plasmid pTX0384 which contains, the UCOE fragment in reverse orientation and the Ad packaging cell line Per.C6, which was developed and supplied by Introgene (Fallaux et al., 1998, Human Gene Therapy, 9, 1909-1917). The procedure supplied by Introgene was used for viral rescue. Essentially pTX0384 was linearised with Swa 1 and co-transfected into, Per.C6 cells with SwaI-linearised backbone vector pPS1160, which carries the right end of Ad5 and a region of overlap with pTX0384 such that a recombinant Ad is generated by homologous recombination. Virus produced by homologous recombination in the transfected cells was pooled and designated CTL208.

NTR Expression in Cell Lines In Vitro

Larger scale virus preparations were made using standard procedures for CTL208, and two other recombinant Ad viruses. These were CTL203, which carries the NTR gene preceded by the AFP promoter and minimal enhancer but no UCOE fragment, and CTL102 which carries the NTR gene preceded by the CMV promoter. The CMV promoter is commonly used in recombinant Ad vectors to give strong expression in a wide range of tissue and tumour types. CTL203 and CTL102 share the same Ad5 backbone as CTL208 and were identical to it except in the elements used for transcription of the NTR gene.

CTL203, 208 and 102 were then used to transduce two cell lines in vitro to investigate the level and specificity of NTR expression. These were the primary human hepatoma cell line HepG2 which expresses AFP, and KLN205, a mouse squamous cell carcinoma line which does not express AFP. Exponentially growing cells were harvested from tissue culture plates by brief trypsinisation, resuspended in infection medium at $1.25 \times 10^4$ viable cells/ml and plated into 6-well plates. The viruses were added to the wells before attachment at a multiplicity of 50, and for CTL203 at multiplicities of 100 and 500 also. After 90 minutes the fetal calf serum concentration was adjusted to 10% and the cells incubated for a total of 24 hours. Cell lysates were made from the infected cells by hypotonic lysis, then cell debris cleared by centrifugation in eppendorf tubes. An ELISA was performed to quantify the NTIR protein in the supernatants. This involved coating Nunc-Immuno Maxisorp Assay Plates with recombinant NTR, adding 50 µl of each hypotonic lysate per well in duplicate and incubating overnight at 4° C. The samples were then washed 3× with 0.5% Tween in PBS and incubated with a sheep anti-NTIR polyclonal antiserum 50 µl per well of a 1 in 2000 dilution in PBS/Tween for 30 minutes at room temperature. After washing off excess primary antibody HRP-conjugated secondary antibody was applied, this being donkey anti-sheep (100 µl per well of 1 ln 5000 in PBS/Tween). After a further 30 minutes incubation the samples were washed with PBS before development with 100 µl per well of TMB substrate (1 ml TMB solution, 1 mg/ml in DMSO+9 ml of 0.05M phosphate-citrate buffer+2 µl of 30% v/v $H_2O_2$ per 10 ml) for 10 minutes at room temperature. The reactions were stopped by addition of 25 µl of 2M $H_2SO_4$ per well and read at 450 nm using a plate reader.

FIG. 46 shows the results of these ELISAs. It shows that CTL203, with NTR expressed, from the AFP promoter/enhancer, gave weak but specific NTR expression, detectable only in the AFP positive cell line. CTLI 02 (with NTR expressed from the CMV promoter) gave much higher and non-specific expression, with very similar levels of NTR in both cell lines. Strikingly, AFP positive HepG2 cells infected with CTL208 (UCOE+AFP promoter driving expression of NTR) expressed NTR at a higher level then CTU 02 infected cells, whereas CTL208 infected AFP negative KLN205 cells expressed significantly less NTR than those infected with CTLI 02. These data show that the UCOE dramatically enhances expression in the context of Ad, with partial retention of specificity.

NTR Expression and -Tumour Effects In Vivo

Tumour-specific promoters are preferable to non-specific promoters for cancer gene therapy from the safety viewpoint, because they will give lower expression of the transgene in normal tissues. This is particularly important for Ad-based gene therapies because after injection into tumours some of the virus tends to escape from the tumour and following systemic dissemination tends to transduce normal tissues. In particular Ad gives very efficient transduction of liver cells, such that liver damage is usually the dose-limiting toxicity for Ad gene therapies. In the case of GDEPT the use of strong promoters able to give expression in normal tissues, such as the CMV promoter, can lead to killing of normal liver cells expressing NTR. This problem can potentially be avoided or minimised using tumour-specific promoters, which would be advantageous providing these give sufficiently strong expression in the tumour cells to give anti-tumour effects. CTL208 was therefore compared to CTL102 for NTR gene expression in tumour cells and liver cells following injection into tumours in mice, and for anti-tumour effects. The congenitally athymic nude mouse strain BALB/c nu/nu was used. The mice were males free of specific pathogens, aged eight to twelve weeks at the commencement of the experiments, and maintained in microisolator cages equipped with filter tops. Exponentially growing HepG2 cells cultured in vitro were used as tumour inocula. The cells were cultured in shake flasks, harvested by trypsinisation and centrifugation for 5 minutes at 800 g, washed and resuspended in sterile saline solution. Cell viability was estimated by trypan blue dye exclusion, and only single cell suspensions of greater than 90% viability were used. Mice were injected sub-cutaneously in the flank with $2-5 \times 10^6$ cells, under general anaesthesia, induced by intraperitoneal injection of 0.2 ml of a xylizine (Chanelle Animal Health Ltd, Liverpool, UK) and ketamine (Willows Francis Veterinary, Crawley, UK) mixture at a concentration of 1 mg/ml and 10 mg/ml respectively. In the first experiment CTL102 or CTL208 were injected into sub-cutaneous HepG2 tumours of size 25-60 mm² (size expressed as surface area determined by multiplying the longest diameter with its greatest perpendicular diameter, length×width'mm²) growing in nude mice. Single doses of $7.5 \times 10^9$ particles were used for each virus. The animals were sacrificed 48 hours later, their tumours and livers excised, fixed in buffered 4% formalin/PBS for 24 hours and processed for paraffin-embedding and sectioning using standard protocols. Serial 3 m sections were cut and immunostained to detect cells expressing NTR by indirect immunoperoxidase staining using a sheep anti-NTR antiserum (Polyclonal Antibodies Ltd) and VECTASTAIN Elite ABC kit (Vector Labs). These histological sections were examined using standard microscopic equipment and the percentage of cells expressing NTR in the entire livers and tumours were estimated by microscopy. FIG. 47 shows the results for each mouse. It demonstrates that the UCOE in combination with the (otherwise weak) AFP promoter gives strong NTR expression in AFIR positive tumours in mice, such that on average CTL208 gives very similar numbers of tumour cells expressing NTR at detectable levels as CTL102 following injection into tumours. Intra-tumoral injection of CTL102, however, led to NTR expression detectable in the liver for 5 out of 6 animals for CTL102, but 0 out of 6 for CTL208. This result confirms that in CTL208 the UCOE-AFP promoter combination gives expression in AFIR positive tumour cells similar to or stronger than the CMV promoter, but shows much less expression in (AFP negative) normal tissues.

To confirm that the UCOE elevates expression from the AFP promoter to therapeutically useful levels CTL208 and CTL102 were compared for their ability to confer anti-tumour effects in combination with the prodrug CB 1 954. Nude mice 2 bearing sub-cutaneous HepG2 tumours of size 25 to 60 mm$^2$ were given single injections of CTL102 or CTL208, at doses of either $7.5 \times 10^9$ or $2 \times 10^{10}$ particles. 24 hours later CB1954 administration to the mice commenced. CB1954 (Oxford Asymmetry, Oxford, UK) was dissolved in DMSO (Sigma, St Louis, Mo., USA) to give a concentration of 20 mg/ml Immediately prior to dosing this solution was diluted 1:5 in sterile saline solution to give a final concentration of 4 mg/ml. Mice received five equal daily doses intraperitoneally without anaesthesia. For a control group of mice the tumours were injected with PBS instead of virus 24 hours before commencing prodrug administration. Tumour size was measured daily using vernier calipers for the next 27 days. FIG. 48 shows the results. For the control group given CB1954 and neither virus, 7/7 tumours continued to grow rapidly. Tumour regressions were observed in some of the mice in an the groups given both NTR expressing virus and CB1954. With CTL102 regressions were observed in ⅜ mice given the lower dose, and ⅘ mice given the higher dose. With CTL208 regressions were observed in ⅝ and ⁶⁄₆ mice respectively. These results confirm that, in CTL208, the UCOE elevates NTR expression from the AFP promoter in permissive tumour cells to levels which exceed those given by the strong CMV promoter and this results in a superior anti-tumour effect in a mouse model of the clinical situation for GDEPT.

These results demonstrate two important and useful properties of the UCOE. First, it substantially improves expression in the context of Ad, a non-integrating vector of great potential in gene therapy. Second, it elevates expression from weak but specific promoters to much more useful levels with retention of useful specificity.

FISH Analysis

Copy number was determined in 31 16 RNP-EGFP clones in mouse Ltk cells. Due to the low amount of DNA used in the transfection (0.5-1.0 μg), the percentage of single. copy clones was very high (83%). Moreover, EGFP expression varied more than two-fold within the single copy clones, indicating that the transgene was susceptible to positive and negative position effects. Nonetheless, three single copy clones had integrated in centromeric heterochromatin, (FIG. 42), indicating that this construct is able to open chromatin. Clones F1 and G6 showed the 16RNP-EGFP transgene had integrated in one of the centromeres of metacentric chromosomes originated by Robertsonian translocations (Figure B, C), whereas in clone 13, integration had occurred in the centromere of a typical mouse acrocentric chromosome (Figure D).

Expression of Erythropoietin (EPO) In Vectors CET300 and CET301

Construction of EPO Expression Vectors CET300 and CET301

The erythropoietin (EPO) coding sequence was amplified by polymerase chain reaction (PCR) from a human fetal liver Quick-Clone™ cDNA library (Clontech, Palo Alto, US.) using primers EP2 (5'-CAGGTCGCTGAGGGAC-3') (SEQ ID NO:21) and EP4 (5'-CTCGACGGGGTTCAGG-3') (SEQ ID NO:22). The resulting 705 bp product, which included the entire open reading frame, was subcloned into the vector pCR3.1 using the Eukaryotic TA cloning kit (Invitrogen, Groningen, The Netherlands), to create the vector pCR-EPO. The EPO sequence was verified by automated DNA sequencing on both strands. A 790 bp Nhe I-Eco RV fragment, containing the EPO coding sequence, was excised from pCR-EPO and subcloned between the Nhe I and Pme I sites of the vectors CET200 and CET210 (containing the 7.5 kb RNP fragments in the forward and reverse orientations respectively), to generate the vectors CET300 and CET301 respectively. A control vector, pCMV-EPO, was generated by excising the EGFP coding sequence from pEGFP-N1 as a Nhe I-NotI fragment and replacing it with a Nhe I-NotI fragment from pCR-EPO containing the EPO coding sequence.

Expression of Erythropoietin in CHO Cells

Plasmids CET300, CET301 and pCMV-EPO were linearised using the restriction endonuclease Dra III. Restricted DNA was then purified by extraction with phenol-chloroform followed by ethanol precipitation. DNA was resuspended in sterile water and equimolar amounts of the plasmids were electroporated into CHO cells. Viable cells were plated in 225 cm$^3$ culture flasks and stable transfected cells were selected by replacing the medium after 24 hrs for complete medium containing 0.6 mg/ml G418. Cells were grown in this medium until G418-resistant colonies were present (about 10 days after electroporation). The flasks were then stripped and cells were seeded at $10^6$ cells/well in a E-well dish containing 1 ml of complete medium. After 48 hrs the medium was removed and the levels of erythropoietin in the media were quantitated by enzyme linked immunosorbent assay (ELISA) using a Quantikine$^R$ IVD$^R$ Human EPO immunoassay kit (R & D systems, Minneapolis, US). The levels of EPO produced by the constructs CET300, CET301 and pCMV-EPO were 1780 U/ml, 1040 U/ml and 128 U/ml respectively (FIG. 40). Therefore, constructs CET300 and CET301, containing the 7.5 kb RNP fragment in forward and reverse orientations, produced EPO in the above experiment at levels approximately 14-fold and 8-fold higher, respectively, than the control plasmid pCMV-EPO which contains the strong ubiquitous CMV promoter to drive expression of EPO.

GFP expression in Hela cells transfected with EBV reporter constructs with or without the 16 kb UCOE fragment of hnRNPA2.

In the initial experiment with cells maintained on hygromycin selection, the RNP16 UCOE-containing construct (p220.RNP16) gave high level, homogeneous expression of EGFP by day 23, whereas a more heterogeneous pattern of EGFP expression was observed with p220.EGFP (construct without the UCOE). EGFP expression in the 220.EGFP-transfected pools was gradually lost, whereas expression remained stable for 160 days with the p220.RNP16 transfected pools.

Three repeat experiments demonstrated the same pattern of high level, homogeneous EGFP expression in p220.RNP16- transfected pools, with heterogeneous expression again observed in the p220.EGFP transfected pools. As with the initial experiment, the expression of EGFP was stable with the RNP16 UCOE and was unstable without the UCOE, with expression dropping dramatically by 30-40 days (FIG. 43).

A further experiment was performed wherein hygromycin selection was removed at day 27. The results show that even without selection EGFP expression is stable with the RNP16 UCOE and was unstable without the UCOE (FIG. 44).

Example 3

Plasmid Containing a UCOE

FIG. 50 shows the constructs generated and fragments used in comparison to the hnRNPA2 endogenous genomic locus.

FIG. 51 shows a graph of the FACS analysis with median fluorescence of the transiently transfected HeLa populations. The cells were transfected using the CL22 peptide condensed reporter plasmids as indicated above. It can be seen that the duration of expression of the control CMV-GFP reporter construct is short lived and dramatically decreases from 24 to 48 hours post transfection.

In contrast to the control, the UCOE containing plasmid 7.5CMV-F continues to show significant GFP expression over an extended period of time, at least 9 days post transfection. In repeat experiments GFP expression can be seen at 14 days post transfection.

FIG. 52 shows representative low magnification field of views of the transiently transfected HeLa cell populations. The data correlates with the FACS analyses and enables the cells to be visibly followed over a similar time-course. At 24 hours post transfection significant numbers of GFP positive cells are visible in both the control CMV-GFP and 7.5CMV transient populations (FIGS. 52A and 8). In fact it can be seen that at 24 hours there were more GFP positive cells in the control population than in the 7.5CMV transfected population. This is due to the fact that the quantity of input DNA in both cases was not gene dosage corrected, resulting in significantly more copies of the control plasmid per transfection. However, at 6 days post transfection there were very few if any positive fluorescent cells left in the CMV-EGFP control population (FIG. 52C). In contrast 6 days post transfection the 7.5CMV transfected HeLa cells continued to show significant numbers of GFP expressing cells (FIG. 52D). In fact even 14 days after transfection positively fluorescing cells could easily be detected (data not shown).

Total DNA was recovered from various time points throughout the experiment, linearised, run on a gel and blotted (see Materials and Methods). Interestingly at day 6 even in the control Population of cells where little or no expression of GFP was detected, the plasmid could be readily detected in an unitegrated state (data not shown). This would suggest that the rapid loss in gene expression seen with the CMV-GFP control plasmid is not due to chronic loss of the plasmid template but rather to a mechanism of chromatin shut down of gene expression.

Transcient Transfection of CHO Cells with Erythopoietin Expression Vectors

Supercoiled forms of plasmids CET300, CET301 and CMV-EPO were electroporated into CHO cells using standard conditions (975 µF, 250V). Viable cells were then seeded at $10^6$ cells in a 6-well dish containing 1 ml of complete CHO medium. The medium was then removed at 24 hr intervals and replaced with 1 ml of fresh medium. Media samples were collected in this fashion for 9 days and erythropoietin levels were then quantitated by ELISA using a Quantikine[R] IVD[R] Human EPO immunoassay kit (R & D systems, Minneapolis, US). The attached figure shows a time-course of erythropoietin expression by cells transfected with CET300, CET301 and CMV-EPO plasmids. Erythropoietin expression continued to rise for 48 hrs in all cell populations. Thereafter, erythropoietin expression by cells transfected with CET300 or M161 continued to rise throughout the 9 day period (FIG. 45).

All References Cited Herein are Hereby Incorporated by Reference in their Entireties.

Altschul, S. F., Madden, T. L., Sch ä ffer, J. Z., Zhang, Z., Miller, W., and Lipman, D. J. (1997). Gapped BLAST and PSI-BLAST: a new generation of protein database search programs. Nucleic Acids Res. 25: 3389-3402.

Antoniou, M. (1991). Induction of erythroid specific expression in murine erythroleukaemia (MEQ cell lines. In: Methods in Molecular Biology, Vol. 7: Gene Transfer and Expression Protocols. Ed. E. J. Murray, Humana Press Inc., Clifton, N.J., U.S.A. pp. 421-434.

Antoniou, M. and Grosveld, F. (1990) 1990), The β-globin gene dominant control region interacts differently with distal and proximal promoter elements. Genes Dev. 4: 1007 1012.

Archer, T. K., Lefebvre, P., Wolford, R. G. and Hager, G. L. (1992) Transcription factor loading on the MMTV promoter: a bimodal mechanism for promoter activation. Science 255: 1573 1576.

Aronow, B. J. Ebert, C. A., Valerius, M. T., Potter, S. S., Wiginton, D. A., Witte, D. P. and Hutton, J. J. (1995) Dissecting a Locus Control Region: Facilitation of Enhancer Function by Extended Enhancer Flanking Sequences. Mol. Cell. Biol. 15: 1123-1135.

Auffray, C., and Rougeon, F. (1980). Purification of mouse immunoglobulin heavy chain RNAs from total myeloma tumor RNA. Eur. J. Biochem. 107: 303-324.

Blom van Assendelft, G., Hanscombe, 0., Grosveld, F., and Greaves, D. R. (1989). The (1989). The β-globin dominant control region activates homologous and heterologous promoters in a tissue-specific manner. Cell 56L 969-977.

Brines R D and Klaus G G (1993) Polyclonal activation of immature B cells by preactivated T-cells: the role of IL-4 and CD40 ligand. Int Immunol 5: 1445-1450.

Chalut, C., Gallois, Y., Poterszman, A., Moncollin, V., and Egly, J.-M. (1995). Genomic structure of the human TATA box binding protein (TBP). Gene 161: 277-282.

Chu, G., Hayakawa, H., and Berg, P. (1987). Electroporation for the efficient transfection of mammalian cells with DNA. Nucleic Acids Res. 15: 1311-1326.

Church, G. M., and Gilbert, W. (1984). Genomic sequencing. Proc. Natl. Acad. Sci. USA 81: 1991-1995.

Collis, P., Antoniou, M. and Grosveld, F. (1990). Definition of the minimal requirements within the human β-globin gene and the dominant control region for high level expression. EMBO J. 9: 233-240.

Cooper, M. J. and Miron, S., 1993, Efficient episomal expression vector for human transitional carcinoma cells, Hum. Gene Ther. 4: 557-566.

Dai, Y., Roman, M., Naviaux, R X and Verma, I. M. (1992) Gene Therapy via primary myoblasts: long-term expression of factor IX protein following transplantation in vivo. Proc. Natl. Acad. Sci. USA 89: 10892-10895.

De Benedetti, A. and Rhoads, R. E., 1991, A novel BK virus based episomal vector for expression of foreign genes in mammalian cells, Nucl. Acids Res., 19:1925-1931.

Deprimo, S. E., Stambrook, P. J. and Stringer, J. R. (1996) Human placental alkaline phosphatase as a histochemical marker of gene expression in transgenic mice.

Diaz, P., Cado, D. and Winoto, A. (1994). A locus control region in the T-cell receptor α/δ locus. Immunity 1: 207-217.

Dillon, N., and Grosveld, F. (1993). Transcriptional analysis using transgenic animals. In Gene Transcription: A practical approach, B. D. Harries and S. J. Higgins, eds. (Oxford: IRL Press), pp. 153-188.

Dillon, N. and Grosveld, F. (1994). Chromatin domains as potential units of eukaryotic gene function. Curr. Opin. Genet. Develop. 4: 260 264.

Dillon, N., Trimborn, T., Strouboulis, J., Fraser, P. and Grosveld F. (1997). The effect of distance on long range chromatin interactions. Mol. Cell. 1: 131-39.

Earle, W. R., Schilling, E. L., Stark, T. H., Straus, N. P., Brown, M. F., and Shelton, E. (1943). Production of malignancy in vitro. IV. The mouse fibroblast cultures and changes seen in the living cells. J. Natl. Cancer Inst. 4: 165-212.

Ellis, J., Tan Un, K. C., Harper, A., Michalovich, D., Yannoutsos, N., Philipsen, S. and Grosveld, F. (1996). A dominant chromatin opening activity in 5=hypersensitive site 3 of the human β-globin locus control region. EMBO J. 15: 562-568.

Festenstein, R., Tolaini, M., Corbella, P., Mamalaki, C., Parrington, J., Fox, M., Millou, A., Jones, M. and Kloussis, D. (1996). Locus control region function and heterochromatin induced position effect variegation. Science 271: 1123-1125.

Flotte, T. R. and Carter, B J. (1995) Adeno associated virus vectors for gene therapy. Gene Ther. 2: 357-362.

Foulds, C. E. and Hawley, D. K. (1997) Analysis of the human TATA binding protein promoter and identification of an ets site critical for activity. Nucl. Acids Res. 25: 2485-2494.

Forrester, W. C., Takegawa, S., Papayannopouplou, T., Starnatoyannopoulos, G., and Groudine, M. (1987). Evidence for a locus activation region: the formation of developmentally stable hypersensitive sites in globin expressing hybrids. Nucleic Acids Res. 15: 10159-10177.

Freshney, R. I. (1994). In Culture of animal cells: a manual of basic techniques (New York: Wiley Liss, Inc.), pp. 169-171.

Greaves, D. R., Wilson, F. D., Lang, G. and Kioussis, D. (1989). Human CD2 3' flanking sequences confer high level, T-cell specific, position independent gene expression in transgenic mice. Cell 56: 979-986.

Grosveld, F., Blom van Assendelft, G. B., Greaves, D. R. and Kollias, G. (1987). Position independent high level expression of the human β-globin gene in transgenic mice. Cell 51: 975-985.

Grosveld, F., Dillon, N. and Higgs, D. R. (1993) The regulation of human globin gene expression. Baillieres Clin. Haematol. 6: 31-55.

Hammekytö, M., Alhonen, L., Wahlfors, J., Sinervirta, R., Janne, O. A., and Janne, J. (1991). Position independent, aberrant expression of the human ornithine decarboxylase gene in transgenic mice. Biochem. Biophys. Res. Comm 180: 262-267.

Hanscombe, O., Whyatt, D., Fraser, P., Yannoutsos, N., Greaves, D., Dillon, N. and Grosveld, F. (1991) Importance of globin gene order for correct developmental expression. Genes Dev. 5: 1387-1394.

Hartman, P. S. (1991). Transillumination can profoundly reduce transformation frequencies. BioTechniques 11: 747-748.

Heng H H, Xiao H, Shi X M, Greenblatt J, Tsui L C (1994) Genes encoding general initiation factors for RNA polymerase 11 transcription are dispersed in the human genome. Hum Mol. Genet. 3: 61-64.

Hong, N. A., Cado, D., Mitchell, J., Ortiz, B. D., Hsieh, S. N. and Winoto, A. (1997) A targeted mutation at the T-cell receptor a locus impairs T-cell development and reveals the presence of the nearby anti-apoptosis gene Dad-1. Mol. Cell. Biol. 17:2151-2157.

Ioannou, P. A., Amemiya, C. T., Gamer, J., Kroisel, P. M., Shizuya, H., Chen, C., Batzer, M. A., and de Jong, P. J. (1994). A new bacteriophage P1-derived vector for the propagation of large human DNA fragments. Nat. Genet. 6: 84-89.

Jarman, A. P., Wood, W. G., Sharpe, J. A., Gourdon, G., Ayyub, H. and Higgs, D. R. (1991) Characterization of the major regulatory element upstream of the human alpha globin gene cluster. Mol. Cell. Biol. 11: 4679-4689.

Jones, B. K., Monks, B. R., Liebhaber, S. A. and Cooke, N. E. (1995) The Human Growth Hormone Gene is Regulated by a Multicomponent Locus Control Region. Mol. Cell. Biol. 15: 7010-7021.

Kaufman, R. J. (1990) Methods in Enzymology 185: 537 566.

Lang, G., Wotton, D., Owen, M. J., Sewell, W. A., Brown, M. H., Mason, D. Y., Crumpton, M. J. and Kioussis, D. (1988) The structure of the human CD2 gene and its expression in transgenic mice. EMBO J. 7: 1675-1682.

Larsen, F., Gundersen, G., Lopez, R., and Prydz, H. (1992). CpG-islands as gene markers in the human genome. Genomics 13: 1095-1107.

Lozzio, C. B., and Lozzio, B. B. (1975). Human chronic myelogenous leukemia cell line with positive Philadelphia chromosome. Blood 45: 321-334.

McBurney, M. W., Staines, W. A., Boekelheide, K., Parry, D., Jardine, K. and Pickavance, L. (1994) Murine PGK-1 promoter drives widespread but not uniform expression in transgenic mice. Devel. Dynam. 200: 278-293.

Mehtali, M., LeMeur, M. and Lathe, R. (1990) The methylation free status of a housekeeping transgene is lost at high copy-number. Gene 91: 179-184.

Yeoman H and Mellor A L (1992) Tolerance and MHC restriction in transgenic mice expressing a MHC class I gene in erythroid cells. Int Immunol 4: 59-65.

Michelsen, B. K. (1995). Transformation of *Escherichia coli* increases 260-fold upon inactivation of T4 DNA ligase. Anal. Biochem. 225:172-174.

Miller, A. D. (1992) Retroviral vectors. Curr. Top. Microbiol. Immunol. 158: 1-24.

Miller, A. D., Miller, D. G., Garcia, J. V. and Lynch, C. M. (1993) Use of retroviral vectors for gene transfer and expression. Meth. Enzymol. 217: 581-599.

Milot, E., Strouboulis, J., Trimborn, T., Wijgerde, M., de Boer, E., Langeveld, A., Tan-Un, K., Vergeer, W., Yannoutsos, N., Grosveld, F. and Fraser, P. (1996). Heterochromatin effects on the frequency and duration of LCR-mediated gene transcription. Cell 87: 105-114.

Montoliu, L., Umland, T. and Sch a tz, G. (1996). A locus control region at −12 kb of the tyrosinase gene. EMBO J. 15: 6026-6034.

Muzyczka, N. (1992) Use of adeno-associated virus as a general transduction vector for mammalian cells, Curr. Top. Microbiol. Immunol., 158: 97-129.

Needham, M., Egerton, M., Millest, A., Evans, S., Popplewell, M., Cerillo, G., McPheat, J., Monk, A., Jack, A., Johnstone, D. and Hollis, M. (1995). Further development of the locus control region/murine erythroleukemia expression system: high level expression and characterisation of recombinant human calcitonin receptor. Protein Expression and Purification 6: 124-131.

Needham, M., Gooding, C., Hudson, K., Antoniou, M., Grosveld, F. and Hollis, M. (1992). LCR/MEL: A versatile system for high level expression of heterologous proteins in erythroid cells. Nucl. Acids Res. 20: 997-1003.

Ogilvy, S., Elefanty, A. G., Visvader, J., Bath, M. L., Harris, A. W., and Adams, J. M. (1998). Transcriptional regulation of vav, a gene expressed throughout the hematopoietic compartment. Blood 91: 419-430.

Ortiz, B. D., Cado, D., Chen, V., Diaz, P. W. and Winoto, A. (1997) Adjacent DNA elements dominantly restrict the ubiquitous activity of a novel chromatin opening region to specific tissues. EMBO J. 16: 5037-5045.

Peterson, M. G., Tanese, N., Pugh, B F., and Tijan, R. (1990). Functional domains and upstream activation properties of cloned human TATA binding protein. Science 248:1625-1630.

Philipsen, S., Talbot, D., Fraser, P. and Grosveld, F. (1990) The β-globin dominant control region: hypersensitive site 2, EMBO J., 9: 2159-2167.

Piirsoo, M., Ustav, E., Mandel, T., Stenlund, A. and Ustav, M. (1996) Cis and trans requirements for stable episomal maintenance of the BPV-1 replicator. EMBO J. 15: 1-11.

Pruzina, S., Hanscombe, O., Whyatt, D., Grosveld, F. and Philipsen, S. (1991) Hypersensitive site 4 of the human β-globin locus control region, Nucl. Acids Res., 19: 1413-1419.

Raguz, S., Hobbs, C., Yagüe, E., loannou, P. A., Walsh, F. S, and Antoniou, M. (1998) Muscle specific locus control region activity associated with the human desmin gene. Develop. Biol. in press.

Ray P, Higgins K M, Tan J C, Chu T Y, Yee ISIS, Nguyen H, Lacy E, Besmer P (1991) Ectopic expression of a c-kitW42 minigene in transgenic mice: recapitulation of W phenotypes and evidence for c kit function in melanoblast progenitors. Genes Dev. 5: 2265-2273.

Reeves, R., Gorman, C. M. and Howard, B. (1985) Minichromosome assembly of non-integrated plasmid DNA transfected into mammalian cells. Nucl. Acids Res. 13:3599-3615.

Reitmann, M., Lee, E., Westphal, H., and Felsenfeld, G. (1993). An enhancer/locus control region is not sufficient to open chromatin. Mol. Cell. Biol. 13: 3990-3998.

Smith, C. L., Archer, T. K., Hamlin Green, G. and Hager, G. L. (1993) Newly expressed progesterone receptor cannot activate stable, replicated mouse mammary tumor virus templates but acquires transactivation potential upon continuous expression. Proc. Natl. Acad. Sci. USA 90: 11202-11206.

Southern, E. M. 0975). Detection of specific sequences among DNA fragments separated by gel electrophoresis. J. Mol. Biol. 98: 503-517.

Sun, T. Q., Fernstermacher, D. A. and Vos, J. M. (1994) Human artificial episomal chromosomes for cloning large DNA fragments in human cells. Nat. Genet. 8, 33-41.

Talbot, D., Philipsen, S., Fraser, P. and Grosveld, F. (1990) Detailed analysis of the site 3 region of the human β-globin dominant control region, EMBO J., 9: 2169-2178.

Tamura T, Osaka F, Kawamura Y, Higuti T, Ishida N, Nothwang H G, Tsurumi C, Tanaka K, Ichihara A (1994) Isolation and characterization of alpha-type HC3 and beta type HC5 subunit genes of human proteasomes. J. Mol. Biol. 244: 117-124.

Tartof, K. D., and Hobbs, C. A. 0 987). Improved media for growing plasmid and cosmid clones. Bethesda Res. Lab. Focus 9: 12.

Trachtulec Z, Hamvas R M, Forejt J, Lehrach H R, Vincek V, Klein J (1997) Linkage of TATA binding protein and proteasome subunit CS genes in mice and humans reveals synteny conserved between mammals and invertebrates. Genomics 44:1-7.

Vyas P, Vickers M A, Simmons D L, Ayyub H, Craddock C F, Higgs D R (1992).

Winston, J. H., Hong, L., Datta, S. K. and Kellems, R. E. (1996) An intron 1 regulatory region from the murine adenosine deaminase gene can activate heterologous promoters for ubiquitous expression in transgenic mice. Som. Cell Mol. Genet. 22: 261-278.

Yamashita, T., Kasai, N., Miyoshi, I., Sasaki, N., Maki, K., Sakai, M., Nishi, S. and Namioka, S. (1993) High level expression of human alpha fetoprotein in transgenic mice. Biochem. Biophys. Res. Comm 191: 715-720.

Yates, J. L., Warren, N. and Sugden, B. (1985) Stable replication of plasmids derived from Epstein Barr virus in various mammalian cells. Nature 313: 812-815.

Zhumabekov T, Corbella P, Tolaini M, Kioussis D (1995) Improved version of a human CD2 minigene based vector for T-cell specific expression in transgenic mice. J. Immunol. Methods 185: 133-140.

---

What is claimed is:

1. A method of obtaining a desired gene product comprising culturing a host cell, wherein the host cell comprises a vector, and the vector comprises a polynucleotide, the polynucleotide comprising:
   (i) at least one extended methylation-free CpG-island comprising dual or bi-directional promoters that are divergently transcribed;
   (ii) an expressible gene encoding a desired gene product, wherein the expressible gene is operably-linked to the at least one CpG-island; and
   (iii) a promoter, operably-linked to the expressible gene, wherein said promoter is not naturally operably-linked to said CpG-island;
wherein the at least one extended methylation-free CpG island facilitates reproducible activation of transcription of the expressible gene.

2. The method of claim 1, wherein the at least one extended methylation-free CpG island comprises at least one endogenous promoter.

3. The method of claim 1, wherein the at least one extended methylation-free CpG island comprises dual promoters that transcribe divergently.

4. The method of claim 1, wherein the at least one extended methylation-free CpG island extends for more than 300 bp or more than 500 bp.

5. The method of claim 1, wherein the at least one extended methylation-free CpG island comprises a 44 kb DNA fragment spanning the human TATA binding protein gene and 12 kb from each of the 5' and 3' flanking sequence.

6. The method of claim 1, wherein the at least one extended methylation-free CpG island comprises a 25 kb DNA fragment spanning the human TATA binding protein gene with 1 kb 5' and 5 kb 3' flanking sequence.

7. The method of claim 1, wherein the at least one extended methylation-free CpG island comprises the sequence according to FIG. 21 or a functional fragment thereof.

8. The method of claim 1, wherein the at least one extended methylation-free CpG island comprises a 60 kb DNA fragment spanning the human heterogeneous nuclear ribonucleoprotein A2 gene with 30 kb 5' and 20 kb 3' flanking sequence.

9. The method of claim 1, wherein the at least one extended methylation-free CpG island comprises a 16 kb DNA fragment spanning the human heterogeneous nuclear ribonucleoprotein A2 gene with 5 kb 5' and 1.5 kb 3' flanking sequence.

10. The method of claim 1, wherein the vector comprises a heterologous promoter which is a tissue specific promoter or a substantially ubiquitous promoter.

11. The method of claim 10, wherein the promoter is the CMV promoter.

12. The method of claim 1, wherein the expressible gene encodes a therapeutic polypeptide.

13. The method of claim 12, wherein the expressible gene encodes a therapeutic antibody or fragment thereof.

14. The method of claim 1, wherein the at least one extended methylation-free CpG-island increases the expression of the operably linked expressible gene.

15. A method for increasing the expression of an endogenous gene, said method comprising inserting an isolated polynucleotide comprising an extended methylation free CpG island into the genome of a cell in a position operably associated with the endogenous gene thereby increasing the level of expression of the gene, wherein said extended methylation-free CpG island comprises dual or bi-directional promoters that are divergently transcribed.

* * * * *